United States Patent
Annathur et al.

(10) Patent No.: US 9,163,227 B2
(45) Date of Patent: Oct. 20, 2015

(54) ANTI-DIABETIC COMPOUNDS

(71) Applicants: PFIZER INC., New York, NY (US); COVX TECHNOLOGIES IRELAND LIMITED, Ringaskiddy, Co. Cork (IE)

(72) Inventors: Gopinath Vedachalam Annathur, Bangalore (IN); Palani Balu, Cupertino, CA (US); Rory Francis Finn, Manchester, MO (US); Jie Huang, San Diego, CA (US); Olivier Alexandre Laurent, San Diego, CA (US); Nancy Jane Levin, Encinitas, CA (US); Nicholas Gary Luksha, North Andover, MA (US); Joseph Patrick Martin, Jr., Wildwood, MO (US); Haim Moskowitz, San Diego, CA (US); Moorthy Sitharamaiah Suriyanarayana Palanki, Encinitas, CA (US); Mark John Pozzo, Chesterfield, MO (US); Gregory Allan Waszak, O'Fallon, MO (US); Jin Xie, Ballwin, MO (US)

(73) Assignee: COVX TECHNOLOGIES IRELAND LIMITED, Ringaskiddy, Co. Cork (IE)

( * ) Notice: Subject to any disclaimer, the term of this patent is extended or adjusted under 35 U.S.C. 154(b) by 30 days.

(21) Appl. No.: 13/712,873

(22) Filed: Dec. 12, 2012

(65) Prior Publication Data

US 2013/0164310 A1    Jun. 27, 2013

Related U.S. Application Data

(60) Provisional application No. 61/644,831, filed on May 9, 2012, provisional application No. 61/579,609, filed on Dec. 22, 2011.

(51) Int. Cl.
*C12N 9/00* (2006.01)
*C12N 9/96* (2006.01)
*A61K 38/22* (2006.01)
*A61K 47/48* (2006.01)

(52) U.S. Cl.
CPC .............. *C12N 9/96* (2013.01); *A61K 38/2278* (2013.01); *A61K 47/48415* (2013.01); *A61K 47/48538* (2013.01)

(58) Field of Classification Search
CPC ................................ C12N 9/0002; C12N 9/96
See application file for complete search history.

(56) References Cited

FOREIGN PATENT DOCUMENTS

| | | |
|---|---|---|
| EP | 2 292 248 A2 | 3/2011 |
| WO | WO 2009/020802 A2 | 2/2009 |
| WO | WO 2011/020319 A1 | 2/2011 |
| WO | WO 2011/024110 A2 | 3/2011 |

OTHER PUBLICATIONS

Fan, K., et al, "Exendin-4-FGF-21 Fusion Protein Sequence #4," Feb. 24, 2011, GENESEQ AZF43312.
Rader, et al., "A Humanized Aldolase Antibody for Selective Chemotherapy and Adaptor Immunotherapy," Journal of Molecular Biology, 889-899, vol. 332, No. 4.

*Primary Examiner* — Ruixiang Li
(74) *Attorney, Agent, or Firm* — Pfizer Inc.

(57) ABSTRACT

The present invention provides a composition of the formula: [FGF21-$1^{st}$ Linker]-[Ab]-[$2^{nd}$-Linker-Ex4]; wherein FGF21 is an FGF21 homologue; and Ex4 is an Exendin4 homologue; and Ab is an aldolase catalytic antibody or antigen binding portion thereof; and the $1^{st}$ linker is covalently attached to the side chain of a protein-linking residue in FGF21 and to a combining site of the antibody, and the $2^{nd}$ linker is covalently attached to the side chain of a peptide-linking residue in Ex4 and to a combining site of the antibody, and wherein the first and second linker are the same or different. Various uses of the compounds are provided, including methods to prevent or treat diabetes or diabetes-related conditions.

14 Claims, 14 Drawing Sheets

```
                      1         2                 3                    4         5                 6         7         8                 9         10
         1234567890123 4567890123abcde234 567890123456789 0123456 789012345678901234567 8901234567 01234567
              FR1              CDR1              FR2          CDR2          FR3              CDR3       FR4 m38c2    DVVMTQTPLSLPVRLGDQASISC RSSQSLLHTYGSPYLN  WYLQKPGQSPKLLIY  KVSNRFS  GVPDRFSGSGSGTDFTLRISRVEAEDLGVYFC  SQGTHLPYT  FGGGTKLEIK
              ***  *  **        ******      *          * ***        *             * **         * *****        *
h38c2    ELQMTQSPSSLSASVGDRVTITC RSSQSLLHTYGSPYLN  WYLQKPGQSPKLLIY  KVSNRFS  GVPSRFSGSGSGTDFTLTISSLQPEDFAVYFC  SQGTHLPYT  FGGGTKVEIK
              **                 ********                                                                         * *****
DPK-9    DIQMTQSPSSLSASVGDRVTITC RASQS-SS----YLN   WYQQKPGKAPKLLIY  AASSLQS  GVPSRFSGSGSGTDFTLTISSLQPEDFATYYC  QQSYS-P
JK4                                                                                                         LT FGGGTKVEIK
```

VH

```
             -2345678901234567890 1ab2345  5789012345678  5  012abc345678901234  56789012345  5 6789012  345678901234
                     FR1             CDR1       FR2            CDR2                FR3               CDR3             FR4 m38c2    EVKLVESGGGLVQPGGTMKLSCEISCLTFR N  YWMS  WVRQSPEKGLEWVA  E-RLRSDNYATHYAESVKG  KFTISRDDSKSRLYLQMNSLRTEDTGIYYCKY  YFY-SFSY  WGQGTLVTVSA
            *  *       *   *        * *        *        * *   ***  *     *    *                          **
h38c2    EVQLVESGGGLVQPGGSLRLSCAASGFTFS N--YWMS  WVRQSPEKGLEWVS  E-RLRSDNYATHYAESVKG  RFTISRDNSKNTLYLQMNSLRAEDTGIYYCKT  YFY-SFSY  WGQGTLVTVSS
              **               *   *                             * ***   *****  *       **  **                           **
DP-47    EVQLLESGGGLVQPGGSLRLSCAASGFTFS S--YAMS  WVRQAPGKGLRWVS  A-SG--SGGSTYYADSVKG  RFTTSRDNSKNTLYLQMNSLRARDTAVYYCAK
JH4                                                                                                                 YFDY  WGQGTLVTVSS
```

ANTI-DIABETIC COMPOUNDS

This application claims the benefit of U.S. Provisional Application No. 61/579,609 filed Dec. 22, 2011, and U.S. Provisional Application No. 61/644,831 filed May 9, 2012, the contents of which are hereby incorporated by reference in their entireties.

The present invention relates to novel compounds that promote insulin secretion and lower blood glucose levels, and methods of making and using these compounds.

REFERENCE TO SEQUENCE LISTING

This application is being filed electronically via EFS-Web and includes an electronically submitted sequence listing in .txt format. The .txt file contains a sequence listing entitled "PC71861A_seq_list.txt" created on Dec. 12, 2012 and having a size of 93 KB. The sequence listing contained in this .txt file is part of the specification and is herein incorporated by reference in its entirety.

BACKGROUND

Type II diabetes is the most prevalent form of diabetes. The disease is caused by insulin resistance and pancreatic β cell failure, which results in decreased glucose-stimulated insulin secretion. Fibroblast growth factor (FGF) 21, a member of the FGF family, has been identified as a metabolic regulator and is preferentially expressed in the liver and adipose tissue and exerts its biological activities through a cell surface receptor complex composed of FGFR1c and β-Klotho on target cells such as liver and adipose tissues (WO0136640, and WO0118172). The receptor complex is thought to trigger cytoplasmic signaling and to up-regulate the GLUT1 expression through the Ras/MAP kinase pathway. Its abilities to provide sustained glucose and lipid control, and improve insulin sensitivity and β-cell function, without causing any apparent adverse effects in preclinical settings, have made FGF21 an attractive therapeutic agent for type-2 diabetes and associated metabolic disorders.

There have been a number of efforts towards developing therapies based on FGF21. WO2006065582, WO2006028714, WO2006028595, and WO2005061712 relate to muteins of FGF21, comprising individual amino-acid substitutions. WO2006078463 is directed towards a method of treating cardiovascular disease using FGF21. WO2005072769 relates to methods of treating diabetes using combinations of FGF21 and thiazolidinedione. WO03059270 relates to methods of reducing the mortality of critically ill patients comprising administering FGF21. WO03011213 relates to a method of treating diabetes and obesity comprising administering FGF21.

However, many of these proposed therapies suffer from the problem that FGF21 has an in-vivo half-life of between 1.5 and 2 hrs in humans. Some attempts have been made to overcome this drawback. WO2005091944, WO2006050247 and WO2008121563 disclose FGF21 molecules linked to PEG via lysine or cysteine residues, glycosyl groups and non-natural amino acid residues, respectively. WO2005113606 describes FGF21 molecules recombinantly fused via their C-terminus to albumin and immunoglobulin molecules using polyglycine linkers.

However, developing protein conjugates into useful, cost-effective pharmaceuticals presents a number of significant and oftentimes competing challenges: a balance must be struck between in vivo efficacy, in vivo half-life, stability for in vitro storage, and ease and efficiency of manufacture, including conjugation efficiency and specificity. In general, it is an imperative that the conjugation process does not eliminate or significantly reduce the desired biological action of the protein in question. The protein-protein interactions required for function may require multiple regions of the protein to act in concert, and perturbing any of these with the nearby presence of a conjugate may interfere with the active site(s), or cause sufficient alterations to the tertiary structure so as to reduce active-site function. Unless the conjugation is through the N' or C' terminus, internal mutations to facilitate the linkage may be required. These mutations can have unpredictable effects on protein structure and function. There therefore continues to be a need for alternative FGF21-based therapeutics.

Incretins are compounds that stimulate glucose-dependent insulin secretion and inhibit glucagon secretion, have emerged as attractive candidates for the treatment of type II diabetes. Glucagon-like peptide (7-36) amide (GLP1) is one of the incretin family members, and has been shown to increase insulin secretion, decrease glucagon secretion, stimulate pro-insulin gene transcription, slow down gastric emptying time, and reduce food intake (WO98019698). GLP1 exerts its physiological effects by binding to the glucagon-like peptide 1 receptor (GLP1R), a putative seven-transmembrane domain receptor.

A drawback to the therapeutic use of GLP1 is its short in vivo half-life (1-2 mins). This short half-life is the result of rapid degradation of the peptide by dipeptidyl peptidase 4 (DPP-IV). This has led to the identification of GLP1 homologues that exhibit increased half lives while maintaining the ability to agonize GLP1R activity. Examples of these homologues include exendin4 and GLP1-Gly8.

WO2009020802 discloses a method for lowering body weight comprising administering a FGF21 compound in combination with a GLP1 compound.

The reference to any art in this specification is not, and should not be taken as, an acknowledgement of any form or suggestion that the referenced art forms part of the common general knowledge.

SUMMARY OF INVENTION

In some aspects the invention provides a composition of the formula:

[FGF21-1$^{st}$ Linker]-[Ab]-[2$^{nd}$-Linker-Ex4]; wherein

FGF21 is an FGF21 homologue; and
Ex4 is an Exendin4 homologue; and
Ab is an aldolase catalytic antibody or antigen binding portion thereof; and
the 1$^{st}$ linker is covalently attached to the side chain of a protein-linking residue in FGF21 and to a combining site of the antibody, and
the 2$^{nd}$ linker is covalently attached to the side chain of a peptide-linking residue in Ex4 and to a combining site of the antibody, and wherein the first and second linker are the same or different; or stereoisomers, tautomers, solvates, prodrugs, and pharmaceutically acceptable salts thereof.

In some aspects, the present invention relates to a composition comprising a FGF21 molecule covalently attached to a first combining site of an antibody or antigen binding portion thereof via a first linker, wherein the first linker is covalently attached to the side chain of a protein-linking residue within FGF21, and further comprising an Exendin4 homologue covalently attached to a second combining site of the antibody via a second linker, wherein the second linker is covalently attached to the side chain of a peptide-linking residue within the Exendin4 homologue; or stereoisomers, tautomers, solvates, prodrugs, and pharmaceutically acceptable salts thereof.

In some aspects, the invention comprises the formula: [FGF21]-[1$^{st}$ Linker]-[Antibody]-[2$^{nd}$-Linker]-[Ex4] wherein FGF21 is an FGF21 homologue, and may be selected from the group consisting of SEQ ID NOs: 3, 4, 5, 6, 7, 8, 9, 10, 11, 12, 13, 14, 15, 16, 17, 18, 19, 20, 21, 22, 23, and 24; and Ex4 is an Exendin4 homologue, and may be selected from the group consisting of SEQ ID NOs: 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, and 72, and the Antibody is an aldolase catalytic antibody or antigen binding portion thereof; and the 1$^{st}$ linker is covalently attached to the side chain of a protein-linking residue in FGF21 and to the combining site of the antibody, and the 2$^{nd}$ linker is covalently attached to the side chain of a peptide-linking residue in Ex4 and to the combining site of the Antibody, and wherein the first and second linker are the same or different. The 1$^{st}$ and 2$^{nd}$ linker may each independently be selected from the group consisting of L1, L2, L3, L4, L5, L6, L7, L8, L9 and L10.

The protein-linking residue may be cysteine or lysine. The protein-linking residue may be located at a position selected from the group consisting of amino acid residue numbers 56, 59, 69, 79, 86, 122, 125 and 129, according to the numbering of SEQ ID NO:1. The protein-linking residue may be located at a position selected from the group consisting of amino acid residue numbers 56, 59, 86, and 122 according to the numbering of SEQ ID NO:1. The protein-linking residue may be located at a position selected from the group consisting of residue 79, 125 and 129 according to the numbering of SEQ ID NO:1. The protein-linking residue may be located at a position selected from the group consisting of residues 125 and 129 according to the numbering of SEQ ID NO:1.

The side chain of the protein-linking residue may comprise a thiol group. The protein-linking residue may be cysteine.

The FGF21 molecule may comprise SEQ ID NO:3. The FGF21 molecule may comprise SEQ ID NO:4. The FGF21 molecule may comprise a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

The protein-linking residue may be located at position 125 according to the numbering of SEQ ID NO:1. The FGF21 molecule may comprise a sequence selected from the group consisting of SEQ ID NO:3, SEQ ID NO:4, SEQ ID NO:5, SEQ ID NO:6, and SEQ ID NO:7. In some embodiments, the FGF21 sequence is SEQ ID NO:7.

The protein-linking residue may be located at position 129 according to the numbering of SEQ ID NO:1. The FGF21 molecule may comprise a sequence selected from the group consisting of SEQ ID NO:3, SEQ ID NO:4, SEQ ID NO:8, SEQ ID NO:9, and SEQ ID NO:10. In some embodiments, the FGF21 sequence is SEQ ID NO:10. The FGF21 molecule may comprise SEQ ID NO:8, SEQ ID NO:9 or SEQ ID NO:10.

The protein-linking residue may be located at position 79 according to the numbering of SEQ ID NO:1. The FGF21 molecule may comprise a sequence selected from the group consisting of SEQ ID NO:3, SEQ ID NO:4, SEQ ID NO:11, SEQ ID NO:12, and SEQ ID NO:13. In some embodiments, the FGF21 sequence is SEQ ID NO:13.

In some embodiments, the protein-linking residue may be located at a position selected from the group consisting of 1, 2, 56, 59, 69, and 122 according to the numbering of SEQ ID NO:1. In some embodiments, the protein-linking residue may be located at a position selected from the group consisting of 1, 2, 56, 59, and 122 according to the numbering of SEQ ID NO:1. The protein-linking residue may be lysine. The FGF21 molecule may comprise SEQ ID NO:17. The FGF21 molecule may comprise a sequence selected from the group consisting of SEQ ID NO:18, SEQ ID NO:19, SEQ ID NO:20, SEQ ID NO:21, and SEQ ID NO:23.

In some aspects, the Exendin4 homologue may comprise the formula: Hx$^2$EGTFTSDLSKQMEEEAVRL FIEWLKNGGPSSGAPPPSx$^{40}$ (SEQ ID NO:38), wherein x$^2$ is Aib and x$^{40}$ is a peptide-linking residue comprising any amino acid or is absent, and wherein one of L$^{10}$, S$^{11}$, K$^{12}$, Q$^{13}$, M$^{14}$, E$^{16}$, E$^{17}$, V$^{19}$, R$^{20}$, L$^{21}$, E$^{24}$, L$^{26}$, K$^{27}$, N$^{28}$, S$^{32}$, S$^{33}$, G$^{34}$, A$^{35}$, P$^{36}$, P$^{37}$, P$^{38}$, S$^{39}$, or X$^{40}$ comprises or is substituted with a peptide-linking residue [LR], such that the peptide linking residue comprises a nucleophilic side chain or C-terminus carboxyl group covalently linked to the second combining site of the antibody via the second linker, and where linkable through the nucleophilic side chain, the peptide linking residue being selected from the group consisting of K, K(SH), K(S-MAL), R, Y, C, T, S, homocysteine, homoserine, Dap, and Dab.

The peptide-linking residue may be located at a position selected from the group consisting of amino acid residue numbers 11, 12, 13, 14, 15, 16, 17, 19, 20, 21, 24, 27, 28, 39, and 40, according to the numbering of SEQ ID NO:38. In some embodiments, the peptide-linking residue is located at one of positions of 12, 13, 14, 16, 17, 19, 20, 21, 24, according to the numbering of SEQ ID NO:38. In some embodiments, the Exendin4 homologue comprises a sequence selected from the group consisting of SEQ ID NO:46, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the peptide-linking residue is located at one of positions of 13, 14, 16, 17, 19, 20, 21, 24, according to the numbering of SEQ ID NO:38. In some embodiments, the Exendin4 homologue comprises a sequence selected from the group consisting of SEQ ID NO:46, SEQ ID NO:48, SEQ ID NO:49, SEQ ID NO:50, SEQ ID NO:51, SEQ ID NO:52, SEQ ID NO:53, and SEQ ID NO:54.

In some embodiments, the peptide-linking residue is located at one of positions of 12, 14, 17, 19, 20, or 21, according to the numbering of SEQ ID NO:38. In some embodiments, the Exendin4 homologue comprises a sequence selected from the group consisting of SEQ ID NO:48, SEQ ID NO:49, SEQ ID NO:50, SEQ ID NO:51, SEQ ID NO:53, and SEQ ID NO:55.

In some embodiments, the peptide-linking residue is located at one of positions of 12, 14, 19, 20, 21, or 40 according to the numbering of SEQ ID NO:38.

The Exendin4 homologue may comprise SEQ ID NO:60. In some embodiments, the Exendin4 homologue comprises a sequence selected from the group consisting of SEQ ID NO:48, SEQ ID NO:49, SEQ ID NO:50, SEQ ID NO:53, SEQ ID NO:55, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, and SEQ ID NO:72.

The Exendin4 homologue may comprise SEQ ID NO:60 when x40 is absent. In some embodiments, the Exendin4 homologue comprises a sequence selected from the group consisting of SEQ ID NO:48, SEQ ID NO:49, SEQ ID NO:50, SEQ ID NO:53, SEQ ID NO:55, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, and SEQ ID NO:70.

In some embodiments, the peptide-linking residue is located at one of positions of 14, 19, 20, or 21, according to the numbering of SEQ ID NO:60. In some embodiments, the Exendin4 homologue comprises a sequence selected from the group consisting of SEQ ID NO:48, SEQ ID NO:49, SEQ ID NO:50, SEQ ID NO:53, SEQ ID NO:63, SEQ ID NO:64, SEQ ID NO:65, SEQ ID NO:66, SEQ ID NO:67, SEQ ID NO:68, SEQ ID NO:69, and SEQ ID NO:70.

In some embodiments, the peptide-linking residue is located at position 14, according to the numbering of SEQ ID NO:60. In some embodiments, the Exendin4 homologue comprises a sequence selected from the group consisting of SEQ ID NO:53, SEQ ID NO:63, SEQ ID NO:64 and SEQ ID NO:77. In some embodiments, the Exendin4 homologue comprises SEQ ID NO:53. In some embodiments, the Exendin4 homologue comprises SEQ ID NO:63. In some embodiments, the Exendin4 homologue comprises SEQ ID NO:64. In some embodiments, the Exendin4 homologue comprises SEQ ID NO:77.

The peptide-linking residue may comprise a nucleophilic sidechain covalently linked to the second linker. The peptide-linking residue may be selected from the group consisting of K, Y, C, Dap, Dab, K(SH) and K(S-MAL). The side chain of the peptide-linking residue may comprise a thiol group.

The peptide-linking residue [LR] may comprise the structure: K(S-MAL)

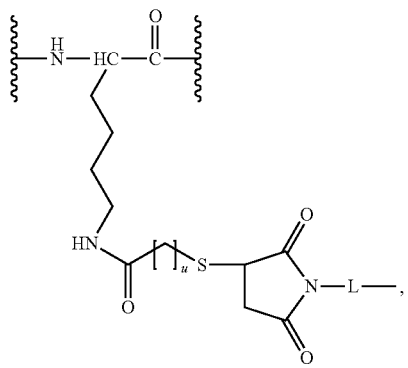

wherein u is 1, 2 or 3, and L is the second linker. In some embodiments is u 1. In some embodiments, u is 2. In some embodiments, u is 3. Unless otherwise stated, where K(SMAL) is used in the examples, u=2.

In some embodiments, the peptide-linking residue comprises the structure K(SH), wherein u is 1, 2 or 3:

Where u = 2, K(SH) =

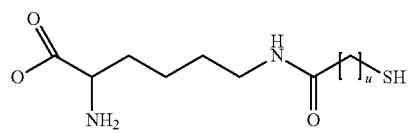

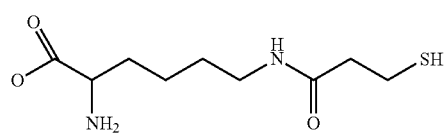

Unless otherwise stated, where K(SH) is used in the examples and sequence listing, u=2.

In some aspects, the Exendin4 homologue further comprises an amino-terminal capping group $R^1$ selected from the group consisting of $CH_3$, $C(O)CH3$, $C(O)CH_2CH_3$, $C(O)CH_2CH_2CH_3$, or $C(O)CH(CH_3)CH_3$. In some aspects, the Exendin4 homologue further comprises a carboxy-terminus capping group $R^2$ selected from the group consisitng of OH, $NH_2$, $NH(CH_3)$, $NHCH_2CH_3$, $NHCH_2CH_2CH_3$, $NHCH(CH_3)CH_3$, $NHCH_2CH_2CH_2CH_3$, $NHCH(CH_3)CH_2CH_3$, $NHC_6H_5$, $NHCH_2CH_2OCH_3$, $NHOCH_3$, $NHOCH_2CH_3$, a carboxy protecting group, a lipid fatty acid group or a carbohydrate. In some embodiments, $R^1$ is $C(O)CH_3$. In some embodiments, $R^2$ is $NH_2$. In embodiments where the Ex4 peptide comprises SEQ ID NO:64 and R1 is $C(O)CH_3$ and R2 is $NH_2$, the Ex4 peptide may be denoted as SEQ ID NO:77.

In some aspects, the Exendin4 homologue comprises the formula:

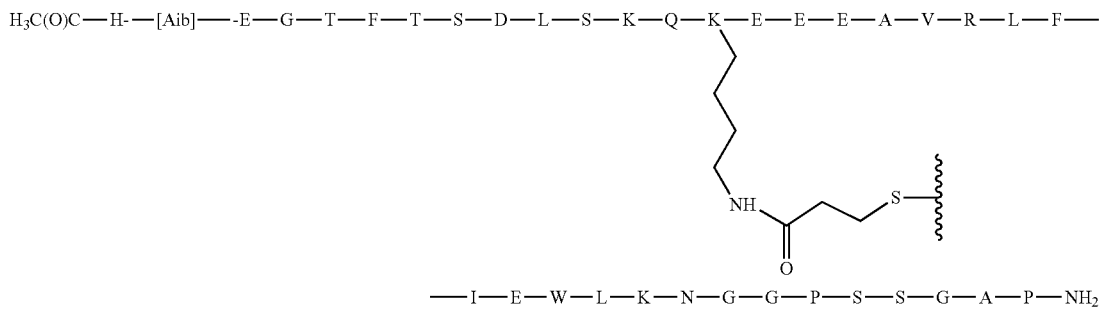

Both the first and second linker each play a critical role in the presentation of the protein and peptide respectively. It is essential that the composition and length of linker be optimized for both protein and peptide in order to maximize the ability of each to interact with their respective cognate. A further complication with an asymmetric bifunctional molecule (i.e. one presenting a different protein/peptide on each of the two arms) is the importance that the linker-peptide arrangement or functionality of one arm does not interfere with the linker-protein arrangement or functionality of the other arm, and vice versa. In some embodiments, a longer linker length has a tendency to reduce interference between the different arms. Balanced against this, however, is the tendency for longer linkers to offer less protection against proteases. In addition, in some circumstances, a short linker can allow a peptide or protein to be optimally presented for cognate interaction: increasing the linker length can increase flexibility, and so lose this advantage. Conversely, some protein or peptide interactions with the respective target are improved by a certain amount of flexibility in the linker. Thus, finding the optimum linker length and composition for each active protein/peptide, and balancing each holistically across the entire assembled molecule is critical in order to strike the right balance between half-life and activity of both protein and peptide. All of this must then be offset against the additional manufacturing cost and complexity inherent in having a different linker for each protein/peptide. Using the same linker for each active molecule has clear cost and manufacturing efficiencies.

Certain suitable linkers are disclosed in US2009098130, the contents of which are incorporated herein by reference. In particular, aspects of US2009098130 pertaining to the general formulae describing linkers, specific linker structure, synthesis of linkers and combinations of different elements of X, Y (which may also be written as yy) and Z groups as specifically and generally described therein are herein included. The first and/or second linker may be linear or branched, and optionally includes one or more carbocyclic or heterocyclic groups. Linker length may be viewed in terms of the number of linear atoms, with cyclic moieties such as aromatic rings and the like to be counted by taking the shortest route around the ring. In some embodiments, the first and/or second linker has a linear stretch of between 5-15 atoms, in other embodiments 15-30 atoms, in still other embodiments 30-50 atoms, in still other embodiments 50-100 atoms, and in still other embodiments 100-200 atoms. Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, and modulation of antibody binding, the ability to be incorporated into a micelle or liposome, and the like.

The first and/or second linker may comprise the formula: X-Y-Z; wherein X is a biologically compatible connecting chain including any atom selected from the group consisting of C, H, N, O, P, S, F, Cl, Br, and I, and may comprise a polymer or block co-polymer, and is covalently linked to the protein-linking residue and/or peptide-linking residue where the linker is linear, Y is an optionally present recognition group comprising at least a ring structure; and Z is an attachment moiety comprising a covalent link to an amino acid side chain in a combining site of an antibody.

When present, Y may have the optionally substituted structure:

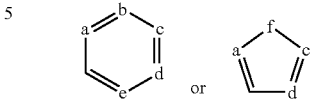

wherein a, b, c, d, and e are independently carbon or nitrogen; f is carbon, nitrogen, oxygen, or sulfur; Y is attached to X and Z independently at any two ring positions of sufficient valence; and no more than four of a, b, c, d, e, or f are simultaneously nitrogen and preferably a, b, c, d, and e in the ring structure are each carbon. In some aspects, Y may be phenyl. Although not wishing to be bound by any theory, it is believed that the Y group can assist in positioning the reactive group into an antibody combining site so that the Z group can react with a reactive amino acid side chain.

The first and/or second linker may be designed such that it contains a reactive group capable of covalently or non-covalently forming a bond with a macromolecule, such as an antibody, protein, or fragment thereof. The reactive group is chosen for use with a reactive residue in a particular combining site. For example, a chemical moiety for modification by an aldolase antibody may be a ketone, diketone, beta lactam, active ester haloketone, lactone, anhydride, maleimide, alpha-haloacetamide, cyclohexyl diketone, epoxide, aldehyde, amidine, guanidine, imine, enamine, phosphate, phosphonate, epoxide, aziridine, thioepoxide, masked or protected diketone (ketal for example), lactam, haloketone, aldehyde, and the like. In embodiments of the present invention linking a peptide of the invention with a linker, the Z is the reactive group.

In some embodiments, Z, prior to conjugation with the side-chain of a residue in the combining site of an antibody, includes one or more C=O groups arranged to form an azitidinone, diketone, an acyl beta-lactam, an active ester, a haloketone, a cyclohexyl diketone group, an aldehyde, a maleimide, an activated alkene, an activated alkyne or, in general, a molecule comprising a leaving group susceptible to nucleophilic or electrophilic displacement. Other groups may include a lactone, an anhydride, an alpha-haloacetamide, an imine, a hydrazide, or an epoxide. Exemplary linker electrophilic reactive groups that can covalently bond to a reactive nucleophilic group (e.g., a lysine or cysteine side chain) in a combining site of antibody include acyl beta-lactam, simple diketone, succinimide active ester, maleimide, haloacetamide with linker, haloketone, cyclohexyl diketone, aldehyde, amidine, guanidine, imine, enamine, phosphate, phosphonate, epoxide, aziridine, thioepoxide, a masked or protected diketone (a ketal for example), lactam, sulfonate, and the like, masked C=O groups such as imines, ketals, acetals, and any other known electrophilic group. In certain embodiments, the reactive group includes one or more C=O groups arranged to form an acyl beta-lactam, simple diketone, succinimide active ester, maleimide, haloacetamide with linker, haloketone, cyclohexyl diketone, or aldehyde. Z may be a substituted alkyl, substituted cycloalkyl, substituted aryl, substituted arylalkyl, substituted heterocycle, or substituted heterocycloalkyl, wherein at least one substituent is a 1,3-diketone moiety, an acyl beta-lactam, an active ester, an alpha-haloketone, an aldehyde, a maleimide, a lactone, an anhydride, an alpha-haloacetamide, an amine, a hydrazide, or an epoxide. In some aspects, the Z group is covalently linked to a macromolecule scaffold that can provide increased half-life to the peptides of the invention. In some aspects, the Z group if present is covalently linked to the combining site of an antibody.

In some aspects, prior to conjugation (for example, with the combining site of an antibody), Z has the structure:

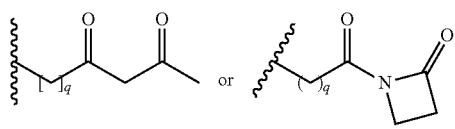

wherein q=0-5. q may be 1 or 2. q may be 1. In other aspects, q may be 2.

In some aspects, following conjugation with the antibody combining site, Z has the structure:

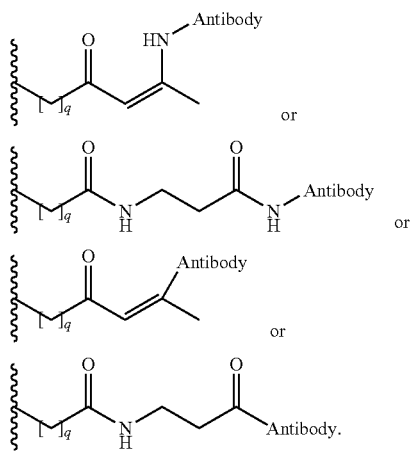

wherein q=0-5 and Antibody-N— is a covalent bond to a side chain in a combining site of an antibody (wherein the NH is the ε-amino group of a lysine the side chain in the antibody combining site). q may be 1 or 2. q may be 1. In other aspects, q may be 2.

X may be a group comprising three components; Xp-Xs-Xy, wherein Xp is a group specifically adapted to be combinable with the side chain of the protein-linking residue of the FGF21 protein and/or the peptide linking residue of an Exendin4 homologue, Xs is a spacer region of the X group, and Xy is a group adapted to bind to the Y group. In some aspects, Xy is selected from an amide bond, an enamine bond, or a guanidinium bond. Xy may be selected so as to provide a hydrogen molecule adjacent (within two atoms) to the Y group. While not wishing to be bound by theory, it is believed that the H atom can assist the Y group recognition of a hydrophobic pocket through H-bond interaction, particularly in respect of the hydrophobic pocket of the binding cleft of a catalytic antibody, such as h38C2. Thus the amide bond, for example, may be oriented such that the NH group is directly bonded to the Y group, providing the H of the NH group for hydrogen bonding. Alternatively, the C=O group of an amide may be bonded to the Y group, with the H of the NH group nay 2 atoms adjacent to the Y group, but still available for H-bonding. In some embodiments, Xy is absent. In some embodiments the Xy group has the formula:

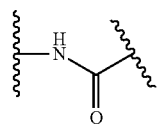 [SMILES: *NC(*)=O]

In some aspects, Xs is selected such that Xs does not provide any overly reactive groups. Xs may be selected so as to provide an overall length of the X groups of between 2-15 atoms. Xs may be selected so that the overall length of the X group is between 2 and 10 atoms. Xs may be selected so that the overall length of X group is 4-8 atoms. Xs may be selected so that the overall length of X group is 5 atoms. Xs may be selected so that the overall length of X group is 6 atoms. In some aspects, Xs may comprise one of the following formulae:

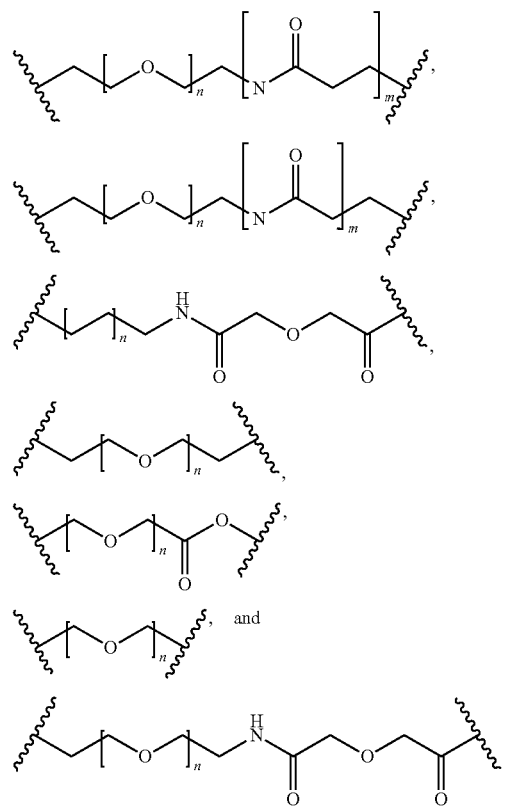

where n=1, 2, 3, 4, 5, 6, 7, 8, 9, or 10, and m is present or absent; n may be 1, 2, 3, 4, 5, or 6; n may be 1, 2, 3, or 4; n may be 1; n may be 2; n may be 3; n may be 4.

In some aspects, Xs comprises one of the following formulae:

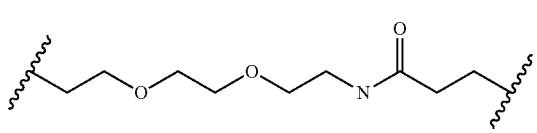

(exemplified in L1 and L2)

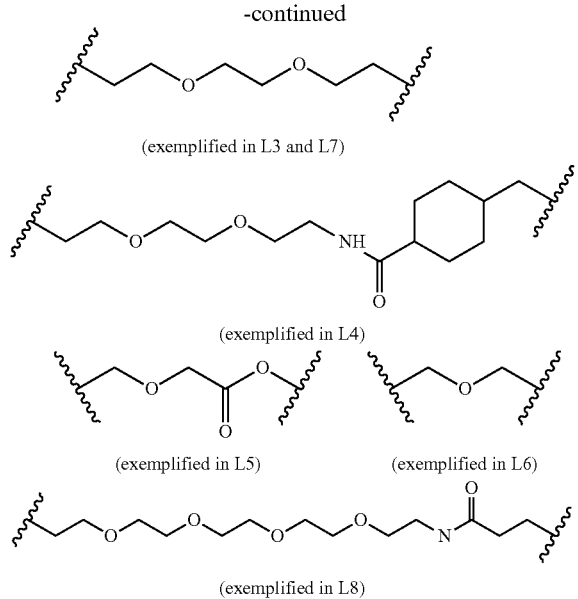

(exemplified in L3 and L7)

(exemplified in L4)

(exemplified in L5)    (exemplified in L6)

(exemplified in L8)

Xp ideally is selected so as to enable a specific directional covalent linking strategy to the protein-linking residue of the FGF21 protein and/or the peptide-linking residue of the Exendin4 homologue. For example, where the linking residue comprises a nucleophilic group, Xp may be an electrophilic group and vice versa. For example, if the linking residue side chain comprises an amine group, such as K, H, Y, ornithine, Dap, or Dab, Xp may be COOH, or other similarly reactive electrophile. If the linking residue is D or E, Xp may comprise a nucleophilic group, such as an amine group. Either of these strategies permits a covalent bond to be formed between the Xp group and the linking residue by amide bond formation strategies. Where the linking residue comprises an amine group, Xp may comprise the formula:

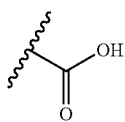

Where the linking residue is C, homologs of C, or other thiol-group containing residues such as K(SH), Xp may comprise a maleimide group (or similar) permitting a thiol-maleimide addition reaction strategy to covalently link the Xp group to the linking residue. In some aspects, Xp may also comprise a thiol group, allowing a disulphide bridge to be formed between the linking residue and Xp group. In some aspects, Xp may be maleimide:

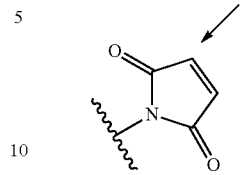

wherein the arrow indicates the point of attachment to the linking residue and the parallel line represents the attachment to the Y group of the linker. Where the linking residue is a cysteine residue or other thiol bearing side chain, the mechanism of conjugation may be as follows:

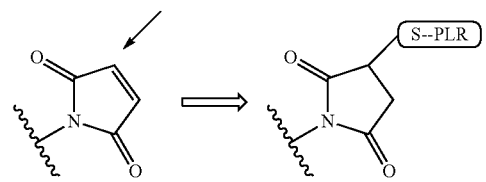

where PLR is the protein-linking residue or peptide-linking residue, and S is the sulphur atom of the thiol group of the cysteine or other thiol bearing amino acid, such as K(SH).

In some aspects, the Xp group comprises a substituted maleimide:

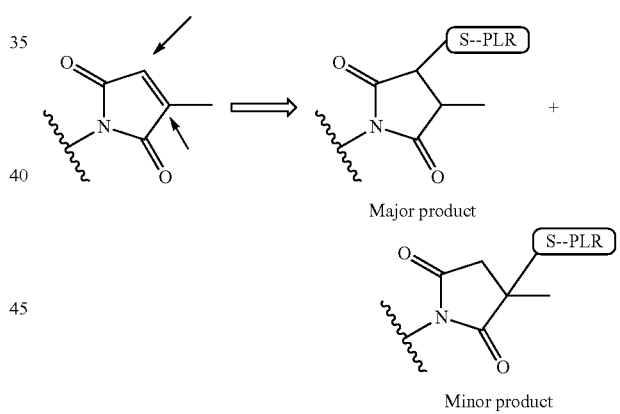

Major product

Minor product

In some aspects, the XY components of the linker prior to conjugation and following conjugation may be selected from the following:

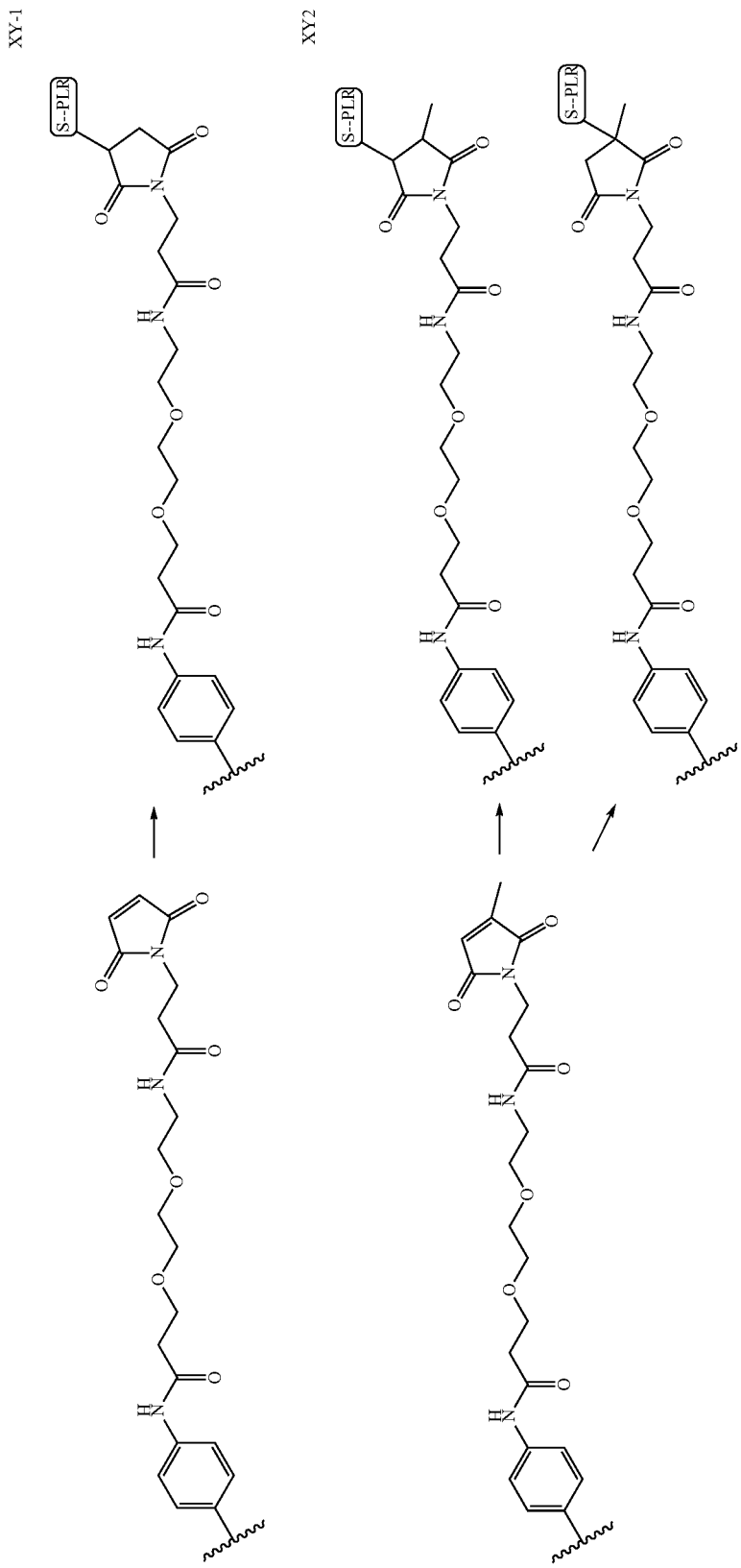

-continued
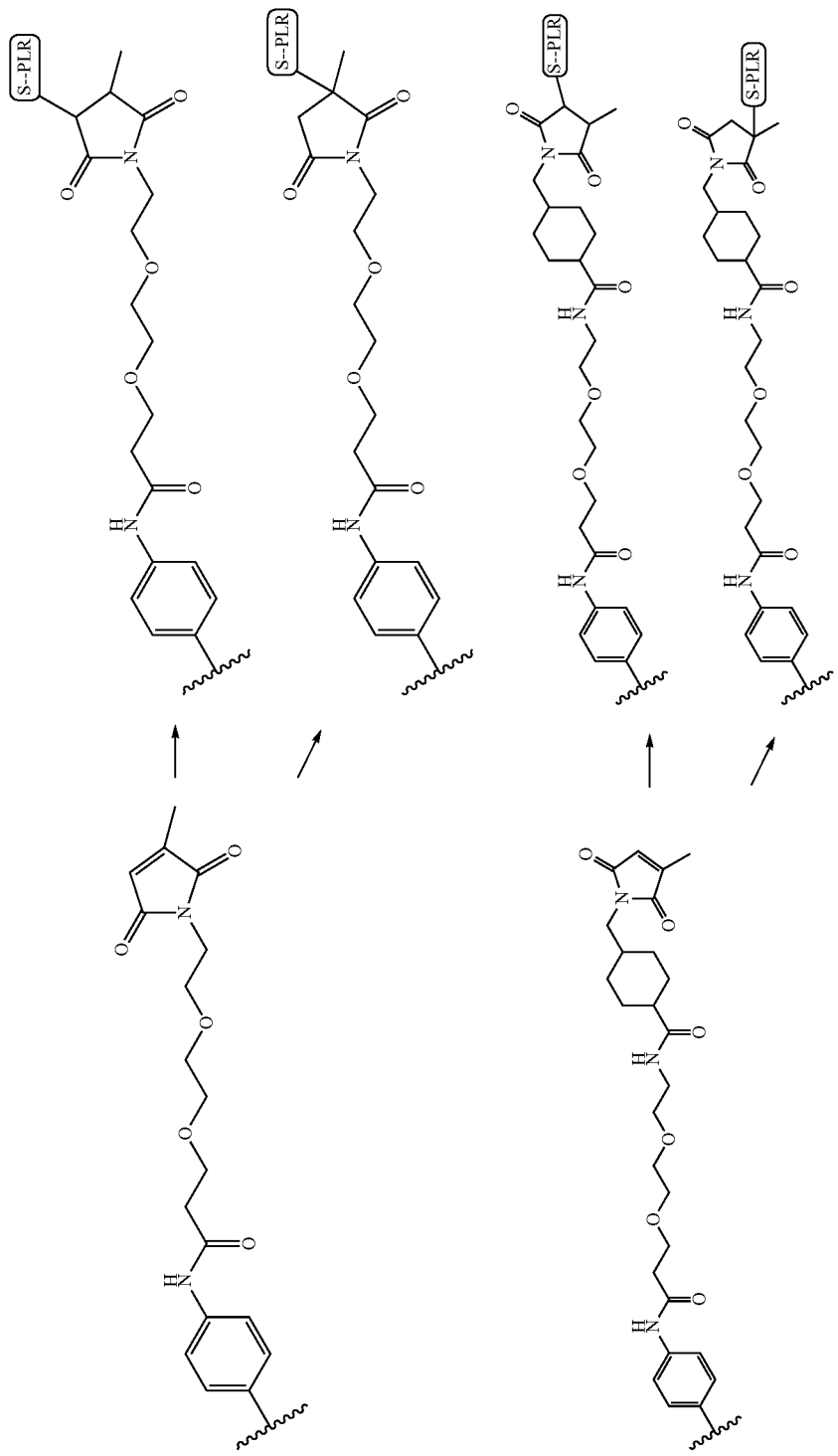

Components XY-1, XY-2, XY-3, and XY-4 are particularly useful in embodiments conjugating to a thiol-group bearing side chain on the linking residue.

In some embodiments, the linker may be Linker-1 (L1):

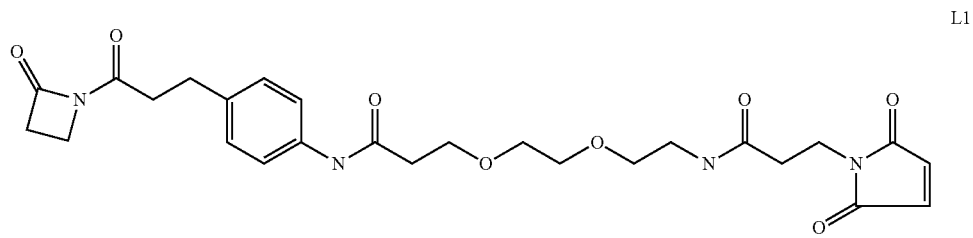 [SMILES: O=C(CCN1C(=O)C=CC1=O)NCCOCCOCCC(=O)Nc1ccc(CCC(=O)N2CCC2=O)cc1]

L1

When L1 is conjugated to the PLR, the L1-PLR complex may comprise the formula:

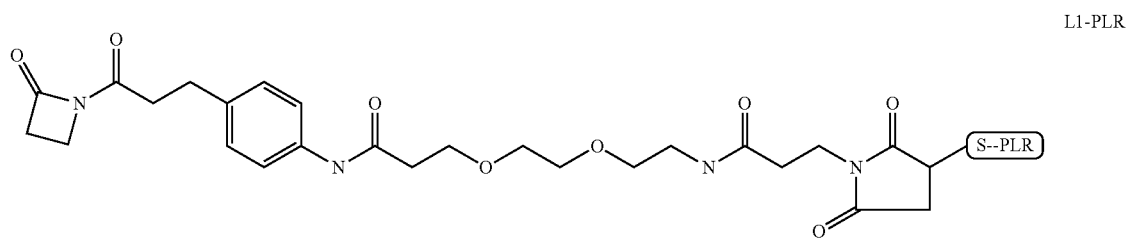 [SMILES: CC1CC(=O)N(CCC(=O)NCCOCCOCCC(=O)Nc2ccc(CCC(=O)N3CCC3=O)cc2)C1=O]

L1-PLR

When L1 is conjugated to the antibody and PLR, the antibody-L1-PLR complex may comprise the formula:

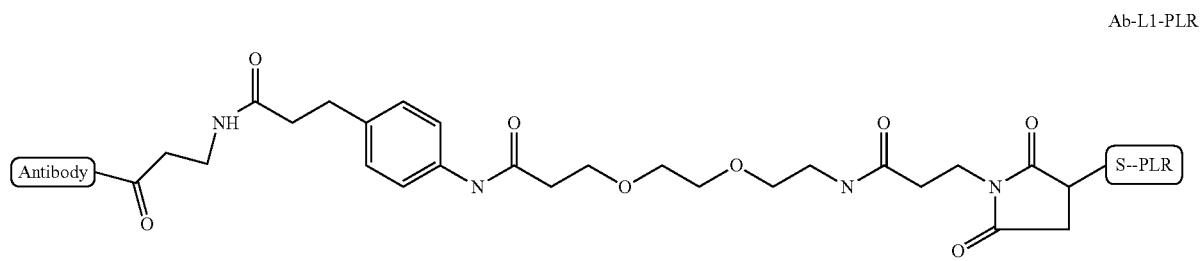 [SMILES: CC(=O)CCNC(=O)CCc1ccc(NC(=O)CCOCCOCCNC(=O)CCN2C(=O)CC(C)C2=O)cc1]

Ab-L1-PLR

In some embodiments, the linker may be Linker-2 (L2):

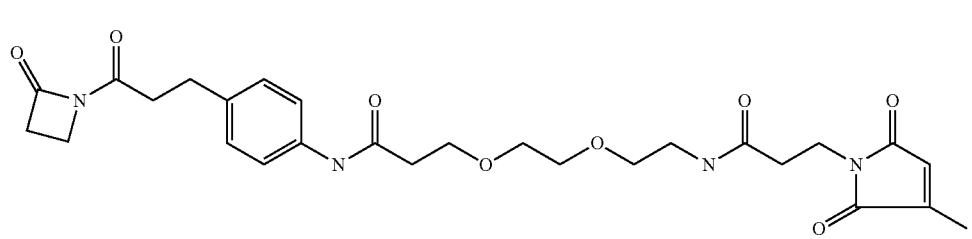

L2

When L2 is conjugated to the PLR, the L2-PLR complex may comprise one of the following formulae:
L2-PLR
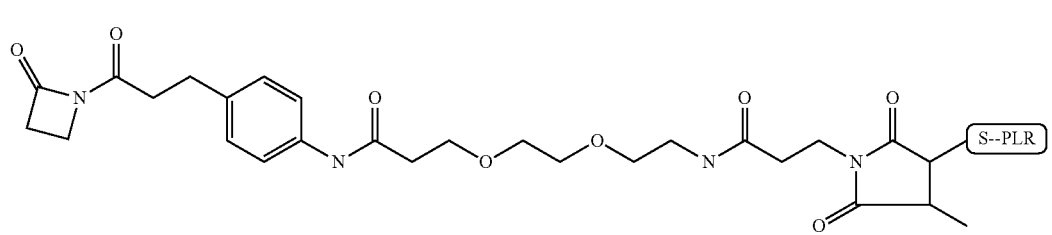
L2-PLR
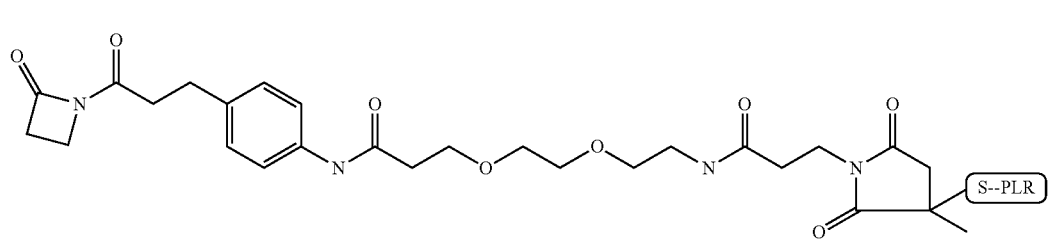
When L2 is conjugated to the antibody and the PLR, the antibody-L2-PLR complex may comprise one of the following formulae:
Ab-L2-PLR
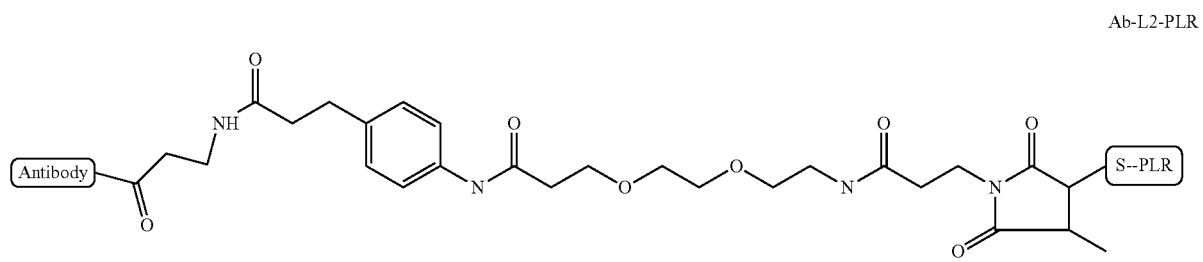
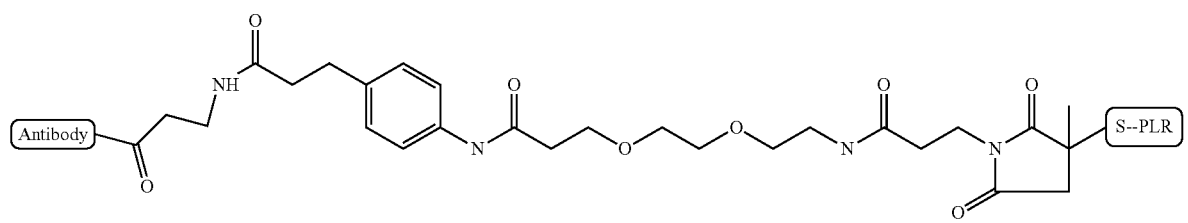
In some embodiments, the linker may be Linker-3 (L3):
L3
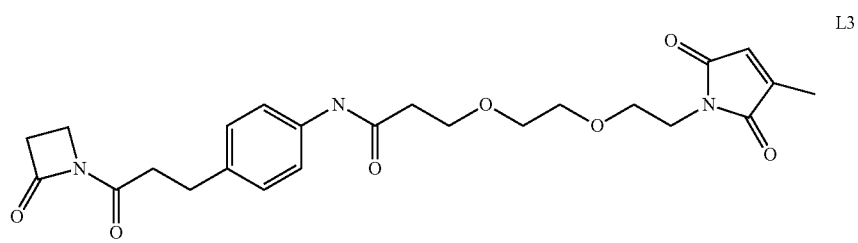 [SMILES: CC1=CC(=O)N(CCOCCOCCC(=O)Nc2ccc(CCC(=O)N3CCC3=O)cc2)C1=O]

When L3 is conjugated to the PLR, the L3-PLR complex may comprise one of the following formulae:
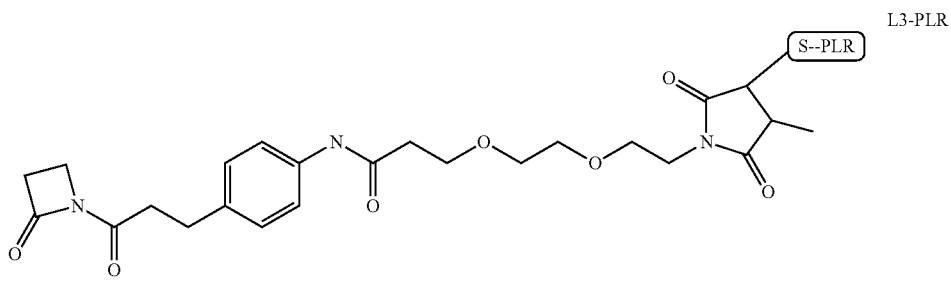
L3-PLR
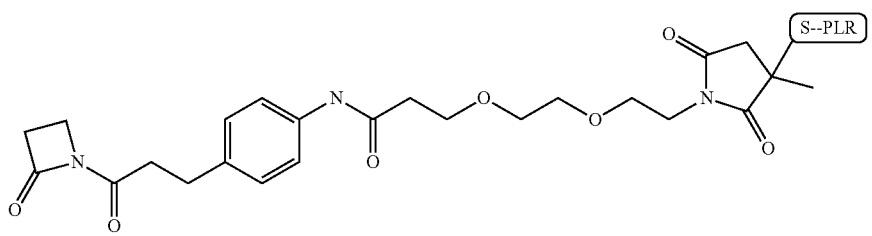
When L3 is conjugated to the antibody and the PLR, the antibody-L3-PLR complex may comprise the formula:
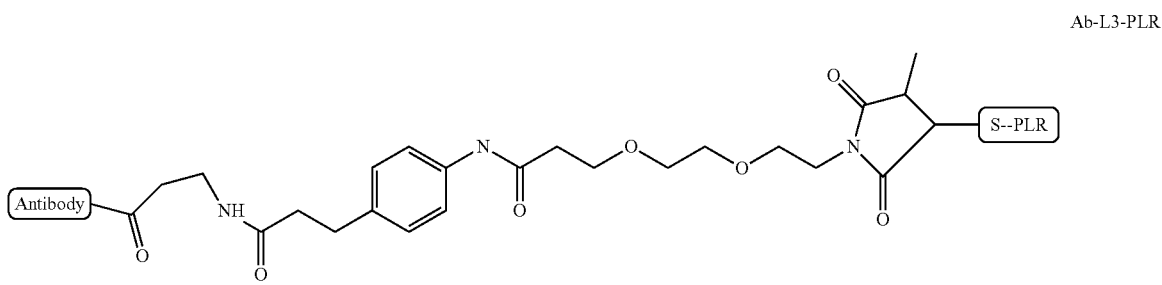
Ab-L3-PLR
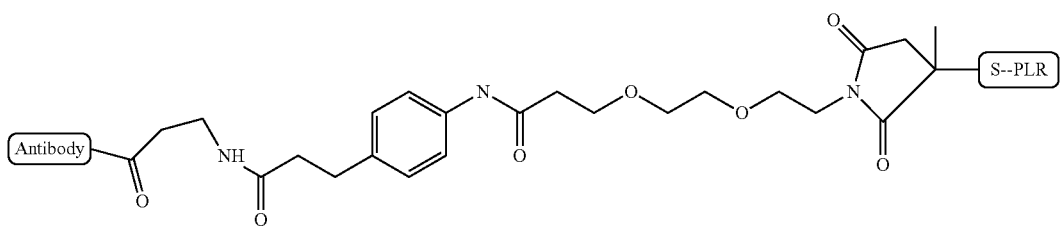
In some embodiments, the linker may be Linker-4 (L4):
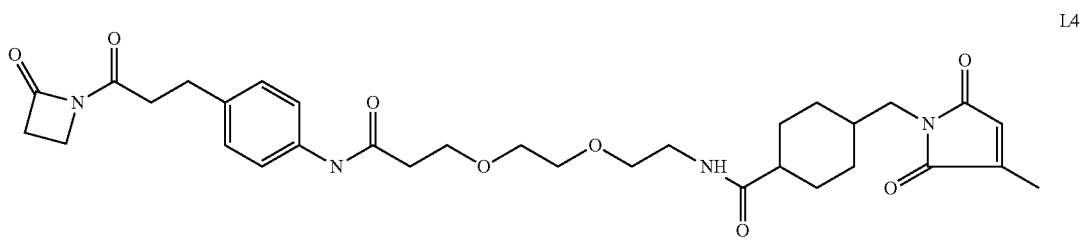 [SMILES: CC1=CC(=O)N(CC2CCC(C(=O)NCCOCCOCCC(=O)Nc3ccc(CCC(=O)N4CCC4=O)cc3)CC2)C1=O]
L4

When conjugated to the PLR, the L4-PLR complex may comprise the formula:
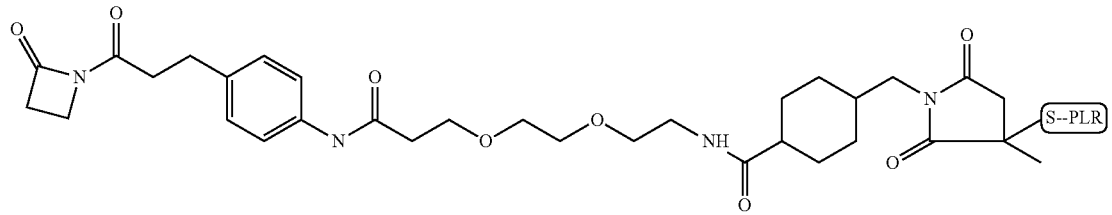
L4-PLR
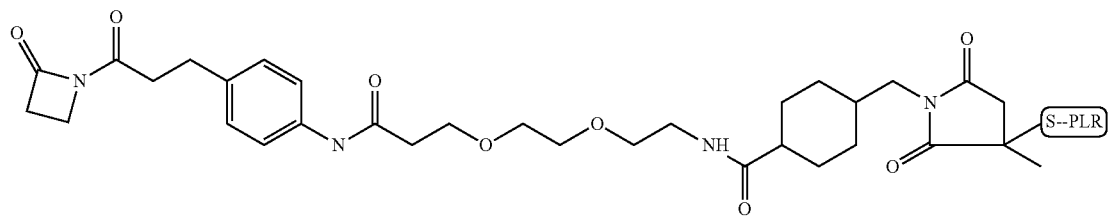
When L4 is conjugated to the antibody and the PLR, the antibody-L4-PLR complex may comprise the formula:
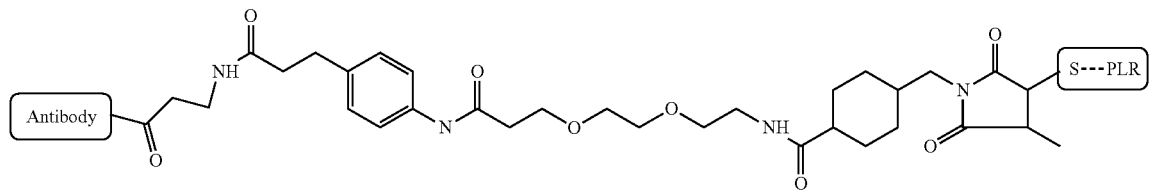
Ab-L4-PLR
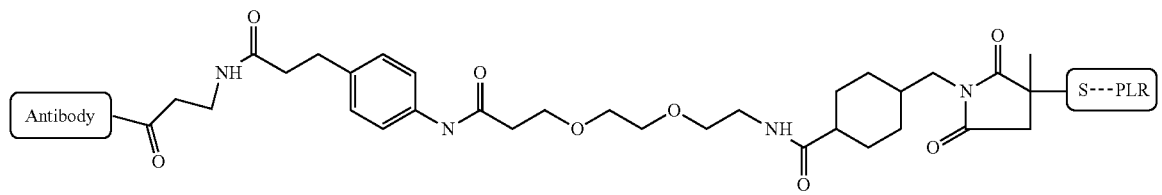
In some embodiments, the linker may be Linker-5 (L5):
When L5 is conjugated to the PLR, the L5-PLR complex may comprise the formula:
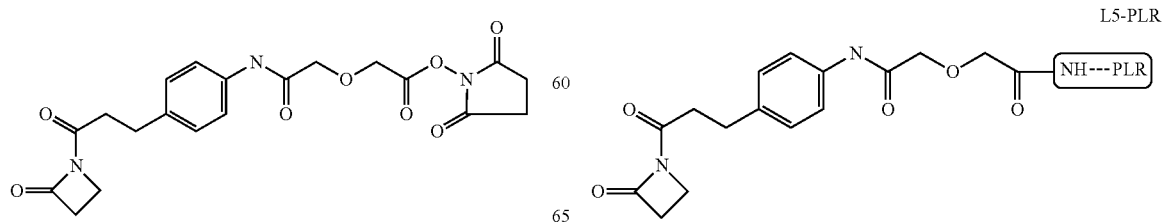
L5
L5-PLR When L5 is conjugated to the antibody and PLR molecule, the antibody-L5-PLR complex may comprise the formula:

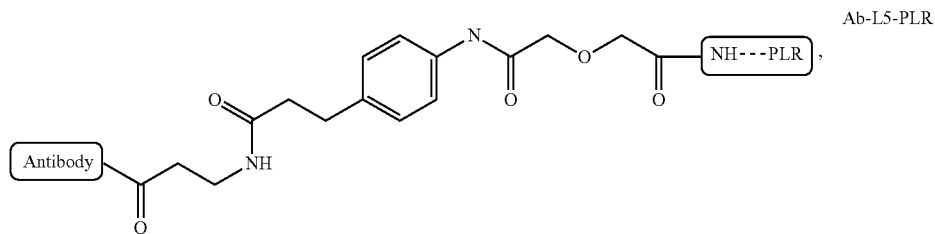
Ab-L5-PLR wherein NH is the amino group at the end of a side chain of the LR, such as lysine.

In some aspects, the linker may be Linker-6 (L6).

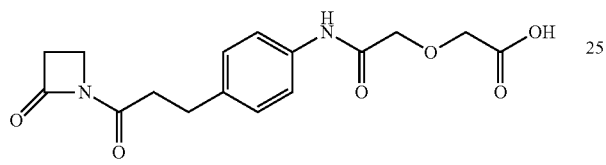
L6

When L6 is conjugated to the PLR, the L6-PLR complex may comprise the same formula as that for L5-PLR1. Similarly, when L6 is conjugated to the antibody and the PLR, the antibody-L6-PLR complex may comprise the same formula as that for Ab-L5-PLR.

In some embodiments, the linker may be Linker-7 (L7):

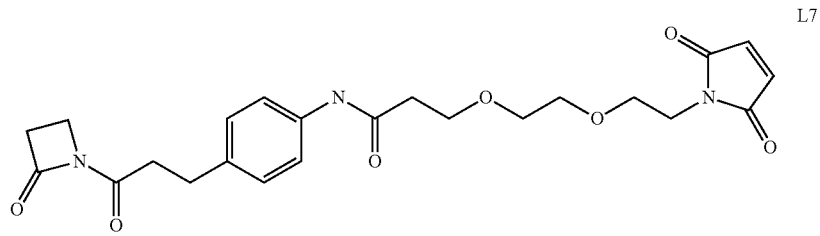 [SMILES: O=C(CCOCCOCCN1C(=O)C=CC1=O)Nc1ccc(CCC(=O)N2CCC2=O)cc1]
L7

When conjugated to the PLR, the L7-PLR complex may comprise the formula:

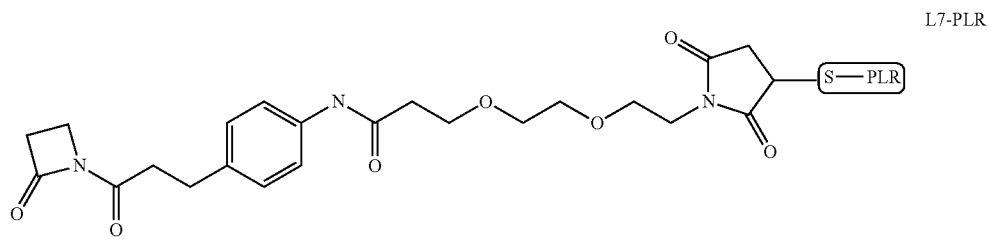
L7-PLR

When conjugated to the antibody and PLR, the antibody-L7-PLR complex may comprise the formula:
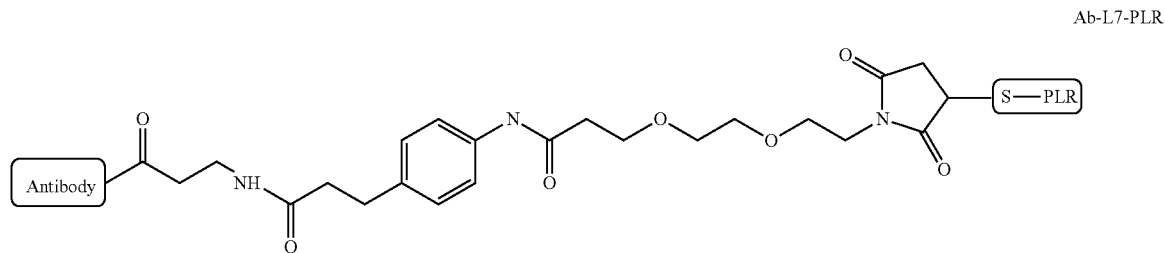
Ab-L7-PLR
In some embodiments, the linker may be Linker-8 (L8):
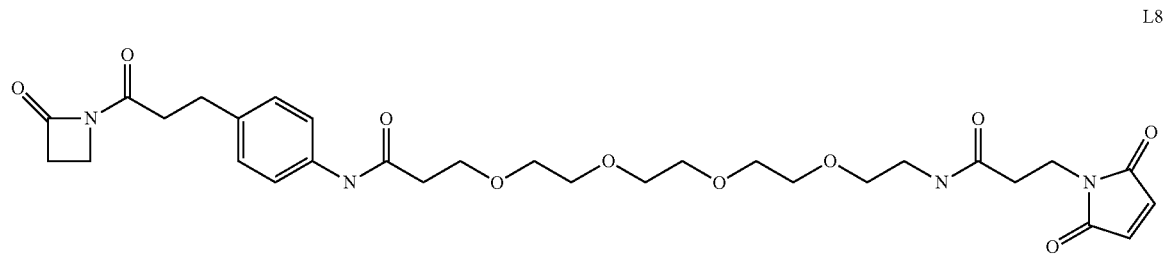 [SMILES: O=C(CCN1C(=O)C=CC1=O)NCCOCCOCCOCCOCCC(=O)Nc1ccc(CCC(=O)N2CCC2=O)cc1]
L8
When L8 conjugated to the PLR, the L8-PLR complex may comprise the formula:
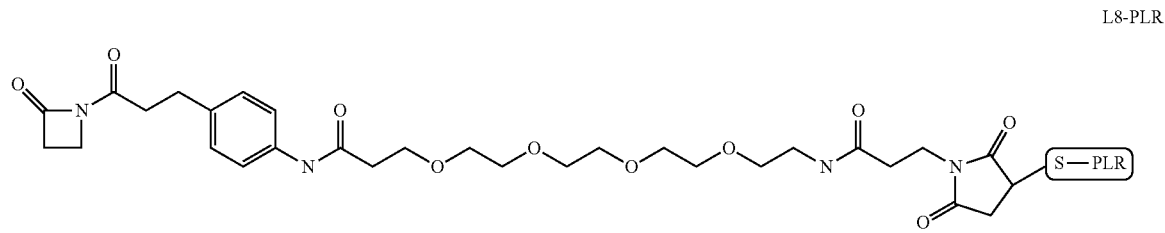
L8-PLR
When L8 is conjugated to the antibody and the PLR, the antibody-L8-PLR complex may comprise the formula:
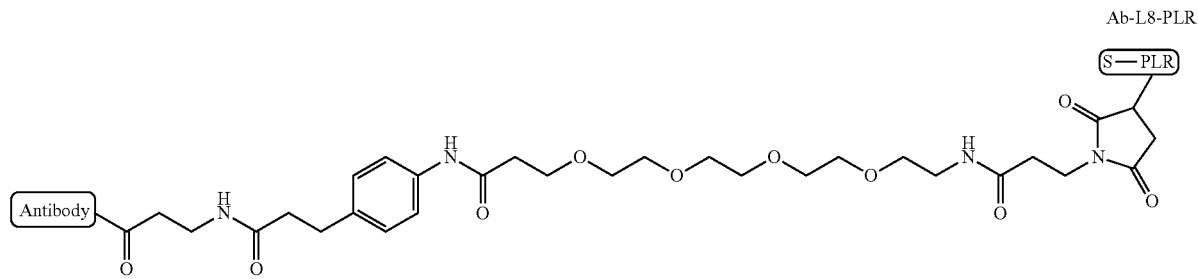
Ab-L8-PLR In some embodiments, the linker may be of the formula:

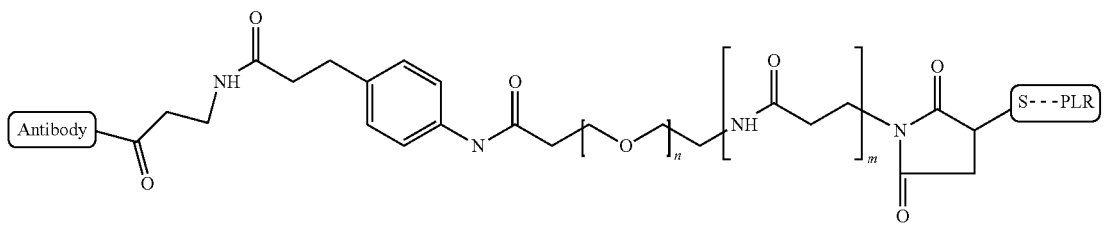

wherein Antibody is a covalent linkage to the combining site of an antibody, S-PLR is the covalent linkage to a thiol-bearing side chain on the protein-linking residue and/or the peptide-linking residue, n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some embodiments, the $1^{st}$ and/or $2^{nd}$ linker, when conjugated to the antibody and PLR, may be of the formula:

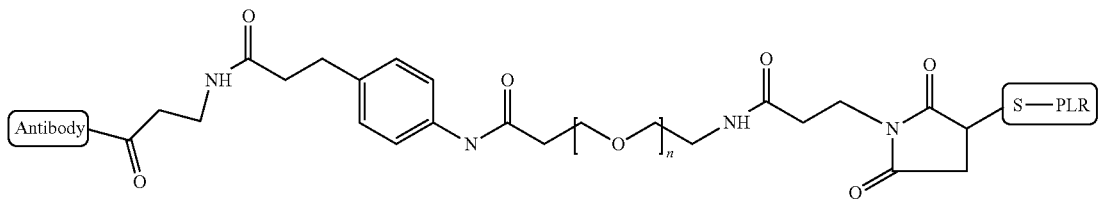

wherein Antibody is a covalent linkage to the combining site of an antibody, S-PLR is a covalent linkage to a thiol-bearing side chain on the protein-linking residue and/or the peptide-linking residue, n=1, or 2, or 3, or 4, 5, 6, 7, 8, 9, or 10; n may be 1, 2, 3, 4, 5, or 6; n may be 1; n may be 2; n may be 3; n may be 4.

In some embodiments, the composition comprises the formula:

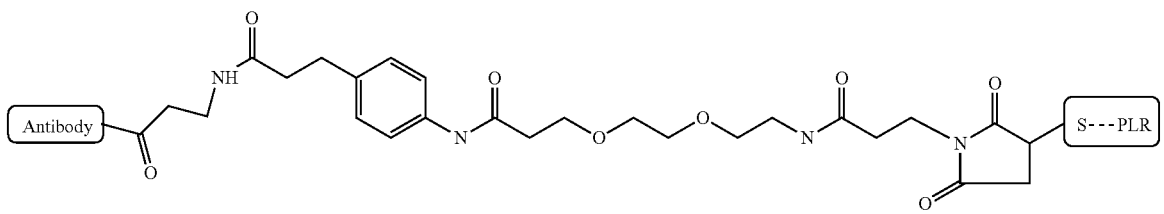

wherein Antibody is a covalent linkage to the combining site of an antibody, and S-PLR is a covalent linkage to a thiol-bearing side chain on the protein-linking residue and/or the peptide-linking residue.

In some embodiments, the protein-linking residue comprises an amino or thiol bearing side chain. In some embodiments, the protein linking residue comprises lysine or cysteine. In some embodiments, the protein-linking residue comprises cysteine.

In some embodiments, the protein-linking residue is located at one of residue numbers 56, 59, 69, 79, 86, 122, 125 and 129, according to the numbering of SEQ ID NO:1 In some embodiments, the FGF21 molecule comprises SEQ ID NO:10. In some embodiments, the FGF21 molecule comprises SEQ ID NO:7.

In some embodiments, the peptide-linking residue is located at one of positions of 10, 11, 12, 13, 14, 16, 17, 19, 20, 21, 24, 26, 27, 28, 32, 33, 34, 35, 36, 37, 38, 39, or 40 according to the numbering of SEQ ID NO:60.

In some embodiments, the $1^{st}$ and $2^{nd}$ linkers are the same. In some embodiments, the $1^{st}$ and $2^{nd}$ linker both comprise L1.

In some aspects, the structure of the protein linking residue [S-PLR] and/or the peptide-linking residue [S-PLR] when attached to the antibody is of the formula:

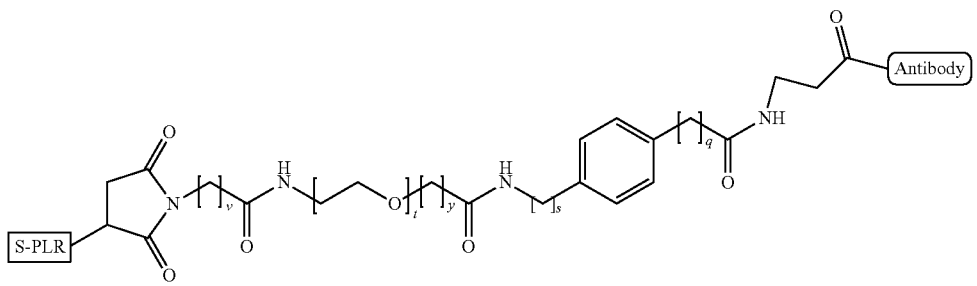

wherein v is 1 or 2, t is 1, 2, 3, 4, 5, 6, 7, 8, 9, or 10, y is 0, 1 or 2; s is 0, 1, 2, 3, 4, 5, 6, 7, 8, 9, or 10, and q is 1, 2, 3, 4, or 5. In some aspects, v is 2, t is 2, y is 1, s is 0 and q is 2.

In some aspects, the invention provides a compound of the formula:

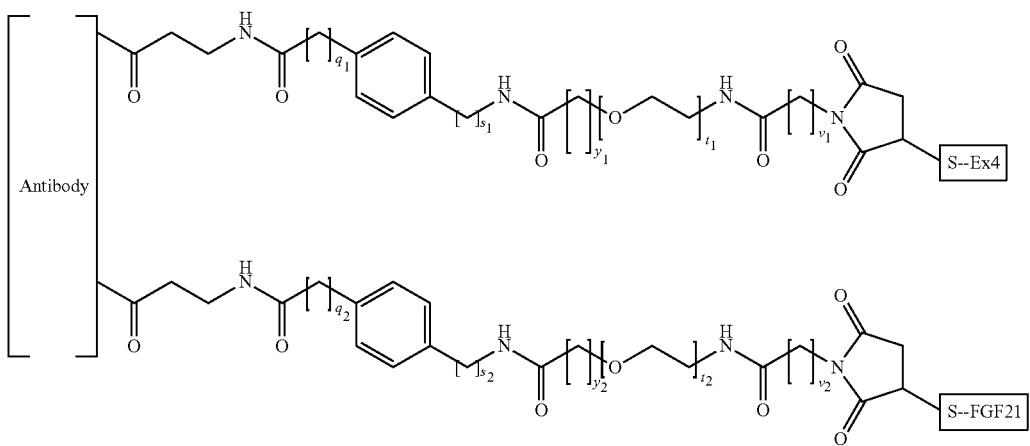

wherein each independently of $v_1$ and $v_2$ is 1 or 2, each independently of $t_1$ and $t_2$ is 1, 2, 3, 4, 5, 6, 7, 8, 9, or 10, each independently of $y_1$ and $y_2$ is 0, 1 or 2; each independently of $s_1$ and $s_2$ is 0, 1, 2, 3, 4, 5, 6, 7, 8, 9, or 10, and each independently of $q_1$ and $q_2$ is 1, 2, 3, 4, or 5. In some aspects $v_1$ and $v_2$ are both 2. In some aspects $t_1$ and $t_2$ are both 2. In some aspects $y_1$ and $y_2$ are both 1. In some aspects $s_1$ and $s_2$ are both 0. In some aspects and $q_1$ and $q_2$ are both 2.

In some aspects, the invention provides a composition of the formula:

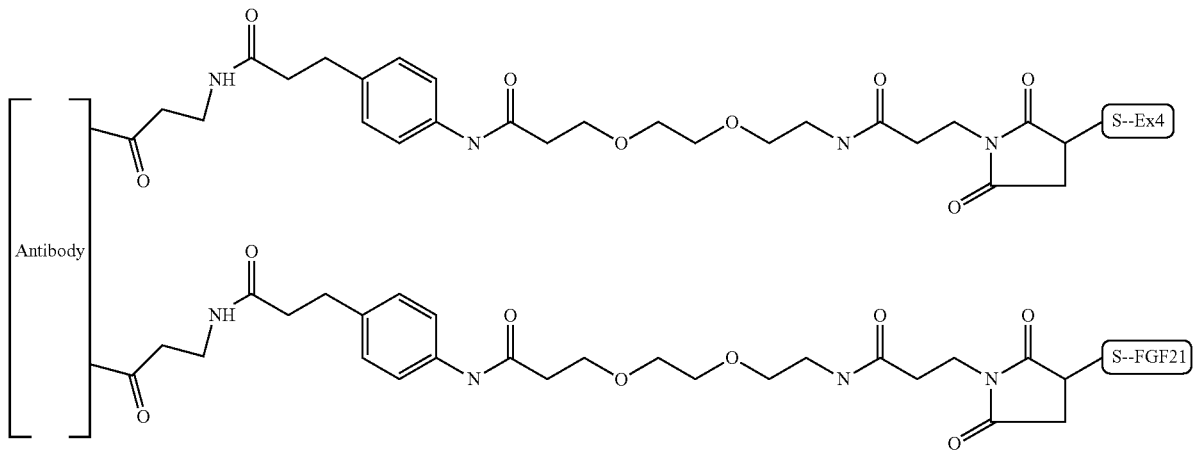

wherein the first and second linker are each covalently connected to one of the two antibody combining sites, and the antibody comprises SEQ ID NO:25 and SEQ ID NO:26, and S-Ex4 denotes a covalent link through a thiol group to K(SH) of SEQ ID NO:64, and S-FGF21 denotes a covalent link through a thiol group to $C^{129}$ of SEQ ID NO:10.

In some aspects, the structure of the peptide-linking residue [LR] when attached to the second linker and second combining site of the antibody is of the formula:

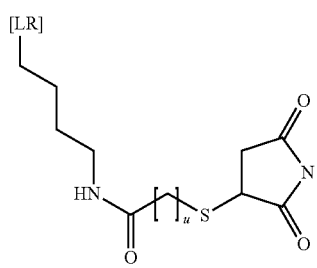
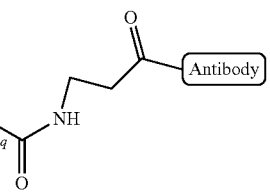

wherein u is 1, 2 or 3; v is 1 or 2, t is 1, 2, or 3, y is 1 or 2; s is 0, 1 or 2 and q is 1 or 2. In some aspects, u is 2, v is 2, t is 2, y is 1, s is 0 and q is 2.

In some aspects of the invention, the Exendin4 homologue and second linker comprise the formula:

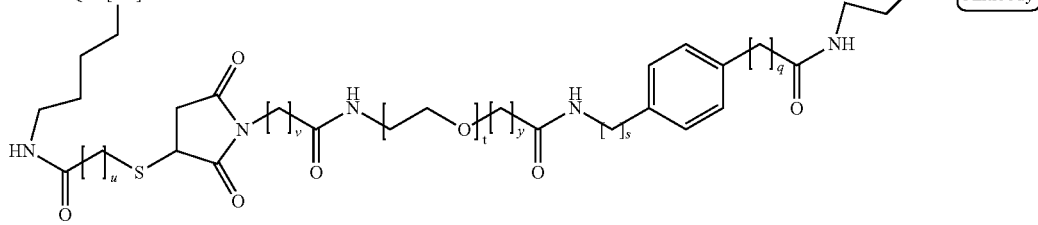

wherein u is 1, 2 or 3; v is 1 or 2, t is 1, 2, or 3, y is 1 or 2; s is 0, 1 or 2 and q is 1 or 2, and [LR] is the peptide linking residue. In some aspects, u is 2, v is 2, t is 2, y is 1, S is 0 and q is 2. In some aspects, [LR] is K, K(S-MAL), or K(SH).

In some embodiments, the invention relates to a composition of the formula: [FGF21-1$^{st}$ Linker]$_1$-[Ab]-[2$^{nd}$-Linker-Ex4]$_1$ wherein FGF21 is an FGF21 homologue; and Ex4 is an Exendin4 homologue; and Ab is an aldolase catalytic antibody; and the 1$^{st}$ linker is covalently attached to the side chain of a protein-linking residue in FGF21 and to the combining site of the antibody, and the 2$^{nd}$ linker is covalently attached to the side chain of a peptide-linking residue in Ex4 and to the combining site of the antibody, and wherein the first and second linker are the same or different, such that the subcutaneous half-life of the conjugated protein-antibody complex is at least about 20 hrs in murine models. In some embodiments, the SC half-life is at least about 25 hrs. In some embodiments, the SC half-life is at least about 30 hrs. In some embodiments, the half-life is at least about 33 hrs. In some embodiments, the SC half-life is at least about 40 hrs in primate models. In some embodiments, the SC half-life is at least about 45 hrs in primate models. In some embodiments, the SC half-life is at least about 48 hrs in primate models. In some embodiments, the invention provides a conjugated antibody-protein complex with an IV half-life of at least about 28 hrs in murine models. In some embodiments, the invention provides a conjugated antibody-protein complex with an IV half-life of at least about 30 hrs in murine models. In some embodiments, the invention provides a conjugated antibody-protein complex with an IV half-life of at least about 34 hrs in murine models. In some embodiments, the invention provides a conjugated antibody-protein complex with an IV half-life of at least about 40 hrs in murine models. In some embodiments, the invention provides a conjugated antibody-protein complex with an IV half-life of at least about 50 hrs in primate models. In some embodiments, the invention provides a conjugated antibody-protein complex with an IV half-life of at least about 55 hrs in primate models. In some embodiments, the invention provides a conjugated antibody-protein complex with an IV half-life of at least about 60 hrs in primate models.

In some embodiments, the invention relates to a composition of the formula: [FGF21-1$^{st}$ Linker]-[Antibody]-[2$^{nd}$-Linker-Ex4] wherein FGF21 is an FGF21 homologue; and Ex4 is an Exendin4 homologue; and Antibody is an aldolase catalytic antibody; and the 1$^{st}$ linker is covalently attached to the side chain of a protein-linking residue in FGF21 and to the combining site of the antibody, and the 2$^{nd}$ linker is covalently attached to the side chain of a peptide-linking residue in Ex4 and to the combining site of the antibody, and wherein the first and second linker are the same or different, such that the subcutaneous bioavailability of the conjugated protein-antibody complex is at least about 80% in murine models. In some embodiments, the SC bioavailability is at least about 85%. In some embodiments, the SC bioavailability is at least about 90%. In some embodiments, the SC bioavailability is at least about 50% in primate models. In some embodiments, the SC bioavailability is at least about 55% in primate models. In some embodiments, the SC bioavailability is at least about 60% in primate models.

In some embodiments, the invention relates to a composition of the formula: [FGF21-1$^{st}$ Linker]-[Antibody]-[2$^{nd}$-Linker-Ex4] wherein FGF21 is an FGF21 homologue; and Ex4 is an Exendin4 homologue; and Antibody is an aldolase catalytic antibody; and the 1$^{st}$ linker is covalently attached to the side chain of a protein-linking residue in FGF21 and to the combining site of the antibody, and the 2$^{nd}$ linker is covalently attached to the side chain of a peptide-linking residue in Ex4 and to the combining site of the antibody, and wherein the first and second linker are the same or different, such that the subcutaneous bioavailability of the conjugated protein-antibody complex has a $EC_{50}$ potency in a hGLP-1R (iAMP) assay of less than about 1 nM. In some aspects, the $EC_{50}$ potency in hGLP-1R (iAMP) assay is less than about 500 pm. In some aspects, the $EC_{50}$ potency in hGLP-1R (iAMP) assay is less than about 100 pm. In some aspects, the $EC_{50}$ potency in hGLP-1R (iAMP) assay is less than about 50 pm. In some aspects, the $EC_{50}$ potency in hGLP-1R (iAMP) assay is between about 10-50 pm.

In some embodiments, the invention relates to a composition of the formula: [FGF21-1$^{st}$ Linker]-[Antibody]-[2$^{nd}$-Linker-Ex4] wherein FGF21 is an FGF21 homologue; and Ex4 is an Exendin4 homologue; and Antibody is an aldolase catalytic antibody; and the 1$^{st}$ linker is covalently attached to the side chain of a protein-linking residue in FGF21 and to the combining site of the antibody, and the 2$^{nd}$ linker is covalently attached to the side chain of a peptide-linking residue in Ex4 and to the combining site of the antibody, and wherein the first and second linker are the same or different, such that the conjugated protein-antibody complex has a EC50 potency in a Glut1 Taqman assay of less than about 5 nM. In some embodiments, the $EC_{50}$ potency in a Glut1 Taqman assay is less than about 4 nM. In some embodiments, the $EC_{50}$ potency in a Glut1 Taqman assay is less than about 3 nM. In some embodiments, the $EC_{50}$ potency in a Glut1 Taqman assay is less than about 2 nM. In some embodiments, the $EC_{50}$ potency in a Glut1 Taqman assay is less than about 1 nM.

In some embodiments, the conjugated protein-antibody complex combines two or more favourable advantages, such as SC half-life, IV half-life, glucose uptake, potency, bioavailability, ease of manufacture, conjugation efficiency, in vivo stability, in vitro stability, resistance to hydrolysis, and compatibility between antibody, linker and protein.

In some aspects, the invention provides a composition comprising a FGF21 molecule covalently connected to at least one half-life-increasing moiety at a linking residue located at residue number 171 according to the numbering of SEQ ID NO:1. In some aspects, the FGF21 molecule is covalently connected to one half life-increasing moiety. In some aspects, the FGF21 molecule is covalently connected to more than one half life-increasing moiety. In some aspects, the linking residue is selected from the group consisting of residue numbers 79,129, and 171. In some aspects, the linking residue is position 171. The FGF21 molecule may comprise SEQ ID NO:73. The FGF21 molecule may comprise SEQ ID NO:74. The FGF21 molecule may comprise SEQ ID NO:75. The term "half life-increasing moiety" refers to any molecule that when connected to the FGF21 molecule, increases the circulating half-life of the FGF21 molecule and/or inhibits or reduces renal clearance of the FGF21 molecule. Examples of half life-increasing moieties include PEG, mPEG, phosphorylcholine containing polymers, Fc domains, Fab, Fab', F(ab')$_2$, F$_v$, dsF$_v$, scF$_v$, V$_H$, V$_L$, diabodies, minibodies, antibodies, catalytic antibodies (discussed below), proteins (such as albumin), and other macromolecules known in the art.

Antibodies

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including, for example without limitation, scFv, single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9): 1126-1136). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

Two types of human light chain constant regions are known: lambda (CL-λ) and kappa (CL-κ). There are three known CL-κ variants, based on the polymorphisms V/A at position 46 and A/L at position 84 (numbering according to SEQ ID NO:78). The 3 identified CL-κ polymorphisms are Km(1):V$^{46}$/L$^{84}$, Km(1,2): A$^{46}$/L$^{84}$, and Km(3) A$^{46}$/V$^{84}$). Antibodies of the present invention may therefore comprise a constant kappa domain according to any one of SEQ ID NOs:78, 79, 80 or 81, or variants thereof that comprise no more than 5, 4, 3, 2, or 1 amino acid insertions, substitutions or deletions. It is understood by the skilled person that residue R$^1$ of SEQ ID NOs:78, 79, 80 and 81 by some counting methods may be included in the variable domain, and that the constant domains may therefore also be considered as beginning from residue T$^2$ of said sequences.

The term "antigen binding portion" of an antibody, as used herein, refers to one or more fragments of an intact antibody that retain the ability to specifically bind to a given antigen (e.g., target X). Antigen binding functions of an antibody can be performed by fragments of an intact antibody. Examples of binding fragments encompassed within the term "antigen binding portion" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., 1989 Nature 341:544-546), and an isolated complementarity determining region (CDR).

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modelling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The contents of US2006205670 are incorporated herein by reference. US2006205670 describes a number of compositions and techniques directly applicable to the present application, in particular at paragraphs [0153]-[0233], describing antibodies, useful fragments and variants and modifications thereof, combining sites and CDRs, antibody preparation, expression, humanization, amino acid modification, glycosylation, ADCC, CDC, increasing serum half life of antibodies, expression vectors, mammalian host systems, and folding, amongst other elements of antibody technology.

"Combining site", as used herein, (also known as the antibody binding site) refers to the region of the immunoglobulin or Ig domains that combine (or can combine) with the determinant of an appropriate antigen (or a structurally similar protein). The term generally includes the CDRs and the adjacent framework residues that are involved in antigen binding.

"Aldolase antibodies" as used herein, refers to antibodies containing combining site portions that, when unencumbered (for example by conjugation), catalyze an aldol addition reaction between an aliphatic ketone donor and an aldehyde acceptor. Aldolase antibodies are capable of being generated by immunization of an immune-responsive animal with an immunogen that includes a 1,3 diketone hapten of the formula:

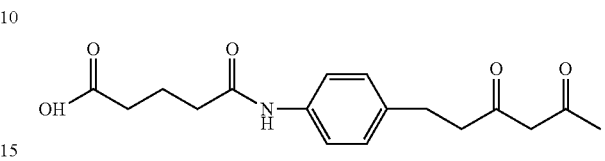

coupled to a carrier protein, and further characterized by having a lysine with a reactive ε-amino group in the combining site of the antibody. Aldolase antibodies are further characterized by their catalytic activity being subject to inhibition with the 1,3-diketone hapten by formation of a complex between the 1,3-diketone hapten and the ε-amino group of the lysine of the catalytic antibody.

As discussed, in certain embodiments, certain antibodies that can be used in conjunction with compounds of the invention may require a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue (e.g. WO 01/22922). The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site. In some embodiments, the amino acid is cysteine, and the reactive group of the side chain is a sulfhydryl group. In other embodiments, the amino acid residue is lysine, and the reactive group of the side chain is the ε-amino group. In some embodiments, the amino acid is Lys93 on the heavy chain according to Kabat numbering. In some embodiments, the amino acid is Lys-99 on HC h38C2 (SEQ ID NO:26).

Catalytic antibodies are one source of antibodies with suitable combining sites that comprise one or more reactive amino acid side chains. Such antibodies include aldolase antibodies, beta lactamase antibodies, esterase antibodies, and amidase antibodies.

One embodiment comprises an aldolase antibody such as the mouse monoclonal antibodies mAb 33F12 and mAb 38C2, as well as suitably chimeric and humanized versions of such antibodies (e.g. h38C2, SEQ ID NOs:25 and 26). Mouse mAb 38C2 (and h38C2) has a reactive lysine near to but outside HCDR3, and is the prototype of a new class of catalytic antibodies that were generated by reactive immunization and mechanistically mimic natural aldolase enzymes. See C. F. Barbas 3$^{rd}$ et al., Science 278:2085-2092 (1997). Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases. Aldolase antibodies and methods of generating aldolase antibodies are disclosed in U.S. Pat. Nos. 6,210,938, 6,368,839, 6,326,176, 6,589,766, 5,985,626, and 5,733,75, which are incorporated herein by reference.

Compounds of the invention may also be formed by linking a compound of the invention to a reactive cysteine, such as those found in the combining sites of thioesterase and esterase catalytic antibodies. Suitable thioesterase catalytic antibodies are described by K. D. Janda et al., Proc. Natl. Acad. Sci. U.S.A. 91:2532-2536 (1994). Suitable esterase antibodies are described by P. Wirsching et al., Science 270: 1775-1782 (1995). Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

The antibody may be a humanized antibody. Where compounds of the invention are covalently linked to the combining site of an antibody, and such antibodies are humanized, it is important that such antibodies be humanized with retention of high linking affinity for the Z group. Various forms of humanized murine aldolase antibodies are contemplated. One embodiment uses the humanized aldolase catalytic antibody h38c2 IgG1 or h38c2 Fab with human constant domains $C_\kappa$ and $C_{\gamma1}$1. C. Rader et al., J. Mol. Bio. 332:889-899 (2003) discloses the gene sequences and vectors that may be used to produce h38c2 Fab and h38c2 IgG1. Human germline $V_k$ gene DPK-9 and human $J_k$ gene JK4 were used as frameworks for the humanization of the kappa light chain variable domain of m38c2, and human germline gene DP-47 and human $J_H$ gene JH4 were used as frameworks for the humanization of the heavy chain variable domain of m38c2. FIG. 1 illustrates a sequence alignment between the variable light and heavy chains in m38c2, h38c2, and human germlines. h38c2 may utilize IgG1, IgG2, IgG3, or IgG4 constant domains, including any of the allotypes thereof. In certain embodiments of compounds of the invention wherein the antibody is h38c2 IgG1 with the G1m(f) allotype, Z binds to the side chain of the lysine residue at position 99 of the heavy chain. Another embodiment uses a chimeric antibody comprising the variable domains ($V_L$ and $V_H$) of h38c2 (SEQ ID NOS:27 and 28) and the constant domains from an IgG1, IgG2, IgG3, or IgG4. The antibody may be a full-length antibody, Fab, Fab', F(ab')$_2$, F$_v$, dsF$_v$, scF$_v$, $V_H$, $V_L$, diabody, or minibody. The antibody may be a full length antibody, and may be selected from the group consisting of IgG1, IgG2, IgG$_{2\Delta a}$, IgG3, IgG4, IgG$_{4\Delta b}$, IgG$_{4\Delta c}$, IgG$_4$ S228P, IgG$_{4\Delta b}$ S228P and IgG$_{4\Delta c}$ S228P. The antibody or antigen binding portion thereof may comprise the $V_H$ and $V_L$ domains from h38c2. The antibody may be an antibody comprising the $V_L$ and $V_H$ domains from h38c2 and a constant domain selected from the group consisting of IgG1, IgG2, IgG$_{2\Delta a}$, IgG3, IgG4, IgG$_{4\Delta b}$, IgG$_{4\Delta c}$, IgG$_4$ S228P, IgG$_{4\Delta b}$ S228P and IgG$_{4\Delta c}$ S228P. The antibody may be h38C2 IgG1 (SEQ ID NOS:25 and 26). The antibody may be h38C2 IgG2 (SEQ ID NOS:25 and 76). The antibody may be a humanized version of a murine aldolase antibody comprising a constant region from a human IgG, IgA, IgM, IgD, or IgE antibody. In another embodiment, the antibody is a chimeric antibody comprising the $V_L$ and $V_H$ region from a murine aldolase antibody and a constant region from a human IgG, IgA, IgM, IgD, or IgE antibody. In some embodiments, the antibody comprises the $V_L$ and $V_H$ regions from m38C2 (SEQ ID NOS:29 and 30). In further embodiments, the antibody is a fully human version of a murine aldolase antibody comprising a polypeptide sequence from natural or native human IgG, IgA, IgM, IgD, or IgE antibody. In some aspects, the antibody may comprise a light chain variable region ($V_L$) comprising a $V_L$ CDR1, $V_L$ CDR2, and $V_L$ CDR3 of the $V_L$ sequence shown in SEQ ID NO:27; and a heavy chain variable region ($V_H$) comprising a $V_H$ CDR1, $V_H$ CDR2, and $V_H$ CDR3 of the $V_H$ sequence shown in SEQ ID NO:28. As outlined above, the CDRs may be determined by a number of known methods of the art.

In some aspects, the antibody the antibody comprises a light chain at least 95% identical to SEQ ID NO:25 and a heavy chain at least 95% identical to SEQ ID NO:26. The light chain may be at least 96% identical to SEQ ID NO:25. The light chain may be at least 96% identical to SEQ ID NO:25. The light chain may be at least 97% identical to SEQ ID NO:25. The light chain may be at least 98% identical to SEQ ID NO:25. The light chain may be at least 99% identical to SEQ ID NO:25. The heavy chain may be at least 96% identical to SEQ ID NO:26. The heavy chain may be at least 97% identical to SEQ ID NO:26. The heavy chain may be at least 98% identical to SEQ ID NO:26. The heavy chain may be at least 99% identical to SEQ ID NO:26. In some aspects, the light chain may differ from SEQ ID NO:25 by one amino acid. In some aspects, the heavy chain may differ from SEQ ID NO:26 by one amino acid. In some aspects, the differences between the light chain and SEQ ID NO:25 may be located in the constant region only. In some aspects, the differences between the heavy chain and SEQ ID NO:26 may be located in the constant region only.

Various forms of humanized aldolase antibody fragments are also contemplated. One embodiment uses h38c2 F(ab')$_2$. h38c2 F(ab')$_2$ may be produced by the proteolytic digestion of h38c2 IgG1. Another embodiment uses an h38c2 scFv comprising the $V_L$ and $V_H$ domains from h38c2 which are optionally connected by the intervening linker (Gly$_4$Ser)$_3$ (SEQ ID NO:31). As an alternative to humanization, human antibodies can be generated. For example, it is now possible to produce transgenic animals (e.g. mice) that are capable, upon immunization (or reactive immunization in the case of catalytic antibodies) of producing a full repertoire of human antibodies in the absence of endogenous immunoglobulin production.

Alternatively, phage display technology can be used to produce human antibodies and antibody fragments in vitro using immunoglobulin variable (V) domain gene repertoires from unimmunized donors. As indicated above, human antibodies may also be generated by in vitro activated B cells, e.g., U.S. Pat. Nos. 5,567,610 and 5,229,275.

Amino acid sequence modification(s) of the antibodies described herein are contemplated. For example, it may be desirable to improve the binding affinity and/or other biological properties of the antibody. Amino acid sequence variants of an antibody are prepared by introducing appropriate nucleotide changes into the antibody nucleic acid, or by peptide synthesis. Such modifications include, for example, deletions from, insertions into, and/or substitutions of residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

An antibody or antibody portion of the invention can be derivatized or linked to another molecule (e.g. another peptide or protein). In general, the antibodies or portion thereof is derivatized such that the ability of the linker to covalently conjugate to the antibody combining is not affected adversely by the derivatization or labelling. Accordingly, the antibodies and antibody portions of the invention are intended to include both intact and modified forms of the antibodies described herein. E.g. an antibody or antibody portion of the invention can be functionally linked (by chemical coupling, genetic fusion, noncovalent association or otherwise) to one or more other molecular entities, such as another antibody (e.g. a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

In other embodiments, the antibody or antigen binding portion thereof of the invention may be a fusion antibody or an antibody linked to another polypeptide. In some aspects, only the variable regions of the antibody are linked to the polypeptide. In some aspects, the antibody is covalently conjugated to a peptide in such a way so as to not interfere with the binding ability of the combining site.

The polypeptide may be a therapeutic agent, such as a targeting agent, peptide, protein agonist, protein antagonist, metabolic regulator, hormone, toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

One type of derivatized antibody is produced by crosslinking two or more antibodies (of the same type or of different types, e.g. to create bispecific antibodies). Suitable crosslinkers include those that are heterobifunctional, having two distinctly reactive groups separated by an appropriate spacer (e.g. m-maleimidobenzoyl-N-hydroxysuccinimide ester) or homobifunctional (e.g. disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. When an antibody is labelled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labelled with biotin, and detected through indirect measurement of avidin or streptavidin binding. An antibody may be labelled with a magnetic agent, such as gadolinium. An antibody may also be labelled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The antibody may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

Conjugation Process

The invention provides for processes for generating compounds of the formula:

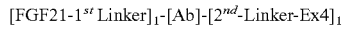

wherein FGF21 is an FGF21 homologue; and
Ex4 is an Exendin4 homologue; and
Ab is an aldolase catalytic antibody or antigen binding portion thereof; and
the $1^{st}$ linker is covalently attached to the side chain of a protein-linking residue in FGF21 and to the combining site of the antibody, and
the $2^{nd}$ linker is covalently attached to the side chain of a peptide-linking residue in Ex4 and to the combining site of the antibody, and
wherein the first and second linker are the same or different.
According to one embodiment, the invention provides a process comprising the steps:
(i) mixing FGF21 and the $1^{st}$ linker together at a ratio of between about 1:4 and about 1:1 to form the complex [FGF21-$1^{st}$ linker];
(ii) mixing [FGF21-$1^{st}$ linker] and Ab together at a ratio of between about 1.1:1 and about 1:5 so as to form a mixture containing [Ab], [Ab]-[FGF21-$1^{st}$ linker]$_1$ and [Ab]-[FGF21-$1^{st}$ linker]$_2$;
(iii) extracting the [Ab]-[FGF21-$1^{st}$ linker]$_1$ molecules from the mixture formed in (ii);
(iv) mixing Ex4 and $2^{nd}$ linker together at a ratio of between about 2:1 and about 1:2, to form the complex [$2^{nd}$ linker-Ex4];
(v) mixing [Ab]-[FGF21-$1^{st}$ linker]$_1$ with [$2^{nd}$ linker-Ex4] at a ratio of between about 2:1 and about 1:2 so as to form a mixture containing [FGF21-$1^{st}$ linker]$_1$-[Ab]-[$2^{nd}$ linker-Ex4]$_1$.

Conjugating FGF21 with $1^{st}$ Linker

In some embodiments, the FGF21 homologue is provided in about 20 mM Tris, about 50 mM NaCl, pH=about 7. In some embodiments, the FGF21 homologue is provided in about 25 mM MES pH=about 6.5. In some embodiments, tris(2-carboxyethyl)phosphine (TCEP) may be added to a final concentration 0.1× to 10× fold in comparison to FGF21 (0.5× and 0.75× have been shown to work particularly well). This has the advantage of minimizing the tendency of FGF21ΔH-A129C to dimerize, such that approximately ≥75% of the protein is in monomeric form. If the protein is dimerized, then TCEP will break it back to monomer. Apart from TCEP, mercaptoethanol (β-ME) or dithiothreitol (DTT) in concentrations between 0.1× to 10× may be used to break dimer break to monomer. The reagents such as β-mercaptoethanol (β-ME) or dithiothreitol (DTT) also react with FGF21 and form a covalent bond with thiol sulphur, and TCEP does not form a covalent bond with FGF21. Other reagents such as tetrakis-hydroxymethyl phosphonium chloride and tris-diethylaminomethyl phosphine can readily reduce disulfide and useful for reducing dimer to monomer. In some embodiments, the $1^{st}$ linker is provided in about 100% DMSO at a concentration of about 10 mM.

In some aspects, the FGF21 and $1^{st}$ linker may be conjugated together by incubation at about room temperature for about 30 mins with gentle swirling. [FGF21-$1^{st}$ linker] complexes may be obtained by eluting the mixture through a pre-equilibrated Zeba column, such that excess linker remains in the Zeba column resin.

The conjugation of FGF21 with $1^{st}$ linker can be carried out at a ratio of between about 1:1 to about 1:4. In some embodiments, the conjugation between FGF21 and $1^{st}$ linker can be carried out at a range of ratios, where the lower limit is selected form the group consisting of about 1:1, about 1:1.25, about 1:1.5, about 1.75, about 1:2, and the upper limit is selected from the group consisting of about 1:2, about 1:2.25, about 1:2.5, about 1:2.75, about 1:3, about 1:3.5, and about 1:4. In some aspects, the amount of linker can be increased to about 2- to about 4-fold excess in equivalent basis compared to FGF21. The increased amount of $1^{st}$ linker can help to expedite the conjugation time. Adding more than about 4-fold excess linker, however, does not produce any further increase in product formation or reaction time. In an excess of about 2-fold of $1^{st}$ linker is preferable which provides the FGF21-linker material. Decreasing the amount of $1^{st}$ linker to less than 1 equivalent results in reduced amount of product formation. As the amount of linker dropped to about 0.9 equivalent, and about 0.8 equivalent, 0.7 equivalent, and so on, the amount of product formed decreases. The highest amount of product formed is when the ratio of FGF21 and the $1^{st}$ linker is between about 1:1 to about 1:2.

Conjugation of [FGF21-$1^{st}$ Linker] to Antibody

In some aspects, the [FGF21-$1^{st}$ linker] is conjugated to the antibody in a MES or phosphate buffer, at a concentration between about 25 mM and about 150 mM, with a pH range of about 5.5 to about 7.5, or about 6.0 to about 7.0, at between about 0° C. and 37° C., and preferably at between about 4° C. and about RT. In some aspects, the [FGF21-$1^{st}$ linker] is conjugated to the antibody in a 100 mM a phosphate buffer with a pH range about 6.0 to about 6.5 at RT. The [FGF21-$1^{st}$ linker] may be conjugated to the antibody in a reaction carried out for a time selected from the group consisting of at least 30 mins, at least about 60 mins, at least about 90 mins, at least about 2 hrs, at least about 3 hrs, at least about four hrs, at least about 6 hrs, at least about 12 hrs, at least about 18 hrs and at least about 24 hrs.

Extracting Ab-[FGF21-$1^{st}$ Linker]

In some aspects, it is advantageous to extract Ab-[FGF21-$1^{st}$ linker]$_1$ molecules from the mixture formed in (ii) by reverse phase chromatography. In part, the invention is based on the surprising application of reverse phase chromatography to isolate Ab-[FGF21-$1^{st}$ linker]$_1$ at high purity.

In some aspects, the reverse phase chromatography is conducted over a hydrophobic interaction chromatography (HIC) butyl column. The HIC resin typically comprises beads (for example of hydroxylated methylacrylated polymer) covalently attached to butyl ligands (—$OCH_2CH_2CH_2CH_3$). In some aspects, the invention provides for a process for extracting Ab-[FGF21-$1^{st}$ linker]$_1$ from a mixture of unconjugated antibody, unconjugated [FGF21-$1^{st}$ linker], Ab-[FGF21-$1^{st}$ linker]$_1$, and Ab-[FGF21-$1^{st}$ linker]$_2$, by reverse phase chromatography over a butyl column.

The particle size of the column beads may be below about 50 µM. The particle size of the column beads may be below about 40 µM. The particle size of the column beads may be between about 50 µM and about 20 µM. The particle size of the column beads may be between about 40 µM and about 30 µM. The particle size of the column beads may be about 35 µM. In some aspects, a butyl column of "S" grade may be used.

In some aspects, the beads may comprise pores of at least about 500 Å. In some aspects, the beads may comprise pores of at least about 750 Å. In some aspects, the beads may comprise pores of at least about 1000 Å. In some aspects, the beads may comprise pores of between about 450 Å and 1050 Å. In some aspects, the beads may comprise pores of between about 950 Å and 1050 Å.

In some aspects, the HIC column may comprise butly conjugated resin beads of about 35 µM comprising pores of between about 1000 Å. In some aspects, the column may be a butyl 650 S column.

This may be at a temperature of between about 0° C. and 37° C. This may be at RT (about 15° C. to about 25° C.). This may be at a temperature of between about 15° C. to about 20° C. This may be at between about 16° C. to about 18° C. In some aspects of the invention, too high a temperature can result in excess Ab-[FGF21-$1^{st}$ linker]$_2$ species, whereas in too low a temperature, not enough of the desired Ab-[FGF21-$1^{st}$ linker]$_1$ species is trapped by the column.

In some aspects, the butyl column may subjected to an isocratic wash step with comprising 1,6 hexanediol at a concentration of about 2% to about 3%, preferably between about 2.2% and about 2.6%, and most preferably about 2.4%. The wash buffer may be between about pH 6.5 and about pH 7.5, and may be pH 7.0. The wash buffer may comprise 50 mM sodium phosphate. In some aspects, the 1,6 hexanediol may be substituted with an alternative organic diol, such as propylene glycol or unoxol. Alcohols such as isopropanol did not provide satisfactory results.

HIC columns are typically run over a steadily decreasing salt concentration: the present invention is in part based on the surprising discovery of particular advantages associated with running a relatively low salt concentration elution buffer with an increasing diol concentration in the isolation of AB-[FGF21-$1^{st}$ linker]$_1$ species from the conjugation reaction.

In some aspects, the elution on the butyl column may be conducted using a linear gradient with a buffer comprising 1,6 hexanediol. The elution linear gradient may progress from an initial concentration of between about 2% to about 3%, and preferably between about 2.2% and about 2.6%, and most preferably about 2.4%.

The diol elution may be run over a large column volume (at least 20, preferably at least 25 column volumes (CV). In such embodiments, while the initial diol concentration may be as described as above, the final concentration of the linear gradient may be over 20% and may be around 25%. In some embodiments, the elution step is run over between 5 and 15 CV, preferably between 8 and 13 CV, more preferably between 10 and 12 CV, most preferably 11 CV. In such embodiments, it can be advantageous to limit the final concentration of the linear gradient to a between about 6% to about 10%, preferably between about 7% and about 9%, more preferably between about 7.5% and about 8.5%, to most preferably about 8%. The elution buffer may be between about pH 6.5 and about pH 7.5, and may be about pH 7.0. The elution buffer may comprise between about 10 and about 100 mM sodium phosphate. The elution buffer may comprise between about 20 mM and about 80 mM sodium phosphate. The elution buffer may comprise between about 40 mM and about 60 mM sodium phosphate. The elution buffer may comprise 50 mM sodium phosphate.

This material may then be diafiltered into suitable buffer (for example, 30 mM sodium lactate pH 4.8 or 20 mM sodium glutamate pH 4.5).

Generation of [$2^{nd}$ Linker-Ex4]

In some aspects, the Exendin4 homologue and the $2^{nd}$ linker may be mixed together a ratio of between about 2:1 to about 1:2 to form the complex [$2^{nd}$ linker-Ex4]. In some aspects, mixing the Exendin4 homologue and the $2^{nd}$ linker together may be done at a ratio of about 1.5:1, to form the complex [$2^{nd}$ linker-Ex4]. In some aspects, mixing the Exendin4 homologue and the $2^{nd}$ linker together may be done at a ratio of about 1:1, to form the complex [$2^{nd}$ linker-Ex4]. In some aspects, mixing the Exendin4 homologue and the $2^{nd}$ linker together may be done at a ratio of about 1:1.5, to form the complex [$2^{nd}$ linker-Ex4]. In some aspects, mixing the Exendin4 homologue and the $2^{nd}$ linker together may be done at a ratio of about 1:2, to form the complex [$2^{nd}$ linker-Ex4].

In some aspects of the invention, the Exendin4 homologues of the invention comprise a peptide linking residue whose side chain comprises a thiol group. In some embodiments, this thiol group may then undergo a Michael reaction or conjugation additions to the maleimide ring of certain linkers disclosed herein.

The conjugation additions between suitable Exendin4 homologues and $2^{nd}$ linkers may be carried out in wide range of solvents including dimethyl sulfoxide, dimethyl formamide, dichloromethane, water, ethanol, acetonitrile acetone, propylene glycol, and any combination of the above solvents. In some aspects, the solvent for the Exendin4/$2^{nd}$ linker reaction is selected from the group consisting of dimethyl sulfoxide, dimethyl formamide and water. The conjugation reaction can also be done in mixed solvent system such as acetonitrile-water, dimethyl sulfoxide-water and dimethyl formamide-water. The use of dimethyl sulfoxide, dimethyl formamide, water-acetonitirle solvents are preferred choice due to the ease of solubility of Exendin4 peptides and the $2^{nd}$ linker, efficiency of conjugation reaction and subsequent ease of purification of product. The key criterion is the solubility of Exendin4 homologues at concentrations that would be suitable for conjugation and efficiency of conjugation with minimal side products. If the Exendin4 peptide and the $2^{nd}$ linker are sparingly soluble (for example, less than about 0.1 M) then the conjugation efficiency will be reduced.

The presence of an organic base or inorganic base greatly facilitates the formation of thiolate anion in Exendin4 peptides and subsequent conjugation to $2^{nd}$ linker. Primary amines and secondary amines generally are not preferred due to their reactivity with the linker. However, primary amines or secondary amines can be used in certain embodiments, provided they react poorly with the linker, tertiary amines such as trimethylamine, triethylamine, diethylmethylamine, diisopropylmethylamine, diethylisopropylamine, triisopropylamine, tributylamine, N-methylmorpholine, and N-methylpiperidine can be used in the conjugation reactions. Most of the above listed amine bases are suited for conjugation reaction. However, the efficiency of the reaction is different among different bases. Some bases are more resistant to react with the linker than the others. In general bulkier bases are preferred, since these bases do not react readily with the linker. Bases such as diisopropylethylamine, triisopropylamine and diethylisopropylamine are preferred as they offer good balance of almost no reactivity with the linker and efficient formation of product.

The reactions may also be carried out in aqueous system using inorganic bases such as sodium bicarbonate, sodium carbonate, potassium bicarbonate, potassium carbonate lithium bicarbonate, lithium carbonate, provided these bases do not react with the linker or peptide. The reactions can also be carried out aqueous buffered systems with or without an organic co-solvent. The addition of thiol to double bond is achieved more readily when pH is about 7 and above. The conjugation reaction is slower at pH<about 7. The conjugation reactions between Ex4 and the linker can generally take place between pH about 5 to about 8. However under more basic conditions the linkers are less stable. The pH closer to neutral level offers both the efficiency and the stability. Wide range of buffers can be used to facilitate the reactions. Many buffers are suitable for the conjugation reactions including but not limited to phosphate buffer, citrate buffer, glycine/histidine buffer, 2-amino-2-hydroxymethyl-propane-1,3-diol buffer, 4-2-hydroxyethyl-1-piperazineethanesulfonic acid, and 3-(N-morpholino)propanesulfonic acid.

Conjugation of [2" Linker-Ex4] to Ab-[FGF21-Linker]$_1$

In some aspects, Ab-[FGF21-$1^{st}$ linker]$_1$ and [$2^{nd}$ linker-Ex4] may be combined at a ratio of about Ab-[FGF21-linker]$_1$:[$2^{nd}$ linker-Ex4] of between about 0.7:1 to about 2:1. In some aspects, the ratio is about 1.1:1 to about 1.7:1. In some aspects, the ratio is about 1:3:1 to about 1.5:1. The ratio may be about 1.4:1.

In some aspects, Ab-[FGF21-$1^{st}$ linker]$_1$ and [$2^{nd}$ linker-Ex4] may be combined at a pH of between about 5.5 and about 6.5. In some aspects, Ab-[$1^{st}$ FGF21-linker]$_1$ and [$2^{nd}$ linker-Ex4] may be combined at a pH of between about 6 and about 6.5. In some aspects, Ab-[FGF21-$1^{st}$ linker]$_1$ and [$2^{nd}$ linker-Ex4] may be combined at a pH of about 6.3.

In some aspects, Ab-[FGF21-$1^{st}$ linker]$_1$ and [$2^{nd}$ linker-Ex4] may be combined at RT. In some aspects, Ab-[FGF21-$1^{st}$ linker]$_1$ and [$2^{nd}$ linker-Ex4] may be combined at between about 17° C. to about 22° C. In some aspects, Ab-[FGF21-$1^{st}$ linker]$_1$ and [$2^{nd}$ linker-Ex4] may be combined at about 19° C.

In some aspects, Ab-[FGF21-$1^{st}$ linker]$_1$ and [$2^{nd}$ linker-Ex4] may be combined following a reaction of at least 6 hrs. In some aspects, Ab-[FGF21-$1^{st}$ linker]$_1$ and [$2^{nd}$ linker-Ex4] may be combined following a reaction of at least 8 hrs. In some aspects, Ab-[FGF21-$1^{st}$ linker]$_1$ and [$2^{nd}$ linker-Ex4] may be combined following a reaction of at least 12 hrs. According to another embodiment of a process for generating compounds of the invention, the process comprises the steps:

(i) mixing Ex4 and $2^{nd}$ linker together at a ratio of between about 2:1 and about 1:2, to form the complex [$2^{nd}$ linker-Ex4];

(ii) mixing [$2^{nd}$ linker-Ex4] and Ab together at a ratio of between about 1:1 and about 1:3 so as to form a mixture containing [Ab], [Ab]-[$2^{nd}$ linker-Ex4]$_1$ and [Ab]-[$2^{nd}$ linker-Ex4]$_2$;

(iii) extracting the [Ab]-[$2^{nd}$ linker][Ex4]$_1$ molecules from the mixture formed in (ii);

(iv) mixing FGF21 and the $1^{st}$ linker together at a ratio of between about 1:4 and about 1:1 to form the complex [FGF21-$1^{st}$ linker];

(v) mixing [FGF21-$1^{st}$ linker] with [Ab]-[$2^{nd}$ linker-Ex4]$_1$ at a ratio of between about 2:1 and about 1:2 so as to form a mixture containing [FGF21-$1^{st}$ linker]$_1$-[Ab]-[$2^{nd}$ linker-Ex4]$_1$.

[FGF21-$1^{st}$ linker] and [Ex4-$2^{nd}$ linker] may be prepared as described above.

Generation of [Ex4-$2^{nd}$ Linker]$_1$-Ab

In some embodiments, [$2^{nd}$ linker-Ex4] and Ab may be conjugated together at a ratio of from about 0.5:1 to about 1:3 to form [Ab]-[$2^{nd}$ linker-Ex4]$_1$. In some embodiments, the ratio may be about 0.6:1. In some embodiments, the ratio may be about 0.7:1. In some embodiments, the ratio may be about 0.75:1. In some embodiments, the ratio may be about 0.8:1. In some embodiments, the ratio may be about 0.9:1. In some embodiments, the ratio may be about 1:1. In some embodiments, the ratio may be about 1.1:1. In some embodiments, the ratio may be about 1.2:1. In some embodiments, the ratio may be between about 1:1 and about 0.5:1. In some embodiments, the ratio may be about 0.7:1.

In some embodiments, where the ratio of [$2^{nd}$ linker-Ex4] and Ab is about 1:1, this provides the maximum amount of [Ab]-[$2^{nd}$ linker-Ex4]$_1$ species, relative to unconjugated Ab and [Ab]-[2nd linker-Ex4]$_2$. Where the ratio is about 1:1, a favourable distribution of about 40-50% [Ab]-[$2^{nd}$ linker-Ex4]$_1$ is observed, together with about 25% unconjugated Ab, and about 25% Ab-[$2^{nd}$ linker-Ex4]$_2$.

However, in order to purify [Ab]-[$2^{nd}$ linker-Ex4]$_1$ from the mixture, it is advantageous to try to minimize the amount of [Ab]-[$2^{nd}$ linker-Ex4]$_2$, as this species can interfere with Ab-[$2^{nd}$ linker-Ex4]$_1$ extraction. Moreover, [Ab]-[$2^{nd}$ linker-Ex4]$_2$ represents material that cannot be recycled. Therefore, it is also advantageous to minimize the formation of Ab-[$2^{nd}$ linker-Ex4]$_2$. To do this, the amount of [$2^{nd}$ linker-Ex4] may be lowered from about 1 equivalent to about 0.7 equivalent, or even as low as and 0.5 equivalent (in comparison to antibody). By reducing the amount of [$2^{nd}$ linker-Ex4] in comparison to Ab, the formation of [Ab]-[$2^{nd}$ linker-Ex4]$_2$ species may be minimized.

While reducing the ratio of [$2^{nd}$ linker-Ex4] to Ab may help improve the balance of products formed to favour Ab-[$2^{nd}$ linker-Ex4]$_1$ in relation to [Ab]-[2nd linker-Ex4]$_2$, this needs to be offset against the need for the reaction to provide a tolerable yield, and to minimise the amount of unconjugated, and therefore strictly unnecessary, antibody at the end of the reaction. Therefore, lowering the ratio of [$2^{nd}$ linker-Ex4]:[Ab] below about 0.5:1 can reduce the overall yield of Ab-[$2^{nd}$ linker-Ex4]$_1$. It has surprisingly found that the optimum ratio of [$2^{nd}$ linker-Ex4]:[Ab] is between about 0.5:1 and about 1:1. In some embodiments, the reaction ratio may be within a range of two ratios, defined by a lower limit selected from the group consisting of about 0.5:1, about 0.6:1, about 0.7:1, about 0.8:1, about 0.9:1 and an upper limit selected from the group consisting of about 0.6:1, about 0.7:1, about 0.8:1, about 0.9:1 and about 1:1. In some aspects, the ratio is between about 0.6:1 and about 0.8:1. In some aspects, the ratio is about 0.7:1.

The advantageous ratios of [$2^{nd}$ linker-Ex4]:[Ab] of the invention help to minimize the formation of [Ab]-[$2^{nd}$ linker-Ex4]$_2$ while maintaining the amount of formation of [Ab]-[$2^{nd}$ linker-Ex4]$_1$. By lowering the amount of [2nd linker-Ex4], the peptide may be conserved while still maintaining the yields. By increasing the amount of [$2^{nd}$ linker-Ex4] beyond 1 equivalent (for example, [$2^{nd}$ linker-Ex4]:[Ab]=about 1.25:1 to about 2:1), the formation of Ab-[$2^{nd}$ linker-Ex4]$_2$ species increases dramatically and reduces the amount of Ab-[$2^{nd}$ linker-Ex4]$_1$, the desired product. Higher amounts of [$2^{nd}$ linker-Ex4] compared to Ab (in equivalent basis) results in a dramatic drop in the amount of formation of Ab-[$2^{nd}$ linker-Ex4]$_1$ The formation of [Ab]-[$2^{nd}$ linker-Ex4]$_1$ between Ex4 peptide and antibody can occur at pH between about 4 to about 8. In some embodiments, especially where $2^{nd}$ linker is L1, the linker connected to Ex4 is relatively more stable under acidic conditions than under basic conditions. However, under acidic conditions the conjugation reaction is slower. Under basic conditions (pH>about 7) the conjugation reaction is faster; however, the linker attached to Ex4 can undergo hydrolysis. It is therefore critical to identify a condition that shows reasonable stability and efficient conjugation.

The conditions closer to neutral pH (about 6.5-about 7.5) show most stability for the linker with concomitant reaction efficiency. While the conjugation works at pH about 7, it appears the stability of the linker and the efficiency of conjugation are better at pH about 6.5.

While the reaction is feasible in plain water, it is far more desirable to have a buffered system where the pH can be maintained to improve the conjugation efficiency. Several buffer systems including formulation buffer (made up of glycine, histdine, sucrose), (4-(2-hydroxyethyl)-1-piperazineethanesulfonic acid) buffer, N-cyclohexyl-3-aminopropanesulfonic acid buffer, 3-(N-morpholino)propanesulfonic acid buffer, 2-(N-morpholino)ethanesulfonic acid buffer, 3-[4-(2-Hydroxyethyl)-1-piperazinyl]propanesulfonic acid buffer.

In some instances phosphate buffer can be used, although may promote antibody aggregation. Other buffers can be used to maintain the pH between about 6 and about 8. Appropriate pH, along with appropriate buffer, plays a critical role in forming maximum amount of Ex4 and antibody adduct. Antibody fusion buffer (comprising histidine, sucrose, glycine, pH 6.5-7.5, preferably about pH 7) appears to have all the qualities that is expected in a buffer for the conjugation reaction. Depending on the buffer, the reaction time to conjugate Ex4 to antibody can vary anywhere between about 2 hrs to about 24 hrs. In most suitable buffers, the reaction times are between about 6 to about 14 hrs. In antibody fusion buffer, the reaction is completed in about 12 to about 15 hrs. The reaction time to conjugate [$2^{nd}$ linker-Ex4] to Ab may be between two time points; the lowest of which may be about 1, about 2, about 4, about 6, about 8, about 12 hrs or about overnight, and the upper of which may be about 2, about 4, about 6, about 8, about 12, about 14, about 15, about 16, about 17, about 18, about 19, about 20, about 21, about 22, about 23, about 24, about 36, and about 48, hrs.

In some embodiments, the conjugation reaction between [$2^{nd}$ linker-Ex4] and Ab may occur between about 5° C. and about 40° C. At higher temperature, the conjugation reaction is faster. However, the stability of peptide and linker may be compromised by keeping them at higher temperature for longer period of time. As the temperature is lowered, the stability of antibody, peptide and linker is improved, but the conjugation efficiency is subjected to temperature gradation. The temperature between about 15° C. and about 25° C. is most preferable. The temperature between about 20° C. and about 25° C. offers efficient conjugation and stability of reagents and products. The temperature at which to conjugate [$2^{nd}$ linker-Ex4] to Ab may be within a range defined by a lower and an upper limit; the lower limit of which may be about 10, about 12, about 13, about 14, about 15, about 16, about 17, about 18, about 19, about 20, about 21 degrees Celsius, and the upper of which may be about 11, about 15, about 16, about 18, about 20, about 22, about 23, about 24, about 25, about 26, about 27, about 28, about 29, about 30, about 31, about 32, about 33, and about 34, degrees Celsius.

Extracting [$2^{nd}$ Linker-Ex4]$_1$-Ab

The conjugation mixture contains free antibody ([Ab]), antibody with one conjugated Ex4 peptide ([Ab]-[$2^{nd}$ linker-Ex4]$_1$), and antibody with 2 conjugated Ex4 peptides ([Ab]-[$2^{nd}$ linker-Ex4]$_2$), in addition to free [$2^{nd}$ linker-Ex4] conjugates. The next step involves purification of [Ab]-[$2^{nd}$ linker-Ex4]$_1$ from rest of the materials. In some aspects, the material can be purified using chromatography columns such as butyl column, carboxymethyl column and ion-exchange column such as strong cation exchange column. Suitable solvents for eluting the antibody conjugates include buffered solutions. The pH of the buffer solutions may be between about 6 and about 8. The aqueous buffers may be made up of either one or combination of ammonium sulphate, sodium phosphate, potassium phosphate, sodium chloride, sodium acetate, ammonium hydroxide, or 2-amino-2-hydroxymethyl-propane-1,3-diol 2-[4-(2-hydroxyethyl)piperazin-1-yl]ethanesulfonic acid, with or without an organic co-solvent such as isopropanol, propanol, butanol, or ethyl alcohol.

Conjugating Ab-[$2^{nd}$ Linker-Ex4]$_1$ with [FGF21-$1^{st}$ Linker]

The mixing of the [$1^{st}$ linker-FGF21] with [Ab]-[$2^{nd}$ linker-Ex4]$_1$ at a ratio between about 3:1 to about 1:1 results in the formation of [FGF21-$1^{st}$ linker]$_1$-[Ab]-[$2^{nd}$ linker-Ex4]$_1$ molecule. While a ratio of about 1:1 provides a reasonable amount of product, increasing the amount of [FGF21-$1^{st}$ linker] to about 2-fold improved the formation of [FGF21-$1^{st}$ linker]$_1$-[Ab]-[$2^{nd}$ linker-Ex4]$_1$ molecule, and by about 3-fold, the formation of [FGF21-$1^{st}$ linker]$_1$-[Ab]-[$2^{nd}$ linker-Ex4]$_1$ was improved further. However, increasing the amount of [FGF21-$1^{st}$ linker] more than about 3-fold does not improve the efficiency of formation of [FGF21-$1^{st}$ linker]$_1$-[Ab]-[$2^{nd}$ linker-Ex4]$_1$ molecule.

In some embodiments, the conjugation of [$2^{nd}$ linker-Ex4] with [Ab] in the ratio of 0.7:1 using the process of the invention as described yields about 35% unconjugated antibody; about 48% [Ab]-[$2^{nd}$ linker-Ex4]$_1$; and about 17% [Ab]-[$2^{nd}$ linker-Ex4]$_2$ at step (ii) above. In some embodiments, the unconjugated antibody, [Ab]-[$2^{nd}$ linker-Ex4]$_1$; and [Ab]-[$2^{nd}$ linker-Ex4]$_2$ were separated using HPLC equipped with CM Sepharose column using loading buffer (ammonium sulphate between 0.6M to 0.9M, sodium phosphate between 25 mM to 75 mM, pH between 6.5 and 7.5) and eluted with an elution buffer (15 to 25% isopropyl alcohol in 25 mM to 75 mM sodium phosphate, pH between =6.5 and 7.5). NaCl was also explored in place of ammonium sulphate as a component in loading buffer. The separation of unconjugated antibody, [Ab]-[$2^{nd}$ linker-Ex4]$_1$; and [Ab]-[$2^{nd}$ linker-Ex4]$_2$ using ammonium sulphate was comparable to NaCl. The HPLC column was packed with CM Sepharose resin as stationary phase. The column was equilibrated with loading buffer mentioned above. The range of buffer concentrations and pHs would work in isolating [Ab]-[$2^{nd}$ linker-Ex4]$_1$ were mentioned above. It was found that the separation using loading buffer (ammonium sulphate 0.75 M, sodium phosphate 50 mM, pH=7) and eluted with an elution buffer (20% isopropyl alcohol in 50 mM sodium phosphate, pH=7) gave consistently better yield. The fractions containing [Ab]-[$2^{nd}$ linker-Ex4]$_1$ were combined, extracted by UF/DF into an Antibody Fusion Buffer, comprising of histidine (5 mM to 25 mM), glycine (5 mM to 25 mM), and sucrose (0.5 to 5%) and pH between 6 to 8. The buffer containing 10 mM Histidine, 10 mM Glycine, 2% Sucrose, pH=about 6.5, gave consistently better yield. The unconjugated antibody separated from [Ab]-[$2^{nd}$ linker-Ex4]$_1$ using the above buffer conditions may be cycled×3 so as to achieve an extraction rate of about 70%.

Pharmaceutical Compositions

Another aspect of the invention provides pharmaceutical compositions comprising compositions and/or compounds of the invention. Agents comprising compositions of the invention may be formulated and administered systemically. Techniques for formulation and administration may be found in *Remington's Pharmaceutical Sciences*, 18$^{th}$ Ed., 1990, Mack Publishing Co., Easton, Pa.

For injection, compositions of the invention may be formulated in aqueous solutions, emulsions or suspensions, or nonaqueous solutions, suspensions, emulsions, dispersions or sterile powders or lyophilisates suitable for reconstitution into sterile injectable solutions or dispersions. Examples of suitable aqueous and nonaqueous diluents, solvents, and carriers include water, ethanol, polyols (such as propylene glycol, polyethylene glycol, glycerol, and the like), suitable mixtures thereof, and oils. Fluidity can be maintained or improved, for example, by the use of a coating such as lecithin, by the maintenance of the required particle size in the case of dispersions, and by the use of surfactants.

Compositions of the invention may be formulated in aqueous solutions containing physiologically compatible buffers such as citrate, acetate, histidine or phosphate. Where necessary, such formulations may also contain various tonicity adjusting agents, solubilizing agents and/or stabilizing agents (e.g., salts such as sodium chloride, sugars such as sucrose, mannitol, and trehalose, proteins such as albumin, amino acids such as glycine and histidine, surfactants such as polysorbates (Tweens), or cosolvents such as ethanol, polyethylene glycol and propylene glycol). Compositions of the invention may also comprise adjuvants, such as wetting agents, emulsifying and suspending agents, dispersing agents, and preserving agents. Compositions of the invention may also comprise suspending agents, such as agar-agar, aluminum metahydroxide, bentonite, ethoxylated isostearyl alcohols, microcrystalline cellulose, polyoxyethylene sorbitol and sorbitan esters, and tragacanth, or mixtures thereof.

Compositions of the invention may also comprise various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable compositions of the invention may be affected by the use of agents capable of delaying absorption, for example, aluminum monostearate and gelatin.

Compositions of the invention may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as L-methionine ascorbic acid, sodium sulfite, or sodium hydrogen-sulfite), buffers (such as sodium acetate, lactate, borate, bicarbonate, Tris-HCl, citrates, phosphates, or other organic acids), bulking agents (such as mannitol or glycine), chelating agents (such as ethylenediamine tetraacetic acid (EDTA), DPTA), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants.

The formulation components may be present in concentrations that are acceptable to the site of administration. Buffers may be used to maintain the composition at physiological pH or at a slightly lower pH, typically within a pH range of from about 5 to about 8.

In some aspects, pharmaceutical compositions of the invention may be prepared wherein compounds of the invention are formulated for the controlled or sustained release of the compound. Examples include hyaluronic acid and the like, polymeric gels, beads, particles, injectable microspheres, liposomes, films, microcapsules, sustained release matrices, and implantable drug delivery devices.

In some aspects, pharmaceutical compositions of the invention are provided in single- or multi-chambered pre-filled syringes.

In some aspects, the invention provides for a kit comprising at least one compound or composition of the invention together with at least one additional ingredient suitable for use in a pharmaceutical composition. In some aspects, the invention provides for a kit comprising at least one compound or composition of the invention together with at least one means for delivery of said composition to a patient.

The invention also for compositions comprising [FGF21-$1^{st}$ Linker]-[Ab]-[$2^{nd}$-Linker-Ex4]; wherein FGF21 is an FGF21 homologue; and Ex4 is an Exendin4 homologue; and Ab is an aldolase catalytic antibody or antigen binding portion thereof; and the $1^{st}$ linker is covalently attached to the side chain of a protein-linking residue in FGF21 and to a combining site of the antibody, and the $2^{nd}$ linker is covalently attached to the side chain of a peptide-linking residue in Ex4 and to a combining site of the antibody, and wherein the first and second linker are the same or different for use in one or more therapies as herein described. Also provided is the use of compositions of the invention in the treatment of one or more conditions herein described. Also provided is the use of compositions of the invention for the manufacture of a medicament for the treatment of one or more diseases or disorders as herein described.

Methods of Use

For therapeutic use in humans, a human, humanized, or human chimeric antibody or antigen binding portion thereof is a preferred antibody form of the antibody portion of the compound or composition of the invention.

One aspect of the invention is a method for treating diabetes or a diabetes-related condition comprising administering a therapeutically effective amount of a composition of the invention to a subject suffering from diabetes or a diabetes-related condition.

Another aspect of the invention is a method for increasing insulin secretion in a subject comprising administering to the subject a therapeutically effective amount of a composition of the invention or a pharmaceutical derivative thereof.

Another aspect of the invention is a method for decreasing blood glucose levels in a subject comprising administering to the subject a therapeutically effective amount of a composition of the invention or a pharmaceutical derivative thereof.

Another aspect of the invention is a method for treating obesity in a subject comprising administering to the subject a therapeutically effective amount of a composition of the invention or a pharmaceutical derivative thereof.

Another aspect of the invention is a method for controlling or reducing weight levels in a subject comprising administering to the subject a therapeutically effective amount of a composition of the invention or a pharmaceutical derivative thereof.

Another aspect of the invention is a method for treating dislipidemia in a subject comprising administering to the subject a therapeutically effective amount of a composition of the invention or a pharmaceutical derivative thereof.

Another aspect of the invention is a method for treating hypertension in a subject comprising administering to the subject a therapeutically effective amount of a composition of the invention or a pharmaceutical derivative thereof.

Another aspect of the invention is a method for treating hepatosteaotosis in a subject comprising administering to the subject a therapeutically effective amount of a composition of the invention or a pharmaceutical derivative thereof.

Another aspect of the invention is a method for treating cardiovascular disease in a subject comprising administering to the subject a therapeutically effective amount of a composition of the invention or a pharmaceutical derivative thereof.

Another aspect of the invention is a method for reducing glucagon levels in a subject comprising administering to the subject a therapeutically effective amount of a composition of the invention or a pharmaceutical derivative thereof.

Another aspect of the invention is a method for reducing triglyceride levels in a subject comprising administering to the subject a therapeutically effective amount of a composition of the invention or a pharmaceutical derivative thereof.

Another aspect of the invention is a method for increasing non-esterified free fatty acid levels in a subject comprising administering to the subject a therapeutically effective amount of a composition of the invention or a pharmaceutical derivative thereof.

Another aspect of the invention is a method for reducing low density cholesterol levels in a subject comprising administering to the subject a therapeutically effective amount of a composition of the invention or a pharmaceutical derivative thereof.

Another aspect of the invention is a method for reducing C-reactive protein levels in a subject comprising administering to the subject a therapeutically effective amount of a composition of the invention or a pharmaceutical derivative thereof.

Another aspect of the invention is a method for reducing fructosamine levels in a subject comprising administering to the subject a therapeutically effective amount of a composition of the invention or a pharmaceutical derivative thereof.

Another aspect of the invention is a method for controlling glycemic control in a subject comprising administering to the subject a therapeutically effective amount of a composition of the invention or a pharmaceutical derivative thereof.

Another aspect of the invention is a method for increasing levels of adipsin in a subject comprising administering to the subject a therapeutically effective amount of a composition of the invention or a pharmaceutical derivative thereof.

Another aspect of the invention is a method for increasing levels HDL in a subject comprising administering to the subject a therapeutically effective amount of a composition of the invention or a pharmaceutical derivative thereof.

In some aspects, the invention provides for a method of treating diabetes related conditions, obesity, dislipidemia, hypertension, hepatosteaotosis, or cardiovascular disease; or controlling or reducing weight levels; or controlling glycemic control; or increasing insulin secretion, or levels of non-esterified free fatty acids, HDL or adipsin; or reducing levels of blood glucose, glucagon, triglyceride, fructosamine, low density cholesterol, or C-reactive protein; comprising administering a therapeutically effective amount of a compound or a pharmaceutical composition of the invention to a subject.

In some aspects, the invention provides for the use of a composition or a pharmaceutical composition of the invention in the preparation of a medicament for treating diabetes related conditions, obesity, dislipidemia, hypertension, hepatosteaotosis, or cardiovascular disease; or controlling or reducing weight levels; or controlling glycemic control; or increasing insulin secretion, HDL, or non-esterified free fatty acid levels; or reducing levels of blood glucose, glucagon, triglyceride, fructosamine, low density cholesterol, or C-reactive protein.

The term "therapeutically effective dose," as used herein, means that amount of compound, composition or pharmaceutical composition of the invention that elicits the biological or medicinal response in a tissue system, animal, or human being sought by a researcher, medical doctor, or other clinician, which includes alleviation of the symptoms of a disease or disorder being treated.

Methods of Administration and Dosages

Administration routes of composition of the invention may include parenteral delivery, including intramuscular, SC, or intramedullary injections, as well as intrathecal, direct intraventricular, IV, and intraperitoneal delivery. In some embodiments, administration is intravenous. The compositions of the invention may be administered through any of the parenteral routes either by direct injection of the formulation or by infusion of a mixture of the formulation of the composition of the invention with an infusion matrix such as normal saline, D5W, lactated Ringers solution or other commonly used infusion media.

In treating mammals, including humans, having diabetes or a diabetes-related condition (or in some aspects, one or more of the following conditions: diabetes, obesity, dislipidemia, hypertension, hepatosteaotosis, cardiovascular disease, high blood glucose, low insulin levels, or any of the conditions discussed herein or a condition associated with a symptom herein discussed), a therapeutically effective amount of a composition of the invention or a pharmaceutically acceptable derivative is administered. For example, a composition of the invention may be administered as a daily IV infusion from about 0.1 mg/kg body weight to about 15 mg/kg body weight. Accordingly, some embodiments provide a dose of about 0.5 mg/kg body weight. Other embodiments provide a dose of about 0.75 mg/kg body weight. Other embodiments provide a dose of about 1.0 mg/kg body weight. Other embodiments provide a dose of about 2.5 mg/kg body weight. Other embodiments provide a dose of about 5 mg/kg body weight. Other embodiments provide a dose of about 10.0 mg/kg body weight. Other embodiments provide a dose of about 15.0 mg/kg body weight. Doses of a composition of the invention or a pharmaceutically acceptable derivative should be administered in intervals of from about once per day to 2 times per week, or alternatively, from about once every week to once per month. In some embodiments, a dose is administered to achieve peak plasma concentrations of a composition of the invention according to the invention or a pharmaceutically acceptable derivative thereof from about 0.002 mg/ml to 30 mg/ml. This may be achieved by the sterile injection of a solution of the administered ingredients in an appropriate formulation (any suitable formulation solutions known to those skilled in the art of chemistry may be used). Desirable blood levels may be maintained by a continuous infusion of composition of the invention according to the invention as ascertained by plasma levels measured by a validated analytical methodology.

One method for administering a composition of the invention to an individual comprises administering a FGF21-linker conjugate to the individual and allowing it to form a covalent compound with a combining site of an appropriate antibody in vivo. The antibody portion of a composition of the invention that forms in vivo may be administered to the individual before, at the same time, or after administration of the FGF21-linker conjugate. Alternatively, or in addition, an antibody may be present in the circulation of the individual following immunization with an appropriate immunogen. For example, catalytic antibodies may be generated by immunizing with a reactive intermediate of the substrate conjugated to a carrier protein. In particular, aldolase catalytic antibodies may be generated by administering with keyhole limpet hemocyanin linked to a diketone moiety.

The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g. orally, through injection by SC, IV, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Combination Therapies

In another aspect of the invention, a composition of the invention may be used in combination with other therapeutic agents used to treat diabetes or diabetes-related conditions, or to increase insulin secretion or decrease blood glucose levels, or to treat any of the conditions discussed herein. In one embodiment, a composition of the invention may be administered in combination with insulin, such as for example synthetic human insulin, including rapid acting, short-acting, intermediate-acting, or long-lasting insulin. In other embodiments, a composition of the invention may be administered in combination with compounds belonging to the α-glucosidase inhibitor, sulfonylurea, meglitinide, biguanide, or thiazolidinedione (TZD) families. Compositions of the invention may also be administered in combination with metabolism-modifying proteins or peptides such as glucokinase (GK), glucokinase regulatory protein (GKRP), uncoupling proteins 2 and 3 (UCP2 and UCP3), glucagon, glucagon like peptide 1 and 2 (Glp1 and Glp2), an exendin, (such as Exendin4), gastric inhibitory polypeptide (GIP), Glp2 peroxisome proliferator-activated receptor α (PPARα), leptin receptor (OB-Rb), DPP-IV inhibitors, sulfonylureas, or other incretin peptides. One of ordinary skill in the art would know of a wide variety of agents that are currently used in the treatment of diabetes or diabetes-related conditions.

In order to evaluate potential therapeutic efficacy of a composition of the invention or a pharmaceutically acceptable derivative thereof in combination with other therapeutic agents used to treat diabetes or diabetes-related conditions, increase insulin secretion, or decrease blood glucose levels, these combinations may be tested using methods known in the art. For example, the ability of a combination of a composition of the invention and another therapeutic agent to increase insulin secretion may be measured using an in vitro glucose-stimulated insulin secretion assay. In such an assay, pancreatic β cells are treated with various concentrations of glucose for a set period of time, and insulin levels are measured using methods known in the art, such as for example a radioimmunoassay. The effect of compositions of the invention and other therapeutic agents on insulin secretion may also be measured in vivo, by administering the agents directly to a subject and measuring insulin levels in bodily fluid samples at various time points. Methods for administering known therapeutic agents to a subject for use in combination therapies will be well known to clinical health care providers.

Effective dosages of composition of the invention to be administered may be determined through procedures well known to those in the art which address such parameters as biological half-life, bioavailability, and toxicity. Effective amounts of therapeutic agents to be used in combination with composition of the invention or pharmaceutically acceptable derivatives thereof are based on the recommended doses known to those skilled in the art for these agents. These recommended or known levels will preferably be lowered by 10% to 50% of the cited dosage after testing the effectiveness of these dosages in combination with a composition of the invention or a pharmaceutically acceptable derivative. It should be noted that the attending physician would know how and when to terminate, interrupt, or adjust therapy to lower dosage due to toxicity, bone marrow, liver or kidney dysfunctions or adverse drug-drug interaction. The attending physician would also know to adjust treatment to higher levels if the clinical response is inadequate (precluding toxicity).

A therapeutically effective dose refers to that amount of the compound sufficient to result in amelioration of symptoms or a prolongation of survival in a patient. The effective in vitro concentration of a composition of the invention may be determined by measuring the $EC_{50}$. Toxicity and therapeutic efficacy of such agents in vivo can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e. the concentration of the test compound which achieves a half-maximal inhibition of RT production from infected cells compared to untreated control as determined in cell culture). Such information can be used to more accurately determine useful doses in humans. Levels in plasma may be measured, for example, by high performance liquid chromatography (HPLC).

In those embodiments wherein compositions of the invention are administered in combination with other therapeutic agents, the combined effect of the agents can be calculated by the multiple drug analysis method of Chou and Talalay (T. C. Chou and P. Talalay, Adv. Enzyme Regul. 22:27-55 (1984)) using the equation:

$$CI = \frac{D_1}{(Dx)_1} + \frac{D_2}{(Dx)_2} + \frac{\alpha D_1 D_2}{(Dx)_1(Dx)_2}$$

where CI is the combination index, $(Dx)_1$ is the dose of drug 1 required to produce x percent effect alone, $D_1$ is the dose of drug 1 required to produce the same x percent effect in combination with $D_2$. The values of $(Dx)_2$ and $(D)_2$ are similarly derived from drug 2. The value of α is determined from the plot of the dose effect curve using the median effect equation:

$$\frac{fa}{fu} = \left(\frac{D}{Dm}\right)^m$$

where fa is the fraction affected by dose D, fu is the uninfected fraction, Dm is the dose required for 50% effect and m is the slope of the dose-effect curve. For mutually exclusive drugs (i.e., similar modes of action), both drugs alone and their parallel lines in the median effect plot. Mutually nonexclusive drugs (i.e., independent mode of action) will give parallel lines in the median effect plot, but in mixture will give a concave upward curve. If the agents are mutually exclusive α is 0, and if they are mutually non-exclusive, α is 1. Values obtained assuming mutual non-exclusiveness will always be slightly greater than mutually exclusive drugs. CI values of <1 indicate synergy, values>1 indicate antagonism and values equal to 1 indicate additive effects. The combined drug effects may also be calculated using the CalcuSyn software package from Biosoft (Cambridge, UK).

The compounds according to the invention may be solvated, especially hydrated. Hydration may occur during manufacturing of the compounds or compositions comprising the compounds, or the hydration may occur over time due to the hygroscopic nature of the compounds. The compounds of the invention may be lyophilized.

The invention also provides for stereoisomers, tautomers, solvates, prodrugs, and pharmaceutically acceptable salts of compounds of the invention. The invention also provides for compounds according to any of the sequences disclosed herein.

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

Aib is 2-aminoisobutyric acid, and has the structure:

"Exendin4 homologue" means a molecule with at least 80%, and preferably at least 85%, more preferably at least 90% and most preferably at least 95% identity with wildtype Exendin4 (SEQ ID NO:35), and that binds the glucagon-like peptide 1 receptor (GLP1R) with an affinity equal to or greater than that of wildtype Exendin4, or within at least 2 log below. Exendin4 homologues include variants (comprising natural amino acid deletions, additions and substitutions) and derivatives (comprising non-natural amino acid additions and substitutions and/or further chemical modification). In some aspects, the Exendin4 homologue may be selected from one of the Ex4 sequences provided herein.

"FGF21 homologue" means a molecule with at least 80%, and preferably at least 85%, more preferably at least 90% and most preferably at least 95% identity with wildtype human FGF21 (SEQ ID NO:2), and binds each of FGFR1c and β-Klotho with an affinity equal to or greater than that of wildtype FGF21, or within at least 2 log below. FGF21 homologues include variants (comprising natural amino acid deletions, additions and substitutions) and derivatives (comprising non-natural amino acid additions and substitutions and further chemical modification). Known polymorphisms are also included (such as P/L[146]). In some aspects, the FGF21 homologue may be selected from one of the FGF21 sequences provided herein.

Sequences

| SEQ ID NO: | Description | Sequence |
|---|---|---|
| 1 | FGF21 genus<br>x1 = H or absent,<br>x146 = L or P. | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPAP RGPARFLPLP GLPPAXPEPP GILAPQPPDV<br>GSSDPLSMVG PSQGRSPSYAS |
| 2 | FGF21ΔH<br>H1 absent, L146. | -PIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPAP RGPARFLPLP GLPPALPEPP GILAPQPPDV<br>GSSDPLSMVG PSQGRSPSYAS |
| 3 | FGF21 Cys mutant genus 1<br>x1 = H or absent,<br>x79 = D or C,<br>x125 = H or C,<br>x129 = A or C,<br>x146 = P or L | xPIPDSSPLL QFGGQVRQRY LYTDDAQQTE AHLEIREDGT<br>VGGAADQSPE SLLQLKALKP GVIQILGVKT SRFLCQRPxG<br>ALYGSLHFDP EACSFRELLL EDGYNVYQSE AHGLPLHLPG<br>NKSPxRDPxP RGPARFLPLP GLPPAXPEPP GILAPQPPDV<br>GSSDPLSMVG PSQGRSPSYAS |
| 4 | FGF21 Cys mutant genus 2<br>x1 = H or absent,<br>x125 = C or H,<br>x129 = A or C,<br>x146 = L or P | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPxRDPxP RGPARFLPLP GLPPAxPEPP GILAPQPPDV<br>GSSDPLSMVG PSQGRSPSYAS |
| 5 | FGF21 H125C genus<br>x1 = H or absent,<br>H125C, x146 = L or P | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPCRDPAP RGPARFLPLP GLPPAxPEPP GILAPQPPDV<br>GSSDPLSMVG PSQGRSPSYAS |
| 6 | FGF21ΔH-H125C-L146<br>H1 absent<br>H125C P146 | -PIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPCRDPAP RGPARFLPLP GLPPAPPEPP GILAPQPPDV<br>GSSDPLSMVG PSQGRSPSYAS |
| 7 | FGF21ΔH-H125C<br>H1 absent<br>H125C L146 | -PIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPCRDPAP RGPARFLPLP GLPPALPEPP GILAPQPPDV<br>GSSDPLSMVG PSQGRSPSYAS |
| 8 | FGF21 A129C genus<br>x1 = H or absent,<br>A129C, x146 = L or P | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPCP RGPARFLPLP GLPPAPPEPP GILAPQPPDV<br>GSSDPLSMVG PSQGRSPSYAS |
| 9 | FGF21ΔH-A129C-L146<br>H1 absent, A129C,<br>P146 | -PIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPCP RGPARFLPLP GLPPAPPEPP GILAPQPPDV<br>GSSDPLSMVG PSQGRSPSYAS |
| 10 | FGF21ΔH-A129C<br>H1 absent, A129C,<br>L146 | -PIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPCP RGPARFLPLP GLPPALPEPP GILAPQPPDV<br>GSSDPLSMVG PSQGRSPSYAS |
| 11 | FGF21 D79C genus<br>x1 = H or absent,<br>D79C, x146 = P or L | xPIPDSSPLL QFGGQVRQRY LYTDDAQQTE AHLEIREDGT<br>VGGAADQSPE SLLQLKALKP GVIQILGVKT SRFLCQRPCG<br>ALYGSLHFDP EACSFRELLL EDGYNVYQSE AHGLPLHLPG<br>NKSPHRDPAP RGPARFLPLP GLPPAxPEPP GILAPQPPDV<br>GSSDPLSMVG PSQGRSPSYAS |

| SEQ ID NO: | Description | Sequence |
|---|---|---|
| 12 | FGF21ΔH-D79C H1 absent, D79C, L146 | -PIPDSSPLL QFGGQVRQRY LYTDDAQQTE AHLEIREDGT VGGAADQSPE SLLQLKALKP GVIQILGVKT SRFLCQRPCG ALYGSLHFDP EACSFRELLL EDGYNVYQSE AHGLPLHLPG NKSPHRDPAP RGPARFLPLP GLPPALPEPP GILAPQPPDV GSSDPLSMVG PSQGRSPSYAS |
| 13 | FGF21ΔH-D79C-L146 H1 absent, D79C, P146 | -PIPDSSPLL QFGGQVRQRY LYTDDAQQTE AHLEIREDGT VGGAADQSPE SLLQLKALKP GVIQILGVKT SRFLCQRPCG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYAS |
| 14 | FGF21ΔH-L86C H1 absent, L86C, L146 | -PIPDSSPLL QFGGQVRQRY LYTDDAQQTE AHLEIREDGT VGGAADQSPE SLLQLKALKP GVIQILGVKT SRFLCQRPDG ALYGSCHFDP EACSFRELLL EDGYNVYQSE AHGLPLHLPG NKSPHRDPAP RGPARFLPLP GLPPALPEPP GILAPQPPDV GSSDPLSMVG PSQGRSPSYAS |
| 15 | FGF21ΔH-T40C H1 absent, T40C, L146 | -PIPDSSPLL QFGGQVRQRY LYTDDAQQTE AHLEIREDGC VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPALPEPP GILAPQPPDV GSSDPLSMVG PSQGRSPSYAS |
| 16 | FGF21ΔH-H1C H1C, L146 | CPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPALPEPP GILAPQPPDV GSSDPLSMVG PSQGRSPSYAS |
| 17 | FGF21 Lys mutant genus x1 = absent or H, x56, x59, x69, x122 = K or R, R69, x146 = L or P | xPIPDSSPLL QFGGQVRQRY LYTDDAQQTE AHLEIREDGT VGGAADQSPE SLLQLxALxP GVIQILGVxT SRFLCQRPDG ALYGSLHFDP EACSFRELLL EDGYNVYQSE AHGLPLHLPG NxSPHRDPAP RGPARFLPLP GLPPAxPEPP GILAPQPPDV GSSDPLSMVG PSQGRSPSYAS |
| 18 | FGF21ΔH-K56-K59R-K69R-K122R-L146 | -PIPDSSPLL QFGGQVRQRY LYTDDAQQTE AHLEIREDGT VGGAADQSPE SLLQLKALRP GVIQILGVRT SRFLCQRPDG ALYGSLHFDP EACSFRELLL EDGYNVYQSE AHGLPLHLPG NRSPHRDPAP RGPARFLPLP GLPPALPEPP GILAPQPPDV GSSDPLSMVG PSQGRSPSYAS |
| 19 | FGF21ΔH-K59 K56R-K69R-K122R-L146 | -PIPDSSPLL QFGGQVRQRY LYTDDAQQTE AHLEIREDGT VGGAADQSPE SLLQLRALKP GVIQILGVRT SRFLCQRPDG ALYGSLHFDP EACSFRELLL EDGYNVYQSE AHGLPLHLPG NRSPHRDPAP RGPARFLPLP GLPPALPEPP GILAPQPPDV GSSDPLSMVG PSQGRSPSYAS |
| 20 | FGF21ΔH-K69 K56R-K59R-K122R-L146 | -PIPDSSPLL QFGGQVRQRY LYTDDAQQTE AHLEIREDGT VGGAADQSPE SLLQLRALRP GVIQILGVKT SRFLCQRPDG ALYGSLHFDP EACSFRELLL EDGYNVYQSE AHGLPLHLPG NRSPHRDPAP RGPARFLPLP GLPPALPEPP GILAPQPPDV GSSDPLSMVG PSQGRSPSYAS |
| 21 | FGF21ΔH-K122 K56R-K59R-K69R-L146 | -PIPDSSPLL QFGGQVRQRY LYTDDAQQTE AHLEIREDGT VGGAADQSPE SLLQLRALRP GVIQILGVRT SRFLCQRPDG ALYGSLHFDP EACSFRELLL EDGYNVYQSE AHGLPLHLPG NKSPHRDPAP RGPARFLPLP GLPPALPEPP GILAPQPPDV GSSDPLSMVG PSQGRSPSYAS |
| 22 | FGF21ΔH-Knull-P2 K56R-K59R-K69R-K122R-L146 | -PIPDSSPLL QFGGQVRQRY LYTDDAQQTE AHLEIREDGT VGGAADQSPE SLLQLRALRP GVIQILGVRT SRFLCQRPDG ALYGSLHFDP EACSFRELLL EDGYNVYQSE AHGLPLHLPG NRSPHRDPAP RGPARFLPLP GLPPALPEPP GILAPQPPDV GSSDPLSMVG PSQGRSPSYAS |
| 23 | FGF21ΔH-Knull-H1K H1K-K56R-K59R-K69R-K122R-L146 | KPIPDSSPLL QFGGQVRQRY LYTDDAQQTE AHLEIREDGT VGGAADQSPE SLLQLRALRP GVIQILGVRT SRFLCQRPDG ALYGSLHFDP EACSFRELLL EDGYNVYQSE AHGLPLHLPG NRSPHRDPAP RGPARFLPLP GLPPALPEPP GILAPQPPDV GSSDPLSMVG PSQGRSPSYAS |
| 24 | FGF21ΔH-Knull-S181K K56R-K59R-K69R- | -PIPDSSPLL QFGGQVRQRY LYTDDAQQTE AHLEIREDGT VGGAADQSPE SLLQLRALRP GVIQILGVRT SRFLCQRPDG |

| SEQ ID NO: | Description | Sequence |
|---|---|---|
| | K122R- L146-S181K- | ALYGSLHFDP EACSFRELLL EDGYNVYQSE AHGLPLHLPG<br>NRSPHRDPAP RGPARFLPLP GLPPALPEPP GILAPQPPDV<br>GSSDPLSMVG PSQGRSPSYAK |
| 25 | h38C2 light chain | ELQMTQSPSS LSASVGDRVT ITCRSSQSLL HTYGSPYLNW<br>YLQKPGQSPK LLIYKVSNRF SGVPSRFSGS GSGTDFTLTI<br>SSLQPEDFAV YFCSQGTHLP YTFGGGTKVE IKRTVAAPSV<br>FIFPPSDEQL KSGTASVVCL LNNFYPREAK VQWKVDNALQ<br>SGNSQESVTE QDSKDSTYSL SSTLTLSKAD YEKHKVYACE<br>VTHQGLSSPV TKSFNRGEC |
| 26 | h38C2 heavy chain | EVQLVESGGG LVQPGGSLRL SCAASGFTFS NYWMSWVRQS<br>PEKGLEWVSE IRLRSDNYAT HYAESVKGRF TISRDNSKNT<br>LYLQMNSLRA EDTGIYYCKT YFYSFSYWGQ GTLVTVSSAS<br>TKGPSVFPLA PSSKSTSGGT AALGCLVKDY FPEPVTVSWN<br>SGALTSGVHT FPAVLQSSGL YSLSSVVTVP SSSLGTQTYI<br>CNVNHKPSNT KVDKRVEPKS CDKTHTCPPC PAPELLGGPS<br>VFLFPPKPKD TLMISRTPEV TCVVVDVSHE DPEVKFNWYV<br>DGVEVHNAKT KPREEQYNST YRVVSVLTVL HQDWLNGKEY<br>KCKVSNKALP APIEKTISKA KGQPREPQVY TLPPSREEMT<br>KNQVSLTCLV KGFYPSDIAV EWESNGQPEN NYKTTPPVLD<br>SDGSFFLYSK LTVDKSRWQQ GNVFSCSVMH EALHNHYTQK<br>SLSLSPGK |
| 27 | VL h38C2 | ELQMTQSPSS LSASVGDRVT ITCRSSQSLL HTYGSPYLNW<br>YLQKPGQSPK LLIYKVSNRF SGVPSRFSGS GSGTDFTLTI<br>SSLQPEDFAV YFCSQGTHLP YTFGGGTKVE IK |
| 28 | VH h38C2 | EVQLVESGGG LVQPGGSLRL SCAASGFTFS NYWMSWVRQS<br>PEKGLEWVSE IRLRSDNYAT HYAESVKGRF TISRDNSKNT<br>LYLQMNSLRA EDTGIYYCKT YFYSFSYWGQ GTLVTVSS |
| 29 | VL m38C2 | DVVMTQTPLS LPVRLGDQAS ISCRSSQSLL HTYGSPYLNW<br>YLQKPGQSPK LLIYKVSNRF SGVPDRFSGS GSGTDFTLRI<br>SRVEAEDLGV YFCSQGTHLP YTFGGGTKLE IK |
| 30 | VH m38C2 | EVKLVESGGG LVQPGGTMKL SCEISGLTFR NYWMSWVRQS<br>PEKGLEWVAE IRLRSDNYAT HYAESVKGKF TISRDDSKSR<br>LYLQMNSLRT EDTGIYYCKY YFYSFSYWGQ GTLVTVSA |
| 31 | (Gly₄ Ser)₃ | GGGGSGGGG SGGGGS |
| 32 | FGF21 leader | MNSNETGFEH SGLWVSVLAG LLLGACQA |
| 33 | FGF21 209 residue sequence, L174 (L146) isoform | MNSNETGFEH SGLWVSVLAG LLLGACQAHP IPDSSPLLQF<br>GGQVRQRYLY TDDAQQTEAH LEIREDGTVG GAADQSPESL<br>LQLKALKPGV IQILGVKTSR FLCQRPDGAL YGSLHFDPEA<br>CSFRELLLED GYNVYQSEAH GLPLHLPGNK SPHRDPAPRG<br>PARFLPLPGL PPALPEPPGI LAPQPPDVGS SDPLSMVGPS<br>QGRSPSYAS |
| 34 | Glp-1 (1227) | HAEGTFTSDV SSYLEGQAAK EFIAWLVKGR |
| 35 | Exendin4 | HGEGTFTSDL SKQMEEEAVR LFIEWLKNGG PSSGAPPPS |
| 36 | Ex4 homologue x2 = Aib | HxEGTFTSDL SKQMEEEAVR LFIEWLKNGG PSSGAPPPS |
| 37 | Ex4 homologue x40 (PLR) = K, KSH, KSMAL, Dap, Dab, R, Y, C, T, S homocysteine, homoserine, | HGEGTFTSDL SKQMEEEAVR LFIEWLKNGG PSSGAPPPSx |
| 38 | Ex4 homologue x2 is Aib x40 = K, KSH, KSMAL, Dap, Dab, R, Y, C, T, S homocysteine, homoserine, or is absent | HxEGTFTSDL SKQMEEEAVR LFIEWLKNGG PSSGAPPPSx |

| SEQ ID NO: | Description | Sequence |
|---|---|---|
| 39 | Ex4 homologue x2 is Aib PLR@x38 = K, KSH, KSMAL, Dap, Dab, R, Y, C, T, S homocysteine, homoserine, | HxEGTFTSDL SKQMEEEAVR LFIEWLKNGG PSSGAPPxS |
| 40 | Ex4 homologue x2 is Aib PLR@x36 = K, KSH, KSMAL, Dap, Dab, R, Y, C, T, S homocysteine, homoserine, | HxEGTFTSDL SKQMEEEAVR LFIEWLKNGG PSSGAxPPS |
| 41 | Ex4 homologue x2 is Aib PLR@x34 = K, KSH, KSMAL, Dap, Dab, R, Y, C, T, S homocysteine, homoserine, | HxEGTFTSDL SKQMEEEAVR LFIEWLKNGG PSSxAPPPS |
| 42 | Ex4 homologue x2 is Aib PLR@x32 = K, KSH, KSMAL, Dap, Dab, R, Y, C, T, S homocysteine, homoserine, | HxEGTFTSDL SKQMEEEAVR LFIEWLKNGG PxSGAPPPS |
| 43 | Ex4 homologue x2 is Aib PLR@x28 = K, KSH, KSMAL, Dap, Dab, R, Y, C, T, S homocysteine, homoserine, | HxEGTFTSDL SKQMEEEAVR LFIEWLKxGG PSSGAPPPS |
| 44 | Ex4 homologue x2 is Aib PLR@x27 = K, KSH, KSMAL, Dap, Dab, R, Y, C, T, S homocysteine, homoserine, | HxEGTFTSDL SKQMEEEAVR LFIEWLxNGG PSSGAPPPS |
| 45 | Ex4 homologue x2 is Aib PLR@x26 = K, KSH, KSMAL, Dap, Dab, R, Y, C, T, S homocysteine, homoserine, | HxEGTFTSDL SKQMEEEAVR LFIEWxKNGG PSSGAPPPS |
| 46 | Ex4 homologue x2 is Aib PLR@x24 = K, KSH, KSMAL, Dap, Dab, R, Y, C, T, S homocysteine, homoserine, | HxEGTFTSDL SKQMEEEAVR LFIxWLKNGG PSSGAPPPS |
| 47 | Ex4 homologue x2 is Aib PLR@x23 = | HxEGTFTSDL SKQMEEEAVR LFxEWLKNGG PSSGAPPPS |

| SEQ ID NO: | Description | Sequence |
|---|---|---|
| | K, KSH, KSMAL, Dap, Dab, R, Y, C, T, S homocysteine, homoserine, | |
| 48 | Ex4 homologue x2 is Aib PLR@x21 = K, KSH, KSMAL, Dap, Dab, R, Y, C, T, S homocysteine, homoserine, | HxEGTFTSDL SKQMEEEAVR xFIEWLKNGG PSSGAPPPS |
| 49 | Ex4 homologue x2 is Aib PLR@x20 = K, KSH, KSMAL, Dap, Dab, R, Y, C, T, S homocysteine, homoserine, | HxEGTFTSDL SKQMEEEAVx LFIEWLKNGG PSSGAPPPS |
| 50 | Ex4 homologue x2 is Aib PLR@x19 = K, KSH, KSMAL, Dap, Dab, R, Y, C, T, S homocysteine, homoserine, | HxEGTFTSDL SKQMEEEAxR LFIEWLKNGG PSSGAPPPS |
| 51 | Ex4 homologue x2 is Aib PLR@x17 = K, KSH, KSMAL, Dap, Dab, R, Y, C, T, S homocysteine, homoserine, | HxEGTFTSDL SKQMEExAVR LFIEWLKNGG PSSGAPPPS |
| 52 | Ex4 homologue x2 is Aib PLR@x16 = K, KSH, KSMAL, Dap, Dab, R, Y, C, T, S homocysteine, homoserine, | HxEGTFTSDL SKQMExEAVR LFIEWLKNGG PSSGAPPPS |
| 53 | Ex4 homologue x2 is Aib PLR@x14 = K, KSH, KSMAL, Dap, Dab, R, Y, C, T, S homocysteine, homoserine, | HxEGTFTSDL SKQxEEEAVR LFIEWLKNGG PSSGAPPPS |
| 54 | Ex4 homologue x2 is Aib PLR@x13 = K, KSH, KSMAL, Dap, Dab, R, Y, C, T, S homocysteine, homoserine, | HxEGTFTSDL SKxMEEEAVR LFIEWLKNGG PSSGAPPPS |
| 55 | Ex4 homologue x2 is Aib PLRx@12 = K, KSH, KSMAL, Dap, Dab, R, Y, C, T, S | HxEGTFTSDL SxQMEEEAVR LFIEWLKNGG PSSGAPPPS |

| SEQ ID NO: | Description | Sequence |
|---|---|---|
| | homocysteine, homoserine, | |
| 56 | Ex4 homologue x2 is Aib PLRx@11 = K, KSH, KSMAL, Dap, Dab, R, Y, C, T, S homocysteine, homoserine, | HxEGTFTSDL xKQMEEEAVR LFIEWLKNGG PSSGAPPPS |
| 57 | Ex4 homologue x2 is Aib PLR@x31 = K, KSH, KSMAL, Dap, Dab, R, Y, C, T, S homocysteine, homoserine, | HxEGTFTSDL SKQMEEEAVR LFIEWLKNGG x |
| 58 | Ex4 homologue x2 is Aib PLR@x21 = K, KSH, KSMAL, Dap, Dab, R, Y, C, T, S homocysteine, homoserine, | HxEGTFTSDL SKQMEEEAVR xFIEWLKNGG PSS |
| 59 | Ex4 homologue x1 is d-His, x2 is Aib PLR@x14 = K, KSH, KSMAL, Dap, Dab, R, Y, C, T, S homocysteine, homoserine, | xxEGTFTSDL SKQxEEEAVR LFIEWLKNGG PSSGAPPPS |
| 60 | Ex4 homologue x2 is Aib x40 when present is any amino acid and is linked through the carboxy termius or a side chain to a linker, and when x40 is absent, one of x12, x14, x19, x20, x21 is a PLR selected from the group K, KSH, KSMAL, Dap, Dab, R, Y, C, T, S homocysteine, or homoserine, and when not a PLR, x12 = K, x14 = M, x19 = V, x20 = R, x21 = L | HxEGTFTSDL SxQxEEEAxx xFIEWLKNGG PSSGAPPPSx |
| 61 | Ex4 homologue x2 is Aib PLR@12 = K | HxEGTFTSDL SKQMEEEAVR LFIEWLKNGG PSSGAPPPS |
| 62 | Ex4 homologue x2 is Aib PLR@x12 = KSH; [u = 2]. | HxEGTFTSDL SxQMEEEAVR LFIEWLKNGG PSSGAPPPS |
| 63 | Ex4 homologue x2 is Aib | HxEGTFTSDL SKQKEEEAVR LFIEWLKNGG PSSGAPPPS |

| SEQ ID NO: | Description | Sequence |
|---|---|---|
| | PLR@14 = K;<br>[u = 2]. | |
| 64 | Ex4 homologue<br>x2 is Aib<br>PLR@14 = KSH;<br>[u = 2]. | HxEGTFTSDL SKQxEEEAVR LFIEWLKNGG PSSGAPPPS |
| 65 | Ex4 homologue<br>x2 is Aib<br>PLR@19 = K;<br>[u = 2]. | HxEGTFTSDL SKQMEEEAKR LFIEWLKNGG PSSGAPPPS |
| 66 | Ex4 homologue<br>x2 is Aib<br>PLR@19 = KSH;<br>[u = 2]. | HxEGTFTSDL SKQMEEEAxR LFIEWLKNGG PSSGAPPPS |
| 67 | Ex4 homologue<br>x2 is Aib<br>PLR@20 = K;<br>[u = 2]. | HxEGTFTSDL SKQMEEEAVK LFIEWLKNGG PSSGAPPPS |
| 68 | Ex4 homologue<br>x2 is Aib<br>PLR@20 = KSH;<br>[u = 2]. | HxEGTFTSDL SKQMEEEAVx LFIEWLKNGG PSSGAPPPS |
| 69 | Ex4 homologue<br>x2 is Aib<br>PLR@21 = K;<br>[u = 2]. | HxEGTFTSDL SKQMEEEAVR KFIEWLKNGG PSSGAPPPS |
| 70 | Ex4 homologue<br>x2 is Aib<br>PLR@21 = KSH;<br>[u = 2]. | HxEGTFTSDL SKQMEEEAVR xFIEWLKNGG PSSGAPPPS |
| 71 | Ex4 homologue<br>x2 is Aib<br>PLR@40 = K;<br>[u = 2]. | HxEGTFTSDL SKQMEEEAVR LFIEWLKNGG PSSGAPPPSK |
| 72 | Ex4 homologue<br>x2 is Aib<br>PLR@40 = KSH;<br>[u = 2]. | HxEGTFTSDL SKQMEEEAVR LFIEWLKNGG PSSGAPPPSx |
| 73 | FGF21 P171C<br>genus<br>x1 = H or absent,<br>x146 = L or P. | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPAP RGPARFLPLP GLPPAxPEPP GILAPQPPDV<br>GSSDPLSMVG CSQGRSPSYA S |
| 74 | FGF21ΔH-P171C<br>X1 = H or absent,<br>L146, P171C | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPAP RGPARFLPLP GLPPALPEPP GILAPQPPDV<br>GSSDPLSMVG CSQGRSPSYA S |
| 75 | FGF21ΔH-P171C<br>X1 = H or absent,<br>P146, P171C, | xPIPDSSPLL QFGGQVRQRY LYTDDAQQTE AHLEIREDGT<br>VGGAADQSPE SLLQLKALKP GVIQILGVKT SRFLCQRPDG<br>ALYGSLHFDP EACSFRELLL EDGYNVYQSE AHGLPLHLPG<br>NKSPHRDPAP RGPARFLPLP GLPPAPPEPP GILAPQPPDV<br>GSSDPLSMVG CSQGRSPSYA S |
| 76 | h38C2-IgG2 HC: | EVQLVESGGG LVQPGGSLRL SCAASGFTFS NYWMSWVRQS<br>PEKGLEWVSE IRLRSDNYAT HYAESVKGRF TISRDNSKNT<br>LYLQMNSLRA EDTGIYYCKT YFYSFSYWGQ GTLVTVSSAS<br>TKGPSVFPLA PCSRSTSEST AALGCLVKDY FPEPVTVSWN<br>SGALTSGVHT FPAVLQSSGL YSLSSVVTVP SSNFGTQTYT<br>CNVDHKPSNT KVDKTVERKC CVECPPCPAP PVAGPSVFLF<br>PPKPKDTLMI SRTPEVTCVV VDVSHEDPEV QFNWYVDGVE<br>VHNAKTKPRE EQFNSTFRVV SVLTVVHQDW LNGKEYKCKV<br>SNKGLPSSIE KTISKTKGQP REPQVYTLPP SREEMTKNQV |

| SEQ ID NO: | Description | Sequence |
|---|---|---|
| | | SLTCLVKGFY PSDIAVEWES NGQPENNYKT TPPMLDSDGS FFLYSKLTVD KSRWQQGNVF SCSVMHEALH NHYTQKSLSL SPGK |
| 77 | Ex4 homologue<br>X1 is C(O)CH₃<br>x3 is Aib<br>x15 = PLR@15 = KSH; [u = 2].<br>X41 = NH₂ | xHxEGTFTSD LSKQxEEEAV RLFIEWLKNG GPSSGAPPPSx |
| 78 | h38C2-IgG1 LC constant region genus<br>x46 = V or A,<br>x84 = V or L | RTVAAPSVFI FPPSDEQLKS GTASVVCLLN NFYPREAKVQ WKVDNxLQSG NSQESVTEQD SKDSTYSLSS TLTLSKADYE KHKxYACEVT HQGLSSPVTK SFNRGEC |
| 79 | h38C2-IgG1 LC constant region Km(1) | RTVAAPSVFI FPPSDEQLKS GTASVVCLLN NFYPREAKVQ WKVDNVLQSG NSQESVTEQD SKDSTYSLSS TLTLSKADYE KHKLYACEVT HQGLSSPVTK SFNRGEC |
| 80 | h38C2-IgG1 LC constant region Km(1, 2) | RTVAAPSVFI FPPSDEQLKS GTASVVCLLN NFYPREAKVQ WKVDNALQSG NSQESVTEQD SKDSTYSLSS TLTLSKADYE KHKLYACEVT HQGLSSPVTK SFNRGEC |
| 81 | h38C2-IgG1 LC constant region Km(3) | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 82 | H38C2 IgG1 HC constant region | AS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |

SEQ ID NO:1 shows the 181-residue expressed protein where H¹ is optional and residue 146 may be L or P. Residue positions tested for conjugation are underlined and in bold. The numbering for SEQ ID NO:1 is used throughout.

The amino acid sequence of the light and heavy chain (SEQ ID NOs:25 and 26, respectively) of one embodiment of a humanized 38c2 IgG1 are also shown. The variable regions (VC and VH) are underlined and complementarity determining regions (CDRs) presented in bold. Lysine 99, whose side chain covalently combines with the linkers described herein, is adjacent HC CDR3.

BRIEF DESCRIPTION OF THE DRAWINGS

FIG. 1. Amino acid sequence alignment of the variable domains of m38c2, h38c2, and human germlines. Framework regions (FR) and CDRs are defined according to Kabat et al. Asterisks mark differences between m38c2 and h38c2 or between h38c2 and the human germlines.

{2.4}) (conjugated with L5), lean control [0.6] {1.0}. *P<0.05, **P<0.01 vs PBS by two-way ANOVA (A) and one-way ANOVA (B).

Figure 6A:
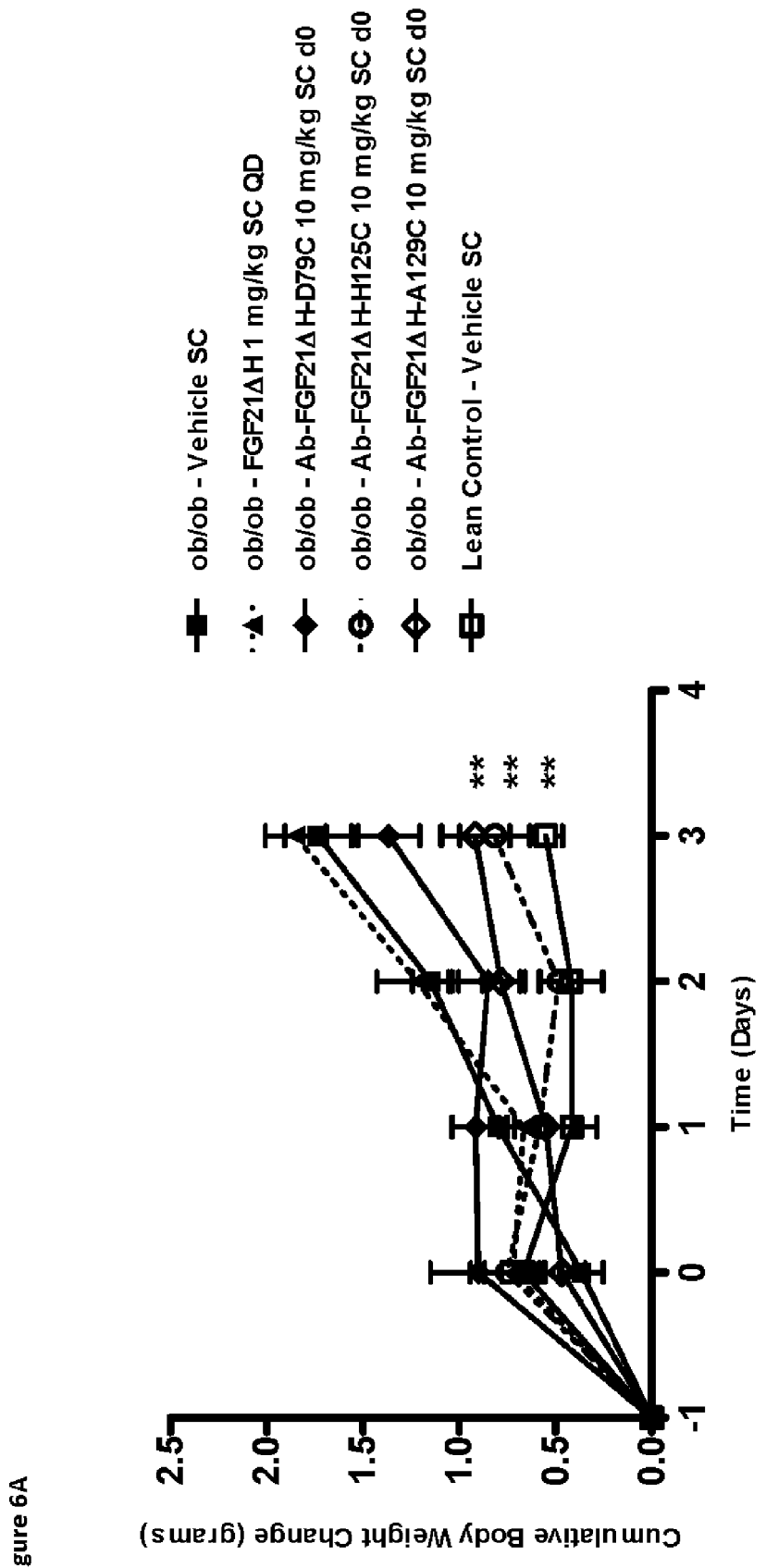

FIG. 6A. Cumulative body weight change in ob/ob mice given a single dose (mean body weight (g) in square brackets): Vehicle [1.7], FGF21ΔH [1.9], FGF21ΔH-D79C (2 mg/kg [2.1]), Ab-FGF21ΔH-D79C (10 mg/kg [1.4]), Ab-FGF21ΔH-H125C (10 mg/kg [0.8]), and Ab-FGF21ΔH-A129C (10 mg/kg [0.9]), lean vehicle [0.6]. d0: day 0. All Ab conjugates used L1. ** P<0.01 vs PBS by two-way ANOVA.

Figure 6B:
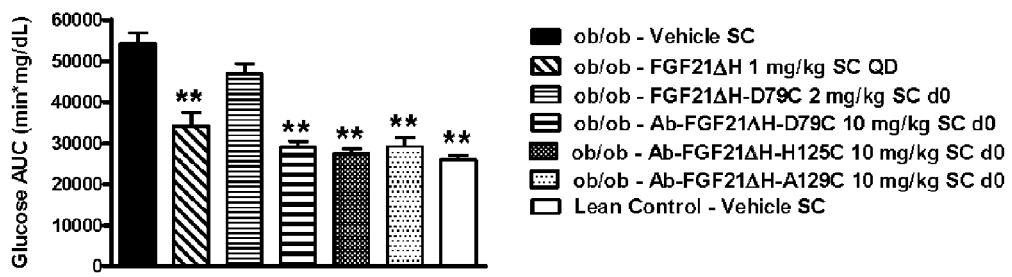

FIG. 6B. Glucose AUC during OGTT in ob/ob mice given a single dose (mean glucose AUC % in square brackets): vehicle [100], FGF21ΔH [63], Ab-FGF21ΔH-D79C (2 mg/kg [86]), FGF21ΔH-D79C (10 mg/ml [54]), Ab-FGF21ΔH-H125C (10 mg/ml [51]), and Ab-FGF21ΔH-A129C (10 mg/kg [54]), lean control [48]. All Ab conjugates used L1. **P<0.01 vs Vehicle by one-way ANOVA.

Figure 6C:
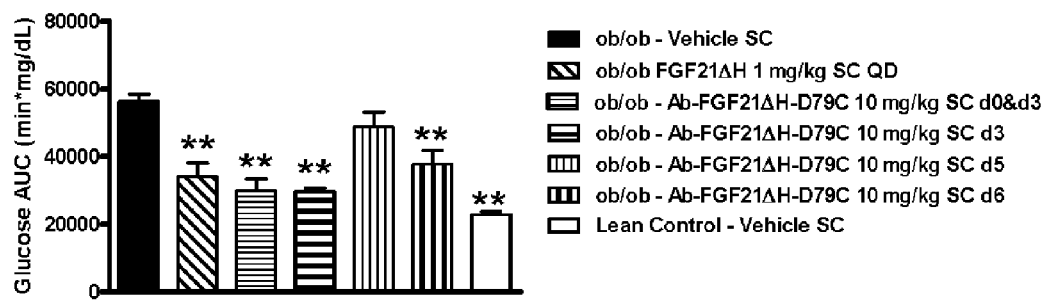

FIG. 6C. Glucose AUC during OGTT in ob/ob mice dosed with FGF21ΔH and Ab-FGF21ΔH-D79C, (10 mg/kg). Ab-FGF21ΔH-D79C was conjugated with Linker-1. **P<0.01 vs Vehicle.

Figure 6D:
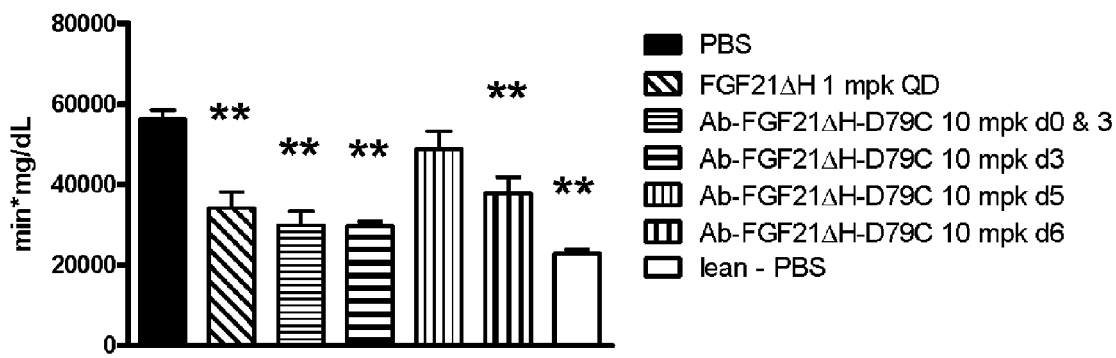

FIG. 6D. Glucose AUC during OGTT in ob/ob mice dosed with FGF21ΔH and Ab-FGF21ΔH-D79C (10 mg/kg) on day 6. Ab-FGF21ΔH-D79C was conjugated with L1. **P<0.01 vs ob/ob-PBS.

Figure 6E:
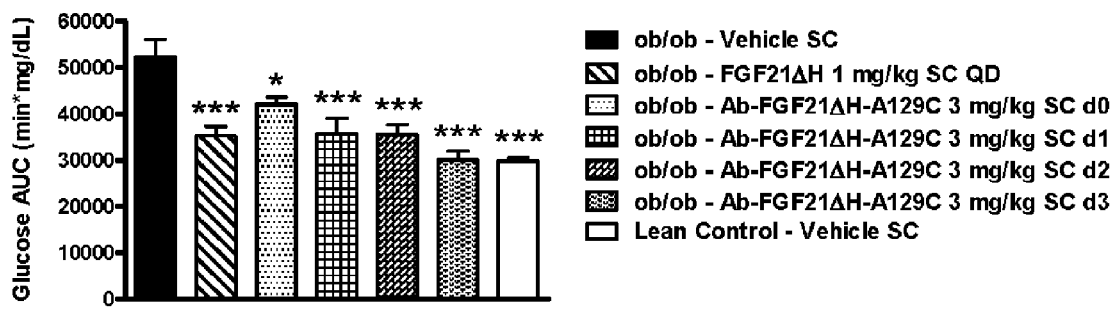

FIG. 6E. Glucose AUC during OGTT conducted on d6 in ob/ob mice given a single dose of Ab-FGF21ΔH-A129C on day 0, 1, 2, or 3 (3 mg/kg). Ab-FGF21ΔH-A129C was conjugated with L1. *P<0.05, ***P<0.001 vs PBS by one-way ANOVA.

Figure 6F:
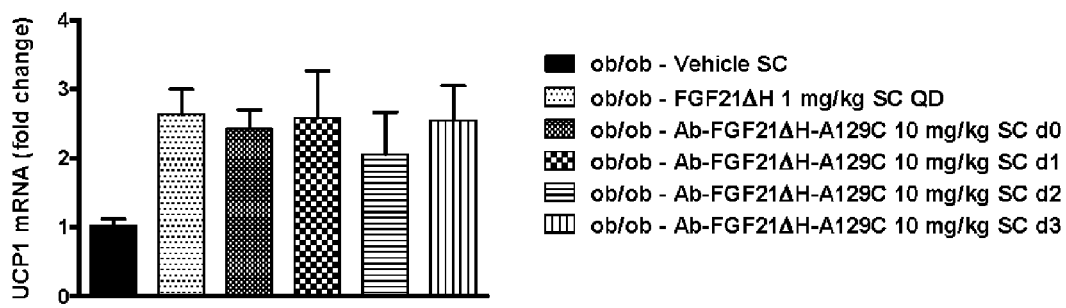

FIG. 6F. A single dose of Ab-FGF21ΔH-A129C increases Ucp1 expression in white adipose tissue in ob/ob mice (10 mg/kg). Ab-FGF21ΔH-A129C was conjugated with L1.

Figure 6G:
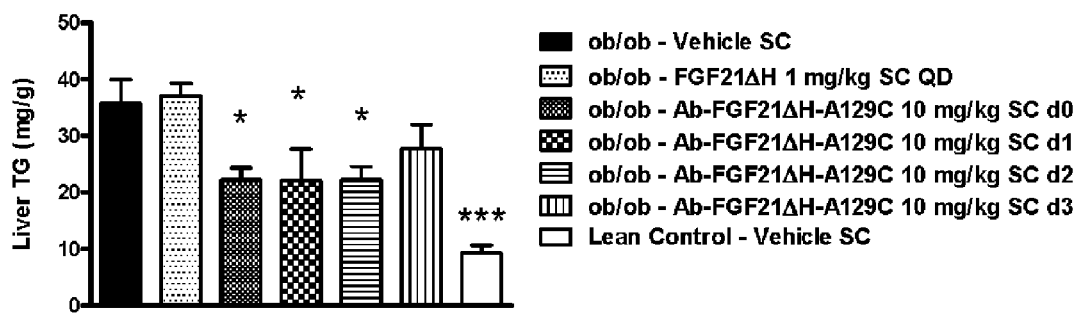

FIG. 6G. A single dose of Ab-FGF21ΔH-A129C decreases liver triglycerides in ob/ob mice (10 mg/kg). Ab-FGF21ΔH-A129C was conjugated with L1. *P<0.05, ***P<0.001 vs Vehicle by one-way ANOVA.

Figure 6H:
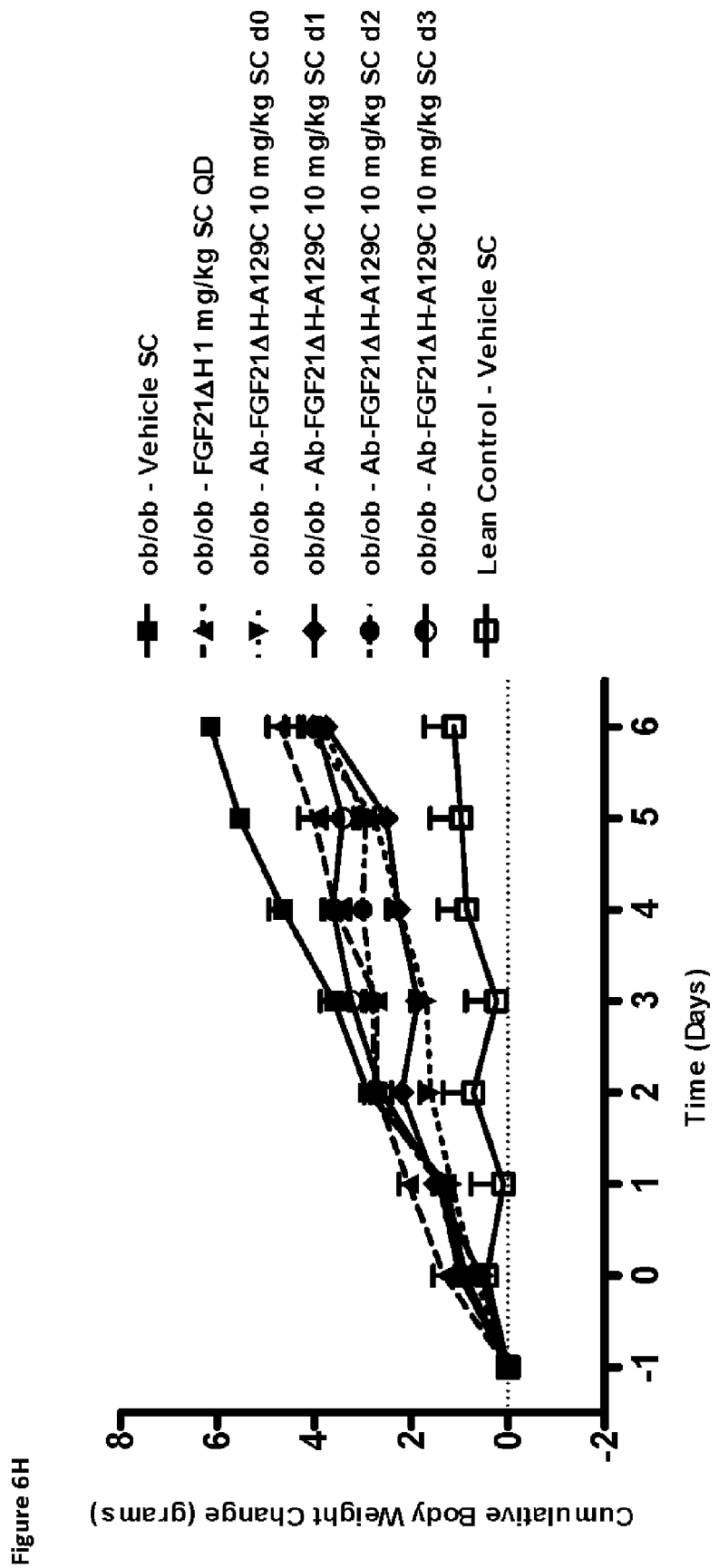

FIG. 6H. Cumulative body weight change in ob/ob mice given a single dose of Ab-FGF21ΔH-A129C on day 0, 1, 2, or 3 (10 mg/kg). Ab-FGF21ΔH-A129C was conjugated with L1.

Figure 7A:
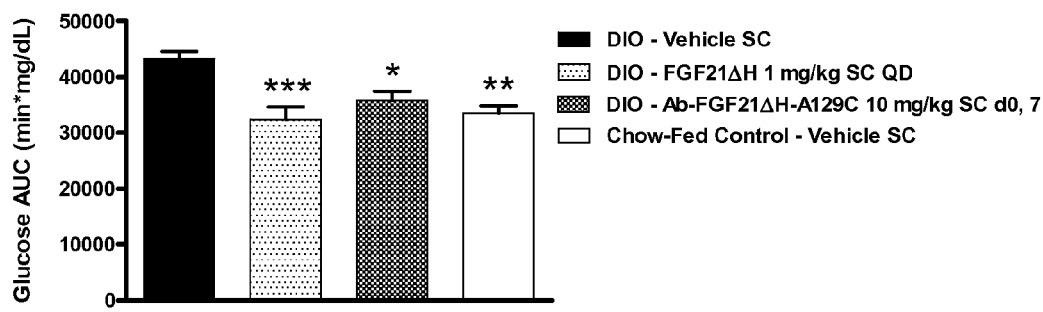

FIG. 7A. Repeat dose of Ab-FGF21ΔH-A129C (10 mg/kg on day 0 and 7) improves glucose tolerance in DIO mice. OGTT was conducted on day 10. Ab-FGF21ΔH-A129C was conjugated with L1. *P<0.05, P<0.01, *P<0.001 vs Vehicle by one-way ANOVA.

Figure 7B:
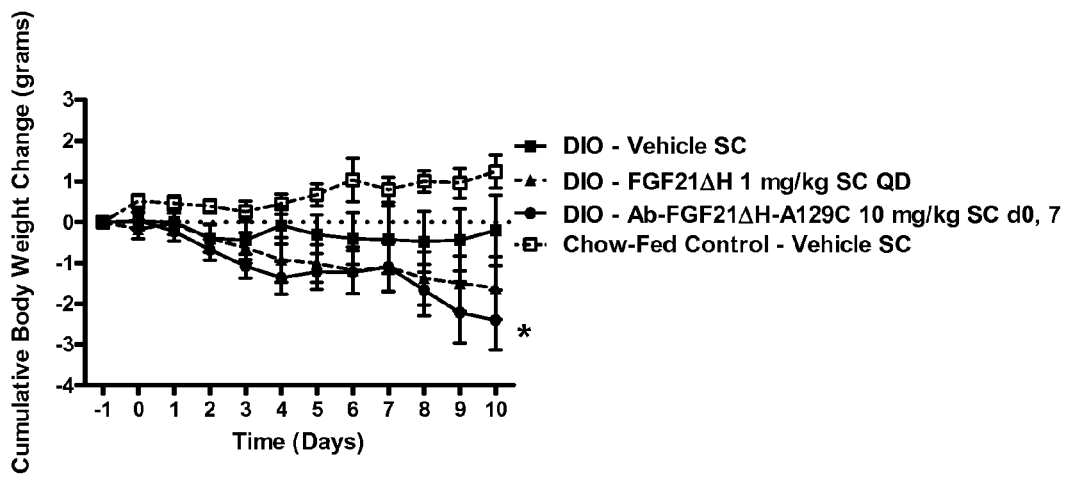

FIG. 7B. Cumulative body weight change in DIO mice given two doses of Ab-FGF21ΔH-A129C on day 0 and 7 (10 mg/kg). Ab-FGF21ΔH-A129C was conjugated with L1. *P<0.05, vs Vehicle by two-way ANOVA.

Figure 7C:

FIG. 7C. Repeat dose of Ab-FGF21ΔH-A129C increases Ucp1 expression in white adipose tissue in DIO mice (10 mg/kg). Ab-FGF21ΔH-A129C was conjugated with L1. **P<0.01 vs Vehicle by one-way ANOVA.

Figure 7D:
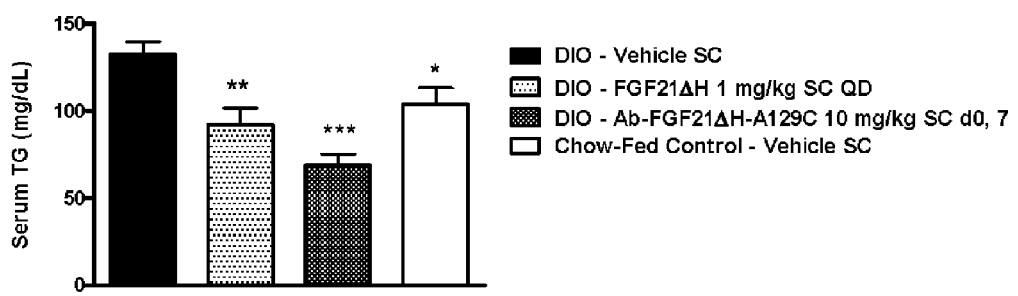
Figure 7E:
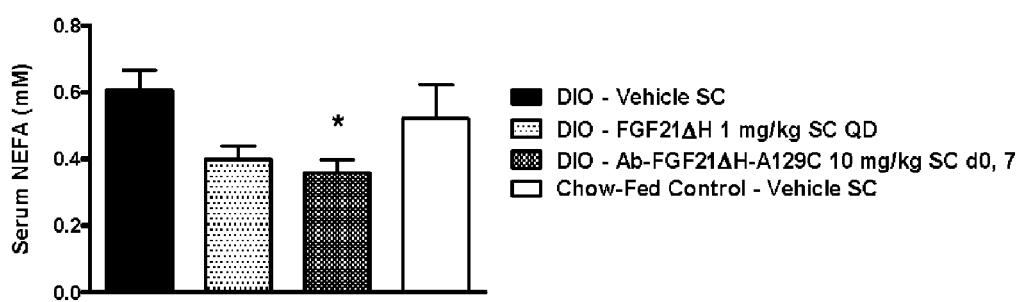
Figure 7F:
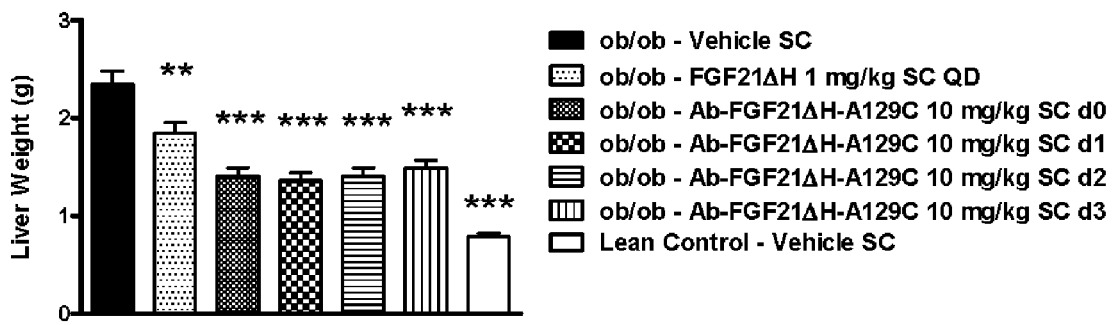

FIG. 7D. Ab-FGF21ΔH-A129C lowers serum triglycerides in DIO mice (10 mg/kg). FIG. 7E. Ab-FGF21ΔH-A129C lowers serum non-esterified fatty acids in DIO mice (10 mg/kg). FIG. 7F. Ab-FGF21ΔH-A129C Liver weight. Ab-FGF21ΔH-A129C was conjugated with L1. *P<0.05, P<0.01, *P<0.001 vs Vehicle (A, B) and vs PBC (C) by one-way ANOVA.

Figure 7G:
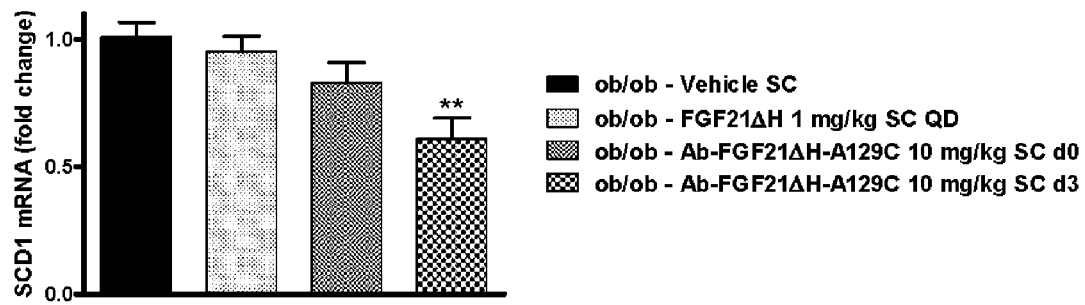
Figure 7H:
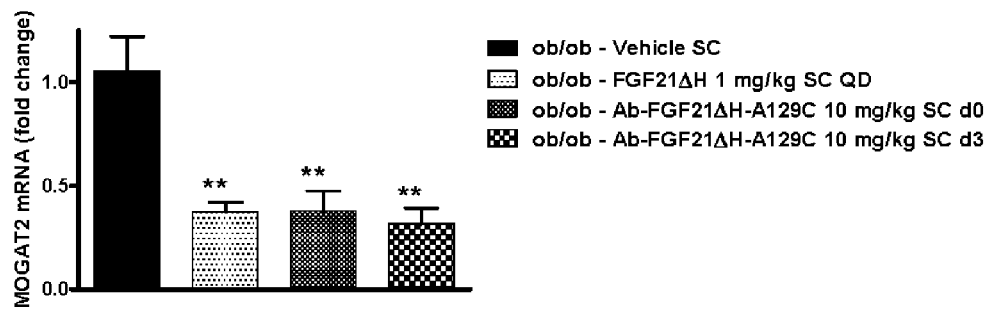
Figure 7I:
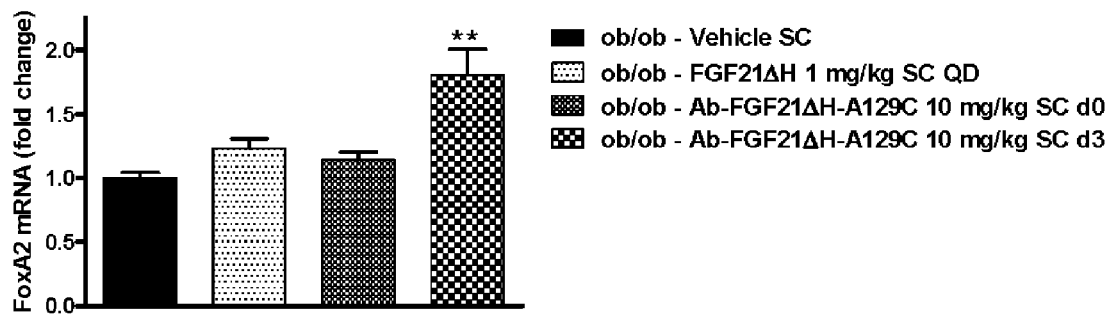

FIG. 7G, 7H, 7i. Effect of Ab-FGF21ΔH-A129C on Hepatic Gene Expression in ob/ob Mice. (7G) SCD1: stearoyl-CoA desaturase 1, (7H) MOGAT2: monoacyglycerol acyltransferase 2 (7i) FoxA2: forkhead transcription factor A2. Ab-FGF21ΔH-A129C was conjugated with L1. **P<0.01 vs Vehicle by one-way ANOVA.

Figure 8:
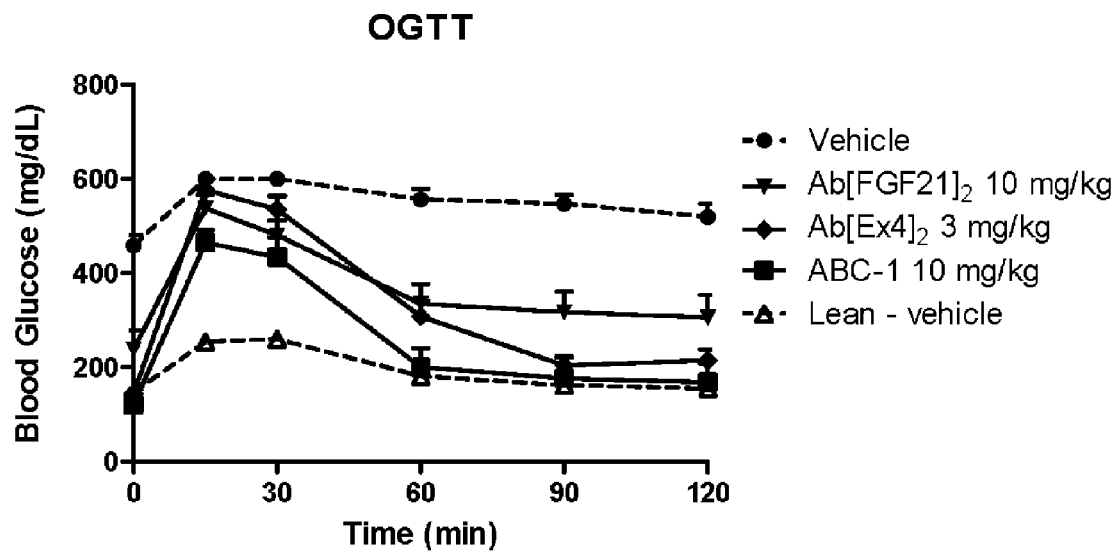

FIG. 8. Blood glucose during the OGTT 3 days after the repeat SC injection of compounds in db/db mice. Ab[FGF21]$_2$=h38C2(IgG2)-[SEQ ID NO:10-L1]$_2$. Ab[Ex4]$_2$=h38C2(IgG1)-[SEQ ID NO:64-L1]$_2$. ABC-1= [SEQ ID NO:10-L1]$_1$-[h38C2-IgG1]-[L1-SEQ ID NO:64]$_1$.

EXAMPLES

The versatility of the invention is illustrated by the following Examples, which illustrate typical embodiments of the invention and are not limiting of the claims or specification in any way.

Example 1

Identifying Optimal Tether Site on FGF-21

A study was undertaken to identify the optimal site for conjugation of FGF21 via a linker to a catalytic antibody combining site. Two conjugation strategies were considered: conjugation through a surface lysine side-chain, and conjugation through a surface cysteine side-chain. Generally, globular proteins do not have unpaired cysteine residues on their surface, and thus incorporation of a single cysteine in the protein surface can be used to engineer in a single site for specific conjugation. However, the mutation of surface residues with cysteine can often cause problems such as intermolecular dimerization, mis-pairing of native disulphide bonds, and interference with receptor binding. For these reasons, protein conjugation is most commonly affected through lysine residues.

Homology Modelling of FGF21 Receptor and its Activation Mechanism

FGF21 binds to both FGFR1c and FGFR4, but the receptor complex can be activated only through FGFR1c. Although FGFR1b and FGFR1c share 87% identity (FGFR1b is identical to FGFR1c except for the 111b/c alternative splicing region), FGF21 specifically recognizes only FGFR1c. Here, homology modelling of the complex structure of FGF21-FGFR1c was performed by using the FGFR2-FGFR1c crystal structure as a template. MOE software was used for homology modelling and structural analyses. The activation of the receptor requires another cell-surface receptor, βKlotho. βKlotho has two domains which are very similar (~35% identical) to human cytosolic β-glucosidase. The human βKlotho structure was modelled by using human cytosolic β-glucosidase, and the structure in the modelled structure of FGF21-FGFR1c aligned. This modelled complex structure provided rational guidelines for the optimum lysine conjugation sites and optimum cysteine residue incorporation in FGF21, which should not interrupt the binding interfaces between FGF21 and FGFR1c and between FGF21 and βKlotho.

The following criteria were used for conjugation site selection: (1) residues should be exposed to the solvent in the structure as much as possible; (2) residues should be far from the disulphide bond; (3) residues should be far from the receptor and β-Klotho binding surfaces.

Exposure to solvent can be assessed based on the accessible surface area (ASA). Calculation of ASA from the modelled structure of FGF21 was done with CCP4 software (The CCP4 Suite: Programs for Protein Crystallography". (1994) Acta Cryst. D50, 760-763) and an in-house program. Briefly the program in CCP4 calculates a value in square angstroms per residue in its log file. In order to calculate the fraction of ASA (fASA), an in-house program was used to normalize ASA per residue. Table 1 shows residues of ASA as well as fASA. Residues whose side chain is predicted to be obscured the surface are not included. Column 1 is the amino acid name, 2 is the residue number, 3 is ASA (as square angstrom), 4 is the fraction exposed. The fASA value defines the accessibility of solvent to the amino acid residue in a given polypeptide. A fASA value close to zero indicates that the residue is predicted to be inaccessible to solvent, suggesting that it is more unlikely to be accessible to the linkers for conjugation. An absolute minimum fASA value of 0.3 was used, with surface area values>1.00 suggestive of particularly likely candidate conjugation sites.

Based on the ASA analysis, K122 (surface area of 164.4) and K59 (surface area of 117.2) were considered the most promising candidate sites for conjugation. K69 (surface area 91) and K56 (surface area 73) were also conjugated for comparative purposes.

TABLE 1

Comparison of surface residues of FGF21.

| Amino Acid | Residue Number | Surface Area | Fraction Exposed |
|---|---|---|---|
| GLY | 14 | 105.2 | 1.25387 |
| GLN | 15 | 158.5 | 0.83774 |
| VAL | 16 | 81.5 | 0.50216 |
| ARG | 17 | 91.6 | 0.36743 |
| ARG | 19 | 78.6 | 0.31528 |
| ALA | 26 | 93.9 | 0.8067 |
| GLN | 27 | 126.5 | 0.66861 |
| GLN | 28 | 169.4 | 0.89535 |
| THR | 29 | 64.2 | 0.43349 |
| GLU | 30 | 103.9 | 0.55502 |
| GLU | 37 | 117.1 | 0.62553 |
| ASP | 38 | 90.5 | 0.58237 |
| THR | 40 | 49.8 | 0.33626 |
| GLY | 43 | 38.1 | 0.45411 |
| ALA | 45 | 93.6 | 0.80412 |
| ASP | 46 | 95 | 0.61133 |
| PRO | 49 | 82.4 | 0.56906 |
| GLN | 54 | 66.8 | 0.35307 |
| LYS | 56 | 73 | 0.35181 |
| ALA | 57 | 46.6 | 0.40034 |
| LEU | 58 | 82.7 | 0.41768 |
| LYS | 59 | 117.2 | 0.56482 |
| PRO | 60 | 153.8 | 1.06215 |
| GLY | 61 | 27.9 | 0.33254 |
| VAL | 68 | 58.8 | 0.36229 |
| LYS | 69 | 91 | 0.43855 |
| SER | 71 | 69 | 0.54893 |
| ARG | 77 | 129.4 | 0.51905 |
| PRO | 78 | 98.9 | 0.68301 |
| ASP | 79 | 109.8 | 0.70656 |
| TYR | 83 | 84.4 | 0.35418 |
| LEU | 86 | 119.4 | 0.60303 |
| HIS | 87 | 104.8 | 0.52796 |
| PHE | 88 | 123 | 0.55083 |
| ASP | 89 | 50.7 | 0.32626 |
| PRO | 90 | 107.5 | 0.7424 |
| GLU | 91 | 121.5 | 0.64904 |
| ARG | 96 | 92.6 | 0.37144 |
| LEU | 98 | 114 | 0.57576 |
| LEU | 99 | 113.2 | 0.57172 |
| GLU | 101 | 182.1 | 0.97276 |
| ASP | 102 | 94.6 | 0.60875 |
| GLY | 103 | 56.1 | 0.66865 |
| GLN | 108 | 72.6 | 0.38372 |
| GLU | 110 | 132.4 | 0.70727 |
| ALA | 111 | 62.7 | 0.53866 |
| GLY | 113 | 56.8 | 0.677 |
| LYS | 122 | 164.4 | 0.79229 |
| PRO | 124 | 67.4 | 0.46547 |
| HIS | 125 | 168.4 | 0.84836 |
| ARG | 126 | 131.4 | 0.52708 |
| PRO | 128 | 91.3 | 0.63053 |
| ALA | 129 | 78.8 | 0.67698 |
| ARG | 131 | 225.5 | 0.90453 |

TABLE 1-continued

Comparison of surface residues of FGF21.

| Amino Acid | Residue Number | Surface Area | Fraction Exposed |
|---|---|---|---|
| GLY | 132 | 65.8 | 0.78427 |
| PRO | 133 | 84.9 | 0.58633 |
| ARG | 135 | 106.2 | 0.42599 |
| GLY | 141 | 30.4 | 0.36234 |
| LEU | 142 | 69.1 | 0.34899 |
| PRO | 143 | 71.4 | 0.49309 |
| ALA | 145 | 86.4 | 0.74227 |
| LEU | 146 | 123.3 | 0.62273 |
| PRO | 147 | 131.1 | 0.90539 |
| GLU | 148 | 67.3 | 0.35951 |
| PRO | 149 | 170 | 1.17403 |

Example 2

Generation of FGF21 Proteins and Mutants

FGF21 cDNA was purchased from ATCC. Mammalian and bacterial expression vectors were constructed by using pcDNA3.1 (Invitrogen®) and pET21b (EMD), respectively. For the mutational variants of FGF21, mutations were introduced into the expression vectors using a QuikChange® site-directed mutagenesis kit (Stratagene®). The presence of the desired mutations was verified by DNA sequencing.

For mammalian expression, HEK293F cells (Invitrogen®) were transfected with the mammalian expression vector of FGF21 using 293 fectin reagent (Invitrogen®) and grown in serum-free medium. Sterile-filtered, conditioned media were dialyzed against buffer A (20 mM Tris-HCl, pH 7.5) and loaded onto a HiTrap Q column (GE Healthcare®) preequilibrated with buffer A. FGF21 protein was eluted with a linear gradient from buffer A to buffer B (20 mM Tris-HCl, pH 7.5, and 100 mM NaCl). The pooled fraction was concentrated and loaded onto Sephadex 300 with phosphate buffer saline (PBS, pH 7.4). The resulting protein solution was concentrated and stored below -80° C. The purity was confirmed by SDS-PAGE and RP-HPLC.

For production of FGF21ΔH from E. coli, the bacterial expression vector was transformed into the host strain BL21-(DE3)-RIL (Stratagene®). The transformed cells were grown in 1 liter of LB medium at 37° C., and expression was initiated by addition of 1 mM isopropyl β-D-thiogalactopyranoside. After 4 hr, cells were harvested and frozen at −20° C. The frozen cell paste was suspended in lysis buffer (50 mM Tris, 10 mM EDTA, pH 7.5), and passed through the microfluidizer 4 times. After 30 min centrifugation at 17,000×g, 4° C., the inclusion body (IB) containing pellet was resuspended in 50 mM Tris, pH 7.5. The washed IB slurry was centrifuged (30 min, 17,000×g, 4° C.). The IB pellet was stored at −80° C. The frozen IB pellet was solubilized with 7 M urea, 5 mM DTT and 50 mM bis-tris propane, pH 10.5 at 1 to 10 mg/ml FGF21 and stirred for 1 hr to dissolve and reduce protein. The solubilized IB was then diluted 10 times into 50 mM Bis-Tris propane, pH 8.0. Final protein concentration was 0.1 to 1 mg/mL. The solution was stirred for ~2 days and dialyzed against 4 liters of 20 mM Tris-HCl, pH7.5. The protein solution was centrifuged at 14,000×g for 30 min. The supernatant was loaded to HiTrap Q HP (GE Healthcare®) and equilibrated with buffer A (see above). Unbound bacterial proteins were washed with buffer A and FGF21 protein was eluted with a linear gradient of buffer B. The FGF21 fraction was then loaded onto a HiTrap chelating HP column (GE Healthcare®) pre-equilibrated with PBS buffer. FGF21 protein was eluted with a linear gradient from PBS to PBS buffer plus 100 mM imidazole (pH was adjusted to 7.4). The fractions were collected and concentrated (up to 50 mg/mL) and the protein solution applied to a size exclusion column (Hiload 26/60, superdex 300) equilibrated with PBS (Gibco®, pH7.4). Purified protein was sterilized by 0.22 μm filter and stored at −80°. Typical yield of FGF21ΔH from 8 L culture media was 600~700 mg. Typical purity was >95%. Typical endotoxin level was ~1 EU/mg. The cysteine and lysine-to-arginine mutants of FGF21 were produced and purified in a similar manner to FGF21ΔH. A typical yield of purified protein was 350~400 mg. Free cysteine was confirmed by using Ellman's reagent.

Example 3

Synthesis of Linker 1

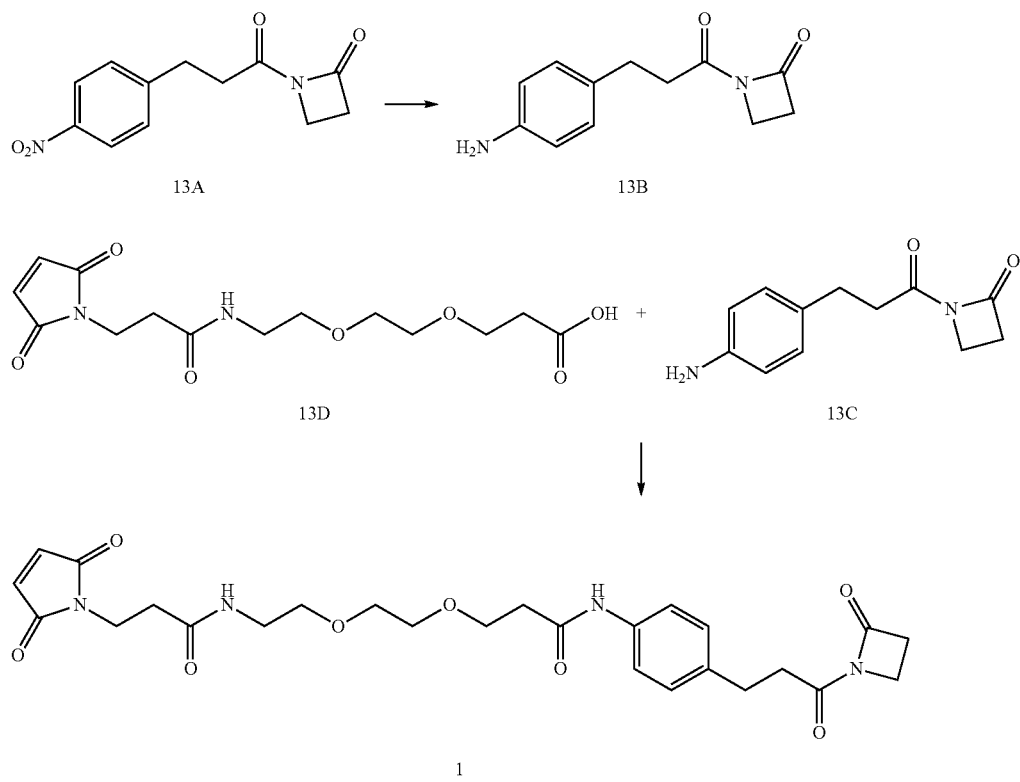

Synthesis of Linker 1: Palladium on carbon (e.g. about 1.0 g, about 0.47 mmol) was added in one portion followed by hydrochloric acid (e.g. about 2.5 mL, about 30.2 mmol) dropwise to a suspension of 13A (e.g. about 5 g, about 20.1 mmol) in methanol (e.g. about 200 mL) at about 35° C. under an atmosphere of nitrogen. Hydrogen was slowly bubbled in to the solution at about 35° C. and the solution was stirred for about 2 hrs at that temperature. The solid was filtered through a bed of celite, and collected. The filtrate was concentrated under reduced pressure and the solid was dried under vacuum to give 13B as hydrochloride salt. Compound 13B was mixed with dichloromethane (e.g. about 200 mL) and saturated solution of sodium bicarbonate (for example, about 250 mL), and the dichloromethane layer was separated. The dichloromethane layer was washed with saturated sodium chloride (e.g. about 250 mL) and dried on sodium sulphate. The organic layer was filtered, concentrated under reduced pressure and purified using flash chromatography (SiO$_2$, about 60% ethyl acetate in hexanes) to give a yield of about 68% (e.g. about 2.94 g) of 13C. A solution of 13C (e.g. about 4.65 g, about 21.3 mmol), 13D (e.g. about 7.00 g, about 21.3 mmol) N-(3-dimethylaminopropyl)-N'-ethylcarbodiimide hydrochloride (e.g. about 3.3 g, about 21.3 mmol), and N,N-diisopropylethylamine (e.g. about 2.75 g, about 21.3 mmol) in dichloromethane (e.g. about 200 mL) at about 0° C. under nitrogen was stirred for 5 mins and at room temperature for about 4 hrs. The organic layer was washed with dilute sodium bicarbonate solution, and, saturated sodium chloride solution, concentrated under vacuum, and purified using flash chromatography (SiO$_2$, acetonitrile) to afford Linker 1 (e.g. about 8.25 g a yield of about 73%).

Example 4

Synthesis of Linker 2

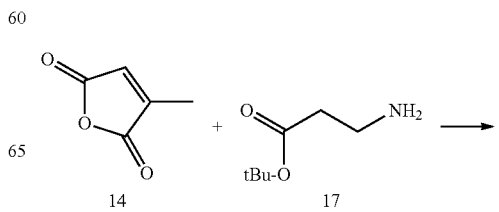

79
-continued
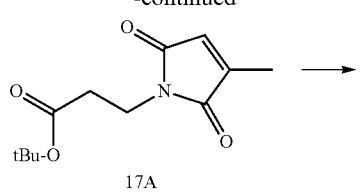
17A
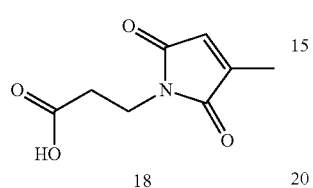
18
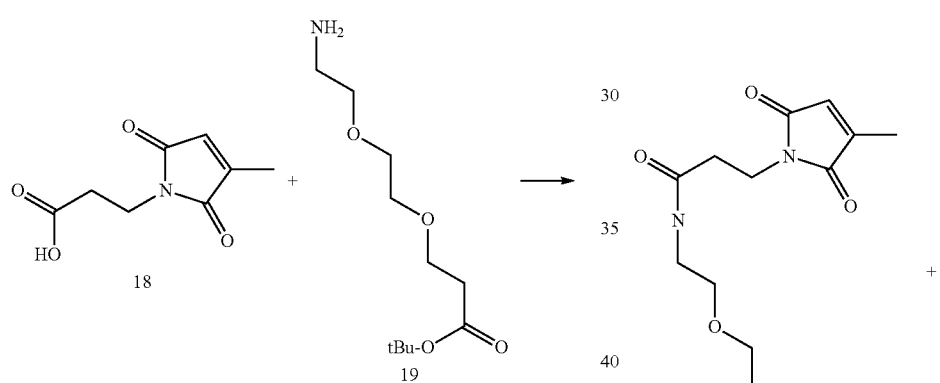
19
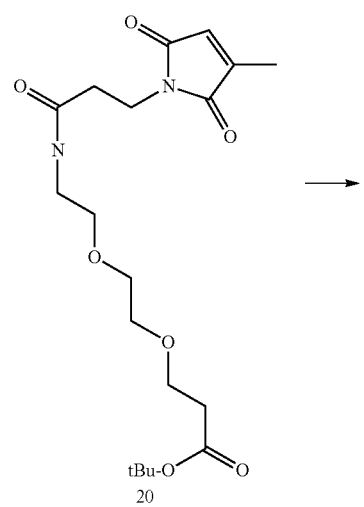
20
80
-continued
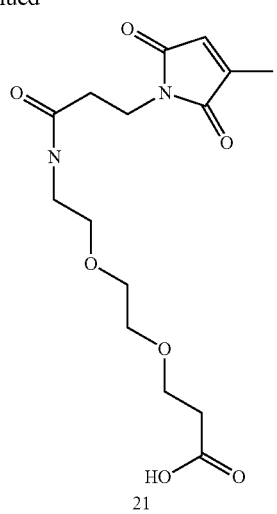
21
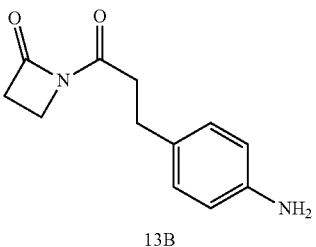
13B

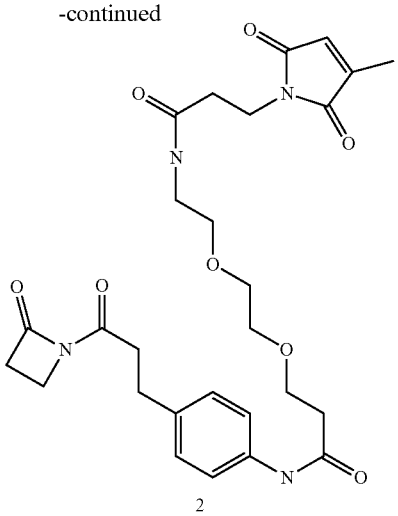

A solution of citraconic anhydride, 14 (e.g. about 2.0 mg, about 16.7 mmol), β-alanine, 17 (e.g. about 1.5 g, about 16.7 mmol) in DMF (e.g. about 10 mL) was stirred at room temperature for about 5 hrs. Then reaction solution was cooled to about 0° C. and a DMF (e.g. about 10 mL) solution containing diisopropylcarbodiimide (e.g. about 2.6 mL, about 16.7 mmol) and HOBT (e.g. about 1.9 g, about 16.7 mmol) was added. Diisopropylethylamine (e.g. about 5 eq, about 83.5 mmol) was added and the reaction mixture was warmed to room temperature and stirred for another about 16 hrs. The reaction was poured into water, acidified with 1N HCl, and extracted with ethyl acetate (e.g. about 3× about 30 mL). The organic layer was washed with water (e.g. about 2× about 30 mL) and brine (e.g. about 30 mL), and then dried over sodium sulphate. The solvent was removed under vacuum and the crude mixture was purified by column chromatography. The desired fractions were pooled and concentrated under reduced pressure to give 17A.

Compound 17A (e.g. about 0.5 g, about 2.09 mmol) was stirred in about 15% trifluoroacetic acid in dichloromethane at room temperature for about 2 hrs and concentrated to dryness under reduced pressure. The free acid 18 was added to N-hydroxysuccinimide (e.g. about 0.25 g, about 2.09 mmol) in tetrahydrofuran (e.g. about 20 mL), followed by diisopropylcarbodiimide (e.g. about 0.33 ml, about 2.09 mmol) and was stirred for about 4 hrs at room temperature. Diisopropyl urea was filtered off. The filtrate was evaporated to dryness. Petroleum ether (e.g. about 30 mL) was added to the residue, triturated, shaken and the petroleum ether layer was decanted. This procedure was repeated one more time with petroleum ether and the product 18 dried under vacuum.

Amine-peg2-tbutyl ester, 19 (e.g. about 0.5 g, 2.09 mmol) was added to a THF solution of the activated 18 followed by excess DIPEA (e.g. about 3 equivalents). The solution was stirred at room temperature for a minimum of 1 hr and purified by HPLC-MS collecting Mass of 343 and 399. The fractions containing the desired product were pooled and lyophilized to collect 20. The residue was dissolved in about 15% trifluoroacetic acid in dichloromethane and few drops of water and stirred at room temperature for about 2 hrs. The reaction was concentrated to approximately 1 ml and treated with water precipitate the product. The crude material was purified using HPLC-MS to yield 21 (M+343).

A solution of acid 21 (e.g. about 60 mg, about 0.18 mmol), HBTU (e.g. about 137 mg, about 0.36 mmol), and aniline hydrochloride 13B (e.g. about 45 mg, about 0.18 mmol), diisopropylethylamine (e.g. about 0.14 ml, about 0.90 mmol) in DMF (e.g. about 2 mL) was stirred at room temperature for about 30 mins and purified on the HPLC-MS. The desired fraction was pooled and concentrated to collect L2 (e.g. about 16 mg, about 0.03 mmol).

Example 5

Synthesis of Linker 3

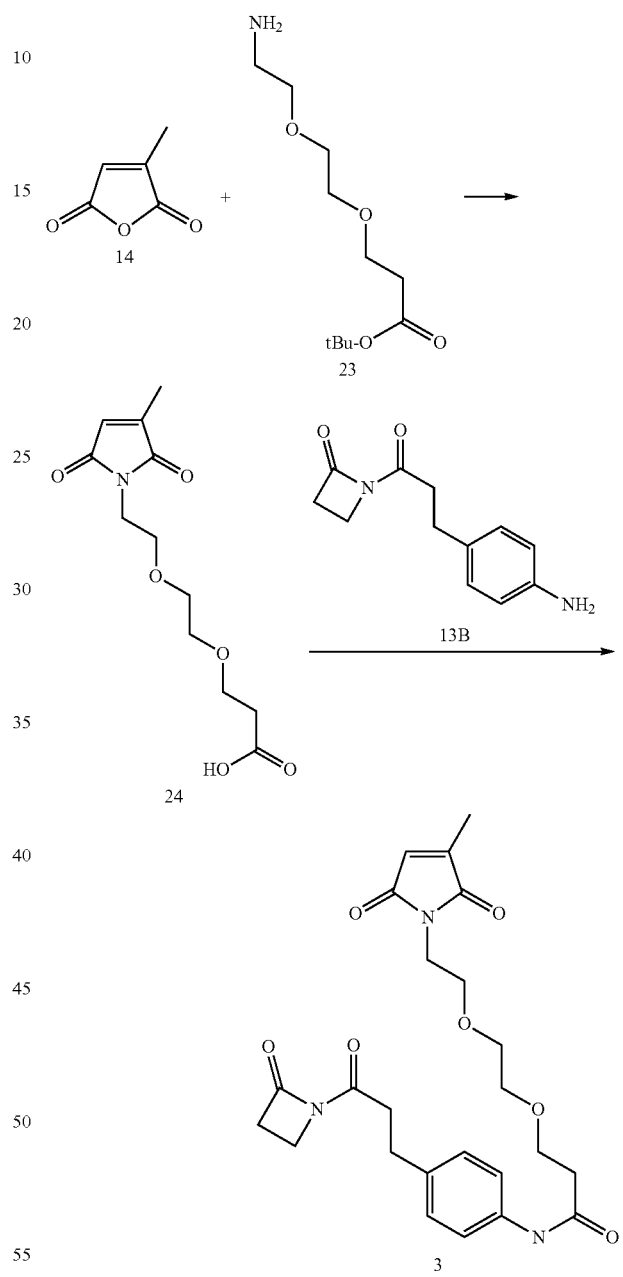

A solution of citraconic anhydride, 14 (e.g. about 0.5 g, about 16.4 mmol), amine-peg2-tbutyl ester 23 (e.g. about 1.0 g, about 4.2 mmol) in DMF (e.g. about 10 mL) was stirred at room temperature for about 2 hrs. Diisopropylcarbodiimide (e.g. about 0.8 mL, about 5.2 mmol) and HOBT (e.g. about 0.7 g, about 6.1 mmol) were added and the reaction was heated at about 80° C. for about 2 hrs. The reaction was allowed to cool to room temperature overnight and the urea filtered. The filtrate was poured into water and extracted with DCM. The organic layer was washed with brine and concentrated to oil. The crude product was dissolved in about 50% 6N HCl in acetonitrile to deprotect the acid. The product was dissolved in DMF, filtered, and purified using HPLC-MS to collect 24 (e.g. about 208 mg, about 0.7 mmol).

A solution of maleimide, 24 (e.g. about 0.16 g, about 0.6 mmol) and aniline hydrochloride 13B (e.g. about 150 mg, about 0.6 mmol) in DMF was added excess HBTU and DIEA (e.g. about over 3 equivalents of each). The crude material was purified via about 2 injections on an HPLC-MS. The desired fractions containing the purest material were pooled and lyophilized to collect L3 (e.g. about 17.3 mg, about 36.7 mmol).

Example 6

Synthesis of Linker 4 mixture was warmed to room temperature and stirred for another about 16 hrs under $N_2$. The solid was filtered, and the filtrate was poured into about 30 mL of water, extracted with dichloromethane (e.g. about 2× about 30 mL) and the dichloromethane layer was dried over $Na_2SO_4$. The solvent was removed under vacuum and the crude mixture was purified by column chromatography to yield about 550 mg of the pentafluorophenyl ester intermediate (15, e.g. about 29% yield).

N-Methyl morpholine (e.g. about 290 µL, about 2.64 mmol) was added to the solution of the pentafluorophenyl ester intermediate (15, e.g. about 550 mg, about 1.32 mmol) and 3-[2-(2-amino-ethoxy)-ethoxy]-propionic acid tert-butyl ester (e.g. about 295 mg, about 1.32 mmol) in terahydrofuran (THF, e.g. about 5 mL) and stirred at room temperature for about 2 hrs. The solvent was removed under vacuum and the residue was dissolved in DMF and purified by preparative

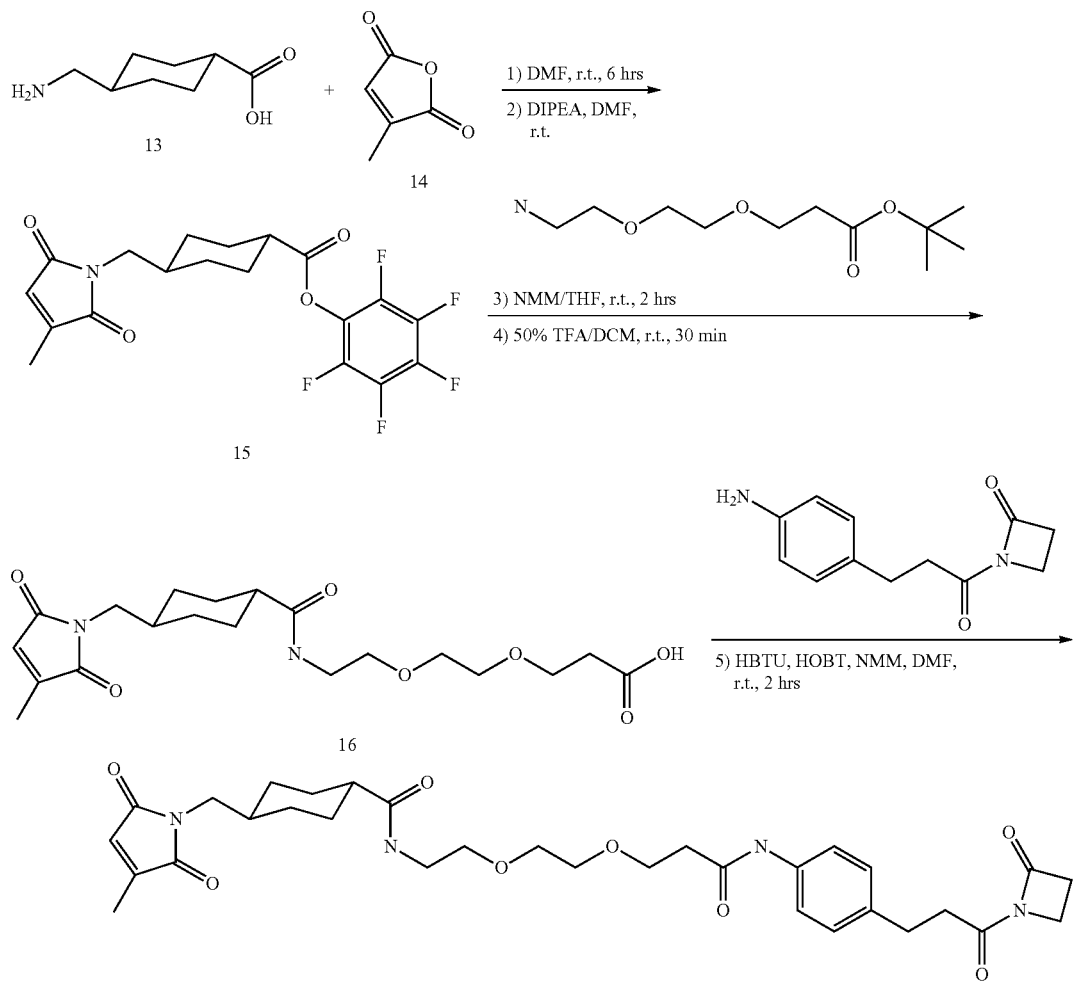

A solution of citraconic anhydride (14, e.g. about 510 mg, about 4.55 mmol) and trans-4-aminomethyl cyclohexane carboxylic acid (13, e.g. about 716 mg, about 4.55 mmol) in dimethylformamide (e.g. about DMF, about 5 mL) under nitrogen ($N_2$) was stirred at room temperature for about 6 hrs. The reaction solution was cooled to about 0° C., DIPEA (e.g. about 1.98 mL, about 11.4 mmol) followed by pentafluorophenyl trifluoroacetate (e.g. about 1.96 mL, about 11.4 mmol) in DMF (e.g. about 3 mL) were added. The reaction HPLC. The tert-butyl ester intermediate obtained was treated with about 50% trifluoroacetic acid in dichloromethane (e.g. about 4 mL) for about 30 mins. The solvent was removed under vacuum and the residue was purified by preparative HPLC to afford about 300 mg of the acid intermediate 16 as white solid (e.g. about 55% yield; MS: 411.2 (M+H$^+$)).

A solution of the above acid intermediate (16, e.g. about 33 mg, about 0.08 mmol), 1-[3-(4-amino-phenyl)-propionyl]-azetidin-2-one (13B e.g. about 18 mg, about 0.08 mmol), HOBT (e.g. about 25 mg, about 0.16 mmol) and HBTU (e.g. about 61 mg, about 0.16 mmol), and N-methyl morpholine (e.g. about 44 μL, about 0.4 mmol) in DMF (e.g. about 1 mL) was stirred at room temperature for about 2 hrs. The crude mixture was purified by preparative HPLC to afford L4 as colourless oil (e.g. about 22 mg, 45% yield; MS: 611.4 (M H⁺)).

Example 7

Synthesis of Linker 5

L5

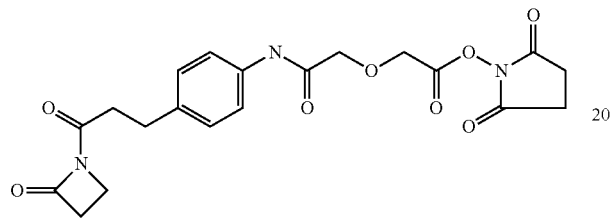

Diisopropyl carbodiimide (e.g. about 3.11 mL, about 19.86 mmol, about 2.95 eq) was added to a solution of Linker 6 (f e.g., about 6.63 g, about 20.69 mmol, about 3.07 eq) and N-hydroxysuccinimide (e.g. about 2.29 g, about 19.86 mmol, about 2.95 eq) in dry tetrahydrofuran (e.g. about 500 mL) at about 0° C. The mixture was stirred at about 0° C. for about 1 hr and then stirred at room temperature overnight. The solvent was removed in vacuo and the residue was washed with petroleum ether (e.g. about 2× about 200 mL) and the powder was dried under vacuo for about 2 hrs, and used in the subsequent steps.

Example 8

Synthesis of Linker 6

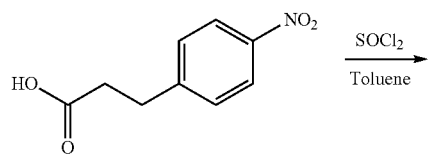

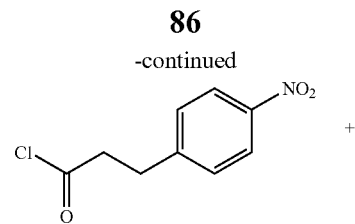

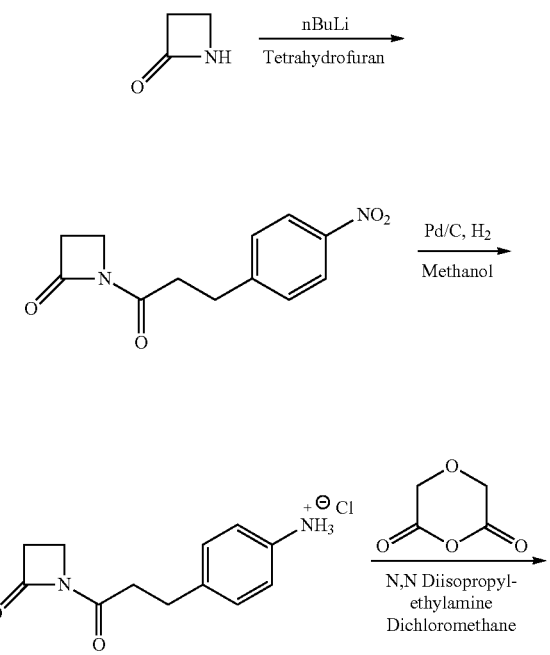

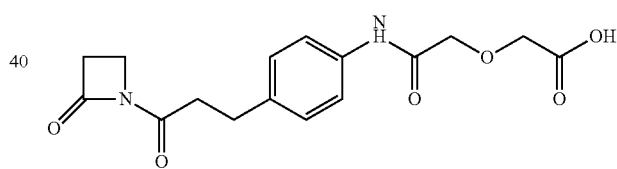

Example 9

Synthesis of Linker 7

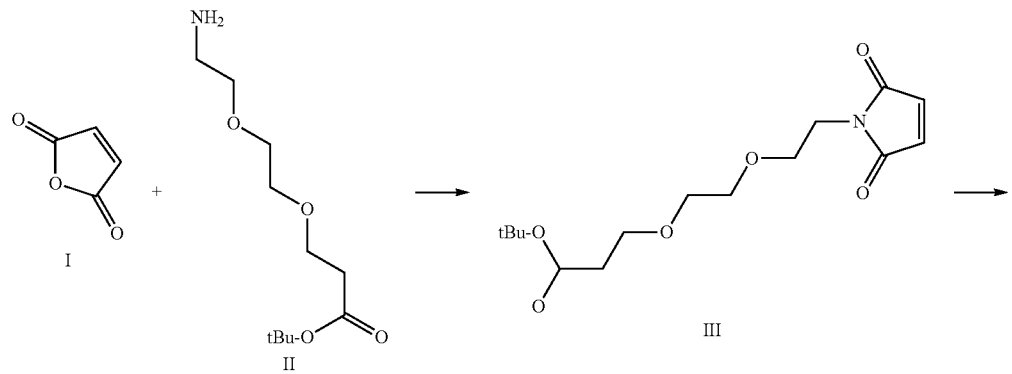

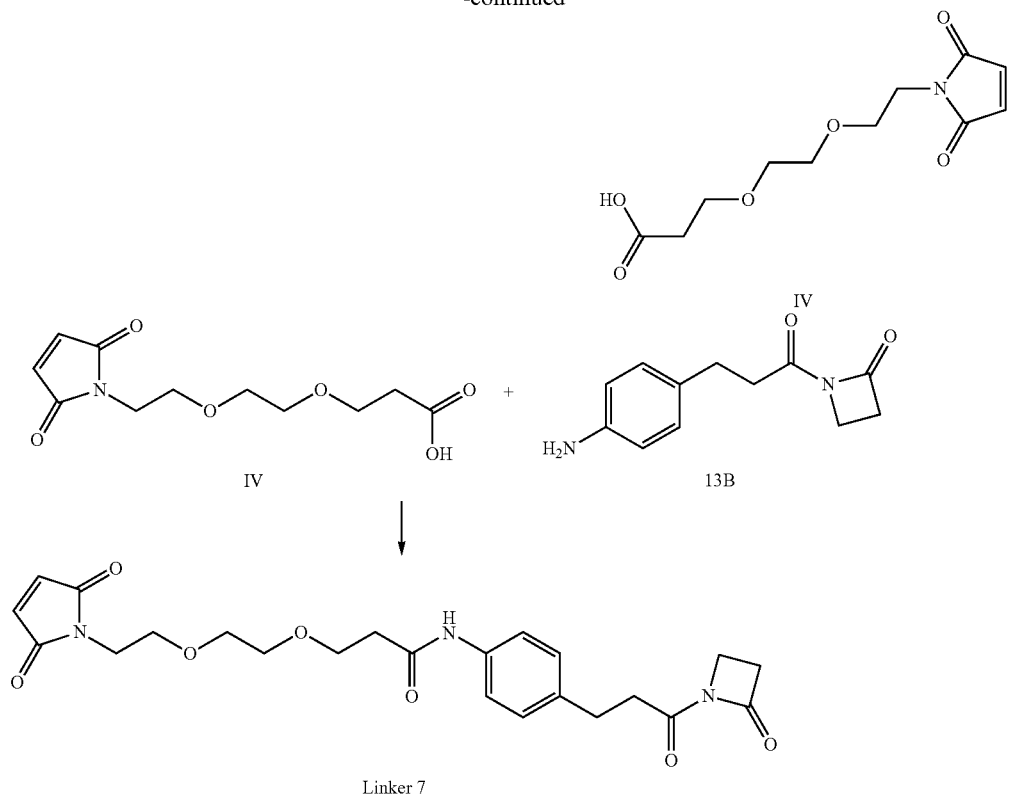

A solution of I (e.g. about 438 mg, about 4.47 mmol) and II (e.g. about 1.04 g, about 4.47 mmol) in diemthyl formamdie (e.g. about 25 mL) was stirred under an atmosphere of nitrogen for about 2.5 hrs. The reaction was cooled to about 0° C. using an ice bath. 1-Hydroxypyrrolidine-2,5-dione (e.g. about 647 mg, about 5.62 mmol), and N-(3-dimethylaminopropyl)-N'-ethylcarbodiimide hydrochloride (e.g. about 1.71 g, about 8.92 mmol) were added and stirred at about room temperature overnight. The organic layer was diluted with dichloromethane, washed with water, concentrated under reduced pressure and purified using flash chromatography (SiO2, about 75% ethyl acetate in hexanes to about 5% methanol in dichloromethane to afford III (e.g. about 767 mg). A solution of III (e.g. about 573 mg, about 1.83 mmol) in dichloromethane (e.g. about 15 mL) and trifluoroacetic acid (e.g. about 1.16 mL) was stirred for about 9.5 hrs at about room temperature. The material was concentrated under reduced pressure and dried on a vacuum pump overnight to afford IV. The crude IV was dissolved in dichloromethane (e.g. about 15 mL), and dimethyl formamide (about 2 drops) and stirred with oxalyl chloride (e.g. about 465 mg, about 3.66 mmol) for about 2 hrs. The solvent was removed under reduced pressure and the oil was dried under vacuum for 1 hr. The oil was dissolved in dichloromethane (e.g. about 15 mL) and stirred with 13B (e.g. about 464 mg, about 1.83 mmol) and diisopropyl ethylamine (e.g. about 2.9 mL, about 16.5 mmol) under nitrogen for about 30 mins. The organic layer was washed with saturated sodium bicarbonate solution, saturated sodium chloride solution, concentrated under reduced pressure and purified using flash chromatography (SiO$_2$, about 85% ethyl acetate in hexanes to about 100% ethyl acetate) to afford Linker 7 (e.g. about 323 mg, about 39%).

Example 10

Synthesis of Linker 8

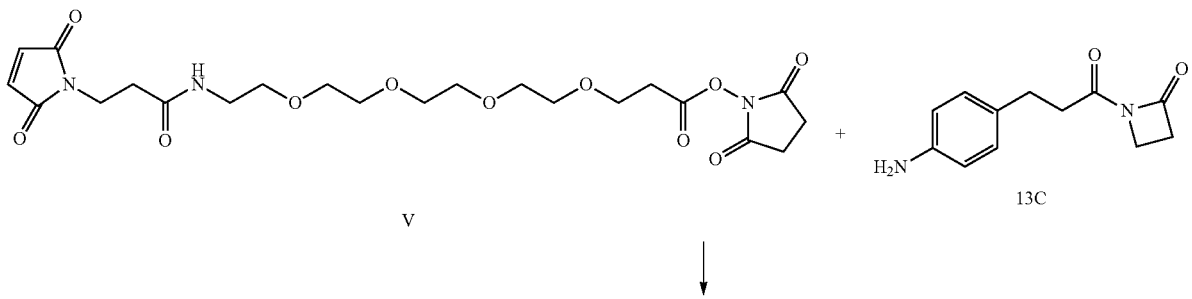

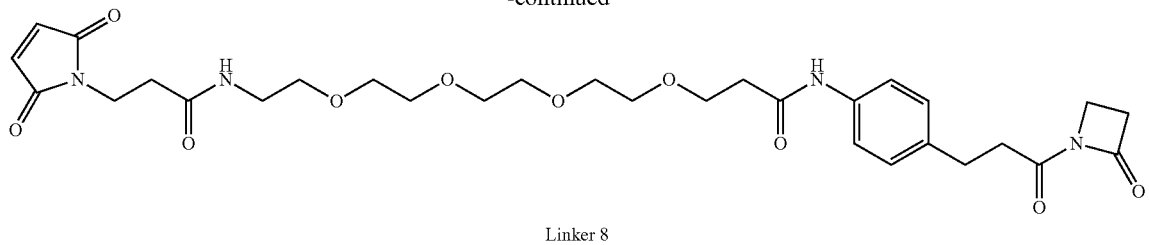

Linker 8

A solution of V (e.g. about 980 mg, about 1.91 mmol), 13C (e.g. about 484 mg, about 1.91 mmol), diisopropylethylamine (e.g. about 2 mL, about 11.5 mmol) in dichloromethane was stirred for about 6 hrs at about room temperature. Another about 1 eq of 13C (e.g. about 484 mg, about 1.91 mmol) and about 3 eq of diisopropylethylamine (e.g. about 1 mL, about 5.73 mmol) were added and stirred at about room temperature overnight. The reaction mixture was washed with saturated sodium bicarbonate solution, saturated sodium chloride solution, dried (sodium sulphate), filtered, concentrated under reduced pressure and purified using flash chromatography (about 100% ethyl acetate to about 5% methanol in ethyl acetate to about 10% methanol in ethyl acetate) to afford Linker 8 (e.g. about 285 mg, about 24%)

Example 11

Conjugation of Protein and Linker

FGF21 mutant proteins were reacted with the relevant linker at 1:10 molar ratio at room temperature for 2 hrs. All linker-attached FGF21 proteins were then purified using PD-10 column and buffer exchanged into 20 mM Tris-HCl, 20 mM NaCl, pH 7.0.

Example 12

Conjugating Protein-Linker Complex with Antibody

All linker-attached FGF21 proteins were fused with h38C2 IgG1 (SEQ ID NOS: 25 and 26) (20 mM Tris-HCl, 20 mM NaCl, pH 7.0) at 6:1 molar ratio at room temperature for overnight. Protein-linker-antibody complexes were purified by SEC. Conjugation efficiency was confirmed by LCMS analysis.

Example 13

Protein Production Assay

All FGF21 proteins were expressed in *E. coli*. Bacterially expressed FGF21 proteins were found in inclusion bodies. After lysing the cells and removal of the supernatant, the pellets were dissolved in 7 M urea, 50 mM Bis-Tris propane, pH 10.5 at 4° C. The solubilized inclusion bodies were diluted into 50 mM Bis-Tris propane, 10 mM oxidized glutathione, ph 9.0 and stirred for 2 hrs, followed by dialysis against 20 mM Tris-HCl, ph 7.5 at 4° C. overnight. The soluble fractions were purified by HiTrap Q column. Proteins were characterized by SDS-PAGE analysis. Expression levels of the lysine mutants were 10-50 mg/L.

Example 14

Glut1 Taqman Assay

Differentiated 3T3-L1 adipocytes were used to measure the Glut1 mRNA expression by qPCR method. Overnight serum starved day 10-14 differentiated 3T3-L1 adipocytes were treated with compounds for 6 hrs. Total RNA was extracted from these cells, and Glut1 and GAPDH mRNA expression was measured using a Quantitect Probe RT-PCR kit and running a quantitative real time PCR reaction in a Taqman machine (Applied Biosystems®). The bioactivity of the compounds was determined by a fold change in Glut1 mRNA levels normalized by the GAPDH mRNA levels from each sample. EC__values as measurements of the potency of the compounds were obtained from the dose response curves in the assay.

Example 15

Glucose Uptake Assay

Differentiated 3T3-L1 adipocytes were treated with compounds in the absence of serum for 24 hrs. Cells were then incubated with $^{14}$C-2-deoxyglucose for 1 hr and glucose uptake into the cells was quantitated in Wallac 1450 Micro-Beta (Trilux) instrument. Glucose uptake was expressed in counts per min (CPM). $EC_{50}$ values as measurements of the potency of the compounds were obtained from the dose response curves in the assay.

Example 16

Mouse Pharmacokinetics

The PK of FGF21 antibody conjugates were examined in mice after IV or SC administration. Antibody conjugates were injected into young adult male Swiss-Webster mice (20-25 g), and blood samples were obtained at time points from 5 mins to 120 hrs after dosing. Antibody conjugates concentrations in serum were determined using an ELISA which captured the FGF21 portion of the antibody conjugates through a monoclonal anti-hFGF21 antibody bound to a 96-well plate. FGF21 antibody conjugates bound to the plate were detected through an anti-hFc monoclonal antibody, and concentrations were determined using a standard curve of the PK dosing solution diluted into serum-containing assay buffer. SC bioavailability was calculated as the ratio of the area-under the curve (AUC) of the SC serum concentration profile divided by the AUC of the IV serum concentration profile.

Example 17

Mouse Efficacy

The efficacy of FGF21 antibodies conjugates was evaluated in two murine obese insulin resistant models—ob/ob mice and high-fat diet-induced obese mice. For both models, male mice (6-8 weeks of age for ob/ob, 12-14 weeks of age for DIO with high-fat diet initiated at 6 weeks of age) were housed 2-4/cage and FGF21 antibody conjugates were administered by SC injection. Body weight was measured daily in the morning. Glucose tolerance was assessed by oral glucose tolerance test. Briefly, mice were fasted for 4-5 hrs in the morning of the day of testing. A basal blood sample was obtained and blood glucose levels were determined using a portable glucometer. Following basal sample, glucose was administered by oral gavage, and blood samples were drawn from 15 to 120 mins thereafter. Glucose tolerance was calculated as the AUC from the basal to the 120 min time point.

Example 18

K56 Ab-L5-FGF21ΔH-K56 Activity

FGF21ΔH-K56-K59R-K69R-K122R (SEQ ID NO:18) was generated and purified as described above. FGF21ΔH-K56-K59R-K69R-K122R was found to be potent in the Glut1 Taqman assay ($EC_{50}$=0.9 nM; n=2). Glucose uptake was shown to be 5.5 nM. FGF21ΔH-K56-K59R-K69R-K122R was combined with L5 at K56 and conjugated with h38C2 as described to form Ab-L5-FGF21ΔH-K56. Ab-L5-FGF21ΔH-K56 retained potency in Glut1 Taqman assay ($EC_{50}$=1.9 nM; n=1), and showed an IV half-life of 17 hrs, and a SC half-life of 13 hrs. Bioavailability was 66%.

Example 19

K59 Ab-L5-FGF21ΔH-K59 Activity

FGF21ΔH-K56R-K59-K69R-K122R (SEQ ID NO:19) was generated and purified as described. FGF21ΔH-K56R-K59-K69R-K122R was potent in the Glut1 Taqman assay ($EC_{50}$=0.6 nM; n=1). Glucose uptake was 0.9 nM. FGF21ΔH-K56R-K59-K69R-K122R was combined with L5 at K59 and conjugated with h38C2 to form Ab-L5-FGF21ΔH-K59. Ab-L5-FGF21ΔH-K59 retained in vitro potency in the Glut1 Taqman assay ($EC_{50}$=6.5 nM; n=2) and showed an IV half-life of 13 hrs.

Example 20

K69 Ab-L5-FGF21ΔH-K69 Activity

FGF21ΔH-K56R-K59R-K69-K122R (SEQ ID NO:20) was generated and purified as described. FGF21ΔH-K56R-K59R-K69-K122R was found to be potent in both a Glut 1 Taqman assay ($EC_{50}$=1.3 nM; n=1) and a glucose uptake assay ($EC_{50}$=5.2 nM). FGF21ΔH-K56R-K59R-K69-K122R was combined with L5 at K69, and conjugated with h38C2 to form Ab-L5-FGF21ΔH-K69.

Example 21

K122 Ab-L5-FGF21ΔH-K122 Activity

FGF21ΔH-K56-K59R-K69R-K122 (SEQ ID NO:21) was generated and purified as described. FGF21ΔH-K56R-K59R-K69R-K122 was potent in both Glut 1 Taqman assay ($EC_{50}$=2.6 nM; n=2) and glucose uptake assay ($EC_{50}$=1.7 nM). FGF21ΔH-K56-K59R-K69R-K122 was combined with L5 at K122, and conjugated with h38C2 to form Ab-L5-FGF21ΔH-K122. Ab-L5-FGF21ΔH-K122 retained in vitro potency ($EC_{50}$=1.6 nM in Glut1 Taqman assay; n=2) and showed an IV half-life of 16 hrs, and a SC half-life of 14 hrs. Bioavailability was 40%.

Example 22

K-Null-P2 Ab-L5-FGF21ΔH-Knull-P2 Activity

FGF21ΔH-Knull-P2 (SEQ ID NO:22) was generated and purified as described. FGF21ΔH-Knull-P2 was potent in Glut 1 Taqman assay ($EC_{50}$=1.2 nM; n=2). FGF21ΔH-Knull-P2 was combined at the N' terminus of $P^2$ with L5, and conjugated with h38C2 to form Ab-L5-FGF21ΔH-Knull-P2. Ab-L5-FGF21ΔH-Knull-P2 displayed reduced in vitro potency ($EC_{50}$=16.6 nM in Glut1 Taqman assay; n=1) and an IV half-life of 17 hrs.

Example 23

Knull-H1K Ab-L5-FGF21ΔH-Knull-H1K Activity

FGF21ΔH-Knull-H1K (SEQ ID NO:23) was generated and purified as described. FGF21ΔH-Knull-H1K was potent in Glut 1 Taqman assay ($EC_{50}$=6.4 nM; n=2). FGF21ΔH-Knull-H1K was combined with L5 at H1K and conjugated with h38C2 to form Ab-L5-FGF21AK-Knull-H1K. FGF21ΔH-Knull-H1K retained in vitro potency ($EC_{50}$=4.3 nM in Glut1 Taqman assay; n=2), and showed an IV half-life of 16 hrs, a SC half-life of 11 hrs and SC bioavailability of 51%.

Example 24

K-Null-S181K Ab-L5-FGF21ΔH-Knull-S181K Activity

FGF21ΔH-Knull-S181K (SEQ ID NO:24) was generated and purified as described. FGF21ΔH-Knull-S181K was potent in Glut 1 Taqman assay ($EC_{50}$=7.5 nM; n=2). FGF21ΔH-Knull-S181K was combined with L5 at S181K and conjugated with h38C2 to form Ab-L5-FGF21ΔH-Knull-S181K. Ab-L5-FGF21ΔH-Knull-S181K showed a loss of in vitro potency ($EC_{50}$=>500 nM in Glut1 Taqman assay; n=2).

Example 25

Summary of Results of Activity of Lysine Mutants

All lysine mutant proteins were active in Glut1 Taqman assay. When conjugated, the majority of the conjugates (K56, K59, K122, Knull-H1K) retained activity in Taqman assay, with $EC_{50}$ values similar to that of the native FGF21 protein. The Knull-P2 conjugate showed some reduction in initial potency, and Knull-S181K conjugate showed loss of activity in the Taqman assay.

Example 26

Identifying Optimal Tether Sites on FGF21 Using Cysteine—Maleimide Conjugation One of the challenges when introducing a cysteine substitution mutation as a linking residue is that the cysteine residue may find itself in contact with other residues, and/or form a salt bridge or hydrogen bond. Although it can be difficult to predict the atom-level distances using modelled structures, a number of residues were selected based on potential for being distally located from the FGFR1c and βKlotho binding sites: His1, Thr40, Asp79, Leu86, His125 and Ala129.

All six residues are distinct to each other in terms of structural elements (turn and loop), accessible surface area (ASA), and shape of environment (convex and concave), and all were modelled on the opposite side of the protein to the FGFR1c interactions (Table 2). In particular, His1, Asp79, Leu86 and His125 were identified as being potentially attractive conjugation sites due to the high ASA values associated with these sites.

TABLE 2

Comparison of candidate residues for cysteine substitution.

| Residues | Structure | Shape | % ASA | ASA | βKlotho site |
|---|---|---|---|---|---|
| His1 | disorder | N/A | N/A | | |
| Thr40 | β-strand | concave | 34 | 49.8 | less far |
| Asp79 | β-turn | convex | 71 | 109.8 | far |
| Leu86 | β-strand | convex | 60 | 119.4 | less far |
| His125 | disorder | convex | 85 | 169.4 | far |
| Ala129 | disorder | concave | 68 | 78.8 | far |

Example 27

H1C FGF21ΔH-H1C

FGF21ΔH-H1C (SEQ ID NO:16) was generated and expressed. However, FGF21ΔH-H1C mutants lacked the N' cysteine group, and therefore investigation of this mutant was discontinued.

Example 28

T40C FGF21ΔH-T40C

Generation of FGF21ΔH-T40O (SEQ ID NO:15) presented significant challenges. The cysteine mutation of threonine at position 40 caused multiple species of FGF21ΔH-T400 in RP-HPLC after refolding. Further attempts were made to improve the refolding process by changing the concentration of protein and pH, with and without addition of glutathione. The refolding process was monitored by RP-HPLC. Addition of glutathione resulted in efficient refolding of T400; however, it was found that glutathione was attached on FGF21, most likely through the introduced cysteine at position 40. The glutathione adduct showed the same biological activity as wild type FGF21ΔH, indicating that the position 40 is not involved in the receptor activation by FGF21.

Example 29

D79C Ab-L1-FGF21ΔH-D79C Activity

FGF21ΔH-D79C (SEQ ID NO:12) was generated and purified as described. FGF21ΔH-D79C was potent in Glut 1 Taqman assay ($EC_{50}$=2.1 nM; n=4). FGF21ΔH-D79C was combined with L1 at D79C and conjugated with h38C2 to form Ab-L1-FGF21ΔH-D790. Ab-L1-FGF21ΔH-D790 retained in vitro potency ($EC_{50}$=3.7 nM in Glut1 Taqman assay; n=3), and showed an IV half-life of 17 and 19 hrs (n=2), a SC half-life of 20 and 20 hrs (n=2) and SC bioavailability of 55% and 70 (n=2).

Example 30

Stability Assay of FGF21ΔH-D79C

FGF21ΔH-D790 mutant protein was produced in E. coli and purified as described above. FGF21ΔH-D790 was expressed from 1 L of culture. A 150 mg inclusion body was obtained and 85 mg purified protein was obtained, representing a 60% yield. To test the stability of FGF21ΔH-D790 as well as FGF21ΔH (SEQ ID NO:2), freshly thawed samples were kept at 4° C. over seven days, and examined for their integrity by RP-HPLC, SEC_HPLC, Ellman assay and SDS-PAGE on day 0, 3 and 7. It was found that FGF21ΔH-D790 is stable at neutral pH 7.4: only slight amounts of FGF21ΔH-D790 appeared oxidized and dimerized even after seven-day incubation at 4° C., while more than half of FGF21ΔH-D790 was oxidized at lower pH 6.0 after three-day incubation at 4° C. PBS (pH7.4) and 20 mM Tris-HCl 50 mM NaCl (pH7.5) made no significant difference of stability of FGF21ΔH-D79C.

It is not apparent why the free cysteine of FGF21ΔH-D79C was more stable at pH 7.4 than at pH 6.0. The calculated isoelectric point (pI) of WT FGF21 was 5.43 (e.e., FGF21-H1-P146); the pI of FGF21ΔH was 5.27; and the pI of FGF21ΔH-D79C was 5.47. It is possible that the solubility of FGF21ΔH-D79C may be reduced at pH6.0. The stability of FGF21ΔH-D79C was examined upon multiple freeze/thaw cycles. The proteins were repeated to freeze (−80 C) and thaw (4° C.) 9 times. Neither sample showed any difference between cycle 1 and cycles 9 in RP-HPLC, SEC and Ellman assay. In conclusion, FGF21ΔH-D79C appeared to be significantly less stable at 4° C. than at −80° C.

Example 31

L86C FGF21ΔH-L86C

FGF21ΔH-L86C (SEQ ID NO:14) was generated and purified as described. Although most hydrophobic residues are buried in protein cores, some residues are exposed to solvent which may cause insolubility of the protein. Leu86 is a hydrophobic residue, and appears solvent exposed in the modelled structure of FGF21. It was postulated that the mutation L86C may provide solubility benefits.

The L86C mutation resulted in inefficient refolding and low protein yield. Addition of glutathione resulted in efficient refolding of L86C; however, it was found that more than one glutathione was attached on one FGF21 molecule, most likely through the introduced C86 as well as native cysteine residues. The glutathione adduct showed approximately 10-fold reduction of biological activity, and therefore investigation of FGF21ΔH-L86C was discontinued.

Example 32

H125C Ab-L1-FGF21ΔH-H125C Activity

FGF21ΔH-H125C (SEQ ID NO:7) was generated and purified as described. FGF21ΔH-H125C was potent in Glut 1 Taqman assay ($EC_{50}$=1.2 nM; n=3). FGF21ΔH-H125C was combined with L1 and conjugated with h38C2 at H125C to form Ab-L1-FGF21ΔH-H125C. When conjugated, Ab-L1-FGF21ΔH-H125C retained in vitro potency ($EC_{50}$=3.2 nM in Glut1 Taqman assay; n=4), and showed an IV half-life of 37 hrs, a SC half-life of 32 hrs and SC bioavailability of 67%.

Example 33

A129C Ab-L1-FGF21ΔH-A129C Activity

FGF21ΔH-A129C (SEQ ID NO:10) was generated and purified as described. FGF21ΔH-A129C was potent in Glut 1 Taqman assay ($EC_{50}$=1.4 nM; n=6). FGF21ΔH-A129C was combined with L1 at A129C and conjugated with h38C2 to form Ab-L1-FGF21ΔH-A129C. Ab-L1-FGF21ΔH-A129C retained in vitro potency ($EC_{50}$=2.7 nM in Glut1 Taqman assay; n=7), and showed an IV half-life of 33 hrs, a SC half-life of 37 hrs and SC bioavailability of 69% (in mice). Ab-L1-FGF21ΔH-A129C showed an IV half-life in rat of 60 hrs, a SC half-life in rat of 39 hrs, and SC bioavailability in rat of 52%. In monkey, the IV half-life was 65 hrs, the SC half-life was 48 hrs, and the SC bioavailability was 68%.

Example 34

Improvement of Endotoxin Purity

FGF21ΔH-H1250 and FGF21ΔH-A129C protein were produced by *E. coli* fermentation culture. To reduce endotoxin levels, an additional Q step was utilized after the first Q which reduced the endotoxin levels from 10 EU/ml ->0.1 EU/mL. The purification protocol was modified as follows. Approximately 10 g IB was obtained from 1 L culture media, and solubilized with 40 mL of 7M Urea, 5 mM DTT, 50 mM BTP (Bis-tris Propane) pH10.5 (1~2 hrs). Reduction of FGF21 protein was monitored by RP-HPLC. The solubilized protein was refolded by dilution into 400 mL of 50 mM BTP, pH 8.0 (24~36 hrs). Oxidation of native disulphide bond of FGF21 was monitored by RP-HPLC. Once refolding was almost completed, the solution was dialyzed twice against 4 L of 20 mM Tris-HCl, pH 7.5. Unsolubilized proteins were precipitated out by centrifugation at 20,000×g for 60 min, 4° C. The supernatant was loaded onto a Hitrap Q FF and the FGF21 protein was eluted with 0~200 mM NaCl gradient (20 CV, 20 mM Tris-HCl, 0.01 mM TCEP, pH 7.5). The collected fractions were loaded onto a Hitrap Ni-NTA FF with 0~100 mM imidazole gradient (10 CV, 0.01 mM TCEP, PBS, pH 7.4) to remove residual DNA efficiently. The desired fractions were dialyzed twice against 4 L of 20 mM Tris-HCl, 0.01 mM TCEP, pH 7.5 and loaded onto a Hitrap Q HP column with 0~100 mM NaCl gradient (20 CV, 20 mM Tris-HCl, pH 7.5) for elution. Purified protein fractions were collected, sterilized with a 0.22 mm filter and stored at −80°.

The typical yield from 1 L culture media was about 350 to about 400 mg. The typical yield of purified protein was about 220 to about 280 mg. This purification technique yielded protein with a purity of >95%, and a typical endotoxin level of about 1 EU/mg. Using a fermentor in place of shake flasks improved the yield about 4 to about 5 times.

Example 35

Linker Selection

It is known that the maleimide ring of L1, below, may be susceptible to opening and subsequent product degradation over time (Woodnutt, G; IBC Conference "Beyond Antibodies/Protein Engineering Design", San Diego, 21-23 Sep. 2009).

Maleimide linker such as L1 can react with thiol to form a thiol adduct with maleimide part as shown in Scheme 1. This addition reaction of thiol to maleimide is referred as to a Michael reaction. Subsequently, a group containing amine (such as antibody h38C2) can react with AZD (β-lactam) as shown in Scheme 1 to yield 6. The resulting thiol-succinimide adduct is stable. However, the succinimide ring can undergo a slow hydrolytic cleavage over time resulting in 7 and/or 8. Therefore it is desirable to have a maleimide ring with improved stability towards hydrolytic cleavage, while preserving its ability to undergo Michael reaction.

Scheme 1

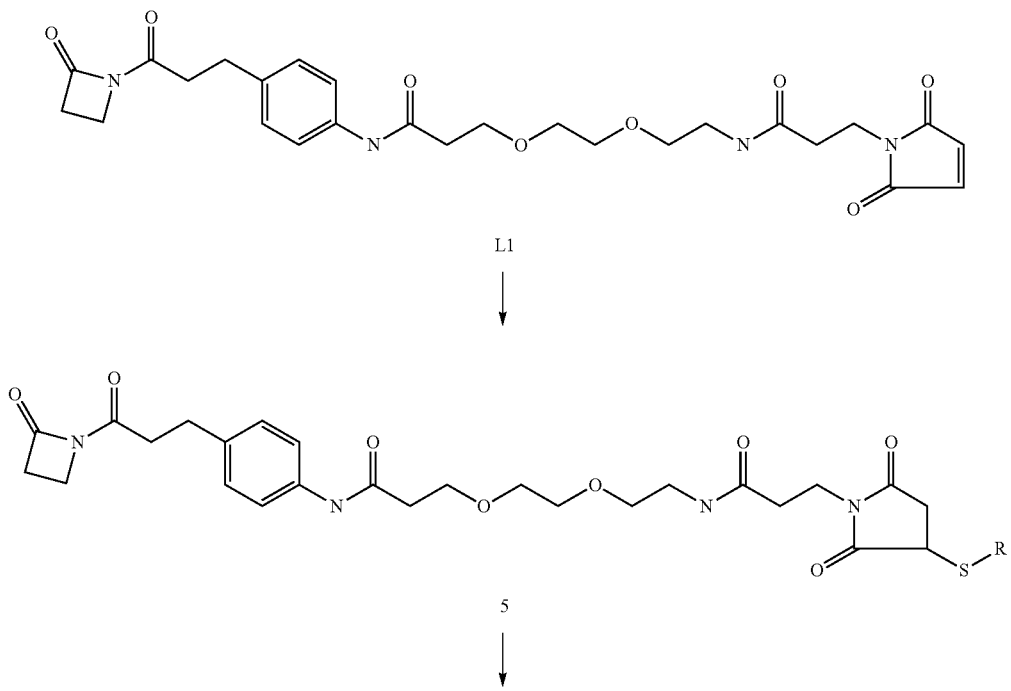

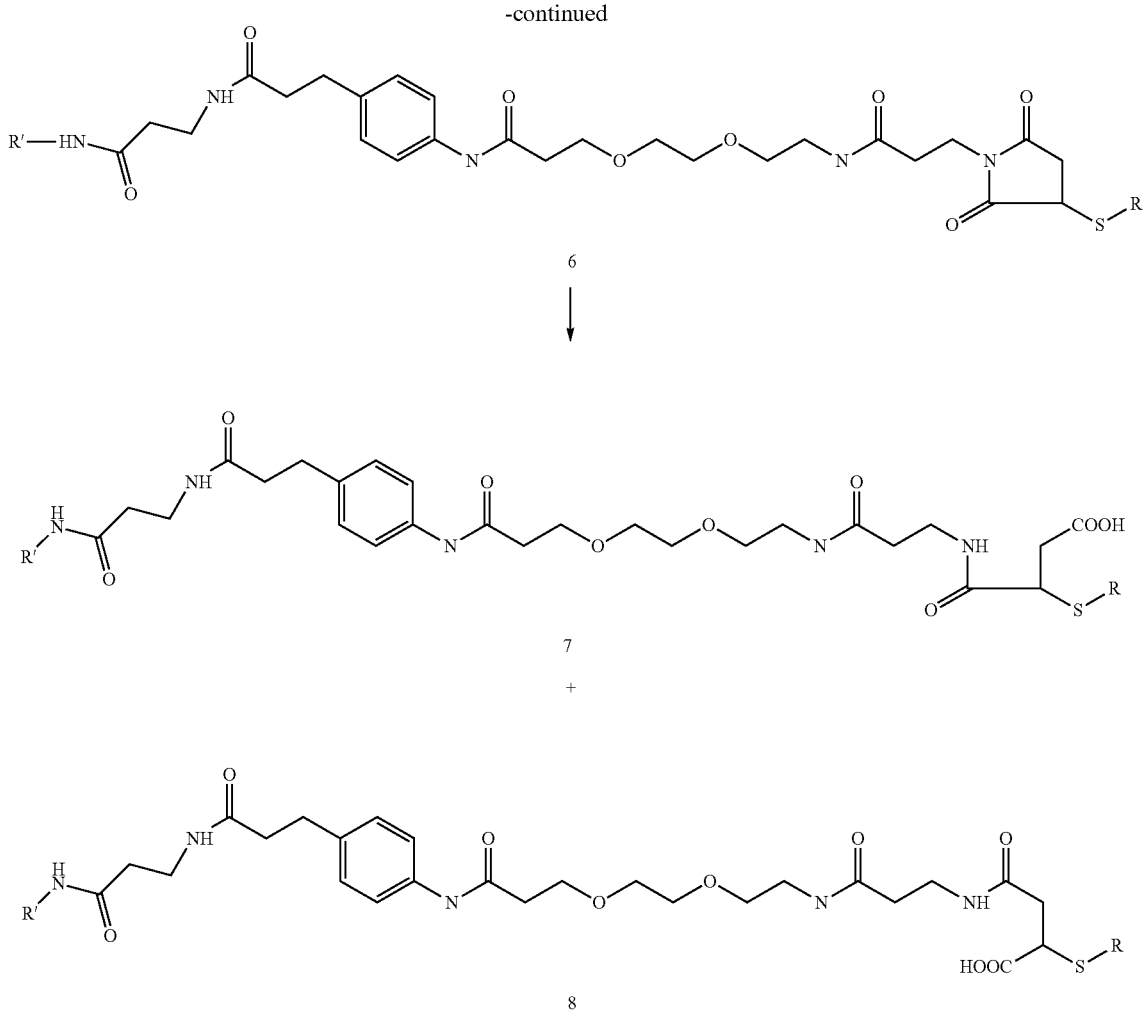

Example 36
Maleimide Modification

Accordingly, the stability of the maleimide ring in L1 was examined, with the expectation that more stable linkers could be generated by modifying the maleimide ring. In order to slow the potential hydrolytic cleavage of the maleimide ring by water, three different approaches (L2-L4) were taken to modify the ring and improve the stability.

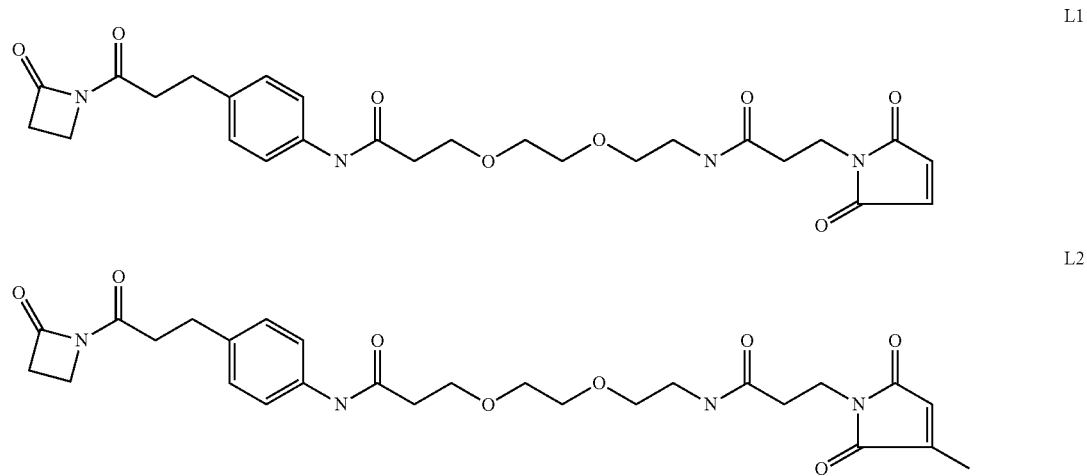

L3

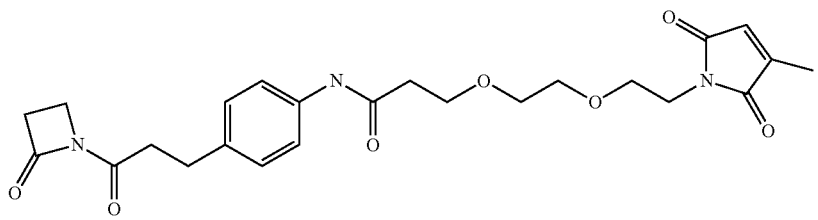

L4

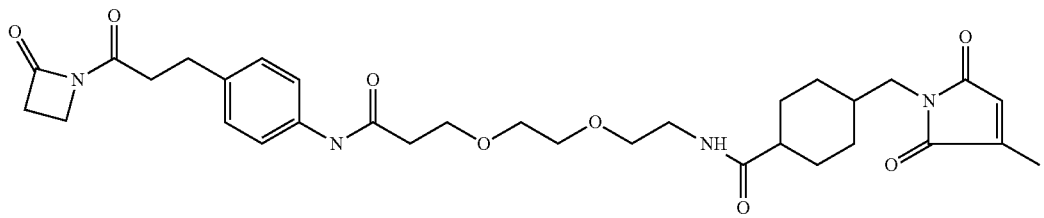

First, it was envisioned that a small alkyl group attached to the ring might slow the hydrolytic cleavage of the succinimide ring. Linker 2, which has a methyl group on the succinimide ring, was prepared. In order for the ring to undergo hydrolytic cleavage, a water molecule adds to the carbonyl group and forms a tetrahedral intermediate as transition state. The presence of the methyl group would sterically and electronically limit the formation of the tetrahedral intermediate, and slow down the hydrolysis rate considerably.

The second modification was focused on the propionamide carbonyl group in close vicinity to the carbonyl group of the maleimide ring. Carbonyl groups in general attract water. Having a carbonyl group in close proximity to the maleimide ring helps attract water and facilitates the attack on the carbonyl group of the maleimide ring. By removing the propionamide carbonyl group, the hydrolytic ring opening reaction is slowed down. This modification was seen in L3.

The third modification was the introduction of a cyclohexylmethylene group in the place of propionamide group as seen in L4. The bulky hydrophobic nature of the cyclohexyl ring would interfere both electronically and sterically towards the formation of a tetrahedral intermediate by the addition of water to the carbonyl group of the ring which is required for the ring opened hydrolytic cleavage. It was anticipated that this would slow down the hydrolytic cleavage.

Stability Studies

For the stability studies, the 1-(3-(4-aminophenyl)propanoyl)azetidin-2-one portion from linkers L1-L4 was removed. Four test compounds were made (30-33) where the maleimide was conjugated with glutathione, a three amino acid peptide.

<

Example 37

Synthesis of Compound 30

A solution of 3-(2-(2-(3-(2,5-dioxo-2,5-dihydro-1H-pyrrol-1-yl)propanamido)-ethoxy)ethoxy)propanoic acid (164 mg, 0.5 mmol) and reduced glutathione (154 mg, 0.5 mmol) in dimethylsulfoxide (5 mL) was stirred at room temperature for 17 hrs. Ethyl acetate (25 mL) was added to the reaction mixture and the solid was filtered. The solid was washed with additional 25 mL of ethyl acetate, dried to give 252 mg of compound 30.

30

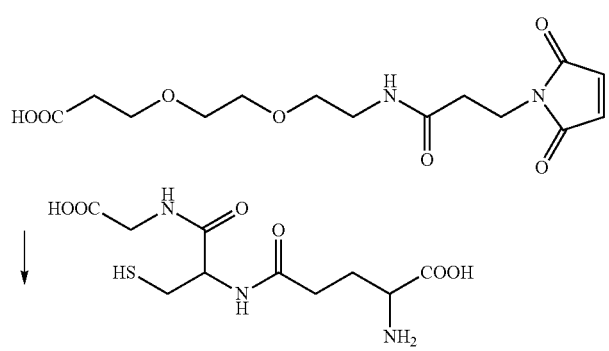

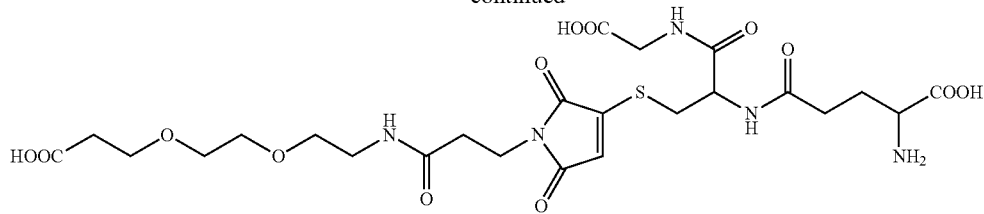

Example 38

Synthesis of Compound 31

A solution of 3-(2-(2-(3-(3-methyl-2,5-dioxo-2,5-dihydro-1H-pyrrol-1-yl)propanamido)ethoxy)ethoxy)propanoic acid (42 mg, 0.12 mmol) and reduced glutathione (37 mg, 0.12 mmol) in dimethylsulfoxide (1.2 mL) was stirred at room temperature for 22 hrs. 50% Ethyl acetate in ether (10 mL) was added to the reaction mixture and the solid was filtered. The solid was washed with additional 25 mL of ethyl acetate, dried to give 67 mg of compound 31.

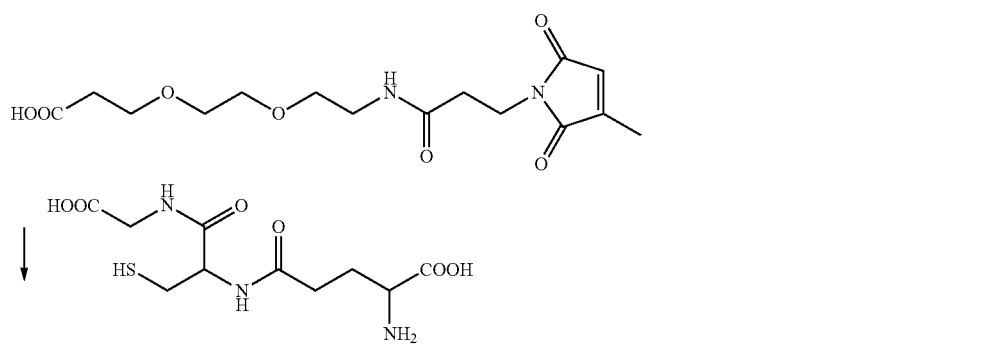

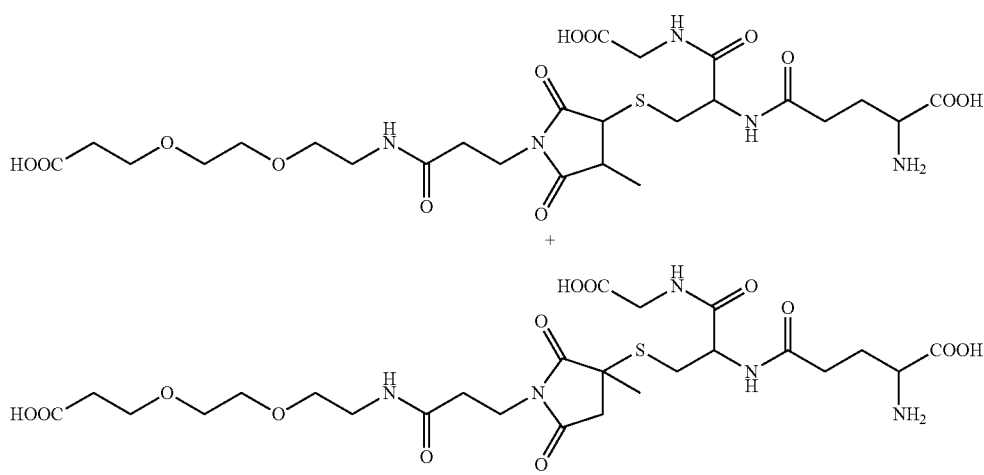

Example 39

Synthesis of Compound 32

A solution of 3-(2-(2-(3-methyl-2,5-dioxo-2,5-dihydro-1H-pyrrol-1-yl)ethoxy)ethoxy)propanoic acid (50 mg, 0.2 mmol) and reduced glutathione (61 mg, 0.2 mmol) in dimethylsulfoxide (2 mL) was stirred at room temperature for 25 hrs. 65% Ethyl acetate in ether (30 mL) was added to the reaction mixture and the solid was filtered. The solid was washed with additional 25 mL of ethyl acetate, dried to give 92 mg of compound 32.

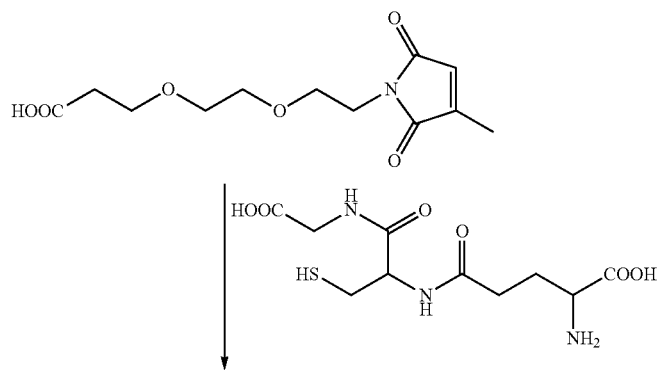

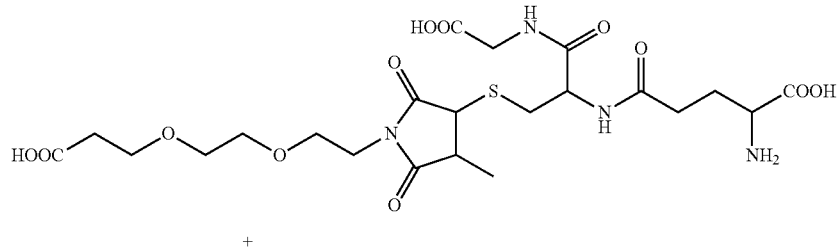

+

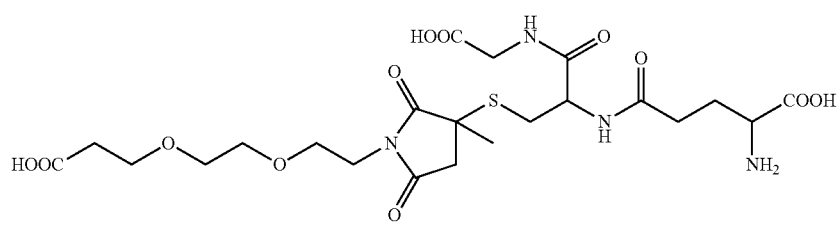

Example 40

Synthesis of Compound 33

A solution of 3-(2-(2-(4-((3-methyl-2,5-dioxo-2,5-dihydro-1H-pyrrol-1-yl)methyl)cyclohexanecarboxamido)ethoxy)ethoxy)propanoic acid (50 mg, 0.12 mmol) and reduced glutathione (37 mg, 0.12 mmol) in dimethylsulfoxide (1.2 mL) was stirred at room temperature for 22 hrs. 50% Ethyl acetate in ether (10 mL) was added to the reaction mixture and the solid was filtered. The solid was washed with additional 25 mL of ethyl acetate, dried to give 75 mg of compound 33.

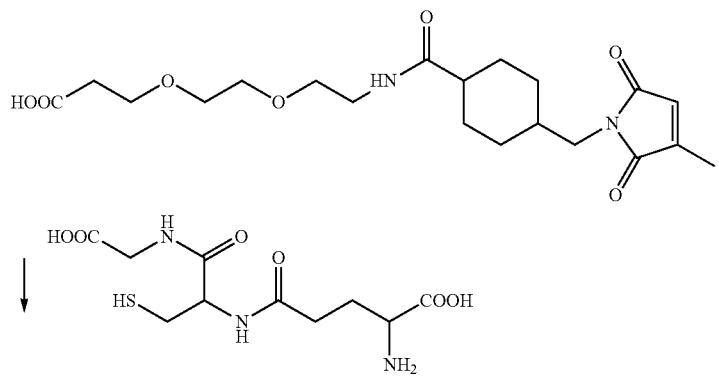

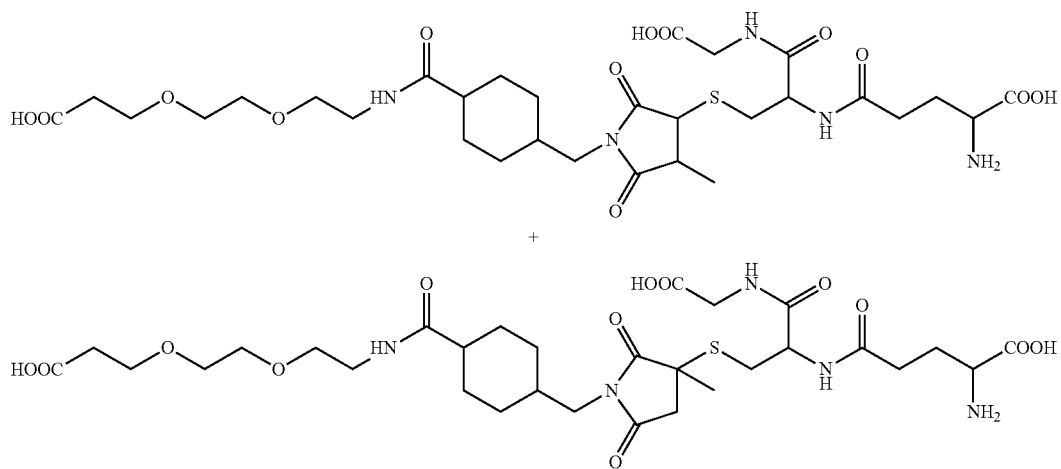

33

Example 41

Stability Study of Compounds 30-33

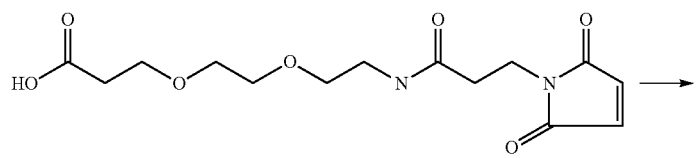

L1

-continued

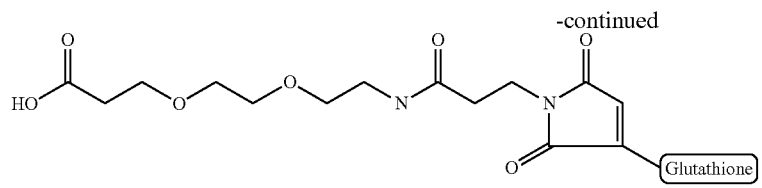
30

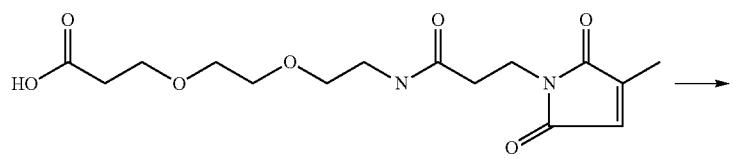
L2

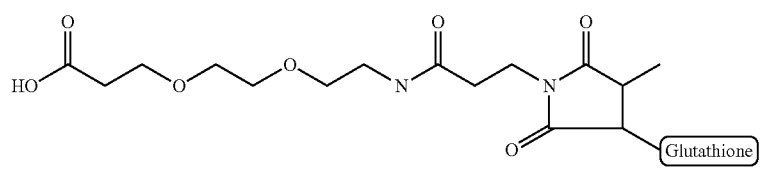
31

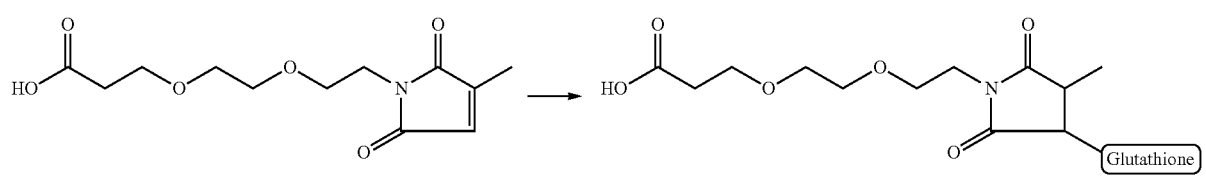
L3                32

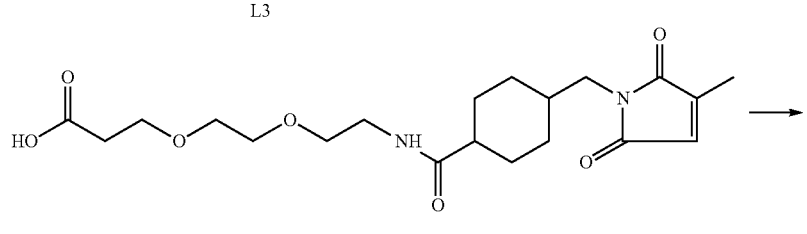
L4

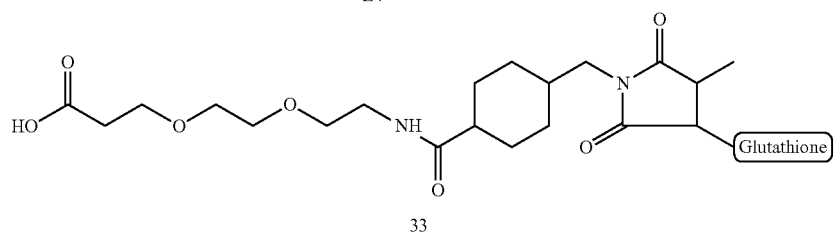
33

Compounds 30, 31, 32, and 33 were monitored on LC-MS for formation of the ring-opened products as well as glutathione cleavage. These new homologues were examined for their stability at pH=6.5 buffer at 40° C., at pH=7.5 buffer at 40° C., and at pH=7.5 buffer at 4° C., all over a two-week period (Tables 3A-C).

Compounds 30, 31, 32, and 33 were dissolved in a buffer at room temperature. The samples were incubated at 40° C. and the buffer solution was analyzed at the set intervals. At defined intervals, 10 µL of the buffer solution was injected on Agilent high performance liquid chromatography and mass spectrometer for analysis. The eluents from the column were monitored using UV spectrometer at 210 and 254 nm and also using mass spectrometer. The hydrolysis by-products were monitored using mass spectrometer and the percentage hydrolysis was calculated based on the total ion current of a particular mass.

It was evident from the LC-MS data showing % hydrolysis in Tables 3A-3C that the modified maleimide rings of L2, L3 and L4 (31-33) were 5-10 times more stable at pH=6.5 at 40° C. compared to maleimide ring in L1 (30), 4-15 times more stable at pH=7.5 buffer at 40° C., and up to 20 times more stable at pH=7.5 buffer at 40° C. The results of the glutathione conjugations (including the data in Tables 3A, 3B and 3C) were discussed at the IBC Conference "Beyond Antibodies/ Protein Engineering Design", San Diego, 21-23 Sep. 2009.

TABLE 3A

Stability Studies at 40° C., pH = 6.5 (10 mM His, 130 mM Gly, 130 mM Suc buffer).

|    | Cmpd # | 0 hr % | 1 hr % | 5 hr % | 24 hr % | 48 hr % | 72 hr % | 96 hr % | 120 hr % | 168 hr % | 192 hr % |
|----|--------|--------|--------|--------|---------|---------|---------|---------|----------|----------|----------|
| L1 | 30     | 0.0    | 0.4    | 0.6    | 4.9     | 11.6    | 14.8    | 18.3    | 17.0     | 25.0     | 25.9     |
| L2 | 31     | 0.1    | 0.1    | 0.3    | 0.8     | 1.8     | 2.6     | 3.0     | 3.1      | 5.0      | 5.1      |
| L3 | 32     | 0.0    | 0.1    | 0.3    | 0.9     | 1.7     | 2.4     | 2.8     | 4.2      | 4.6      | 4.9      |
| L4 | 33     | 0.1    | 0.1    | 0.1    | 0.3     | 0.4     | 0.6     | 0.6     | 0.3      | 1.1      | 1.1      |

TABLE 3B

Stability Studies at 40° C., pH = 7.5 (100 mM His, 200 mM Gly, 200 mM Suc).

|    | Cmpd # | 0 hr % | 1 hr % | 5 hr % | 24 hr % | 48 hr % | 72 hr % | 96 hr % | 120 hr % | 144 hr % | 168 hr % | 264 hr % | 336 hr % |
|----|--------|--------|--------|--------|---------|---------|---------|---------|----------|----------|----------|----------|----------|
| L1 | 30     | 0.1    | 0.3    | 2.0    | 10.0    | 15.0    | 29.0    |         |          |          |          |          |          |
| L2 | 31     | 0.1    | 0.2    | 0.6    | 3.2     | 4.6     | 7.1     | 8.2     | 9.4      | 12.6     | 12.2     | 13.1     | 15.0     |
| L3 | 32     | 0.1    | 0.1    | 0.1    | 1.0     | 1.1     | 2.2     | 2.8     | 3.3      | 3.3      | 3.9      | 4.4      | 5.0      |
| L4 | 33     | 0.1    | 0.2    | 0.3    | 0.6     | 1.8     | 2.8     | 3.0     | 4.3      | 4.1      | 4.7      | 6.5      | 8.8      |

TABLE 3C

Stability Studies at 4° C., pH = 7.5 (100 mM His, 200 mM Gly, 200 mM Suc)

|    | Cmpd # | 0 hr % | 1 hr % | 5 hr % | 24 hr % | 48 hr % | 72 hr % | 96 hr % | 120 hr % | 144 hr % | 168 hr % | 264 hr % | 336 hr % |
|----|--------|--------|--------|--------|---------|---------|---------|---------|----------|----------|----------|----------|----------|
| L1 | 30     | 0.1    | 0.1    | 0.1    | 0.7     | 2.0     | 2.2     | 4.4     | 5.5      | 6.9      | 7.5      | 8.7      | 12.2     |
| L2 | 31     | 0.1    | 0.1    | 0.1    | 0.1     | 0.2     | 0.2     | 0.2     | 0.1      | 0.4      | 0.3      | 0.6      | 0.7      |
| L3 | 32     | 0.1    | 0.1    | 0.0    | 0.2     | 0.3     | 0.3     | 0.4     | 0.6      | 0.6      | 0.7      | 1.1      | 1.3      |
| L4 | 33     | 0.1    | 0.1    | 0.1    | 0.2     | 0.2     | 0.2     | 0.1     | 0.3      | 0.3      | 0.2      | 0.5      | 0.6      |

Example 42

Stability of Linkers L1-L4 Conjugated to FGF21

The following experiment was performed to investigate the chemical stability over 2 weeks of the four linkers upon conjugation to FGF21: each linker was conjugated to FGF21, placed at +4° C. storage conditions, and aliquots were removed and quenched by freezing at specific time points, and linker stability was monitored by LCMS analysis.

The four linkers were dissolved in DMSO from lyophilized stock material. FGF21ΔH-A129C protein was partially reduced with 0.1 mM TCEP for 30 min prior to addition of the linker stock at a 1:1 linker:protein ratio; FGF21ΔH-A129C protein concentration in the conjugation reaction was 5 mg/ml. L1 was reacted with protein for 30 mins; L2, L3 and L4 were reacted for 2 hrs. The conjugation reaction was quenched by removal of excess linkers through size-exclusion resin. Conjugated FGF21ΔH-A129C protein was placed at +4° C. for stability storage. Aliquots were removed at t=0 (prior to stability storage) and at t=1, 3, 8, and 14 days. Analysis of linker stability was performed by LC-MS analysis to determine the relative amount of unconjugated protein, protein+linker conjugation, and single and double hydrolysis events of the conjugated protein+linker.

Linker hydrolysis is the critical analytical variable in this experiment. Hydrolysis was monitored by observing the subsequent addition of $H_2O$ to the FGF21-linker complex. A single addition of $H_2O$, +(1) $H_2O$, likely indicates the hydrolysis of the active AZD group that is present on all 4 linkers. The addition of a second $H_2O$ molecule, +(2) $H_2O$, is a strong indicator of hydrolysis (eg—chemical instability) in the linker. L1 is particularly susceptible because of the presence of a maleimide functional group.

The experimental results in Table 4 below demonstrate that L1 undergoes the largest increase in +(2) $H_2O$. At t=0, each of L1-L4 had a measured value of +(2) $H_2O$ between 6-8% of the total measured protein. During the 2 weeks these samples were monitored, the +(2) $H_2O$ observed in L1 had increased to 18% while the value for each of the remaining linkers L2-L4 was constant at 6-8%. This data suggests that L1 is relatively unstable compared to L2-L4.

TABLE 4

Hydrolysis analysis of L1-L4 conjugated with FGF21.

| Linker | Time (hrs) | 0 linker | 1 linker | +(1) H2O | +(2) H2O |
|--------|------------|----------|----------|----------|----------|
| L1     | 0          | 13       | 49       | 30       | 8        |
| L1     | 24         | 14       | 41       | 34       | 11       |
| L1     | 72         | 14       | 40       | 35       | 11       |
| L1     | 168        | 10       | 33       | 40       | 18       |
| L1     | 336        | 12       | 28       | 41       | 18       |
| L2     | 0          | 22       | 45       | 27       | 6        |
| L2     | 24         | 23       | 43       | 26       | 8        |
| L2     | 72         | 24       | 37       | 32       | 8        |
| L2     | 168        | 24       | 40       | 29       | 7        |
| L2     | 336        | 26       | 38       | 28       | 8        |
| L3     | 0          | 19       | 45       | 30       | 6        |
| L3     | 24         | 18       | 47       | 27       | 8        |
| L3     | 72         | 19       | 43       | 30       | 8        |
| L3     | 168        | 19       | 43       | 29       | 8        |
| L3     | 336        | 20       | 43       | 29       | 8        |
| L4     | 0          | 20       | 46       | 28       | 6        |
| L4     | 24         | 20       | 46       | 27       | 7        |
| L4     | 72         | 21       | 42       | 30       | 7        |

TABLE 4-continued

Hydrolysis analysis of L1-L4 conjugated with FGF21.

| Linker | Time (hrs) | 0 linker | 1 linker | +(1) H2O | +(2) H2O |
|--------|-----------|----------|----------|----------|----------|
| L4 | 168 | 21 | 41 | 32 | 6 |
| L4 | 336 | 22 | 41 | 31 | 6 |

Example 43

Ab-FGF21ΔH-A129C Conjugated with L1-L4

L2-L4 had previously been shown to be more stable than L1 with glutathione conjugations under various conditions (see Tables 3A-C) and FGF21 (Table 4). The modified maleimide linkers L2-L4 were fused to FGF21ΔH-A129C (conjugation efficiencies shown in Table 5), and showed activity in the Glut1 Taqman assay (Table 5): $EC_{50}$ values are normalized against the relative value for FGF21ΔH).

TABLE 5

Conjugation efficiencies of L1-L4.

| Linker | [Compound] | FGF21-Linker conjugation | FGF21-Linker-Ab conjugation | Glut1Taqman activity $EC_{50}$ (nM) Relative to FGF21ΔH |
|--------|-----------|--------------------------|-----------------------------|----------------------------------------------------------|
| L1 | 30 | 95% | 95% | 1.68 |
| L2 | 31 | 67% | 95% | 1.00 |
| L3 | 32 | 87% | 89% | 0.35 |
| L4 | 33 | 90% | 94% | 2.71 |

Figure 2A:
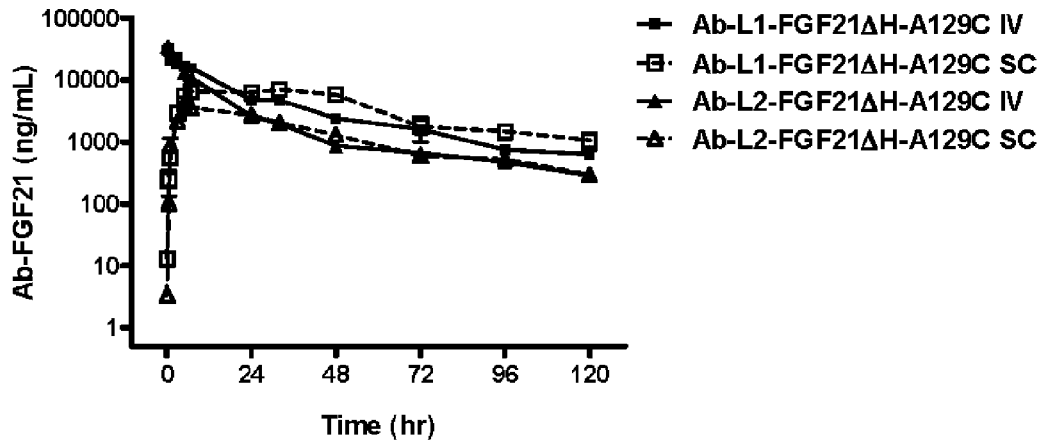
FIG. 2A, 2B, and 2C. Single dose mouse pharmacokinetic studies with Ab-FGF21ΔH-A129C conjugated with Linker-1 (L-1) in comparison with L-2, L-3, or L-4. Young adult male Swiss-Webster mice were dosed either IV or SC at 3 mg/kg. In all cases, the conjugate with L-1 performed better with respect to half-life (~33 hrs SC and IV for L-1 conjugate, 13-23 hrs SC and 22-37 hrs IV for L-2, -3, and -4 conjugates) and/or SC bioavailability (~100% for L-1 conjugate, 48-53% for L-2, -3, or -4 conjugates).
Figure 2B:
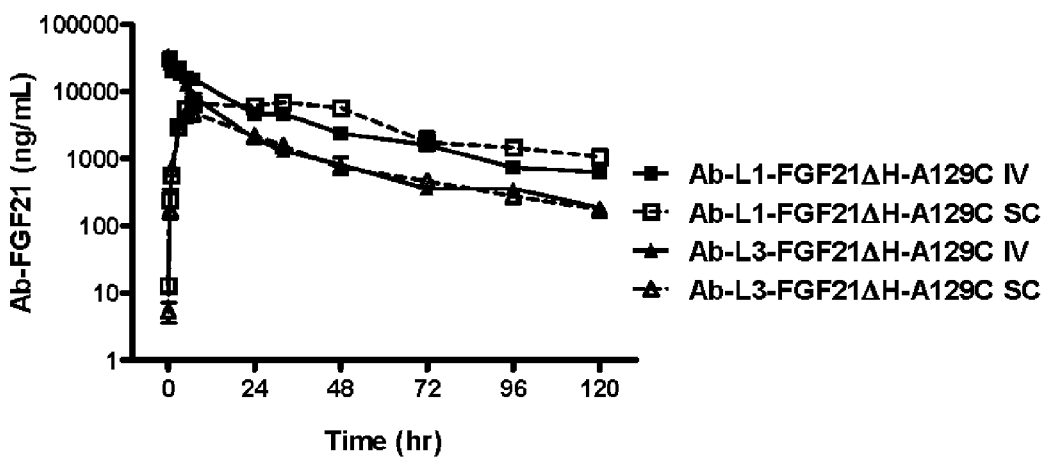
Figure 2C:
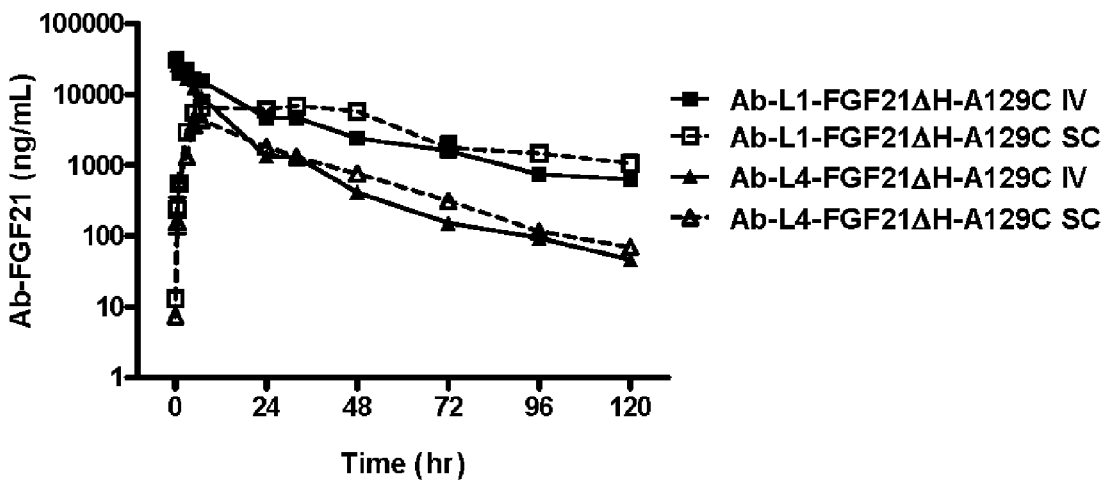

However, despite the foregoing, Ab-L2-FGF21ΔH-A129C, Ab-L3-FGF21ΔH-A129C, Ab-L4-FGF21ΔH-A129C were each less stable in vivo than Ab-L1-FGF21ΔH-A129C. This was evident as lower sustained levels in the circulation after IV dosing, and lower peak and sustained levels in the circulation after SC dosing (FIGS. 2A-C, Table 6). Surprisingly, these results ran counter to the results of the stability studies conducted with the linkers fused to a small peptide in buffer systems.

TABLE 6

Mouse PK parameters of FGF21 conjugates with L1, L2, L3, and L4 following IV and SC administration at 3 mg/kg.

| Cmpd | T½ (hr) IV | T½ (hr) SC | AUC (hr*ug/ml) IV | AUC (hr*ug/ml) SC | SC Bioavailability (%) |
|------|-----------|-----------|-------------------|-------------------|------------------------|
| Ab-L1-FGF21ΔH-A129C | 33 | 33 | 491 | 511 | ~100 |
| Ab-L2-FGF21ΔH-A129C | 37 | 23 | 314 | 165 | 53 |
| Ab-L3-FGF21ΔH-A129C | 32 | 13 | 254 | 129 | 51 |
| Ab-L4-FGF21ΔH-A129C | 22 | 14 | 219 | 106 | 48 |

These results were borne out in an additional study in mouse serum. FGF21ΔH-A129C was conjugated to h38C2 using each of L1, L2, L3 and L4. Each sample was diluted in mouse serum to 0.3 mg/ml and incubated at 37° C. before freezing, followed by subsequent analysis by 2DLC/MS. Compared against a reference standard, Ab-L1-FGF21ΔH-A129C was detected at 149% after 5 mins, 66% after 34 hrs, 81% after 72 hrs, and was undetectable by 120 hrs. In contrast, Ab-L2-FGF21ΔH-A129C, Ab-L3-FGF21ΔH-A129C, Ab-L4-FGF21ΔH-A129C were undetectable in all samples.

Example 44

Rat Study of Ab-FGF21ΔH-A129C Conjugated with L1 & L2

Figure 3A:
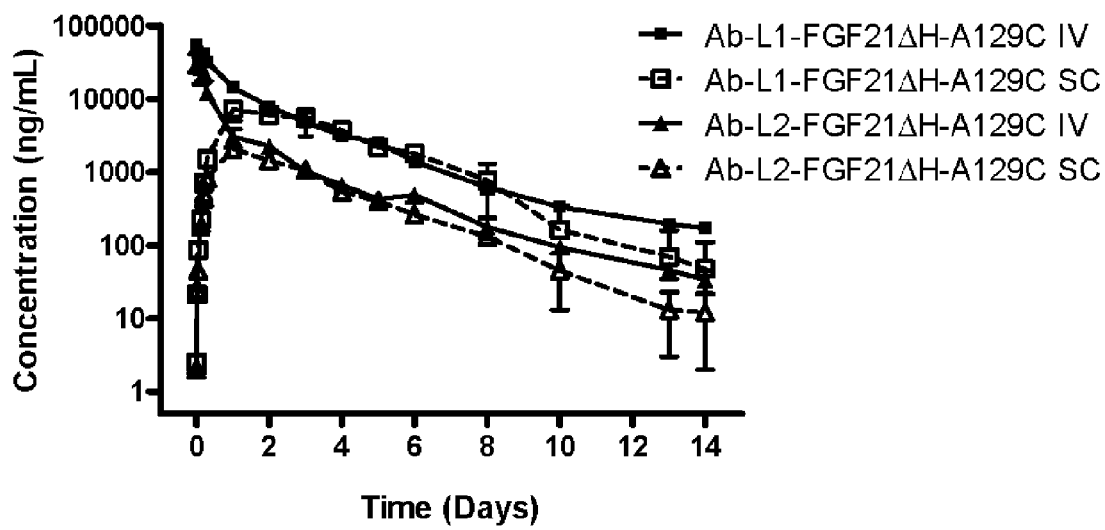
FIG. 3A. Single dose rat pharmacokinetic study with Ab-FGF21ΔH-A129C conjugated with L-1 in comparison with L-2. Adult male Sprague Dawley rats were dosed either IV or SC at 3 mg/kg. For both routes of administration, the conjugate with L-1 performed better than the L-2 conjugate with respect to half-life (~39 hrs SC and ~60 hrs IV for L-1 conjugate, ~33 hrs SC and ~52 hrs IV for L-2 conjugate) and SC bioavailability (~52% for L-1 conjugate, 36% for L-2 conjugate).

Single dose pharmacokinetics (PK) of two versions of Ab-FGF21ΔH-A129C differing by the linker used to conjugate the FGF21 protein to the antibody scaffold were determined in male Sprague Dawley rats. Rats were dosed IV or SC (3 mg/kg) with either Ab-L1-FGF21ΔH-A129C (maleimide linker) or Ab-L2-FGF21ΔH-A129C (methyl maleimide linker), and blood samples were drawn at intervals from 5 mins to 14 days post dose. Serum Ab-FGF21ΔH-A129C levels were determined by ELISA, in which the FGF21 conjugate was captured via a monoclonal antibody specific for FGF21 and detected by anti-human Fc. The resulting PK data demonstrated that the Ab-L1-FGF21ΔH-A129C conjugate had superior PK characteristics ($T_{1/2}$: IV=60 hrs, SC=38 hrs; SC bioavailability=52%) in comparison with the Ab-L2-FGF21ΔH-A129C conjugate ($T_{1/2}$: IV=52 hrs, SC=33 hrs; SC bioavailability=36%), (FIG. 3A and Table 7). These results were not anticipated given the results of stability studies conducted in buffer systems with these linkers fused to a small peptide.

TABLE 7

Rat PK parameters of FGF21 conjugates with L1 and L2 following IV and SC administration at 3 mg/kg (for FIG. 3A).

| Cmpd | T½ (hr) IV | T½ (hr) SC | AUC (hr*ug/ml) IV | AUC (hr*ug/ml) SC | SC Bioavailability (%) |
|------|-----------|-----------|-------------------|-------------------|------------------------|
| Ab-L1-FGF21ΔH-A129C | 60 | 38 | 1382 | 717 | 52 |
| Ab-L2-FGF21ΔH-A129C | 52 | 33 | 419 | 152 | 36 |

Example 45

Effect of Ab-FGF21ΔH-A129C with L1 and L2 on Glut1 RNA

3T3-L1 adipocytes were seeded at day 8 in 24-well tissue culture plates (Falcon®, Cat#353047), and incubated in DMEM complete medium (10% FBS, 2 mM L-glutamine, 1% P/S) at 37° C., 5% $CO_2$. The cells were starved (day 12) with serum-free DMEM medium with 0.2% BSA overnight and treated with Ab-L1-FGF21ΔH-A129C and Ab-L2-FGF21ΔH-A129C in serum-free DMEM containing 0.2% BSA at 37° C. for 6 hrs. The medium was aspirated, and then RNA extracted from the cells using the RNeasy mini Kit according to the manufacturer's instructions. RNA was measured at A260 nm using the Spectramax® Plus spectrophotometer.

TABLE 8

Taqman quantitative real-time PCR.

| Compound | Glut1 RNA expression EC50 (nM) |
| --- | --- |
| FGF21ΔH | 3.39 |
| FGF21ΔH-A129C | 16.03 |
| Ab-L1-FGF21ΔH-A129C | 1.72 |
| Ab-L2-FGF21ΔH-A129C | 9.33 |

Stimulation of 3T3-L1 adipocytes by FGF21ΔH, FGF21ΔH-A129C, Ab-L1-FGF21ΔH-A129C, and Ab-L2-FGF21ΔH-A129C resulted in dose-dependent Glut1 induction. Ab-L1-FGF21ΔH-A129C appeared to be more potent than Ab-L2-FGF21ΔH-A129C (Table 8).

Example 46

Linker Length Study

Ab-L1-FGF21ΔH-D79O, Ab-L7-FGF21ΔH-D79O, and Ab-L8-FGF21ΔH-D79O were tested against each other to assess the tolerance of linker length. All showed similar PK (FIG. 3B and Table 9) and comparable potency (data not shown) in cell-based assays.

TABLE 9

Figure 3B:
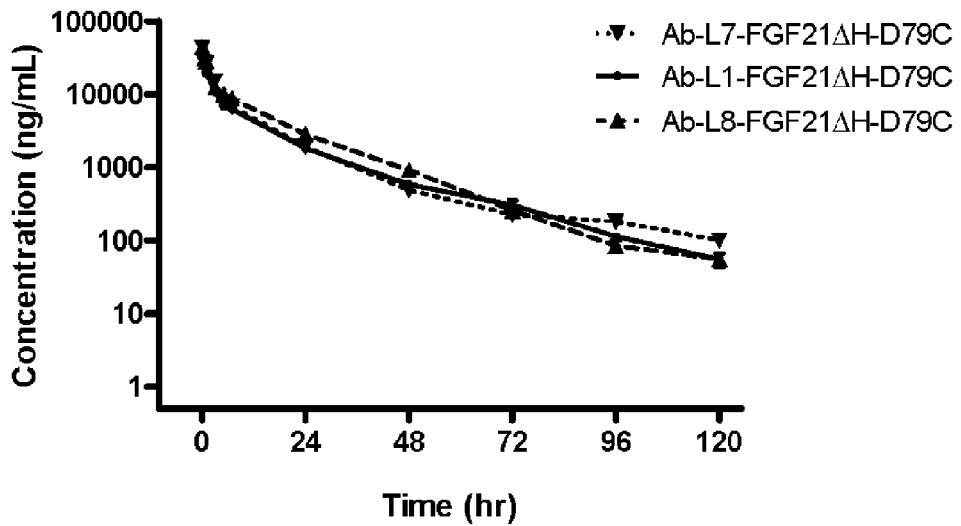
FIG. 3B. Comparison of PK of Ab-L1-FGF21ΔH-D79C, Ab-L7-FGF21ΔH-D79C, and Ab-L8-FGF21ΔH-D79C.
Figure 4A:
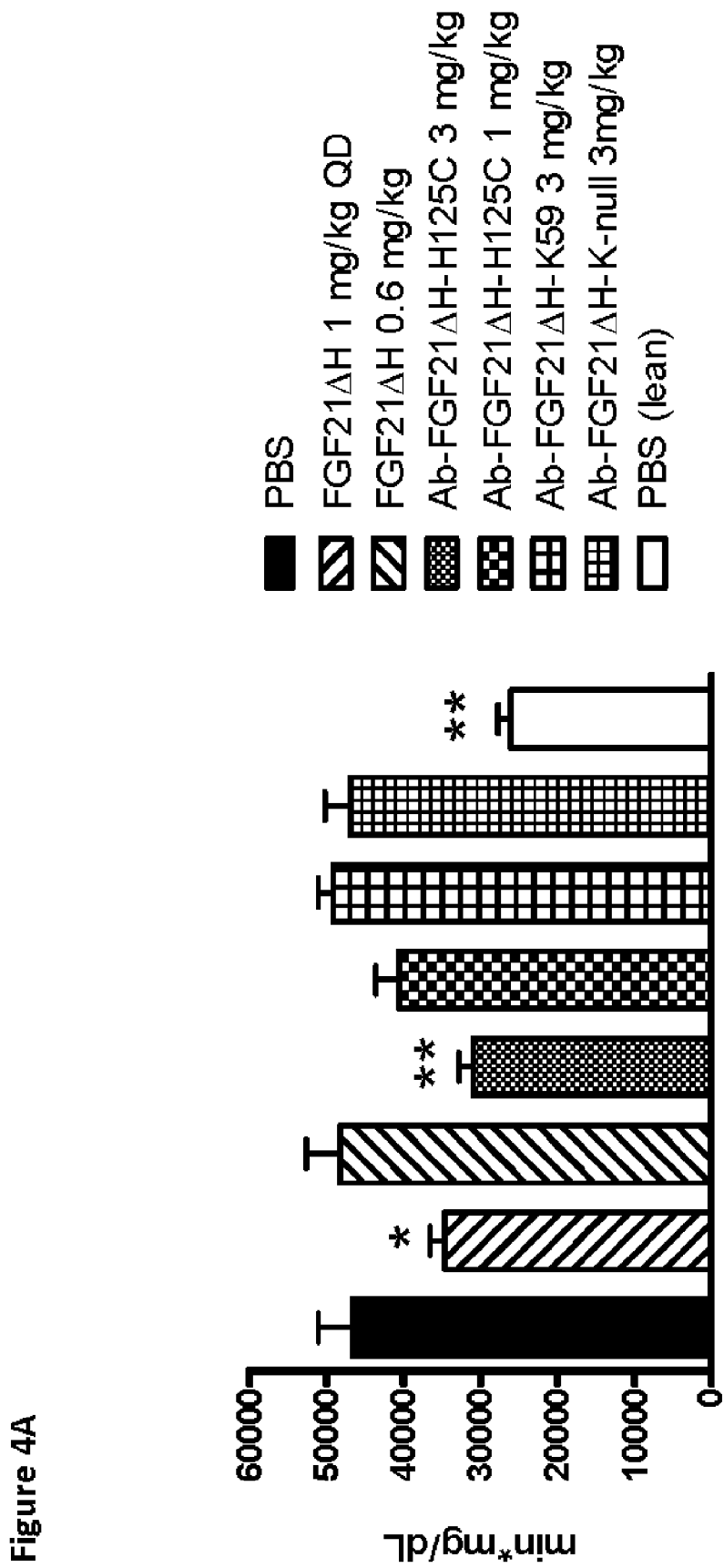
FIGS. 4A and 4B. Glucose area under the curve (AUC) during oral glucose tolerance test (OGTT) in ob/ob mice given a single SC dose (Mean Glucose AUC (% of vehicle control) in square brackets):Vehicle [100], FGF21ΔH (1 mg/kg [74]), FGF21ΔH (0.6 mg/kg [103]) (not shown in FIG. 4B for clarity), Ab-FGF21ΔH-H125C (3 mg/kg [66] and 1 mg/kg [87]) (conjugated with L1), Ab-FGF21ΔH-K59 (3 mg/kg [105]) (conjugated with L5), Ab-FGF21ΔH-Knull-H1K (3 mg/kg [100]) (conjugated with L5), Lean control [56]. *P<0.05, **P<0.01 vs PBS by one-way ANOVA.
Figure 4B:
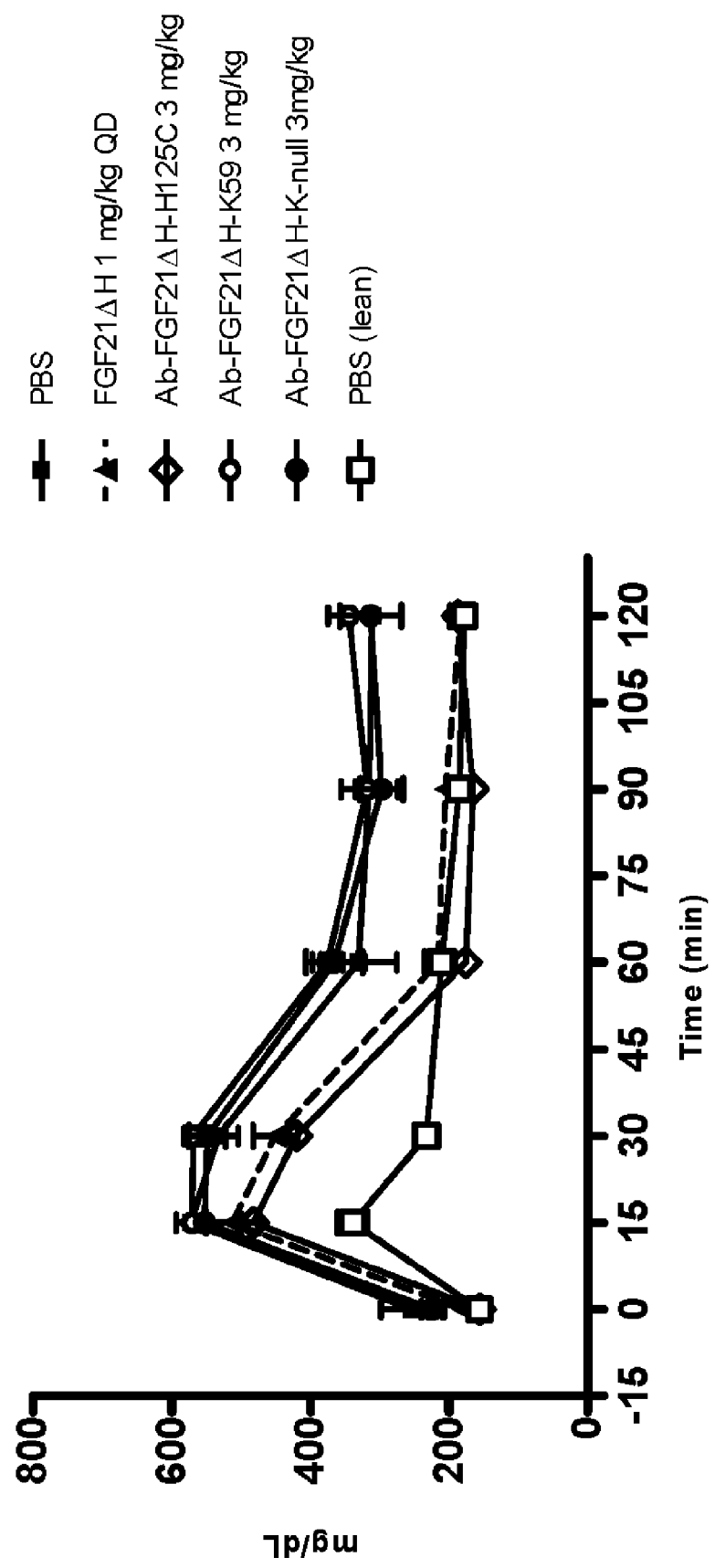

Mouse PK parameters of FGF21 conjugates with L1, L7, and L8 linkers following IV administration at 3 mg/kg (for FIG. 3B).

| Cmpd | IV T½ (hr) | IV AUC (hr*ug/ml) |
| --- | --- | --- |
| Ab-L1-FGF21ΔH-D79C | 19 | 176 |
| Ab-L7-FGF21ΔH-D79C | 27 | 183 |
| Ab-L8-FGF21ΔH-D79C | 15 | 248 |

Example 47

Summary of Residue Positions and Linker Selection

H1C, T40C, D79C, L86C, H125C and A129C were tested as potential conjugation sites using a thiol-maleimide conjugation strategy. Of these, H1C, T40C and L86C showed problems with expression and refolding. D79C, H125C and A129C were explored further as all showed acceptable levels of protein production and demonstrated that the unconjugated mutant protein remained potent. Ab-FGF21ΔH-D790, Ab-FGF21ΔH-H1250, and Ab-FGF21ΔH-A129C showed similar bioactivity as FGF21ΔH, suggesting that conjugating the antibody at these locations does not interfere the receptor binding. D79C, H125C and A129C have similar stability and bioactivity as FGF21ΔH.

All lysine mutant antibody conjugates tested showed inferior mouse PK to the H125C and A129C antibody conjugates, with IV half-lives of 13-17 hrs (Table 10).

TABLE 10

Summary of conjugation sites on FGF21.

| | Protein yield of fermentation (mg/L) | Glucose uptake $EC_{50}$ (nM) | Glut1 Taqman unconjugated Protein $EC_{50}$ (nM) | Glut1 Taqman Conjugate $EC_{50}$ (nM) | IV $T_{1/2}$ (hr) | SC $T_{1/2}$ (hr) | % SC BioAv | GTT* (% AUC of Ctrl) |
| --- | --- | --- | --- | --- | --- | --- | --- | --- |
| FGF21ΔH** | | 12 (12) | 2.3 (7) | N/A | 0.4 | 0.5 | 96 | 67 |
| K56 | 10-50 | 5.5 | 0.9 (2) | 1.9 (1) | 17 | 13 | 66 | 100 |
| K59 | 10-50 | 0.9 | 0.6 (1) | 6.5 (2) | 13 | ND | N/A | 100 |
| K69 | 10-50 | 5.2 | 1.3 (1) | ND | ND | ND | ND | ND |
| K122 | 10-50 | 1.7 | 2.6 (2) | 1.6 (2) | 16 | 14 | 40 | 100 |
| Knull-P2 | 10-50 | ND | 1.2 (2) | 16.6 (2) | 17 | ND | N/A | 100 |
| Knull-H1K | 10-50 | ND | 6.4 (2) | 4.3 (2) | 16 | 11 | 51 | 99 |
| Knull-S181K | 10-50 | ND | 7.5 (2) | >500 (2) | ND | ND | ND | ND |
| D79C | | 9.9 | 2.1 (4) | 3.7 (3) | 17, 19 | 20, 17 | 55, 70 | 54 |
| L86C | | 62 | ND | ND | ND | ND | ND | ND |
| H125C | | 0.65 | 1.2 (3) | 3.2 (4) | 37 | 32 | 67 | 48, 66 |
| A129C | | 5.7 | 1.4 (6) | 2.7 (7) | 28, 33 | 37, 33 | 69, 100 | 64, 67, 72 |

*3 days after a single SC dose of 3 mg/kg, except 10 mg/kg for D79C and 1 mg/kg Qd for FGF21dH.
**protein;
ND: not determined.

Although Ala129 was not highly exposed to the solvent, and is less so than D79 or H125, FGF21ΔH-A129C was surprisingly one of the most stable mutants and the best position tested for antibody conjugation. This was unexpected as the mutation is non-conservative. Although not wishing to be bound by theory, there are several possible reasons for the unique suitability of conjugating at A129C. First; Ala129, as well as His125, are both located in the loop region which is flexible in the modelled structure of FGF21. These regions are usually heparin binding sites for other heparin binding FGF members. Since FGF19, FGF21 and FGF23 do not interact with heparin, maintaining sequence fidelity of this region may not be critical for their biological function. The flexibility of the position may be beneficial for antibody-conjugation to avoid interference of receptor binding. Second; Ala129 is surrounded by positively charged resides, namely His125, Arg126, Arg131, and Arg135. This positively charged patch may avoid the SS-dimerization of FGF21ΔH-A129C due to the strong charged repulsion. Third; these charged resides may favour the stabilization of the maleimide linker L1, which in their absence, may generate a carboxylate after ring-opening of maleimide. Thus, when conjugating FGF21 using a maleimide linkage strategy, linking at the specific residue position of A129 appears to be particularly advantageous.

Ab-L1-FGF21ΔH-A129C and Ab-L1-FGF21ΔH-H125O both show high IV half-lives and SC half-lives of at least 30 hrs in murine models as well as good bioavailability Both conjugates demonstrate potency below 4 nM in the Glut1 Taqman assay. In general, Ab-L1-FGF21ΔH-A129C shows slightly improved half-life and potency compared to Ab-L1-FGF21ΔH-H125O. Use of L1 in Ab-L1-FGF21ΔH-A129C also showed surprising in vivo advantages over what in vitro tests suggested, and appeared overall the most advantageous linker compared with those tested.

The specific combination of the components of Ab-L1-FGF21ΔH-A129C, (antibody, linker, linking residue position, linking residue, protein) appear to provide the optimum in half-life, bioavailability, potency, activity, ease of production, and resistance to hydrolysis compared with multiple alternatives.

Example 48

Efficacy of Compounds

Figure 5A:
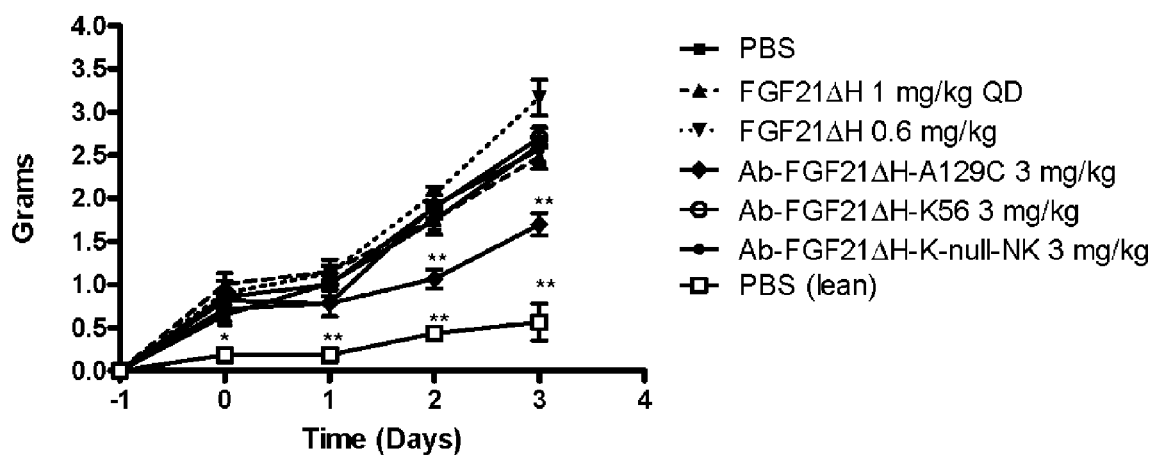
FIGS. 5A and 5B. Cumulative body weight (A) and liver weight (B) change during OGTT in ob/ob mice given a single SC dose (mean body weight (g) in square brackets, mean liver weight (g) in curly brackets):Vehicle [2.6] {2.4}, FGF21ΔH (1 mg/kg [2.5] {2.2}), FGF21ΔH (0.6 mg/kg [3.2] {2.4}), Ab-FGF21ΔH-A129C (3 mg/kg [1.7] {2.0}) (conjugated with L1), Ab-FGF21ΔH-K59 (3 mg/kg [2.7] {2.4}) (conjugated with L5), Ab-FGF21ΔH-Knull-H1K (3 mg/kg [2.6]
Figure 5B:
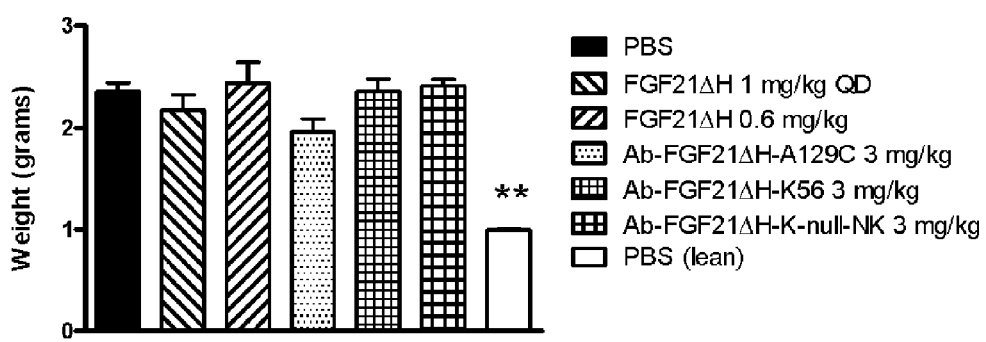

Glucose tolerance was tested for in ob/ob mice treated with compounds Ab-FGF21ΔH-K56 and Ab-FGF21ΔH-Knull-H1K. Both compounds compared poorly against Ab-FGF21ΔH-H125C (FIGS. 4A and 4B) and Ab-FGF21ΔH-A129C (FIGS. 5A and 5B). In contrast, Ab-FGF21ΔH-D79C and Ab-FGF21ΔH-H125C were shown to improve glucose tolerance and reduce body weight gain (FIGS. 4A, 4B, 6A, 6B, 6C, 6D, and Table 11).

TABLE 11

Glucose AUC during the OGTT conducted on day 6 after SC injection of Ab-FGF21ΔH-D79C at 10 mg/kg at indicated time in ob/ob mice (see FIGS. 6C and 6D).

| Treatment | Mean Glucose AUC (% of vehicle control) |
|---|---|
| Vehicle | 100 |
| FGF21ΔH 1 mg/kg QD | 61** |
| Ab-FGF21ΔH-D79C, day 0 & 3 | 53** |
| Ab-FGF21ΔH-D79C, day 3 | 53** |
| Ab-FGF21ΔH-D79C, day 5 | 87 |
| Ab-FGF21ΔH-D79C, day 6 | 67** |
| Lean control (vehicle) | 41** |

**$p < 0.01$ vs vehicle (glucose AUC) by One-way ANOVA with Dunnett's post-tests.

Ab-FGF21ΔH-A129C was found to improve glucose tolerance, and reduced body weight gain, due to increased energy expenditure evidenced by increased Ucp1 expression in white adipose tissue (WAT), and reverses hepatic steatosis in ob/ob mice (FIGS. 6E, 6F, 6G, 6H and Table 12). For Ucp1 expression, frozen visceral WAT samples collected from the in vivo efficacy studies were homogenized. Total RNA was extracted from the tissue homogenates, and Glut1 and GAPDH mRNA expression was measured using a Quantitect Probe RT-PCR kit and running a quantitative real time PCR reaction in a Taqman machine (Applied Biosystems). The effect of treatment was determined by a fold change in Glut1 mRNA levels normalized by the GAPDH mRNA levels from each sample. Ab-FGF21ΔH-A129C caused body weight loss due to increased energy expenditure as suggested by increased Ucp1 expression in WAT, reduced serum triglycerides and fatty acid levels in DIO mice and decreased liver weight (FIGS. 7A, 7B, 7C, 7D, 7E, and Table 13). A reduction in liver weight was also observed in ob/ob mice (FIG. 7F and Table 14). Further tests in ob/ob mice demonstrated a reduction in RNA levels of stearoyl-coenzyme A desaturase-1 (SCD1), and monoacylglycerol O-acyltransferase (MOGAT2), and an increase in RNA levels of forkhead box A2 (FoxA2), (FIGS. 7G, 7H and 7i and Table 15).

TABLE 12

Results after a single SC injection of Ab-FGF21ΔH-A129C at day 6 in ob/ob mice; see FIGS. 6E, 6F, 6G, 6H.

| Treatment | Glucose AUC during OGTT 3 mg/kg. (% of vehicle control) | UCP1 mRNA expression in WAT 10 mg/kg. (SEM) | Triglycerides content in liver 10 mg/kg. (SEM) | Body weight change (g) on day 6 from day-1 10 mg/kg. (SEM) |
|---|---|---|---|---|
| Vehicle | 100 | 1.0 (0.1) | 35.7 (4.2) | 6.2 (0.2) |
| FGF21ΔH 1 mg/kg QD | 67*** | 2.6 (0.4) | 37.0 (2.3) | 4.7 (0.3) |
| Ab-FGF21ΔH-A129C, day 0 | 80* | 2.4 (0.3) | 22.2 (2.1)* | 4.2 (0.4)** |
| Ab-FGF21ΔH-A129C, day 1 | 68*** | 2.6 (0.7) | 22.1 (5.6)* | 3.8 (0.3)*** |
| Ab-FGF21ΔH-A129C, day 2 | 68*** | 2.1 (0.6) | 22.2 (2.4)* | 3.8 (0.4)*** |
| Ab-FGF21ΔH-A129C, day 3 | 57*** | 2.5 (0.5) | 27.7 (4.3) | 4.0 (0.4)** |
| Lean control (vehicle) | 57*** | — | 9.3 (1.4)*** | 1.1 (0.6)*** |

*$p < 0.05$, $p < 0.01$, *$p < 0.001$ vs vehicle by One-way ANOVA with Dunnett's post-tests.

SEM values provided in parentheses.

TABLE 13

Results on day 10 after a repeat SC injection of Ab-FGF21ΔH-A129C at 10 mg/kg on day 0 & 7 in DIO mice (see FIGS. 7A, 7B, 7C, 7D, 7E).

| Treatment | Glucose AUC during OGTT (% of vehicle control) | Body weight change (g) on day 10 from day-1 (SEM) | UCP1 mRNA expression in WAT (SEM) | Mean values of serum lipids | |
|---|---|---|---|---|---|
| | | | | TG (mg/dL) (SEM) | NEFA (mM) (SEM) |
| Vehicle | 100 | −0.2 (0.9) | 1.2 (0.3) | 133 (7.0) | 0.61 (0.06) |
| FGF21ΔH 1 mg/kg QD | 75*** | −1.6 (0.8) | 1.6 (0.2) | 92 (9.6)** | 0.40 (0.04) |
| Ab-FGF21ΔH-A129C, d 0 & 7 | 83* | −2.4 (0.7) | 4.8 (1.1)** | 69 (6.4)*** | 0.36 (0.04)* |
| Chow-fed control (vehicle) | 78** | +1.2 (0.4) | 0.5 (0.1) | 104 (9.2)* | 0.52 (0.10) |

*$p < 0.05$, $p < 0.01$, *$p < 0.001$ vs vehicle by One-way ANOVA with Dunnett's post-tests.
SEM values provided in parentheses.

TABLE 14

Liver weight on day 6 after a single SC injection of Ab-FGF21ΔH-A129C at 10 mg/kg at indicated time in ob/ob mice (for FIG. 7F).

| Treatment | Liver Weight (g) (SEM) |
|---|---|
| Vehicle | 2.3 (0.1) |
| FGF21ΔH 1 mg/kg QD | 1.8 (0.1)** |
| Ab-FGF21ΔH-A129C, day 0 | 1.4 (0.1)*** |
| Ab-FGF21ΔH-A129C, day 1 | 1.4 (0.1)*** |
| Ab-FGF21ΔH-A129C, day 2 | 1.4 (0.1)*** |
| Ab-FGF21ΔH-A129C, day 3 | 1.5 (0.1)*** |
| Lean control (vehicle) | 0.8 (0.0)*** |

$p < 0.01$, *$p < 0.001$ vs vehicle by One-way ANOVA with Dunnett's post-tests.
SEM values provided in parentheses.

TABLE 15

Mean fold changes of mRNA expression using qPCR from liver tissue samples collected on day 6 after a single SC injection of Ab-FGF21ΔH-A129C at 10 mg/kg at indicated time in ob/ob mice (for FIG. 7G, 7H, 7i).

| Treatment | SCD1 (SEM) | MOGAT2 (SEM) | FoxA2 (SEM) |
|---|---|---|---|
| Vehicle | 1.01 (0.06) | 1.05 (0.17) | 1.00 (0.04) |
| FGF21ΔH 1 mg/kg QD | 0.95 (0.06) | 0.37 (0.05)** | 1.23 (0.08) |
| Ab-FGF21ΔH-A129C, day 0 | 0.83 (0.08) | 0.38 (0.10)** | 1.14 (0.06) |
| Ab-FGF21ΔH-A129C, day 3 | 0.61 (0.08)** | 0.31 (0.08)** | 1.81 (0.20)** |

**$p < 0.01$ vs vehicle by One-way ANOVA with Dunnett's post-tests.
SEM values provided in parentheses.

Example 49

GSIS Assay on Exendin4 Compounds

The ability of certain Exendin4 homologues to stimulate insulin secretion from pancreatic β cells in vitro was tested using a glucose-stimulated insulin secretion (GSIS) assay. Briefly, the relevant Exendin4 homologue was conjugated to both combining sites of h38C2, and this conjugated molecule was applied, together with glucose, at various concentrations to pancreatic β cell cultures. Insulin secretion was detected by measuring insulin levels over time. EC50 was calculated for each compound. The results of this assay are set forth in Table 16 below.

Example 50

Glucose Tolerance Test (GTT), Body Weight Change and Food Intake on Exendin4 Compounds In vivo efficacy of exemplary Exendin4 homologues were assessed using a single- or repeat-dose glucose tolerance testing paradigm. Young adult male ob/ob mice (Jackson Laboratories, Bar Harbor, Me.) were dosed with 0.3 mg/kg of test compounds of the invention subcutaneously (SC) in the mid-scapular region, using brief manual restraint, with injection volumes of 0.2-0.3 ml. Lean littermate control mice (n=8/group, Jackson Laboratories, Bar Harbor, Me.) were similarly dosed with Vehicle. Food intake and cumulative body weight change were monitored daily in the morning (08:00-09:00 H; lights on at 06:00 H and off at 18:00 H). Results are shown as average values over days 0-9, as well as the value at day 9. Each compound was tested with 8-10 animals.

Mice underwent oral glucose tolerance testing (OGTT) following a standard protocol. Briefly, mice were fasted for 4-5 hrs at the beginning of the lights-on phase in the colony. At the end of this period (early afternoon), mice were tail-bled immediately prior to and at regular intervals from 15 to 120 mins after an oral glucose challenge (1.5 g/kg). Food was returned to the cages following collection of the 120 minute time point. Glucose levels were determined using self-test blood glucose meters, and the area-under-the-curve (AUC) for glucose as a function of time after oral glucose challenge was calculated using a linear trapezoidal equation. Results were calculated as % of the vehicle control, and are shown for 48 and 72 hrs tests (Table 16).

TABLE 16

Analysis of Exendin4 peptides.

| SEQ ID NO: | Link site | EC$_{50}$ Peptide | EC$_{50}$ pep-Ab conj | SC T½ | SC bio avail | Food intake % of vehicle | Food intake % of vehicle at 9 days | Body weight % of vehicle | Body weight % of vehicle at 9 days | GTT 48 hrs % of vehicle control | GTT 72 hrs % of vehicle control |
|---|---|---|---|---|---|---|---|---|---|---|---|
| 38 | C-20 | 0.03, 0.078, | 2.63 | 26.8 | 85 | 78 | 86 | 61 | 84 | | 88 |
| 39 | K38 | | | 24.9 | 39 | 82 | 100 | 52 | 69 | | 106 |
| 43 | K28 | | | 33.9 | 46 | | | | | | |

TABLE 16-continued

Analysis of Exendin4 peptides.

| SEQ ID NO: | Link site | EC$_{50}$ Peptide | EC$_{50}$ pep-Ab conj | SC T½ | SC bio avail | Food intake % of vehicle | Food intake % of vehicle at 9 days | Body weight % of vehicle | Body weight % of vehicle at 9 days | GTT 48 hrs % of vehicle control | GTT 72 hrs % of vehicle control |
|---|---|---|---|---|---|---|---|---|---|---|---|
| 44 | K27 |  |  | 39.1 | 72 |  |  |  |  |  |  |
| 45 | K26 | 0.01 |  | 66.0 | 100 | 105 | 88 | 121 | 122 | 74.86 |  |
| 46 | K24 | 0.14, |  | 36.0 | 57 | 78 | 91 | 45 | 54 |  | 108 |
| 47 | K23 | 0.03 |  | 84.9 | 82 | 92 | 90 | 102 | 102 | 97 |  |
| 48 | K21 | 0.010, | 2.12 | 52.0 | 72 | 72 | 88 | 55 | 58 | 66 |  |
| 49 | K20 | 0.047 |  | 53.4 | 78 | 75 | 92 | 60 | 76 | 69 | 94 |
| 50 | K19 | no fit |  | 88.6 | 100 | 69 | 76 | 67 | 70 |  | 65 |
| 51 | K17 | 0.22, |  | 51.7 | 48 | 81 | 94 | 45 | 59 |  | 121 |
| 52 | K16 | 0.01 |  | 57.6 | 88 |  |  |  |  |  |  |
| 53 | K14 | 0.027, 0.040 |  | 90.5 | 100 | 72 | 93 | 62 | 73 | 72 | 76 |
| 54 | K13 | 0.031 |  | 55.9 | 80 |  |  |  |  |  |  |
| 55 | K12 | 0.091 | 1.76 | 49.5 | 94 | 84 | 91 | 67 | 91 | 75 |  |
| 56 | K11 | 0.08 |  | 60.9 | 100 |  |  |  |  |  |  |

Linking at position 23 (SEQ ID NO:47) did not decrease body weight or feeding and did not improve glucose tolerance @ 48 hrs. Linking at positions 17, 24, 38 and at the C-terminus (SEQ ID NOs: 51, 46, 39, and 38) decreased body weight and feed but did not improve glucose tolerance at 72 hrs. Linking at position 26 (SEQ ID NO:45) did not decrease body weight or feeding but did improve glucose tolerance at 48 hrs. Clear advantages are seen for linking at positions 12, 14, 19, 20 and 21. Linking at position 14 was seen as providing the graeatest overall advantage. All examples used K or K(SH) residues as the linking residue.

Example 51

Assessing Parameters for Generating Asymmetric Bifunctional Antibody Conjugates

Different fusion ratios between [$2^{nd}$ linker-Ex4] and Ab in formulation buffer (10 mM histidine, 10 mM glycine, 2% sucrose, pH=7) at room temperature were examined. As the amount of [$2^{nd}$ linker-Ex4] increased, the formation of [Ab]-[$2^{nd}$ linker-Ex4]$_1$ also increased, and remained around 45% (Table 17). Further increases in [$2^{nd}$ linker-Ex4] resulted in increased amount of [Ab]-[$2^{nd}$ linker-Ex4]$_2$.

TABLE 17

Conjugation efficiency of [L1-SEQ ID NO: 64] to h38C2.

| [$2^{nd}$ linker-Ex4]$_1$:Antibody | % Unconjugated antibody | % Ab-[$2^{nd}$ linker-Ex4]$_1$ | % Ab-[$2^{nd}$ linker-Ex4]$_2$ |
|---|---|---|---|
| 0.25:1 | 61 | 26 | 13 |
| 0.5:1 | 50 | 35 | 15 |
| 0.75:1 | 40 | 41 | 19 |
| 1:1 | 32 | 45 | 23 |
| 1.25:1 | 23 | 45 | 33 |
| 1.5:1 | 19 | 45 | 36 |
| 1.75:1 | 17 | 45 | 39 |
| 2:1 | 11 | 39 | 49 |

The conjugation of [$2^{nd}$ linker-Ex4] and [Ab] (20 mg/mL, 0.6:1 ratio) to form Ab-[$2^{nd}$ linker-Ex4]$_1$ was examined using different co-solvent systems. These different co-solvents (shown in Table 18) were added to see if the formation of Ab-[$2^{nd}$ linker-Ex4]$_1$ could be improved. Increasing the concentrations of co-solvents such as ethanol, isopropyl alcohol (IPA), dimethyl formamide (DMF), dimethyl sulfoxide (DMSO) from 5% to 10% to 15% did not affect the formation of Ab-[$2^{nd}$ linker-Ex4]$_1$ but did affect the formation of Ab-[$2^{nd}$ linker-Ex4]$_2$, and the recovery of unconjugated antibody. It appears that as the amount of organic co-solvent was increased, a higher amount of antibody remained unconjugated. Similarly, as the co-solvent concentration was increased, there was a decrease in the formation of Ab-[$2^{nd}$ linker-Ex4]$_2$. Co-solvents such as ethanol, DMF, and DMSO inhibit the formation of Ab-[$2^{nd}$ linker-Ex4]$_2$, whereas propylene glycol did not have any effect on the formation of Ab-[$2^{nd}$ linker-Ex4]$_1$ or Ab-[$2^{nd}$ linker-Ex4]$_2$. The analysis was done using HPLC.

TABLE 18

Conjugation efficiency of [L1-SEQ ID NO: 64] to h38C2.

| Organic co-solvent | % Unconjugated antibody | % Ab-[$2^{nd}$ linker-Ex4]$_1$ | % Ab-[$2^{nd}$ linker-Ex4]$_2$ |
|---|---|---|---|
| No co-solvent | 26 | 48 | 24 |
| Ethanol 5% | 27 | 49 | 23 |
| Ethanol 10% | 30 | 49 | 20 |
| Ethanol 15% | 30 | 48 | 20 |
| IPA 5% | 29 | 49 | 21 |
| IPA 10% | 26 | 49 | 24 |
| IPA 15% | 25 | 49 | 25 |
| DMF 5% | 28 | 49 | 21 |
| DMF 10% | 32 | 49 | 18 |
| DMF 15% | 38 | 46 | 14 |
| DMSO 10% | 24 | 49 | 25 |
| DMSO 20% | 31 | 49 | 19 |
| DMSO 30% | 36 | 47 | 16 |
| Propylene Glycol 10% | 25 | 49 | 25 |
| Propylene Glycol 20% | 27 | 49 | 23 |
| Propylene Glycol 30% | 26 | 49 | 24 |

The effects of urea (0.5, 1.0 and 2 M) and EDTA (5, 10 and 15 mM) on the formation of Ab-[$2^{nd}$ linker-Ex4]$_1$ was examined. Neither urea nor EDAT have any noticeable effect on the formation of either Ab-[$2^{nd}$ linker-Ex4]$_1$ or Ab-[$2^{nd}$ linker-Ex4]$_2$.

The effect of guanidine hydrochloride on the formation of Ab-[$2^{nd}$ linker-Ex4]$_1$ from [$2^{nd}$ linker-Ex4] and [Ab] (20 mg/mL) was also examined at different concentrations of guanidine hydrochloride (0, 0.2, 0.4 and 0.5 M) and ratios of [$2^{nd}$ linker-Ex4]$_1$:Ab (0.85:1 and 1:1). At both ratios, increasing the concentrations of guanidine hydrochloride decreased the formation of Ab-[$2^{nd}$ linker-Ex4]$_2$, yet failed to offer a significant improvement in the yield of Ab-[$2^{nd}$ linker-Ex4]$_1$.

The effect of NaCl concentration (0, 100, 250, 500 mM) on the conjugation reaction between [$2^{nd}$ linker-Ex4] and antibody (20 mg/mL) at 0.5:1, 0.75:1 and 1:1 ratios was investigated, using formulation buffer (10 mM histidine, 10 mM glycine, and 2% sucrose, pH=7). No significant difference was observed in the generation of Ab-[$2^{nd}$ linker-Ex4]$_1$ across the NaCl concentrations tested.

The effect of pH on the conjugation reaction between [$2^{nd}$ linker-Ex4]$_1$ and antibody (20 mg/mL) was studied using formulation buffer (10 mM histidine, 10 mM glycine, and 2% sucrose). The results are shown in Table 19. The formation of [$2^{nd}$ linker-Ex4]$_1$ was the highest at pH=6.5 and 7.

TABLE 19

Conjugation efficiency of [L1-SEQ ID NO: 64] to h38C2.

| [$2^{nd}$ linker-Ex4]$_1$:Antibody | pH | % Unconjugated antibody | % Ab-[$2^{nd}$ linker-Ex4]$_1$ | % Ab-[$2^{nd}$ linker-Ex4]$_2$ |
|---|---|---|---|---|
| 1:1 | 5   | 44 | 43 | 12 |
| 1:1 | 5.5 | 38 | 45 | 16 |
| 1:1 | 6   | 26 | 45 | 29 |
| 1:1 | 6.5 | 40 | 47 | 22 |
| 1:1 | 7   | 29 | 47 | 23 |

A systematic investigation of the ratio between [$1^{st}$ linker-FGF21]:[Ab]-[$2^{nd}$ linker-Ex4]$_1$ was studied to evaluate the formation of [FGF21-$1^{st}$ linker]$_1$-[Ab]-[$2^{nd}$ linker-Ex4]$_1$. Table 20 shows the concentration of [Ab]-[$2^{nd}$ linker-Ex4]$_1$ and [$1^{st}$ linker-FGF21] and the formation of [FGF21-$1^{st}$ linker]$_1$-[Ab]-[$2^{nd}$ linker-Ex4]$_1$. The ratios were established using HPLC equipped with HIC columns. The concentration of [Ab]-[$2^{nd}$ linker-Ex4]$_1$ was varied as the added amount of [$1^{st}$ linker-FGF21] varied. Based on these results, it appears the maximum efficiency of [FGF21-$1^{st}$ linker]$_1$-[Ab]-[$2^{nd}$ linker-Ex4]$_1$ formation was achieved when the concentration of [Ab]-[$2^{nd}$ linker-Ex4]$_1$ was between about 2 and about 5 mg, and the amount of [$1^{st}$ linker-FGF21] was between about 3 to about 6 fold excess compared to [Ab]-[$2^{nd}$ linker-Ex4]$_1$

TABLE 20

Conjugation efficiency of h38C2-[L1-SEQ ID NO: 64] to [FGF21ΔH-A129C-L1].

| [Ab]-[$2^{nd}$ linker-Ex4]$_1$ Conc. (mg/mL) | [$1^{st}$ linker-FGF21]:[Ab]-[$2^{nd}$ linker-Ex4]$_1$ Ratio | % [FGF21-$1^{st}$ linker]$_1$-[Ab]-[$2^{nd}$ linker-Ex4]$_1$ |
|---|---|---|
| 5.85 | 2:1 | 54 |
| 4.85 | 3:1 | 65 |
| 3.20 | 6:1 | 65 |
| 2.42 | 6:1 | 68 |
| 1.63 | 6:1 | 66 |
| 0.99 | 6:1 | 63 |
| 0.55 | 6:1 | 51 |
| 0.30 | 6:1 | 39 |

The concentration of TCEP required to break inter disulphide bond between FGF21ΔH-A129C dimer without affecting intra disulfide bond inside FGF21ΔH-A129C was studied. The results are shown in Table 21. A sample containing FGF21ΔH-A129C in 20 mM Tris, 50 mM NaCl, pH=7 (about 2 mg/mL) was treated with various concentrations of TCEP for 30 mins. The samples were analyzed by LC-MS. Based on the data, 0.3 mM of TCEP is the optimum concentration to break inter disulphide bond between FGF21ΔH-A129C protein without affecting intra disulphide bond.

TABLE 21

Analysis of FGF21ΔH-A129C dimer formation.

| TCEP (mM) | % FGF21ΔH-A129C Monomer | % FGF21ΔH-A129C Reduced intra disulfide Monomer | % FGF21ΔH-A129C Dimer |
|---|---|---|---|
| 0.00 | 34.5 | 0.0 | 61.5 |
| 0.04 | 75.8 | 0.0 | 24.2 |
| 0.06 | 90.2 | 0.0 | 9.8 |
| 0.08 | 94.8 | 0.0 | 5.2 |
| 0.10 | 95.9 | 0.0 | 4.1 |
| 0.12 | 96.4 | 0.0 | 3.6 |
| 0.15 | 96.4 | 0.0 | 3.6 |
| 0.20 | 96.4 | 0.0 | 3.6 |
| 0.30 | 95.5 | 0.0 | 3.5 |
| 0.50 | 92.9 | 3.6 | 3.5 |
| 0.75 | 91.3 | 3.3 | 5.4 |
| 1.00 | 87.8 | 3.3 | 8.9 |

The reduction of inter disulphide bond was followed using HPLC over 140 mins using three different TCEP concentrations. All the inter disulphide bonds were cleaved using TCEP within 30 to 40 mins. These experiments suggest that the inter disulphide bond can be cleaved using 0.3 mM TCEP within 30 mins (Table 22).

TABLE 22

Effect of different molar rations of TCEP.

| TCEP Molar Ratio | Time (Min) | | % FGF21 | | % Reduced FGF21 Impurity mg/ml FGF21 | | % FGF21 Dimer | |
|---|---|---|---|---|---|---|---|---|
|  | 6.8 | 7.3 | 6.8 | 7.3 | 6.8 | 7.3 | 6.8 | 7.3 |
| 0.1 Molar Ratio of TCEP:rFGF21 0.03 mg/ml TCEP | 0 | 0 | 28.9 | 33.4 | 0.0 | 0.0 | 69.8 | 65.4 |
| | 0 | 0 | 27.1 | 31.1 | 0.0 | 0.0 | 71.5 | 67.7 |
| | 4 | 6.5 | 36.1 | 43.4 | 0.0 | 0.0 | 63.9 | 56.6 |
| | 27 | 29.5 | 63.5 | 70.3 | 0.0 | 0.3 | 36.5 | 29.4 |
| | 50 | 52.5 | 68.0 | 76.5 | 0.0 | 0.3 | 32.0 | 23.2 |
| | 73 | 75.5 | 70.2 | 79.8 | 0.0 | 0.4 | 29.8 | 19.8 |
| | 96 | 98.5 | 72.2 | 82.9 | 0.0 | 0.3 | 27.8 | 16.8 |
| | 119 | 121.5 | 72.9 | 82.6 | 0.0 | 0.3 | 27.1 | 17.1 |
| | 142 | 144.5 | 73.8 | 81.8 | 0.0 | 0.0 | 26.2 | 18.2 |

TABLE 22-continued

Effect of different molar rations of TCEP.

| TCEP Molar Ratio | Time (Min) | | % FGF21 | | % Reduced FGF21 Impurity mg/ml FGF21 | | % FGF21 Dimer | |
|---|---|---|---|---|---|---|---|---|
| | 6.8 | 7.3 | 6.8 | 7.3 | 6.8 | 7.3 | 6.8 | 7.3 |
| 0.3 Molar Ratio of TCEP:rFGF21 0.09 mg/ml TCEP | 0 | 0 | 28.9 | 33.4 | 0.0 | 0.0 | 69.8 | 65.4 |
| | 0 | 0 | 27.1 | 31.1 | 0.0 | 0.0 | 71.5 | 67.7 |
| | 4 | 8 | 45.9 | 59.3 | 0.0 | 0.0 | 54.1 | 40.7 |
| | 27 | 31 | 94.2 | 93.7 | 1.0 | 1.0 | 4.8 | 5.3 |
| | 50 | 54 | 96.5 | 94.4 | 1.4 | 1.3 | 2.2 | 4.3 |
| | 73 | 77 | 96.6 | 95.1 | 1.4 | 1.4 | 2.0 | 3.5 |
| | 96 | 100 | 96.6 | 94.7 | 1.6 | 1.6 | 1.7 | 3.7 |
| | 119 | 123 | 96.3 | 94.3 | 1.9 | 2.0 | 1.8 | 3.7 |
| | 142 | 146 | 96.0 | 94.9 | 2.1 | 2.3 | 1.8 | 2.8 |
| 0.5 Molar Ratio of TCEP:rFGF21 0.14 mg/ml TCEP | 0 | 0 | 28.9 | 33.4 | 0.0 | 0.0 | 69.8 | 65.4 |
| | 0 | 0 | 27.1 | 31.1 | 0.0 | 0.0 | 71.5 | 67.7 |
| | 4 | 11 | 55.7 | 69.5 | 0.0 | 0.0 | 44.3 | 30.5 |
| | 27 | 34 | 96.4 | 95.2 | 1.4 | 1.3 | 2.3 | 3.5 |
| | 50 | 57 | 96.4 | 95.2 | 1.8 | 1.7 | 1.8 | 3.1 |
| | 73 | 80 | 96.1 | 94.2 | 2.1 | 2.0 | 1.8 | 3.8 |
| | 96 | 103 | 95.5 | 94.9 | 2.4 | 2.2 | 2.1 | 2.9 |
| | 119 | 126 | 95.4 | 94.2 | 3.0 | 3.0 | 1.6 | 2.8 |
| | 142 | 149 | 94.9 | 93.6 | 3.5 | 3.6 | 1.6 | 2.8 |

Example 52

Generating Asymmetric Bifunctional Conjugates (Strategy 1)

H38C2+Exendin 4 Reaction: 2.76 gm of h38C2 (SEQ ID NO:25 and SEQ ID NO:26) (in 10 mM Histidine, 10 mM Glycine, 2% sucrose, pH 6.5, 136 mL) was treated with 62.3 mg of Ex4 peptide (SEQ ID NO:64 with K(SH) as peptide linking residue) conjugated to linker L1 in 1.29 ml (concentration 10 mM) of deionized water and left at room temperature overnight. A small amount of material was analyzed using high performance liquid chromatography equipped with HIC-Butyl column and mass spectroscopy to monitor the formation of Ab-[L1-SEQ ID NO:64]$_1$.

Extraction of Ab-Exendin 4 1 FA Species: A crude reaction mixture containing mixture of antibody, Ab-[L1-SEQ ID NO:64]$_1$ and Ab-[L1-SEQ ID NO:64]$_2$ (2.7 gm in 136 mL of buffer made of 10 mM histidine, 10 mM glycine, 2% sucrose, pH=6.5) was diluted with 409 mL of buffer (50 mM sodium phosphate, 1 M sodium chloride, pH=7.0) and loaded on to a column packed with 681 mL of CM sepharose resin. The product was eluted fractionwise using gradient of solvent B (50 mM sodium phosphate, pH=7.0+20% isopropanol) in A (0.75 M ammonium sulphate and 50 mM sodium phosphate, pH=7.0). The fractions containing Ab-[L1-SEQ ID NO:64]$_1$ were combined. (1100 mL) Ultrafiltration-Diafiltration device equipped with 50 KD membrane was sanitized with 1 N sodium hydroxide and equilibrated with a buffer containing 20 mM 2-Amino-2-hydroxymethyl-propane-1,3-diol, 50 mM sodium chloride at pH=7.0. The above pooled fraction containing Ab-[L1-SEQ ID NO:64]$_1$ was buffer exchanged using 20 mM tris(hydroxymethyl) aminomethane, 50 mM sodium chloride, pH=7.0 and concentrated to 62 mL and filtered through 0.2 um filter to give 1.02 g of Ab-[L1-SEQ ID NO:64]$_1$ in 20 mM tris(hydroxymethyl) aminomethane+50 mM sodium chloride at pH=7.0.

Hydrophobic Interaction Chromatography (HIC) separation is based on the interaction between the stationary phase and hydrophobic characteristics of the molecules. The antibody h38C2 is less hydrophobic than Ab-[L1-SEQ ID NO:64]$_1$, which is less hydrophobic than Ab-[L1-SEQ ID NO:64]$_2$. During the elution, unreacted antibody elutes earlier, followed by Ab-[L1-SEQ ID NO:64]$_1$. Ab-[L1-SEQ ID NO:64]$_2$ elutes at the end. By adjusting the ratio of the antibody to peptide, the above mentioned three different compounds % can vary.

The unreacted antibody has been isolated and subjected to UF/DF and taken into 10 mM Histidine, 10 mM Glycine, 2% Sucrose, pH=6.5 buffer. This isolated antibody was again fused with Ex4 peptide (SEQ ID NO:64 with K(SH) as peptide linking residue) and purified. In some aspects of the invention, this can be cycled 3-fold to yield ~70% Ab-[L1-SEQ ID NO:64]$_1$.

FGF21+Linker: FGF21ΔH-A129C (715 mg in 105 mL of 20 mM tris(hydroxymethyl)-aminomethane+50 mM sodium chloride at pH=7.0) was treated with tris(2-carboxyethyl) phosphine (TCEP) (0.3 mM solution) for 40 mins. FGF21ΔH-A129C can have a problem with dimer formation due to the unreacted thiol at position 129, which can be particularly disadvantageous if the unreacted protein is to be stored between generation and subsequent attachment to the linker. This problem can be overcome by adding TCEP to a final concentration of about 0.1 mM.

L1 (3-(2,5-dioxo-2,5-dihydro-1H-pyrrol-1-yl)-N-(2-(2-(3-oxo-3-(4-(3-oxo-3-(2-oxoazetidin-1-yl)propyl)phenylamino)propoxy)ethoxy)ethyl)propanamide, (27.2 mg in 2.57 mL dimethyl sulfoxide) was added to the FGF21ΔH-A129C solution (at approximately 2:1 molar ratio of linker:protein) and left at room temperature for 30 mins with intermittent swirling. L1 was generally maintained at 10 mM (48.28 mg/ml) in 100% DMSO, although other solvents are also suitable, such as dimethyl formamide, methanol, ethanol, water, propylene glycol and mixtures thereof. L1 has potential to undergo hydrolysis in both methanol and ethanol. The solubility of L1 is higher in both dimethyl sulfoxide and dimethyl formamide. Since dimethyl sulfoxide readily mixes with buffer system used in linker-protein conjugation, dimethyl sulfoxide is preferred for preparing the L1 stock solution.

An UFDF membrane was sanitized with 1N sodium hydroxide for 30 mins and equilibrated with 20 mM tris (hydroxymethyl) aminomethane+50 mM sodium chloride at pH=7.0. The above FGF21ΔH-A129C incubation mixture was concentrated using UFDF, to give 613 mg of [L1-FGF21ΔH-A129C] in 81 mL of buffer.

The [L1-FGF21ΔH-A129C] solution was diluted with 42 mL of 20 mM tris(hydroxymethyl)aminomethane+50 mM sodium chloride at pH=7.0 and added to Ab-[L1-SEQ ID NO:64]$_1$ (1.02 g, in 61 mL of 20 mM tris(hydroxymethyl)aminomethane+50 mM sodium chloride at pH=7.0) and the reaction mixture was left overnight. This incubation mixture (184 mL) was then diluted with 366 mL of buffer A (0.75 M ammonium sulphate+50 mM sodium phosphate pH 7.0) and purified on HIC-butyl column using buffer B (50 mM sodium phosphate+20% isopropanol, pH=7.) in buffer A. It has been found that the HIC-butyl column has the advantage of being suitable scale up to quantities suitable for commercial manufacture. The fractions containing [FGF21ΔH-A129C-L1]$_1$-Ab-[L1-SEQ ID NO:64]$_1$ molecules were collected to give 970 mL.

A UF/DF 50 kD 50 cm2 cassette was sanitized with 1N sodium hydroxide, and the UF/DF membrane was equilibrated with a buffer containing 20 mM 2-amino-2-hydroxymethyl-propane-1,3-diol, 50 mM sodium chloride at pH=7.0. The above combined fraction was concentrated using UF/DF membrane and 20 mM Tris, 50 mM sodium chloride, pH=7 to give 594 mg of [FGF21ΔH-A129C-L1]$_1$-Ab-[L1-SEQ ID NO:64]$_1$ in 67 mL buffer which was filtered through 0.2 uM filter.

After concentration, the sample was filtered through a 0.2 um membrane, and stored at 4C. The final sample was analyzed for endotoxin, and the purity and structural identity was established by butyl HIC HPLC and mass spectrometer. Analysis of the sample using HPLC equipped with HIC-butyl column showed a yield of approximately 78% [FGF21ΔH-A129C-L1]$_1$-Ab-[L1-SEQ ID NO:64]$_1$ and about 22% unreacted Ab-[L1-SEQ ID NO:64]$_1$

Example 53

Alternative Strategy for Developing ABC Molecules

The present invention provides a first strategy (strategy 1) for the conjugation process wherein Ab-[Ex4-2$^{nd}$ linker]$_1$ is conjugated to [FGF21-1$^{st}$ linker]. While this process is advantageous, it requires two high resolution chromatography steps for the final bispecific antibody ABC-1: one HIC for Ab-[Ex4-2$^{nd}$ linker]$_1$ and the other for product ABC-1 purification. In some favorable aspects, the process gave the final product ABC-1 with 74% purity with 14% unreacted Ab-[Ex4-2$^{nd}$ linker]$_1$ process intermediate and other impurities in poor yield.

The present invention also provides for an alternative method of producing asymmetric bifunctional antibody conjugates, according to strategy 2. Strategy 2 provides significant advantages over strategy 1: dramatically improving FGF21 stoichiometry (~1.25× mole ratio in strategy 2 vs. 3× in strategy 1) and reducing the amount of FGF21 required, resulting in significant cost savings.

The Strategy 2 also reduced chromatography steps to only one HIC chromatography for Ab-[SEQ ID NO:10-L1]$_1$ process intermediate purification. The conjugation efficiency of [L1-SEQ ID NO:64] with Ab-[SEQ ID NO:10-L1]$_1$ intermediate to form ABC-1 was near completion using well defined starting material [L1-SEQ ID NO:64] in Strategy 2.

A Butyl 650 S reverse phase chromatographic step was developed to generate

Ab-[SEQ ID NO:10-L1]$_1$ as process intermediate. Single conjugated Ab-[SEQ ID NO:10-L1]$_1$ species was selectively recovered at high yield>90% and high purity>90% in the elution step and was well resolved from the other conjugation reaction species including free [SEQ ID NO:10-L1], dimeric [SEQ ID NO:10-L1]$_2$, doubly conjugated Ab-[SEQ ID NO:10-L1]$_2$, aggregates and free h38C2 species. The process scale up was successfully demonstrated on a 19 L scale.

The excess [L1-SEQ ID NO:64] from second conjugation was quickly removed by flow through Capto-Q chromatography to purify the bispecific antibody ABC-1. Strategy 2 demonstrated an unprecedented yield of about 40% calculated from fully reactive h38C2 into ABC-1, and excellent purity of about 91% of ABC-1 by SEC. The overall process efficiency was dramatically increased by reducing the expensive material FGF21 utilization and minimization of chromatography steps.

Example 54

Improvement of Conjugation Parameters for ABCs

Effect of Mole Ratio of [FGF21-Linker]:Ab on Ab-[FGF21-Linker]$_1$ Yield

A preliminary evaluation of different ratios of [FGF21-1$^{st}$ linker]:Ab to maximize the yield for Ab-[SEQ ID NO:10-L1]$_1$ process intermediate was carried out. The optimal mole ratio of [FGF21-1$^{st}$ linker]:Ab was about 1.25:1 with acceptable range about 1.5:1 to about 1:1 (see Table 23). A ratio of about 1.25:1 gave about 42% yield for the desired intermediate with least % of aggregates.

TABLE 23

Effect of mole ratio of [SEQ ID NO: 10-L1]: Antibody on yield of Ab-[SEQ ID NO: 10-L1]$_1$.

| FGF21-linker:Ab Ratio | % Large Aggregate | % Aggregate | % Ab-[FGF21ΔH-A129C-L1]$_2$ | % Ab-[FGF21ΔH-A129C-L1]$_1$ | % Ab | % [FGF21ΔH-A129C-L1]$_2$ | % [FGF21Δ H-A129C-L1]$_1$ |
|---|---|---|---|---|---|---|---|
| 4.7:1 | 1.5 | 16.4 | 52.6 | 10.7 | 0.3 | 1.7 | 16.8 |
| 1.5:1 | 0.8 | 7.5 | 20.0 | 42.9 | 25.0 | 0.2 | 3.7 |
| 1.25:1 | 1.1 | 5.7 | 14.3 | 41.8 | 34.4 | 0.0 | 2.7 |
| 1:1 | 0.7 | 5.1 | 9.9 | 38.7 | 43.8 | 0.0 | 1.9 |
| 0.75:1 | 0.6 | 3.5 | 5.7 | 32.0 | 56.6 | 0.0 | 1.5 |

Screening of Buffer, pH and Conjugation Temperature for Ab-[FGF21-Linker]$_1$

Different parameters to improve conjugation efficiency were screened, including buffers MES (2-(N-morpholino)ethanesulfonic acid) and phosphate, pHs (pH 6 & 7), and temperatures (RT vs. 4° C.). The results (Table 24) indicated % aggregates remained stable across pH, temperature, and different concentration ranges for both MES and phosphate buffer. 100 mM Phosphate buffer pH 6.0 at RT gave significantly more Ab-[FGF21]$_1$ compared to other conditions. Conjugation at 4° C. showed a similar product profile but with lower yields for h38C2-[SEQ ID NO:10-L1]$_1$. The acceptable operating conditions for conjugation for h38C2-[SEQ ID NO:10-L1]$_1$ was identified as using a MES or phosphate buffer, at a concentration between about 25 mM and about 150 mM, with a pH range of about 5.5 to about 7.5, or about 6.0 to about 7.0, at between about 0° C. and 37° C., and preferably at between about 4° C. and about RT. The optimum conjugation conditions for h38C2-[SEQ ID NO:10-L1]$_1$ comprised about 100 mM a phosphate buffer with a pH range about 6.0 to about 6.5 at RT.

hydrolysis of reactive group of SEQ ID NO:10-L1 occurs over time (Table 27), post activation diafiltration of SEQ ID NO:10-L1 should be operated at between about 2 and about 10° C. The amount of SEQ ID NO:10-L1 after post activation diafiltration varied in different experiments, and the difference could contribute to the variation of the conjugation efficiency for h38C2-[SEQ ID NO:10-L1]$_1$. About 100 mM Phosphate pH about 6.3 gave the least aggregates and highest h38C2 remaining for recycle purpose.

TABLE 24

Results of conjugation efficiency at 0° C. and RT by SEC. Conjugation conditions: total volume: 0.5 ml; h38C2 = 4.9 mg/ml; mole ratio of [SEQ ID NO: 10-L1]: h38C2 = 0.8:1; 4° C., 26 hrs; RT overnight.

| | % Large Aggregate | | % Aggregate | | % Ab-[FGF21ΔH-A129C-L1]$_2$ | | % Ab-[FGF21ΔH-A129C-L1]$_1$ | | % Ab | | % [FGF21ΔH-A129C-L1]$_1$ | |
|---|---|---|---|---|---|---|---|---|---|---|---|---|
| | 0° C. | RT | 0° C. | RT | 0° C. | RT | 0° C. | RT | 0° C. | RT | 0° C. | RT |
| 100 mM MES, pH 7.0 | 0.6 | 0.5 | 3.7 | 4.1 | 6.6 | 6.5 | 34.2 | 35.5 | 53.4 | 52.0 | 1.5 | 1.3 |
| 100 mM MES, pH 6.0 | 0.3 | 0.6 | 1.4 | 2.8 | 2.2 | 6.6 | 21.7 | 35.6 | 70.6 | 52.6 | 3.7 | 1.8 |
| 100 mM phos, pH 7.0 | 0.5 | 0.6 | 3.1 | 3.8 | 5.1 | 5.7 | 32.2 | 33.7 | 56.5 | 54.1 | 2.5 | 2.0 |
| 100 mM phos, pH 6.0 | 0.3 | 0.7 | 3.1 | 6.6 | 8.5 | 19.9 | 37.9 | 44.8 | 43.2 | 24.1 | 7.0 | 3.9 |
| 25 mM MES, pH 7.0 | 0.8 | 0.7 | 4.4 | 4.6 | 8.0 | 7.9 | 36.6 | 36.7 | 48.9 | 48.7 | 1.3 | 1.3 |
| 25 mM MES, pH 6.0 | 0.4 | 0.7 | 2.7 | 3.9 | 5.9 | 8.1 | 34.3 | 37.6 | 54.5 | 48.5 | 2.1 | 1.3 |
| 25 mM phos, pH 7.0 | 0.7 | 0.7 | 4.2 | 4.2 | 7.0 | 7.5 | 36.2 | 36.4 | 50.2 | 49.8 | 1.7 | 1.4 |
| 25 mM phos, pH 6.0 | 0.7 | 0.8 | 3.6 | 4.2 | 6.8 | 7.8 | 36.5 | 37.5 | 51.1 | 48.4 | 1.3 | 1.2 |

Time Course Study for Ab-[FGF21-Linker]$_1$: A time course study was generated for use in modeling the conjugation of [FGF21-1$^{st}$ linker] with h38C2. After 18 hrs at RT, the conjugation efficiency for h38C2-[SEQ ID NO:10-L1]$_1$ intermediate reached maximum as shown in Table 25. Accordingly, the conjugation reaction may be carried out for a time selected from the group consisting of at least 30 mins, at least about 60 mins, at least about 90 mins, at least about 2 hrs, at least about 3 hrs, at least about four hrs, at least about 6 hrs, at least about 12 hrs, at least about 18 hrs and at least about 24 hrs.

TABLE 25

| | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|
| 30 min | 2.0 | 2.0 | 0.0 | 12.5 | 83.1 |
| 60 min | 0.4 | 3.3 | 1.7 | 19.4 | 77.0 |
| 90 min | 0.4 | 4.2 | 2.8 | 24.0 | 71.4 |
| 120 min | 0.3 | 4.8 | 3.4 | 27.4 | 67.5 |
| 180 min | 0.4 | 6 | 4.2 | 31.0 | 62.6 |
| 1080 min | 0.4 | 8.6 | 5.1 | 33.6 | 57.3 |

Kinetic data for h38C2-[SEQ ID NO: 10-L1]$_1$ at RT by SEC: Conjugation conditions: total volume: 0.5 ml; h38C2 = 4.0 mg/ml; mole ratio: [FGF21-1$^{st}$ linker]-: Antibody = 0.8:1; RT; in 25 mM MES pH 6.0.

Fine Tune of Conjugation Conditions for FGF21-Linker: The laboratory scale-ups were performed at different scales with a variety of optimized buffers and pHs. The conjugation efficiency for h38C2-[SEQ ID NO:10-L1]$_1$ remained comparable in the range of about 40%~about 45% (Table 26). Since

TABLE 26

The comparison of conjugation efficiency by SEC.

| | Scale (g) | % Aggregate | % Ab-[FGF21ΔH-A129C-L1]$_2$ | % Ab-[FGF21ΔH-A129C-L1]$_1$ | % Ab |
|---|---|---|---|---|---|
| 25 mM phos pH 6 | 50 | 8.4 | 28 | 43.4 | 20.2 |
| 50 mM phos pH 6.5 | 150 | 6.3 | 19.5 | 43.1 | 31.1 |
| 100 mM phos pH 6 | 50 | 5.6 | 19.9 | 45.3 | 29.3 |
| 25 mM MES pH 6; | 50 | 6.3 | 24.4 | 44.9 | 23.7 |
| 50 mM phos pH 6.5 | 4 | 6.6 | 17.2 | 42.3 | 30.3 |
| 100 mM phos pH 6.3 | 0.5 | 4.7 | 15.3 | 41.3 | 36.1 |

TABLE 27

| | % FGF21 | % Hydrolyzed reactive FGF21ΔH-A129C-L1 | % reactive FGF21ΔH-A129C-L1 | % FGF21 dimer | % Other |
|---|---|---|---|---|---|
| 0 hour | 13.4 | 6.5 | 76.7 | 1.8 | 1.6 |
| 1 hour | 13.2 | 8.8 | 73.6 | 2.8 | 1.6 |
| 2 hrs | 14.4 | 10.6 | 69.1 | 4.0 | 1.9 |
| 3 hrs | 13.3 | 13.6 | 67.1 | 4.1 | 1.9 |
| 4 hrs | 13.9 | 14.9 | 64.9 | 4.5 | 1.8 |
| 5 hrs | 14.3 | 16.9 | 61.9 | 5.0 | 1.9 |
| 6 hrs | 13.9 | 18.8 | 60.3 | 5.2 | 1.8 |
| 8 hrs | 14.5 | 22.3 | 55.8 | 5.7 | 1.7 |
| 10 hrs | 15.0 | 25.0 | 52.3 | 5.9 | 1.8 |

The time course study of hydrolysis of reactive group of [SEQ ID NO: 10-L1] at 4° C. by FGF21 RP chromatography. Activation conditions: total volume: 1.0 ml; [SEQ ID NO: 10-L1] = 1.8 mg/ml; mole ratio: TCEP:[SEQ ID NO: 10-L1] = 0.5:1, TCEP treatment 60 mins; then mole ratio: SEQ ID NO: 64:[SEQ ID NO: 10-L1] = 1.4:1; linker activation 30 mins; RT; in 25 mM Tris pH 7.5 and 200 mM Na$_2$SO$_4$.

Screening of Buffer and pH for Conjugation of [2Nd Linker-Ex4] and Ab-[FGF21-Linker]$_1$: The conjugation reaction solution from the first conjugation step involving activated [SEQ ID NO:10-L1] and h38C2 was purified over Butyl 650 S reverse phase chromatography step to generate h38C2-[SEQ ID NO:10-L1]$_1$. This material was then diafiltered into suitable buffer (either 30 mM sodium lactate pH 4.8 or 20 mM sodium glutamate pH 4.5). The spontaneous selective fusion reaction between the AZD ring of a linker such as L1 and K$^{99}$ of SEQ ID NO:26 normally takes place at pH 6.5, but not at pH 4.5. The optimal pH parameter for conjugation of h38C2-[SEQ ID NO:10-L1]$_1$ to [L1-SEQ ID NO:64] was investigated. 100 mM MES buffer pH 7.0 was used to adjust the pH of h38C2-[SEQ ID NO:10-L1]$_1$ solution. The results (Tables 28 and 29) indicated the optimum range of between about pH 6.0 and about pH 6.5. Higher conjugation efficiency was achieved in MES/Lactate buffer. Excellent fusion efficiency for ABC-1 ([SEQ ID NO:10-L1]$_1$-h38C2 (IgG1)-[L1-SEQ ID NO: 64]$_1$ was achieved using the higher mole ratio of [2$^{nd}$ linker-Ex4]:Ab-[FGF21-1$^{st}$ linker]=about 1.3:1.

TABLE 28

| pH | % Ab | % Ab-[Ex4-L1]$_1$ | Ab-[FGF21ΔH-A129C]$_1$ | ABC-1 |
|---|---|---|---|---|
| 6.5 | 0.9 | 3.4 | 10.3 | 82.5 |
| 6.0 | 1.0 | 3.3 | 10.9 | 81.9 |
| 5.9 | 1.0 | 3.2 | 12.3 | 80.2 |
| 5.65 | 1.1 | 3.1 | 13.7 | 79.2 |
| 5.4 | 1.2 | 3.0 | 15.4 | 77.7 |
| 5.1 | 1.6 | 2.9 | 23.7 | 68.3 |
| 4.75 | 2.2 | 2.9 | 33.8 | 54.2 |

Results of second conjugation efficiency in MES/glutamate solution at different pH by HIC: Conjugation conditions: total volume: 0.5 ml; h38C2-[SEQ ID NO: 10-L1]$_1$ = 10.0 mg/ml; mole ratio: [L1-SEQ ID NO: 64]:/h38C2-[SEQ ID NO: 10-L1]$_1$ = 1:1; RT; in MES/glutamate solution.

TABLE 29

| pH | % Ab | % Ab-[Ex4-L1]$_1$ and h38C2-[FGF21ΔH-A129C]$_1$ | ABC-1 ([FGF21-A129C-L1]$_1$-h38C2-(IgG1)-[L1-SEQ ID NO: 64]$_1$ |
|---|---|---|---|
| 6.5 | 0.2 | 9.0 | 90.8 |
| 6.38 | 0.1 | 9.6 | 90.3 |
| pH 6.13 | 0.1 | 9.1 | 90.8 |
| pH 5.8 | 0.1 | 11.0 | 88.8 |
| pH 5.5 | 0.1 | 10.6 | 89.3 |
| pH 5.1 | 0.2 | 15.8 | 84.0 |
| pH 4.8 | 0.9 | 60.9 | 38.3 |

Results of second conjugation efficiency in MES/Lactate solution at different pH by HIC: Conjugation conditions: total volume: 0.2 ml; h38C2-[SEQ ID NO: 10-L1]$_1$ = 6.0 mg/ml; mole ratio: [L1-SEQ ID NO: 64]:/h38C2-[SEQ ID NO: 10-L1]$_1$ = 1.3:1; RT; in MES/Lactate solution.

Time Course Study for [2nd Linker-Ex4]$_1$-Ab-[FGF21-Linker]$_1$: A time course study was generated for use in modeling of conjugation of h38C2-[SEQ ID NO:10-L1]$_1$ with [L1SEQ ID NO:64]. After 18 hrs at RT, the conjugation efficiency for h38C2-[SEQ ID NO:10-L1]$_1$ approached maximum as shown in Table 30.

TABLE 30

| | % Ab | % Ab + 1 CVX2025 | h38C2-[FGF21ΔH-A129C]$_1$ | ABC-1 ([FGF21-A129C-L1]$_1$-h38C2-(IgG1)-[L1-SEQ ID NO: 64]$_1$ |
|---|---|---|---|---|
| 2 hrs | 2.0 | 2.2 | 29.6 | 58.4 |
| 4 hrs | 1.6 | 2.6 | 23.1 | 67.5 |
| 6 hrs | 1.3 | 2.6 | 18.0 | 73.9 |
| 8 hrs | 1.2 | 2.8 | 15.5 | 77.0 |
| 10.5 hrs | 0.8 | 3.5 | 11.4 | 81.8 |
| 18 hrs | 0.8 | 3.5 | 8.4 | 85.3 |

Kinetic data for ABC-1 at RT by HIC: Conjugation conditions: total volume: 1.0 ml; h38C2-[SEQ ID NO: 10-L1]$_1$ = 6.0 mg/ml; mole ratio: [L1-SEQ ID NO: 64]:h38C2-[SEQ ID NO: 10-L1]$_1$ = 1.3:1; RT; in MES/Glutamate solution, pH 5.8.

Example 55

Conjugation of FGF21 to Linker

The monomer and dimer ratio for FGF21 was checked before the experiment. FGF21 RHPLC analysis showed the monomer: dimer ratio was 27%:73%. 0.207 mM of SEQ ID NO:10 (17.1 g in 20 mM TRIS, 50 mM NaCl, 2.346 L, pH 7.0 was first diluted with 100 mM MES buffer pH 7.0 (1.920 L) to target concentration 4 g/L as measured by absorbance at 280 nm. 7.631 mL TCEP stock solution (50 g/L) was added next. The mixture was mixed thoroughly for 5 min and then mixing was reduced at ambient condition. The reaction lasted for 90 min. After the reduction with TCEP, the sample was analyzed by FGF21 RF showing the monomer: dimer ratio was 89%:6.3% as the in-process control.

After 90 min, the L1 (656.7 mg) was dissolved in 8.76 ml of DMSO (the final concentration of L1 was 0.29 mM, or about 0.15 mg/ml), and the solution was added to the SEQ ID NO:10 solution. The container of L1 was flushed with buffer to ensure all L1 was added. Activation started after all of L1 had been added to the [SEQ ID NO:10 pool. The reaction was mixed thoroughly for 5 min and then mixing was reduced at RT. This mixture was left at RT for 30 min with swirling to complete the reaction between SEQ ID NO:10 and the linker L1. Activation temperature could be lowered if necessary. Further analysis by FGF21 reverse phase HPLC (RP) showed the 73% formation of [SEQ ID NO:10-L1].

The above sample was further passed through the UFDF to remove excess linker and TCEP. The membrane was sanitized with 1N NaOH for 30 min, drained, and equilibrated with 100 mM MES, pH 7.0. Buffer 100 mM MES, pH 7.0 was used for diafilteration (7x diafilteration). Diafiltration was done at 4 g/L retentate concentration. Foaming and splashing may be avoided during UF/DF. Hydrolysis of the reactive group of [SEQ ID NO:10-L1] occurred over the diafiltration process. The hold time for post-activation DF pool should be minimized. UF may be operated at 2-10° C. using 10K Sartorius Hydrosart membrane. The combined species [SEQ ID NO:10-L1] confirmed by FGF21 RP was down from 73% to 64% after UF/DF.

The concentration was estimated by UV 280 nm using extinction coefficient of 0.47 OD equal 1 mg for both SEQ ID NO:10 (Filtered Q Seph Pool) and [SEQ ID NO:10-L1] (post activation UF/DF Pool). This reaction mechanism, and variations thereof, are also suitable for use in strategy 1, as well as with other FGF21 variants and linkers.

Example 56

Conjugation of [FGF21-Linker] to Ab 95.0 g of h38C2 (SEQ ID NO:25 and SEQ ID NO:26: 17.05 g/L, 5.6 L in 10 mM histidine, 10 mM glycine, pH 6.5) was diluted with 100 mM phosphate buffer (14.4 L, pH 6.2).

Then 17.72 gm of [SEQ ID NO:10-L1] in 100 MES buffer pH 7.0 (4.4 g/L, 3.8 L, 1.35 moles [SEQ ID NO:10-L1]:1 mole h38C2 was added to the h38C2 mixture. Final reaction mixture may be about 4 g/L of h38C2 at RT. The reaction started once the [SEQ ID NO:10-L1] component was added. The reaction was mixed thoroughly for about 5 min and then mixing was reduced at RT. This mixture was left at RT overnight, between about 15 and about 20 hrs with gentle stirring. A small amount of material was taken for analysis by SEC chromatography to confirm the formation h38C2-[SEQ ID NO:10-L1]$_1$ conjugate in the mixture. SEC analysis showed the conjugation step yield of h38C2-[SEQ ID NO:10-L1]$_1$ as 40% as shown in Table 33. The conjugation step yield was calculated as purity of h38C2-[SEQ ID NO:10-L1]$_1$ valency by SEC (%).

Example 57

Enrichment of the Reactive Ab-[FGF21-Inker]$_1$ Process Intermediate h38C2-[SEQ ID NO:10-L1]$_1$ was enriched using a 19 L scale column packed with Tosoh© Butyl 650S resin using a 35 cm diameter XK column packed to a bed height of 20 cm. The column was pre-equilibrated and washed with 3 CV (column volume) of WFI and 5 CV of 50 mM sodium phosphate pH 7.0. The filtered conjugation pool of h38C2-[SEQ ID NO:10-L1]$_1$ was loaded at 5 mg/mL onto the Butyl 650S column at 17° C. Then the Butyl 650S load was processed through the Tosoh Butyl 650 S resin using a programmed Unicorn method on the automated chromatography skid at 17-18° C. Elution was performed using a linear gradient: first with 2.4% 1,6 hexanediol isocratic wash (88% Buffer A (50 mM sodium phosphate, pH 7.0) and 12% Buffer B (50 mM sodium phosphate, 20% hexanediol, pH 7.0) with 7 CV; followed by an elution gradient of 88% A+12% B to 60% A+40% B with 11 CV; gradient hold at 60% A+40% B with 5 CV. Fractions were collected and analyzed by SEC assay for purity to determine which fractions would be pooled. SEC analytical results for final pool are shown in Table 31. h38C2-[SEQ ID NO:10-L1]$_1$ was selectively recovered at high yield which corresponded to ~90% recovery of h38C2-[SEQ ID NO:10-L1]$_1$ species loaded on the column, and also with high purity>90% in the elution step and was well resolved from the other conjugation reaction species including free [SEQ ID NO:10-L1], [SEQ ID NO:10-L1]$_2$ dimers, h38C2-[SEQ ID NO:10-L1]$_2$, aggregates and free h38C2 (+0 FGF21) species. The fractions from Butyl 650S chromatography were pooled together and further concentrated and diafiltered. Concentration was estimated by UV 280 nm using extinction of 1.47 equal 1 mg of protein.

Example 58

Conjugation of [2Nd Linker-Ex4] to Ab-[FGF21-Linker]$_1$ 34.6 g of h38C2-[SEQ ID NO:10-L1]$_1$ in 30 mM sodium lactate buffer pH 4.8 (9.7 g/L, 3.569 L) was treated with 25 mM MES buffer pH 7.0 (2.1 L) to adjust the pH to 6.3. Then 1.81 g of [L1-SEQ ID NO:64] dissolved in 90.2 ml of WFI (water for injection) (the final concentration of [L1-SEQ ID NO:64] was 0.065 mM, or about 0.31 mg/ml) was added to the h38C2-[SEQ ID NO:10-L1]$_1$ solution. The container of the [SEQ ID NO:10-L1] was flushed with buffer to ensure all peptide was added. Final reaction mixture may be 6.0 g/L for h38C2-[SEQ ID NO:10-L1]$_1$. The reaction was mixed thoroughly for about 5 min and then mixing was reduced at RT. This mixture was left at RT overnight, between about 15 and about 20 hrs with gentle stirring. A small amount of material was taken for analysis by HIC chromatography to confirm the formation of [SEQ ID NO:10-L1]-[SEQ ID NOs:25 and 26]-[L1-SEQ ID NO:64]$_1$ (ABC-1). HIC analysis showed a 90% yield of (ABC-1). The conjugation step yield was calculated as purity of [SEQ ID NO:10-L1]-[SEQ ID NOs:25 and 26]-[L1-SEQ ID NO:64]$_1$ (ABC-1)+2 valency by HIC (%).

The excess [L1-SEQ ID NO:64] was removed using anion exchange chromatography Capto Q, and fractions from Capto Q chromatography were pooled together and further concentrated and diafiltered to give final drug substance.

Example 59

Enrichment of Fully Reactive Ab Using Phenyl 650 S Column

The fully reactive Ab (h38C2) was enriched using a 9.5 L scale column packed with Tosoh phenyl 650S resin using a 30 cm diameter column packed to a bed height of 14 cm. The column was pre-equilibrated and washed with 2 CV (column volume) of WFI and 5 CV of 20 mM sodium phosphate, 1M NaCl, pH 7.0. The h38C2 pool (153 g) was loaded at 15 mg/mL onto the phenyl 650S column at RT. Then h38C2 load was processed through the Tosoh phenyl 650 S resins using a programmed Unicorn method on the automated chromatography skid. Elution was performed first with 1 CV wash using 20 mM sodium phosphate, 1M NaCl, pH 7.0; then the salt reduction from 100% A (20 mM sodium phosphate, 1M NaCl, pH 7.0) to 67% B (20 mM sodium phosphate, pH 7.0) in 7 CV, hold at 67% B for 6 CV, then to 100% B in 3 CV, followed by elution from 100% B to 70% C (20 mM sodium phosphate, 20% hexanediol, pH 7.0) in 1 CV, then gradient hold at 70% C for 5 CV. Fractions were collected and analyzed by HIC assay for purity to determine which fractions would be pooled. The fully conjugatable h38C2 can serve as feed material for subsequent bioconjugation steps leading to desired final product.

TABLE 31

Conjugation efficiency for h38C2-[SEQ ID NO: 10-L1]$_1$.

| | % Large Aggregate | % Aggregate | % Ab-[FGF21ΔH-A129C-L1]2 | % Ab-[FGF21ΔH-A129C-L1]1 | % Ab |
|---|---|---|---|---|---|
| Conjugation Mix (E Tox) | 0.0 | 3.8 | 12.3 | 40.2 | 43.6 |
| Butyl 650S reverse phase Pool | 0.0 | 1.0 | 4.5 | 91.9 | 2.6 |

Conclusions: Three conjugation steps were developed as part of the production process for ABC-1 bioconjugate bispecific antibody drug substance. Two different strategies were explored to conjugate and purify the process intermediates that would lead to generation of the final drug substance. Strategy 2 was successfully scaled up in the laboratory and performed consistently on repeated trials.

Example 60

Optimization of Butyl RP for Ab-[SEQ ID NO:10-L1]$_1$ Purification Experimental Protocols Chromatography experiments were performed at 4 mL or 103 mL scale using protocols and operating conditions shown below:
4 mL column—0.5 cm diameter×20 cm height operated under ambient conditions
Buffer A: 50 mM Phosphate pH 7.0
Buffer B: 50 mM Phosphate pH 7.0, 20% 1,6-hexanediol
Buffer C: 50 mM Phosphate pH 6.5
Flow rate: 125 cm/hr
2 mL fractions across wash and gradient were collected using Frac 950 equipped with deep well microtiter plate from VWR.

the preliminary evaluations were performed using a 4 mL column (0.5 cm diameter×20 cm height) packed with Tosoh Butyl 650S resin.

Run #118: The first Butyl 650 S column run #118 was performed at 5 mg/mL column loading using h38C2-[SEQ ID NO:10-L1]$_1$ conjugation reaction solution. The column was loaded without any added lyotropic salt and operated under ambient temperature conditions. The column was pre-equilibrated and washed with 3 CV (column volume) of WFI and 5 CV of 100% buffer A (50 mM sodium phosphate pH 7.0). The filtered conjugation pool of h38C2-[SEQ ID NO:10-L1]$_1$ was loaded at 5 mg/mL onto the Butyl 650S column and then processed through the Butyl 650 S resin using a programmed Unicorn method. The column was washed with 5 CV of 100% buffer A, then a linear gradient was run from 100% A+0% B (50 mM sodium phosphate, 20% hexanediol, pH 7.0) to 10% A+90% B in 10 CV; the gradient was hold at 100% B with 5 CV. Fractions were collected and analyzed by SEC assay. SEC analytical results are shown in Table 33.

The results indicate good separation between Ab-[SEQ ID NO:10-L1]$_1$ from Ab-[SEQ ID NO:10-L1]$_2$ and free FGF21.

TABLE 32

Experiment details with gradients for each run. Each column run was pre-equilibrated WFI with 3 column volumes (CV). Equilibration took place with 5 CV, following which the columns were loaded with the FGF21 conjugation pools at 4 mg/ml. During the gradient elution step, the mobile phase composition that the column experiences at any given step is expressed as a mixture of buffer A and buffer B which are mixed at the specified ratios. For example, a gradient step from 12% B to 40% B means a starting composition of a mixture of 12% B + 88% A linearly changing with time to the final composition of 40% B + 60% A over the length of 11 column volumes.

| Run # | 118 | 128 | 132 | 134 | 138 | 148 | 152 | 156 |
|---|---|---|---|---|---|---|---|---|
| Temp ° C. | 22 | 22 | 22 | 22 | 22 | 17 | 17 | 17 |
| Equil | 100% A | 100% A | 100% A | 100% A | 100% A | 100% A | 100% C | 100% A |
| Load | 5 mL | 10 mL | 5 mL | 5 mL | 5 mL | 5 mL | 5 mL | 5 mL |
| Wash % Buffer | 100% A 3 CV | 100% A: 5 CV | 100% A: 5 CV | 25% B, 75% A: 10 CV | 12% B, 88% A: 10 CV | 12% B, 88% A: 10 CV | 12% B, 88% C: 10 CV | 12% B, 88% A: 10 V |
| Gradient | 0-90% B 100-10% A 10 CV | 0-90% B, 100-10% A 10 CV | 0-90% B, 100-10% A 20 CV | 25-90% B 75-10% A 30 CV | 12-90% B 88-10% A 30 CV | 12-90% B 88-10% A 30 CV | 12-90% B 88-10% C 30 CV | 12-40% B 88-60% A 11 CV |

Following the Gradient elution step, each column run was flushed with 5CV of 100% Buffer B. Following this, each column run was cleaned with 5CV of 0.5 N NaOH in an upflow direction, and then flushed with 5CV 0.1 N NaOH. All Although some of free mAb (+0) species was found to co-elute in the front end of the Ab-[SEQ ID NO:10-L1]$_1$ product peak most of the mAb (+0) species eluted later in the 1,6-hexanediol gradient.

TABLE 33

SEC results of load and column fractions for run #118.

| | Conc. (mg/mL) | % Large Aggregate | % Aggregate | % Ab-[FGF21ΔH-A129C-L1]$_2$ | % Ab-[FGF21ΔH-A129C-L1]$_1$ | % Ab | % [FGF21ΔH-A129C-L1]$_1$ |
|---|---|---|---|---|---|---|---|
| Crude load | 4 | 0.7 | 3.3 | 8.9 | 37.3 | 48.9 | 1.0 |
| B5 | 0.27 | 0.0 | 1.0 | 98.2 | 0.7 | 0.0 | 0.2 |
| B3 | 0.11 | 0.0 | 2.2 | 65.0 | 25.4 | 7.1 | 0.3 |
| B2 | 0.26 | 0.0 | 2.2 | 9.9 | 47.9 | 39.8 | 0.2 |
| B1 | 1.02 | 0.0 | 1.1 | 1.8 | 85.2 | 11.8 | 0.0 |
| C2 | 0.90 | 0.1 | 2.8 | 1.9 | 82.6 | 12.5 | 0.0 |
| C4 | 0.73 | 0.0 | 0.9 | 0.0 | 1.7 | 97.4 | 0.0 |
| C5 | 1.43 | 0.0 | 1.1 | 0.0 | 0.7 | 98.3 | 0.0 |

Run #128: Effect of increasing the protein loading to 10 mg/mL was assessed in column run #128, while the gradient was kept the same as column run #118. For this experiment a different conjugation reaction was utilized as load material. This reaction had been optimized for higher relative concentration of Ab-[SEQ ID NO:10-L1]$_1$ (i.e. 44.7%) but also had a higher relative concentration of Ab-[SEQ ID NO:10-L1]$_2$ (i.e., 24.4%) and lower concentration of mAb 24.7% species by SEC assay compared to load solution used in column run #118. Higher levels of Ab-[SEQ ID NO:10-L1]$_2$ species and higher protein loading are expected to impact the column performance and elution pool product composition. As evident in Table 34 increased loading results in diminished resolution of Ab-[SEQ ID NO:10-L1]$_2$ species from Ab-[SEQ ID NO:10-L1]$_1$

TABLE 34

SEC results of load and column fractions for run #128.

|  | Conc. (mg/mL) | % Large Aggregate | % Aggregate | % Ab-[FGF21ΔH-A129C-L1]$_2$ | % Ab-[FGF21ΔH-A129C-L1]$_1$ | % Ab | % [FGF21ΔH-A129C-L1]$_1$ |
|---|---|---|---|---|---|---|---|
| Crude load | 4.0 | 0.7 | 3.3 | 24.4 | 44.7 | 24.7 | 1.0 |
| B5 | 1.11 | 0.0 | 2.3 | 81.9 | 14.1 | 1.4 | 0.2 |
| B4 | 0.89 | 0.0 | 2.9 | 64.9 | 23.1 | 8.8 | 0.3 |
| B3 | 1.02 | 0.0 | 3.5 | 34.7 | 22.9 | 38.7 | 0.1 |
| B2 | 1.47 | 0.0 | 3.3 | 9.5 | 59.9 | 27.4 | 0.2 |
| B1 | 2.00 | 0.0 | 2.5 | 3.6 | 86.7 | 7.3 | 0.0 |
| C1 | 1.59 | 0.0 | 3.3 | 3.2 | 86.7 | 6.9 | 0.0 |
| C2 | 0.97 | 0.0 | 7.0 | 6.3 | 69.9 | 16.8 | 0.0 |
| C3 | 0.72 | 0.9 | 10.6 | 4.9 | 42.8 | 40.8 | 0.0 |
| C4 | 0.94 | 0.0 | 6.5 | 1.2 | 10.5 | 81.7 | 0.0 |

Run #132: To improve resolution of Ab-[SEQ ID NO:10-L1]$_1$ species a shallow gradient elution (100% A+0% B to 10% A+90% B in 20 CVs) was performed in column run #132 at 5 mg/mL column loading using the same load material used in column run #128. Table 35 shows the elution profile and relative purity of various conjugated species as determined by SEC for elution fractions. An improved separation between Ab-[SEQ ID NO:10-L1]$_2$ species and Ab-[SEQ ID NO:10-L1]$_1$ species was obtained with shallow 1,6 hexanediol, which suggests that a step elution designed to elute most of the Ab-[[SEQ ID NO:10-L1]$_2$ species with a certain low concentration of 1,6 hexanediol would be beneficial. A 5% hexanediol wash column run #134 after 5 mg/mL load resulted in elution of all of the bound species (data not shown).

TABLE 35

SEC results of load and column fractions for run #132.

|  | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| B3 | 0.19 | 0.0 | 1.4 | 83.3 | 13.0 | 2.2 |
| B2 | 0.32 | 0.1 | 0.8 | 85.6 | 11.2 | 1.8 |
| B1 | 0.20 | 0.0 | 0.9 | 80.9 | 15.8 | 2.5 |
| C1 | 0.22 | 0.0 | 2.0 | 79.1 | 16.9 | 3.1 |
| C5 | 0.27 | 0.0 | 2.1 | 10.2 | 37.2 | 50.6 |
| C6 | 0.36 | 0.0 | 1.6 | 5.6 | 71.1 | 21.2 |
| C8 | 0.58 | 0.0 | 2.7 | 3.5 | 89.8 | 5.1 |
| C10 | 0.29 | 0.0 | 4.7 | 3.9 | 83.1 | 10.3 |
| C11 | 0.20 | 0.0 | 5.8 | 5.3 | 64.4 | 25.5 |

TABLE 35-continued

SEC results of load and column fractions for run #132.

|  | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| C12 | 0.18 | 0.0 | 8.2 | 5.6 | 52.6 | 35.9 |
| D12 | 0.15 | 0.0 | 5.6 | 4.9 | 39.2 | 47.7 |
| D9 | 0.21 | 0.0 | 3.4 | 1.1 | 8.1 | 85.1 |
| D8 | 0.28 | 0.0 | 1.4 | 0.6 | 2.8 | 93.2 |

Run #138: Subsequently an experiment with 2.4% 1,6-hexanediol isocratic wash (i.e. column run #138) followed by an elution gradient of 2.4%-18% in 30 CVs was performed at a loading density of 5 mg/ml. Table 36 shows the elution profile from this run with the SEC assay of fractions. Enhanced separation was obtained using the 2.4% wash step preceding the elution gradient as seen in this elution profile. Based on this, 12% of Buffer B and 88% Buffer A was determined to provide a suitable initial concentration of 1,6 hexanediol to the linear gradient elution over 30 CV, whereas column run #134 appeared to initially wash out too much Ab-[SEQ ID NO:10-L1]$_1$, due to the slightly higher initial 1,6 hexanediol concentration.

TABLE 36

SEC results of load and column fractions for run #138.

|  | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| A5 | 0.20 | 0.0 | 0.7 | 9.6 | 84.6 | 5.1 |
| A10 | 0.15 | 0.0 | 1.0 | 83.6 | 11.5 | 3.8 |
| A12 | 0.17 | 0.1 | 0.8 | 87.9 | 9.4 | 1.8 |
| C8 | 0.10 | 0.2 | 0.7 | 9.9 | 11.1 | 78.2 |
| C11 | 0.11 | 0.2 | 1.7 | 11.9 | 34.0 | 52.1 |
| C12 | 0.12 | 0.2 | 2.0 | 10.0 | 53.1 | 34.8 |
| D1 | 0.15 | 0.1 | 2.0 | 7.1 | 72.4 | 18.3 |
| D5 | 0.39 | 0.1 | 0.9 | 1.5 | 93.3 | 4.2 |
| D8 | 0.27 | 0.0 | 1.5 | 2.3 | 89.7 | 6.4 |
| D9 | 0.24 | 0.1 | 2.2 | 3.0 | 86.0 | 8.7 |
| E2 | 0.13 | 0.2 | 5.6 | 3.2 | 34.1 | 56.9 |
| E4 | 0.10 | 0.2 | 7.9 | 1.4 | 21.9 | 68.5 |
| E9 | 0.28 | 0.0 | 0.3 | 0.0 | 0.0 | 99.7 |

Effect of Temperature and pH

Run #148: Temperature and pH have been shown to be important process parameters influencing column performance and resolution of the various conjugated species. Impact of lower temperature was evaluated in column run

148 for separation of Ab-[SEQ ID NO:10-L1]$_1$ species from other species in this study. For this experiment the column and buffers were stored and operated at 17° C. in a temperature controlled refrigerator. The column was loaded up to 5 mg/mL and washed and eluted using protocol similar to column run #138. Reducing the temperature from 22° C. to 17° C. resulted in greatly diminished binding capacity for Ab-[SEQ ID NO:10-L1]$_2$ species. Operating the column at the decreased temperature (i.e. about 17° C.) was found to enhance the separation of the Ab-[SEQ ID NO:10-L1]$_2$ species in the wash step and improved resolution of product Ab-[SEQ ID NO:10-L1]$_1$ as evident in the profile shown in Table 37.

TABLE 37

SEC results of load and column fractions for run #148 at 17° C.

| | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| Column load | 4.00 | 1.1 | 6.7 | 24.0 | 43.8 | 24.4 |
| A3 | 0.24 | 0.0 | 0.0 | 8.2 | 17.3 | 74.5 |
| A5 | 0.50 | 0.0 | 3.6 | 46.3 | 45.5 | 4.6 |
| A7 | 0.38 | 0.0 | 3.1 | 81.5 | 10.6 | 4.8 |
| A9 | 0.16 | 0.0 | 2.9 | 70.0 | 17.3 | 9.8 |
| B11 | 0.05 | 0.0 | 0.0 | 30.0 | 32.9 | 37.1 |
| C3 | 0.07 | 0.0 | 3.6 | 11.4 | 18.1 | 66.9 |
| C7 | 0.12 | 0.0 | 3.6 | 3.5 | 27.0 | 65.9 |
| C11 | 0.24 | 0.0 | 2.7 | 3.2 | 68.1 | 26.0 |
| D3 | 0.32 | 0.0 | 1.2 | 1.8 | 91.6 | 5.4 |
| D7 | 0.19 | 0.0 | 2.2 | 2.7 | 89.3 | 5.8 |
| D11 | 0.12 | 0.0 | 7.0 | 4.6 | 74.3 | 14.1 |
| E5 | 0.12 | 0.0 | 3.5 | 0.0 | 12.9 | 83.6 |
| E9 | 0.10 | 0.0 | 6.1 | 0.0 | 2.2 | 91.8 |
| F1 | 0.25 | 0.0 | 0.0 | 0.0 | 0.0 | 100.0 |
| F5 | 0.14 | 0.0 | 0.0 | 0.0 | 0.0 | 100.0 |

Run #152: Equilibrating the column at a lower pH of 6.5 but performing the elution at a higher pH of 7.0 was found to be detrimental to the separation performance in 152. Ab-[SEQ ID NO:10-L1]$_2$ species is observed to strongly bind to the column at a lower pH and a shift in the elution profile to the right was seen resulting in poor separation between Ab-[SEQ ID NO:10-L1]$_2$ species and Ab-[SEQ ID NO:10-L1]$_1$ species (Table 38)

TABLE 38

SEC results of load and column fractions for run #152.

| | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| A3 | 0.15 | 0.0 | 0.0 | 0.0 | 0.0 | 5.7 |
| A9 | 0.09 | 0.0 | 0.0 | 8.6 | 87.4 | 3.2 |
| B9 | 0.05 | 0.0 | 0.6 | 74.7 | 15.5 | 8.8 |
| C1 | 0.06 | 0.0 | 0.4 | 81.1 | 14.4 | 3.9 |
| C5 | 0.12 | 0.0 | 0.6 | 86.6 | 10.5 | 2.1 |
| C9 | 0.11 | 0.0 | 0.6 | 73.7 | 22.4 | 3.1 |
| D1 | 0.11 | 0.0 | 1.2 | 29.2 | 49.5 | 20.0 |
| D5 | 0.13 | 0.0 | 1.8 | 13.1 | 25.7 | 59.5 |
| D9 | 0.29 | 0.0 | 1.6 | 3.4 | 84.0 | 11.0 |
| E1 | 0.31 | 0.0 | 1.3 | 2.0 | 93.7 | 2.9 |
| E5 | 0.12 | 0.2 | 6.7 | 4.1 | 74.1 | 14.8 |
| E8 | 0.13 | 0.0 | 5.9 | 2.0 | 24.5 | 67.5 |
| E9 | 0.13 | 0.0 | 6.1 | 1.9 | 19.5 | 72.6 |

TABLE 38-continued

SEC results of load and column fractions for run #152.

| | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| F1 | 0.13 | 0.0 | 4.1 | 0.6 | 1.5 | 93.8 |
| F5 | 0.20 | 0.0 | 0.4 | 0.0 | 0.1 | 99.5 |
| F9 | 0.08 | 0.0 | 0.9 | 0.0 | 0.0 | 99.1 |

Development of Final Conditions and Demonstration of Process Consistency

Run #156: The selected combination of operating conditions i.e. pH, temperature, wash and linear gradient elution conditions used in column run #148 provided adequate resolution of Ab-[SEQ ID NO:10-L1]$_1$ species from Ab-[SEQ ID NO:10-L1]$_2$ species. Further improvement in separation to achieve resolution of Ab-[SEQ ID NO:10-L1]$_1$ species from mAb species was explored in column run #156 using a isocratic hold step at 8% 1,6-hexanediol during the gradient elution. At 8% 1,6-hexanediol most of the Ab-[SEQ ID NO:10-L1]$_1$ species is eluted from the column leaving a large proportion of the mAb species still bound to the column. mAb species was then subsequently eluted during regeneration step with a 100% 1,6-hexanediol isocratic wash. The SEC results of fractions from column run #156 performed at 5 mg/mL column loading density is shown in Table 39. The elution peak observed in the middle of the gradient step is enriched in Ab-[SEQ ID NO:10-L1]$_1$ species with very low levels of Ab-[SEQ ID NO:10-L1]$_2$ species and some mAb species. A representative pool was prepared from fractions # C8-D6 resulting in a pool protein concentration of 0.225 mg/mL corresponding to a column protein yield of 24%.

TABLE 39

SEC results of load and column fractions for run #156.

| | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| A3 | 0.22 | 0.0 | 1.6 | 32.5 | 63.0 | 2.9 |
| A4 | 0.44 | 0.0 | 2.9 | 62.9 | 33.3 | 0.8 |
| A5 | 0.13 | 0.1 | 3.0 | 83.5 | 12.8 | 0.6 |
| C6 | 0.13 | 0.0 | 3.5 | 3.0 | 58.9 | 34.6 |
| C8 | 0.21 | 0.0 | 2.0 | 2.1 | 82.1 | 13.8 |
| C10 | 0.30 | 0.0 | 1.2 | 1.7 | 92.3 | 4.9 |
| D3 | 0.22 | 0.0 | 1.2 | 1.4 | 94.7 | 2.7 |
| D5 | 0.13 | 0.0 | 2.4 | 2.2 | 91.9 | 3.5 |
| D6 | 0.10 | 0.0 | 3.7 | 3.0 | 88.2 | 5.1 |
| E9 | 1.32 | 0.9 | 9.0 | 0.0 | 3.3 | 86.8 |
| E10 | 0.80 | 0.8 | 4.7 | 2.0 | 2.1 | 90.4 |

Run #160: The scale up performance was evaluated in column run #160 using a 103 mL column packed using a 2.6 cm diameter XK column packed to a bed height of 20 cm. The column was loaded up to 5 mg/mL and washed and eluted using protocol similar to column run #156. The SEC results of fractions from column run #160 performed at 5 mg/mL column loading density is shown in Table 40. The elution peak in the linear gradient step contained very high purity fractions enriched in Ab-[SEQ ID NO:10-L1]$_1$ species. An elution pool was prepared by pooling fractions D2-F1 contained 36.4% total protein which corresponded to >85% recovery of +1 species loaded on the column.

TABLE 40

SEC results of load and column fractions for run #160.

| | Conc. (mg/mL) | % Large Aggregate | % Aggregate | % Ab-[FGF21ΔH-A129C-L1]$_2$ | % Ab-[FGF21ΔH-A129C-L1]$_1$ | % Ab |
|---|---|---|---|---|---|---|
| C7 | 0.13 | 0.0 | 2.4 | 5.1 | 56.1 | 36.4 |
| D1 | 0.16 | 0.0 | 2.2 | 4.4 | 68.6 | 24.9 |
| D2 | 0.22 | 0.0 | 1.8 | 3.4 | 81.6 | 13.1 |
| D3 | 0.33 | 0.0 | 1.4 | 2.6 | 89.9 | 6.0 |
| D5 | 0.49 | 0.0 | 0.9 | 1.7 | 95.5 | 1.8 |
| D7 | 0.54 | 0.0 | 0.8 | 1.3 | 96.1 | 1.8 |
| E3 | 0.39 | 0.0 | 0.8 | 1.5 | 95.9 | 1.8 |
| E5 | 0.27 | 0.0 | 1.1 | 1.4 | 95.4 | 2.1 |
| E7 | 0.11 | 0.0 | 1.9 | 2.2 | 93.0 | 2.8 |
| F1 | 0.11 | 0.0 | 2.6 | 2.5 | 90.6 | 4.2 |
| F2 | 0.11 | 0.0 | 2.0 | 82.9 | 14.6 | 0.5 |
| F3 | 0.11 | 0.7 | 6.4 | 0.0 | 4.0 | 88.8 |

Several scale-up column runs (#178, #180 and #182) were performed under identical conditions to test reproducibility of performance at 5 mg/mL loading. An elution pool was prepared for each run, and the elution pool profiles from the 3 runs performed under same operating conditions are shown in Table 41, and results have indicated the consistent results.

TABLE 41

Reproducibility of several scale-up runs.

| | % Large Aggregate | % Aggregate | % Ab-[FGF21ΔH-A129C-L1]2 | % Ab-[FGF21ΔH-A129C-L1]1 | % Ab |
|---|---|---|---|---|---|
| #156 Final Pool | 0.0 | 0 | 7.2 | 84.9 | 7.9 |
| #160 Final Pool | 0.0 | 1.3 | 1.7 | 94.3 | 2.7 |
| #178 Final Pool | 0 | 1.5 | 2.9 | 92.7 | 2.9 |
| #180 Final Pool | 0 | 1.5 | 1.6 | 93.4 | 3.4 |
| #182 Final Pool | 0 | 1.4 | 2.1 | 92.2 | 4.3 |

Conclusions: Butyl 650 S was chosen as the preferred candidate resin for the purification step when conjugation process was carried out with FGF-21 protein was coupled to the mAb first followed by the Exendin4 peptide. The resin provided good binding capacity of 5 mg/mL in the absence of lyotropic salt. Elution of bound product was accomplished using gradient of 1,6-hexanediol at pH 7.0 Single conjugated Ab-[SEQ ID NO:10-L1]$_1$ species was enriched and selectively eluted using a sequential elution strategy i.e., isocratic wash step with 2.4% hexanediol followed by 2.4%-8% hexanediol linear gradient elution. >85% yield was obtained for the mAb+1 FGF 21 species loaded on the column.

Concentration of hexanediol during the wash step, loading density of column, pH and temperature were found to be important parameters that impacted the binding capacity, resolution and column performance. The purification step was scaled up successfully to 100 mL scale in the laboratory and performed consistently on repeated trials.

Example 61

In Vitro Assays of ABC Molecules

In Glut1 Taqman assay, differentiated 3T3-L1 adipocytes were used to measure the Glut1 mRNA expression by real-time quantitative PCR (qPCR) method described below. Overnight serum starved day 10-14 differentiated 3T3-L1 adipocytes were treated with compounds for 6 hrs. Total RNA was extracted from these cells, and Glut1 and GAPDH mRNA expression was measured using a Quantitect Probe RT-PCR kit and running a real time quantitative PCR reaction in a Taqman machine. The bioactivity of the compounds was determined by a fold change in Glut1 mRNA levels normalized by the GAPDH mRNA levels from each sample. In cAMP assay, Chinese hamster ovary (CHO) cells over-expressing human GLP-1R(CHO-hGLP-1R) were seeded in 96-well plates in serum-free medium with 300 uM IBMX. Cells were incubated with compounds at RT for 1 hr. The cAMP levels were measured using a CisBio cAMP Kit according to manufacturer's instructions. The bioactivity of the compounds was determined by the EC$_{50}$ values obtained from the assay (see Table 42).

TABLE 42

In vitro potency of compounds in Glut1 Taqman and cAMP assays.

| Cmpd | FGF21 (Glut1) (N) EC$_{50}$ (nM) | hGLP-1R (cAMP) (N) EC$_{50}$ (pM) |
|---|---|---|
| FGF21 | 2.1 (2) | — |
| Ab[FGF21]$_2$ | 1.1 | — |

TABLE 42-continued

In vitro potency of compounds in Glut1 Taqman and cAMP assays.

| Cmpd | FGF21 (Glut1) (N) EC$_{50}$ (nM) | hGLP-1R (cAMP) (N) EC$_{50}$ (pM) |
|---|---|---|
| Ab[Ex4]$_2$ | — | 2.4 (2) |
| ABC-1 | 0.8 (7) | 25.7 (4) |

Example 62

ABC in vivo Assays in Murine Models

Pharmokinetics. The pharmacokinetics of [SEQ ID NO:10-L1]$_1$-h38C2-(IgG1)-[L1-SEQ ID NO:64]$_1$ also referred to as Asymmetric Bifunctional Conjugate-1(ABC-1), were assessed in male Swiss Webster mice (22-24 g). The mice were administered compounds IV and SC at 3 mg/kg, and blood samples were taken from 3 mice per time point at the different time points up to 120 hrs. Serum samples were prepared and analyzed by two ELISA assays. In the GLP-1 assay, the conjugates were captured by Exendin4 C-terminal specific antibody and detected by GLP-1 N-terminal specific mAb. In the FGF21 assay, the conjugates were captured with anti-Id antibody and detected by an FGF21 mAb. PK parameter estimates are summarized in the Table 43.

TABLE 43

PK parameter estimates of ABC-1 following IV and SC administration at 3 mg/kg in Swiss Webster mice.

| Assay | $T_{1/2}$ (hr) IV | SC | AUC (hr*ug/mL) IV | SC | Cmax (ug/mL) IV | SC | CL (mL/hr/kg) IV | SC | SC BioAv (%) |
|---|---|---|---|---|---|---|---|---|---|
| GLP-1 | 94 | 80 | 1108 | 1028 | 21.7 | 6.9 | 2.7 | 2.9 | 93 |
| FGF21 | 34 | 34 | 872 | 489 | 35.0 | 10.3 | 3.4 | 3.8 | 56 |

Body Weight and Glucose AUC. The in vivo efficacy of ABC-1 was assessed in a single dose study in ob/ob mice. Compounds were dosed SC on day 0 at 1 or 3 mg/kg, and an OGTT was conducted on day 3. ABC-1 significantly reduced body weight at 1 and 3 mg/kg, and significantly improved glucose tolerance at 3 mg/kg 3 days after a single dose (Table 44).

TABLE 44

| Treatment (mg/kg) | Mean Body Weight Change (g) (SEM) | Mean Glucose AUC (% of vehicle control) |
|---|---|---|
| Vehicle | +1.42 (0.32) | 100 |
| ABC-1 (1) | +0.47 (0.30)* | 74 |
| ABC-1 (3) | −1.97 (0.29)*** | 40*** |
| Lean control (vehicle) | +0.95 (0.16) | 62* |

Body weight change from day 0 measured at day 3, and Glucose AUC during the OGTT measured at day 3, after a single SC injection of ABC-1 in ob/ob mice.
*p < 0.05, ***p < 0.001 vs vehicle by One-way ANOVA with Dunnett's post-tests.
SEM values provided in parentheses.

Comparison of Different ABC Molecules In Vivo. Two asymmetric bifunctional molecules (ABCs) ABC molecules were compared: ABC-1 and ABC-2. Both ABCs comprise the formula: [SEQ ID NO:10-L1]$_1$-[Ab]-[L1-SEQ ID NO:64]$_1$. Both ABCs comprise a version of h38C2 as the antibody: ABC-1 comprises an IgG1 version of h38C2 (SEQ ID NOs: 25 and 26) and ABC-2 comprises an IgG2 version of h38C2 (SEQ ID NOs: 25 and 76). A comparison of the in vitro potency of ABC-1 and ABC-2 was assessed in cell-based assays (Glut1 assay for FGF21 arm and cAMP assay for GLP-1 arm), and they showed comparable activities.

The pharmacokinetics of ABC-2 was assessed in male Swiss Webster mice (22-24 g). The mice were administered IV and SC with the compounds at 3 mg/kg, and blood samples were taken from 3 mice per time point at the different time points up to 120 hrs. Serum samples were prepared and analyzed by two ELISA assays. In the GLP-1 assay, the conjugates were captured by anti-Id antibody and detected by GLP-1 N-terminal specific mAb. In the FGF21 assay, the conjugates were captured with anti-Id antibody and detected by an FGF21 mAb. PK parameter estimates are summarized in the Table 45.

TABLE 45

PK parameter estimates of ABC-2 following IV and SC administration at 3 mg/kg in Swiss Webster mice.

| Assay | $T_{1/2}$ (hr) IV | SC | AUC (hr*ug/mL) IV | SC | SC BioAv (%) |
|---|---|---|---|---|---|
| GLP-1 | 137 | 67 | 5618 | 3835 | 68 |
| FGF21 | 63 | 47 | 1454 | 1116 | 77 |

The in vivo efficacy of ABC-1 and ABC-2 was assessed in a single dose study in ob/ob mice. Compounds were dosed SC on day 0 at 0.3 or 3 mg/kg, and OGTT was conducted on day 3. Both compounds at 3 mg/kg significantly reduced body weight and improved glucose tolerance 3 days after a single dose (Table 46).

TABLE 46

| Treatment (mg/kg) | | Mean Body Weight Change (g) (SEM) | Mean Glucose AUC (% of vehicle control) |
|---|---|---|---|
| Vehicle | | +2.2 (0.13) | 100 |
| Ab[Ex4]$_2$ | (0.3) | +1.03 (0.52) | 70* |
| Ab[FGF21]$_2$ | (3) | +0.58 (0.31) | 74* |
| ABC-1 | (0.3) | +1.72 (0.18) | 83 |
| ABC-1 | (3) | −1.97 (0.21)*** | 45*** |
| ABC-2 | (0.3) | +1.88 (0.14) | 77 |
| ABC-2 | (3) | −2.42 (1.01)*** | 50*** |
| Lean control (vehicle) | | +1.03 (0.17) | 61** |

Body weight change from day 0 at day 3, and Glucose AUC during the OGTT at day 3, after a single SC injection of ABC-1 and ABC-2 in ob/ob mice.
*p < 0.05, p < 0.01, *p < 0.001 vs vehicle by One-way ANOVA with Dunnett's post-tests.
SEM values provided in parentheses.

Example 63

ABC In vivo Assays in Cynomolgus Monkeys

The pharmacokinetics of ABC-1 was also investigated in the male Cynomolgus monkey following single IV and SC bolus administration at a dose level of 3 mg/kg. Blood samples were collected from the animals at the designated time points up to 21 days. The serum samples were prepared and analyzed by two ELISA assays. In the GLP-1 assay, the conjugates were captured by exendin4 C-terminal specific antibody and detected by GLP-1 N-terminal specific mAb. In the FGF21 assay, the conjugates were captured with anti-Id antibody and detected by an FGF21 mAb. PK parameter estimates are summarized in the Table 47.

TABLE 47

PK parameter estimates of ABC-1 following a single IV and SC administration at 3 mg/kg in Cynomolgus monkeys.

| Assay | $T_{1/2}$ (hr) IV | SC | AUC (hr*ug/mL) IV | SC | Cmax (ug/mL) IV | SC | CL (mL/hr/kg) IV | SC | SC BioAv (%) |
|---|---|---|---|---|---|---|---|---|---|
| GLP-1 | 77 | 71 | 3088 | 2110 | 65.6 | 19.1 | 1.0 | 1.5 | 68 |
| FGF21 | 60 | 48 | 2233 | 1339 | 77.3 | 17.7 | 1.4 | 2.3 | 60 |

Example 64

Dose Efficacies of ABC-1

Repeat Dose Efficacy of ABC-1. The repeat dose efficacy of ABC-1 was assessed in comparison with Ab-[SEQ ID NO:10-L1]$_2$ (also referred to as Ab[FGF21]$_2$) and Ab[L1-SEQ ID NO:64]$_2$ (also referred to as Ab[Ex4]$_2$) in db/db mice. Compounds were dosed on day 0 and 7. Body weight was measured twice weekly, and an OGTT was conducted on day 10. On day 11, liver, pancreas and serum samples were collected for lipid and immunohistochemistry (IHC) analysis. ABC-1 (10 mg/kg) significantly reduced body weight gain compared with the vehicle-treated group 3 days after the second dose, and also normalized fasting blood glucose level and significantly improved glucose tolerance to a greater extent than the single agents alone 3 days after the second dose in these mice (Table 48). In addition, ABC-1 significantly lowered serum triglycerides and cholesterol levels, and reduced liver triglycerides content by ~43% compared with the vehicle-treated group (Table 49). In pancreas, significant increase in beta cell mass by 2.7-fold analyzed by IHC was observed in ABC-1-treated mice (Table 49).

TABLE 48

| Treatment (mg/kg) | Mean Body Weight Change (g) (SEM) | Mean Glucose AUC (% of vehicle control) |
|---|---|---|
| Vehicle | 2.4 (0.2) | 100 |
| Ab[Ex4]$_2$ (3) | 1.7 (0.2) | 60*** |
| Ab[FGF21]$_2$ (10) | 3.6 (0.2) | 67*** |
| ABC-1 (10) | 0.5 (0.8)* | 47*** |
| Lean control (vehicle) | 1.7 (0.1) | 35*** |

Body weight change from day 0 at day 10, and Glucose AUC during the OGTT at day 3, after the repeat SC injection of compounds in db/db mice.
*$p < 0.05$, ***$p < 0.001$ vs vehicle by One-way ANOVA with Dunnett's post-tests.
SEM values provided in parentheses.

molecule on pancreatic function and beta cell mass. Compounds were dosed on day 0 and 7, and an OGTT was conducted on day 10. At the 15 min timepoint of the OGTT, blood was collected for measurement of glucose-stimulated plasma insulin secretion. On day 11, pancreas samples were collected for biochemical and immunohistochemical analyses. All treatments significantly improved glucose tolerance in comparison with Vehicle-treated controls. Potentiation of glucose-induced insulin secretion and increased proliferation of insulin-immunoreactive cells (% PCNA positive beta cells) were observed in all the treatment groups in comparison with the Vehicle-treated controls, with the exception of the highest dose of ABC-1 (10 mg/kg). Thus at the lower doses of ABC-1 tested, the effects of the compound on the pancreas are consistent with those of the single agents. Unexpectedly, the 10 mg/kg dose of ABC-1 was associated with increased insulin-immunoreactive staining (beta cell mass) and pancreatic insulin content without a significant increase in beta cell proliferation or in glucose-stimulated insulin secretion. These data suggest that at doses of ABC-1 associated with greater weight loss (see Table 48 above and studies in DIO mice below), an

TABLE 49

| Treatment (mg/kg) | Mean Serum Triglyceride (mg/dL) (SEM) | Mean Serum Cholesterol (mg/dL) (SEM) | Mean Liver Triglyceride (mg/g liver) (SEM) | Mean beta cell mass (mg) (SEM) |
|---|---|---|---|---|
| Vehicle | 542 (91) | 177 (8.3) | 13.0 (2.2) | 0.67 (0.09) |
| Ab[Ex4]$_2$ (3) | 302 (21)* | 167 (4.9) | 17.4 (1.4) | 1.39 (0.23) |
| Ab[FGF21]$_2$ (10) | 356 (35) | 171 (7.3) | 9.6 (2.2) | 1.60 (0.13)* |
| ABC-1 (10) | 234 (42)** | 120 (8.3)*** | 7.4 (1.8) | 1.82 (0.30)** |
| Lean control (vehicle) | ND | ND | ND | 1.23 (0.21) |

Serum lipids, liver triglyceride levels, and pancreatic beta cell mass on day 11 after the repeat SC injection of compounds in db/db mice.
*$p < 0.05$, $p < 0.01$, *$p < 0.001$ vs vehicle by One-way ANOVA with Dunnett's post-tests.
SEM values provided in parentheses.

Additional repeat dose efficacy data with ABC-1 in comparison with single agents Ab[FGF21]$_2$ and Ab[Ex4]$_2$ in db/db mice were collected to better define the effects of the insulin-sensitizing effect overrides the drive for proliferation of the beta cells and insulin secretion, resulting in an accumulation of insulin in preexisting beta cells.

TABLE 50

| Treatment (mg/kg) | Mean Glucose AUC (% of vehicle control) | Mean Plasma Insulin at 15 min (ng/ml) (SEM) | Mean Beta Cell Mass (mg) (SEM) | % PCNA Positive Beta Cells (SEM) | Mean Pancreatic Insulin Content (ug/mg total protein) (SEM) |
|---|---|---|---|---|---|
| Vehicle | 100 | 4.2 (0.6) | 0.32 (0.02) | 1.1 (0.4) | 2.26 (0.54) |
| Ab[Ex4]$_2$ (3) | 61*** | 7.8 (1.0) | 0.54 (0.08) | 3.3 (0.4)* | 2.25 (0.42) |
| Ab[FGF21]$_2$ (10) | 73** | 5.8 (1.2) | 0.49 (0.05) | 4.4 (0.3)** | 4.21 (0.88) |
| ABC-1 (1) | 63*** | 7.1 (1.3) | 0.44 (0.05) | 3.6 (0.7)* | 2.72 (0.61) |
| ABC-1 (3) | 39*** | 10.2 (1.8)** | 0.77 (0.12)** | 4.4 (1.0)** | 6.40 (2.86) |
| ABC-1 (10) | 36*** | 3.7 (0.8) | 0.71 (0.13)** | 2.4 (0.3) | 15.98 (3.57)*** |

Glucose tolerance, glucose-stimulated insulin secretion, and pancreatic beta cell status on day 11 after the repeat SC injection of compounds in db/db mice.
*$p < 0.05$, $p < 0.01$, *$p < 0.001$ vs vehicle by One-way ANOVA with Dunnett's post-tests.
SEM values provided in parentheses.

Sub Chronic Dose Efficacy. The sub-chronic dose efficacy of ABC-1 was assessed in comparison with Ab[FGF21]$_2$ and Ab[EX4]$_2$ in DIO mice (results shown in Table 51). All compounds were dosed SC once weekly, body weight and food intake was measured twice weekly, and an OGTT was conducted on day 17, 3 days after the 3$^{rd}$ weekly dose. On day 20, liver and serum samples were collected for lipid analysis. ABC-1 significantly and dose-dependently reduced body weight. At 3 mg/kg, ABC-1 caused greater weight loss than the single agents alone at the same dose. ABC-1 inhibited food intake, up to the amount of Ab[EX4]$_2$ at 3 mg/kg, indicating the GLP-1 effect of ABC-1. However, the amount of the food intake inhibition could not explain the profound weight loss caused by the ABC-1, suggesting the ABC-1-induced weight loss must be due to the combination of both the FGF21 and GLP-1 arms. All ABC treatment groups significantly lowered fasting blood glucose levels and improved glucose tolerance 3 days after the 3$^{rd}$ weekly dose, and also significantly reduced liver triglyceride contents 6 days after the 3$^{rd}$ weekly dose. Similarly as what was observed in the db/db mice, once weekly ABC-1 treatment resulted in significant reduction in serum cholesterol levels in DIO mice, while neither of the single agents had much effect.

TABLE 51

Body weight change, Cummulative food intake, Basal blood glucose and glucose AUC during the OGTT on day 17, and Serum cholesterol and liver triglyceride levels on day 20, after three weekly SC injection of compounds in DIO mice.

| Treatment (mg/kg) | Mean Body Weight Change (g) (SEM) | Mean Cumulative Food Intake (g) | Mean Basal Glucose (mg/dL) (SEM) | Mean Glucose AUC (% of vehicle control) | Mean Serum Cholesterol (mg/dL) (SEM) | Mean Liver Triglyceride (mg/g liver) (SEM) |
|---|---|---|---|---|---|---|
| Vehicle | +1.2 (0.6) | 41.8 | 161 (15) | 100 | 162 (9) | 13.8 (2.9) |
| Ab[FGF21]$_2$(3) | −0.9 (0.6) | 45.0 | 164 (6) | 101 | 164 (8) | 6.3 (1.6)* |
| Ab[Ex4]$_2$ (3) | −3.6 (0.3)*** | 34.6 | 107 (8)*** | 66*** | 131 (7) | 3.5 (1.7)** |
| ABC-1 (1) | −3.6 (0.5)*** | 39.2 | 113 (6)** | 63*** | 130 (8)* | 3.8 (1.8)** |
| ABC-1 (3) | −7.8 (1.2)*** | 34.6 | 95 (6)*** | 64*** | 112 (6)*** | 3.0 (0.9)*** |
| ABC-1 (10) | −10.1 (1.1)*** | 36.9 | 91 (5)*** | 57*** | 95 (21)*** | 4.3 (1.2)* |

*p < 0.05,
**p < 0.01,
***p < 0.001 vs vehicle by One-way ANOVA with Dunnett's post-tests.
SEM values provided in parentheses.

Duration of Effect. To determine the duration of effect of the ABC-1 in vivo, a single dose efficacy study was conducted in DIO mice. 3 mg/kg ABC-1 was administered SC on day 0, body weight was measured daily, and an OGTT was conducted on day 13. ABC-1 demonstrated sustained efficacy in causing and maintaining weight loss and improving glucose tolerance up to 13 days after a single dose in DIO mice.

TABLE 52

| Days post dose | Mean Body Weight Change (g) (SEM) | |
|---|---|---|
| | Vehicle | ABC-1 (3 mg/kg) |
| 2 | −1.0 (0.2) | −2.6 (0.2)*** |
| 4 | −1.0 (0.3) | −3.2 (0.2)*** |
| 6 | −1.2 (0.2) | −2.9 (0.3)*** |
| 8 | −1.4 (0.2) | −3.1 (0.3)*** |

TABLE 52-continued

| Days post dose | Mean Body Weight Change (g) (SEM) | |
|---|---|---|
| | Vehicle | ABC-1 (3 mg/kg) |
| 10 | −1.1 (0.3) | −3.1 (0.3)*** |
| 12 | −0.9 (0.3) | −2.8 (0.3)*** |
| 13 | −0.9 (0.3) | −2.6 (0.3)*** |

Body weight change up to day 13 after a single SC injection of 3 mg/kg ABC-1 in DIO mice.
***p < 0.001 vs vehicle by unpaired t-test.
SEM values provided in parentheses.

TABLE 53

| Treatment (mg/kg) | Mean Glucose AUC (% of vehicle control) |
|---|---|
| Vehicle | 100 |
| ABC-1 (3) | 76** |

Glucose AUC during the OGTT 13 days after a single SC injection of 3 mg/kg ABC-1 in DIO mice.
**p < 0.01 vs vehicle by One-way ANOVA with Dunnett's post-tests.

To determine the duration of effect of the ABC-1 in comparison with Ab[FGF21]$_2$ and Ab[Ex4]$_2$ alone, and the physical combination of the two in vivo, a single dose efficacy study was conducted in DIO mice. All compounds were administered SC on day 0, body weight was measured twice weekly, and OGTT was conducted on day 7, 13, and 21. Results are shown in Table 54. ABC-1 demonstrated sustained efficacy in causing and maintaining weight loss and improving glucose tolerance up to 21 days after a single dose in DIO mice. ABC-1-induced weight loss was greater than the single agents alone, and comparable with the combination of Ab[FGF21]$_2$ and Ab[Ex4]$_2$ together. However, the glucose AUC during the OGTT in the combination group went back to the levels of the vehicle-treated group, while those of ABC-1-treated group were still significantly lowered than the vehicle-treated group. These data indicate the superior and sustained efficacy of the ABC-1 to the single agents alone, as well as the physical combination of the two. The sustained efficacy of the ABC-1 in vivo supports once weekly dosing of the compound.

TABLE 54

Body weight change, and Glucose AUC during the OGTT, on day 7, 13,
and 21 after a single SC injection of compounds in DIO mice.

| Treatment (mg/kg) | Mean Body Weight Change (g) (SEM) | | | Mean Glucose AUC (% of vehicle control) | | |
|---|---|---|---|---|---|---|
| | Day 7 | Day 13 | Day 21 | Day 7 | Day 13 | Day 21 |
| Vehicle | +0.9 (0.5) | +2.2 (0.7) | +4.4 (0.8) | 100 | 100 | 100 |
| ABC-1 (3) | −2.9 (0.2)*** | −1.2 (0.4)*** | +0.7 (0.4)*** | 64*** | 81 | 83* |
| Ab[Ex4]$_2$ (0.3) | +0.6 (0.3) | +2.3 (0.6) | NA# | 77*** | 103 | NA# |
| Ab[Ex4]$_2$ (1.5) | −1.3 (0.4)*** | +0.4 (0.4)* | +2.4 (0.5) | 62*** | 75* | 98 |
| Ab[FGF21]$_2$ (3) | +0.4 (0.3) | NA | NA | 101 | NA | NA |
| FGF21 (0.6) | +1.4 (0.3) | NA | NA | 99 | NA | NA |
| Ab[Ex4]$_2$ (0.3) + Ab[FGF21]$_2$ (3) | −1.7 (0.4)*** | −1.4 (0.5)*** | 0.0 (0.7)*** | 79** | 101 | NA |
| Ab[Ex4]$_2$ (0.3) + FGF21(0.6) | +0.1 (0.2) | +0.8 (0.2) | +3.2 (0.4) | 77*** | 98 | NA | not available due to termination of the group.
*p < 0.05,
**p < 0.01,
***p < 0.001 vs vehicle by One-way ANOVA with Dunnett's post-tests.
SEM values provided in parentheses.

Sub Chronic Dose Efficacy. The sub-chronic dose efficacy of ABC-1 was also assessed in comparison with the physical combination of Ab[FGF21]$_2$ and Ab[Ex4]$_2$ in DIO mice (Table 55). All compounds were administered SC once weekly. Body weight was measured twice weekly, and an OGTT was conducted 3 days after the 3$^{rd}$ weekly dose. ABC-1 significantly reduced weight loss and improved glucose tolerance to the similar extent as the combination groups of the same total amount of dose or the similar doses matched with the in vitro potency.

TABLE 55

Body weight change and Glucose AUC during the OGTT on day 17, and Serum
cholesterol levels on day 18, after three weekly SC injections of compound in DIO mice.

| Treatment (mg/kg) | Mean Body Weight Change (g) (SEM) | Mean Cumulative Food Intake (g) | Mean Glucose AUC (% of vehicle control) | Mean Serum Cholesterol (gm/dL) (SEM) |
|---|---|---|---|---|
| Vehicle | −1.3 (0.5) | 44.0 | 100 | 163 (11) |
| ABC-1 (3) | −5.1 (0.9) | 46.9 | 67*** | 125 (7)** |
| ABC-1 (10) | −9.5 (1.4)*** | 43.9 | 58*** | 102 (5)*** |
| Ab[Ex4]$_2$ (0.3) + Ab[FGF21]$_2$ (3) | −4.8 (0.8) | 50.8 | 62*** | 132 (10)* |
| Ab[Ex4]$_2$ (1) + Ab[FGF21]$_2$ (10) | −9.3 (1.3)*** | 49.0 | 52*** | 107 (5)*** |
| Ab[Ex4]$_2$(5) + Ab[FGF21]$_2$ (5) | −11.4 (1.2)*** | 39.2 | 52*** | 109 (3)*** |

*p < 0.05, p < 0.01, *p < 0.001 vs vehicle by One-way ANOVA with Dunnett's post-tests.
SEM values provided in parentheses.

The larger magnitude reductions in body weight gain induced by treatment with ABC-1 were observed in the absence of greater reductions in food intake than those induced by the single agents Ab[FGF21]$_2$ or Ab[Ex4]$_2$ (see Tables 51 and 55). Indirect calorimetry studies were undertaken in DIO mice to determine if the additional weight loss induced by ABC-1 in comparison with the single agents was due to an increase in energy expenditure. Compounds were injected SC on day 0 and day 7, and parameters were assessed continuously for 48 hrs beginning immediately after the second dose. Ab[Ex4]$_2$ (1 mg/kg) did not alter $O_2$ consumption, $CO_2$ production, heat production, or respiratory quotient. Ab[FGF21]$_2$ (10 mg/kg) increased $O_2$ consumption, $CO_2$ production, and heat production, but did not affect respiratory quotient. Unexpectedly, the effects of ABC-1 (10 mg/kg) on $O_2$ consumption, $CO_2$ production, and heat production were comparable with and no greater than those of Ab[FGF21]$_2$ (10 mg/kg). Therefore, the increased body weight loss induced by ABC-1 may not be explained by increased energy expenditure greater than the effect of the single agents.

Example 65

Gene Array Analysis

Gene array analyses were undertaken to survey a broader number of candidates in liver and white adipose tissue order to elucidate the mechanism for increased weight loss elicited by ABC-1. DIO mice were dosed once weekly for 3 weeks with ABC-1 (10 mg/kg), Ab[FGF21]$_2$ (10 mg/kg), or Ab[Ex4]$_2$ (3 mg/kg), and genes differentially regulated by the ABC-1 treatment but not by Ab[FGF21]$_2$ or Ab[Ex4]$_2$ were identified. Of the >45000 genes assessed by array, subsequent qPCR analyses confirmed selective up or down regulation of a subset genes in liver of ABC-1 treated mice but not in mice treated with Ab[FGF21]$_2$ or Ab[Ex4]$_2$ (Table 56). Some of the genes identified were particularly unexpected and suggest novel mechanisms of action for the ABC-1 therapeutic not anticipated by either of Ab[FGF21]$_2$ or Ab[Ex4]$_2$ (e.g. Acot3, Saa1/2). These genes may also be useful predictive pharmacodynamic markers.

TABLE 56

Gene expression changes on day 20, after three weekly SC injections of compounds in DIO mice.

| Genes | | Function | Fold change |
|---|---|---|---|
| Abcd2 | ATP-binding cassette d2 | Fatty acid transporter | +4 |
| Acot3 | Acyl-CoA thioesterase 3 | Peroxisome fatty acid oxidation | +80 |
| CIDEA | Cell death-inducing DFFA-like effector A | Apoptosis | −10 |
| Cyp2b9 | cytochrome P450, family 2, subfamily b | Fatty acid oxidation | +100 |
| Cyp4a14 | cytochrome P450, family 4, subfamily a, polypeptide 14 | Fatty acid metabolism | +22 |
| Fmo2 | Flavin-containing monooxygenase 2 | Drug metabolism | +2.8 |
| Gstm5 | glutathione S-transferase mu 5 | Detoxification | +2.0 |
| Hmgcr | 3-hydroxy-3-methylglutaryl- CoA reductase | Cholesterol biosynthesis | +5 |
| Klb | β-Klotho | FGF21 co-receptor | +1.6 |
| Lepr | Leptin receptor | Leptin signaling | +7.8 |
| Saa1/2 | Serum amyloid A protein1/2 | Inflammation marker | −5.6 |
| Scd1 | stearoyl-Coenzyme A desaturase 1 | Fatty acid synthesis | +2.9 |
| Srebf2 | Sterol regulatory element binding protein 2 | Cholesterol metabolism | +1.9 |

Accordingly, in some aspects, the invention provides for a method of assessing or determining a patient's suitability for a treatment for a metabolic disorder, comprising measuring the gene expression levels of one or more genes selected from the group consisting of Abcd2, Acot3, Cidea, Cyp2b9, Cyp4a14, Fmo2, Gstm5, Hmgcrk, Klb, Lepr, Saa1/2, Scd1, and Srebf2, and comparing the gene expression level with the respective gene expression level after an initial period of treatment. In some aspects, the genes are selected from the group consisting of Acot3 and Saa1/2. The measurements of gene expression may be in vitro. The measurements of gene expression may be extracorporeal.

In some aspects, the invention provides for a method of determining the relative expression levels of a gene selected from the group consisting of Abcd2, Acot3, Cidea, Cyp2b9, Cyp4a14, Fmo2, Gstm5, Hmgcrk, Klb, Lepr, Saa1/2, Scd1, and Srebf2 comprising measuring the gene expression levels before and after treatment with a compound of the invention, or one or both of an FGF21-receptor agonist and/or a GLP1-receptor agonist. Such a determination may then be used in recommending a clinical course of action.

In some aspects, the method comprises measuring the expression of said genes in the liver. In some aspects, the method relates to method of assessing a patient's likelihood to lose weight as a result of treatment with a compound of the invention; said method relying on an increase in the expression of Acot3 and or a decrease in the expression of Saa1/2 to suggest the patient is more likely to experience weight loss as a result of treatment with a compound of the invention, or an FGF21-receptor agonist and/or a GLP1-receptor agonist.

Example 66

Stability of h38C2-[SEQ ID NO:7-L1]$_2$ & h38C2-[SEQ ID NO:10-L1]$_2$

Various formulations of h38C2-[SEQ ID NO:7-L1]$_2$ (Ab-[FGF21ΔH-H125C-L1]$_2$) and h38C2-[SEQ ID NO:10-L1]$_2$ (Ab-[FGF21ΔH-A129C-L1]$_2$) were prepared and subjected to a range of stress conditions (full details are in US2011/13289533, US61/579,609, and PCT/IB2011/054874, each of whose contents, particularly Examples 72-76 are hereby referenced and incorporated). Comparing data of several stability tests, such as an appearance assay, size exclusion chromatography (SEC), imaged capillary electrophoresis (iCE), and analytical ultracentrifugation, the overall stability profile of Ab-[L1-FGF21ΔH-A129C]$_2$ appeared to be superior than Ab-[L1-FGF21ΔH-H125C]$_2$. It is also evident that lowering the pH of the formulation (e.g. acetate, pH 4) provided better stability compared to higher pH (e.g. pH 6-8).

Example 67

Formulations of [FGF21-L1]$_1$-[Ab]-[L1-Ex4]$_1$ and Ab-[L1-FGF21ΔH-A129C]$_2$

Although liquid formulations can be used with compounds of the invention, lyophilized formulations can provide greater longevity of stability (see Examples 72-76 of US2011/13289533, US61/579,609, and PCT/IB2011/054874, each of whose contents are hereby incorporated). Accordingly, in some aspects the invention provides for a formulation comprising between about 0.1 and about 200 mg/ml of an ABC or Ab-[L1-FGF21ΔH-A129C]$_2$ and between about 1 and 150 mM lactic acid or sodium acetate, pH between about 4 and about 5.5; and at least one of the following:
  (i) between about 10 to about 150 mg/ml cryoprotectant;
  (ii) between about 0.001 and about 1.0 mg/ml chelator;
  (iii) between about 0.01 and about 10 mg/ml anti-oxidant;
  (iv) between about 0.02-2.0 mg/mL surfactant.

In some aspects, formulations of the invention comprise two or more of (i) to (iv). In some aspects formulations of the invention comprise three or more of (i) to (iv). In some aspects, formulations of the invention comprise (i), (ii), (iii), and (iv).

In some aspects the invention provides for a lyophilized formulation comprising:
  (i) between about 0.1 and about 200 mg/ml of an ABC;
  (ii) between about 1 and 150 mM lactic acid pH between about 4 and about 5.5; and
  (iii) between about 10 to about 150 mg/ml cryoprotectant;
  (iv) between about 0.02-2.0 mg/mL surfactant.

In some aspects, the lyophilized formulation may further comprise between about 0.001 and about 1.0 mg/ml chelator. The chelator may be EDTA or DTPA, and may be present in an amount of between about 0.02 to about 0.5 mg/mL. The chelator may be present in an amount of about 0.05 mg/mL.

In some aspects, the lyophilized formulation may further comprise between about 0.01 and about 10 mg/ml anti-oxidant. In some aspects, the antioxidant may be L-methionine. The antioxidant may be present in an amount of between about 0.02 and about 5 mg/mL. The antioxidant may be present in an amount of between about 0.05 and about 0.2 mg/mL. The antioxidant may be present in an amount of about 0.1 mg/mL.

In some aspects, the ABC is a compound of the invention as herein described. In some aspects, the ABC is the specific species [SEQ ID NO:56-L1]$_1$-h38C2-[SEQ ID NO:10-L1]$_1$. In some aspects, the ABC is present in an amount of between about 5 mg/ml and about 200 mg/ml. In some aspects, the ABC is present in an amount of between about 5 mg/ml and about 100 mg/ml. In some aspects, the ABC is present in an amount of between about 5 mg/ml and about 50 mg/ml. In some aspects, the ABC is present in an amount of about 10 mg/ml.

In some aspects, the lactic acid is present in an amount of between about 1 to about 100 mM. In some aspects, the lactic acid is present in an amount of between about 10 mM and about 50 mM. In some aspects, the lactic acid is present in an amount of about 30 mM. The pH may be between about 4.3 and about 5.3. The pH may be about 4.8±0.5. The pH may be about 4.8.

In some aspects, the cryoprotectant is selected from the group consisting of trehalose dihydrate, sucrose, and mannitol. The cryoprotectant may be trehalose dihydrate. The cryoprotectant may be present in an amount of between about 50 and about 120 mg/ml. The cryoprotectant may be present in an amount of about 90 mg/ml.

In some aspects, the surfactant may be selected from the group consisting of polysorbate 80, polysorbate 20 and poloxamer. The surfactant may be polysorbate 20. In some aspects, the surfactant is present in an amount of about 0.05 to about 1.0 mg/mL. In some aspects the surfactant is present in an amount of about 0.1 to about 0.5 mg/mL. In some aspects, the surfactant is present in an amount of about 0.2 mg/mL.

In some aspects, the invention comprises a formulation suitable for lypholization comprising the following:
(i) about 10 mg/mL ABC;
(ii) about 30 mM lactic acid, pH 4.8±0.5;
(iii) about 90 mg/mL trehalose dehydrate;
(iv) about 0.05 mg/mL disodium EDTA dihydrate;
(v) about 0.1 mg/mL L-methionine; and
(vi) about 0.2 mg/mL polysorbate 20.

The above (all of Examples 66 and 67) also relates to formulations comprising Ab-[L1-FGF21ΔH-A129C]$_2$. Accordingly, in some aspects the invention provides for a lyophilized formulation comprising:
(i) between about 0.1 and about 200 mg/ml of Ab-[L1-FGF21ΔH-A129C]$_2$;
(ii) between about 1 and 150 mM lactic acid pH between about 4 and about 5.5; and
(iii) between about 10 to about 150 mg/ml cryoprotectant;
(iv) between about 0.02-2.0 mg/mL surfactant.

The invention also provides for lyophilized formulations that are lyophilized after pre-dilution of starting formulation by a desired amount (e.g. 2x, 3x) to obtain more desirable properties of lyophilized power or cake (e.g. fluffiness, porosity) resulting in superior reconstitution time (i.e. takes lesser time for reconstitution) and patient-friendly dose preparation method. The invention also provides for lyophilized formulations that can be reconstituted at a higher or lower concentration of the ingredients (e.g. 0.33x, 0.5x, 1x, 2x, 3x, 4x), compared to the composition of pre-lyophilized (pre-lyo) liquid formulations, by adding lower or higher volume of diluent (e.g. 3x, 2x, 1x, 0.5x, 0.33x, 0.25x), respectively. Examples of diluent are water, saline, phosphate-buffered saline, dextrose solution (e.g. 5%), or an aqueous solution containing a pharmaceutical agent, enzyme, surfactant, sugar etc.

In some aspects, the invention comprises the following formulation:
(i) between about 10 to about 60 mg/mL Ab-[L1-FGF21ΔH-A129C]$_2$;
(ii) between about 5 and about 30 mM lactic acid, pH 4.8±0.5;
(iii) between about 10 to about 90 mg/mL trehalose dehydrate;
(iv) between about 0.01 to about 0.1 mg/mL disodium EDTA dihydrate;
(v) between about 0.01 to 0.1 mg/mL L-methionine; and
(vi) about 0.04 to about 0.2 mg/mL polysorbate 20.

In some aspects, the invention comprises the following formulation:
(i) between about 10 to about 20 mg/mL Ab-[L1-FGF21ΔH-A129C]$_2$;
(ii) about 10 mM lactic acid, pH 4.8±0.5;
(iii) about 30 mg/mL trehalose dehydrate;
(iv) about 0.017 mg/mL disodium EDTA dihydrate;
(v) about 0.033 mg/mL L-methionine; and
(vi) about 0.067 mg/mL polysorbate 20.

In some aspects, the invention comprises the following formulation:
(i) between about 15 to about 30 mg/mL Ab-[L1-FGF21ΔH-A129C]$_2$;
(ii) about 15 mM lactic acid, pH 4.8±0.5;
(iii) about 45 mg/mL trehalose dehydrate;
(iv) about 0.025 mg/mL disodium EDTA dihydrate;
(v) about 0.05 mg/mL L-methionine; and
(vi) about 0.1 mg/mL polysorbate 20.

In some aspects, the invention comprises the following formulation:
(i) between about 10 to about 50 mg/mL Ab-[L1-FGF21ΔH-A129C]2;
(ii) about 30 mM lactic acid, pH 4.8±0.5;
(iii) about 90 mg/mL trehalose dehydrate;
(iv) about 0.05 mg/mL disodium EDTA dihydrate;
(iv) about 0.1 mg/mL L-methionine; and
(v) about 0.2 mg/mL polysorbate 20.

In some aspects, the invention comprises the following formulation:
(i) between about 10 to about 30 mg/mL Ab-[L1-FGF21ΔH-A129C]2;
(ii) about 15 mM lactic acid, pH 4.8±0.5;
(iii) about 45 mg/mL trehalose dehydrate;
(iv) about 0.025 mg/mL disodium EDTA dihydrate;
(v) about 0.05 mg/mL L-methionine; and
(vi) about 0.1 mg/mL polysorbate 20.

In some aspects, the invention comprises the following formulation:
(i) between about 20 to about 60 mg/mL Ab-[L1-FGF21ΔH-A129C]2;
(ii) about 30 mM lactic acid, pH 4.8±0.5;
(iii) about 90 mg/mL trehalose dehydrate;
(iv) about 0.05 mg/mL disodium EDTA dihydrate;
(vii) about 0.1 mg/mL L-methionine; and
(viii) about 0.2 mg/mL polysorbate 20.

In some aspects, the invention comprises the following formulation:
(i) between about 10 to about 50 mg/mL Ab-[L1-FGF21ΔH-A129C]2;
(ii) about 30 to 60 mM lactic acid, pH 4.8±0.5;
(iii) about 90 to 180 mg/mL trehalose dehydrate;
(iv) about 0.05 to 0.1 mg/mL disodium EDTA dihydrate;
(iv) about 0.1 to 0.2 mg/mL L-methionine; and
(v) about 0.2 to 0.4 mg/mL polysorbate 20.

In some aspects, the invention comprises the following formulation:
(i) between about 5 to about 25 mg/mL Ab-[L1-FGF21ΔH-A129C]2;
(ii) about 30 mM lactic acid, pH 4.8±0.5;
(iii) about 90 mg/mL trehalose dehydrate;
(iv) about 0.05 mg/mL disodium EDTA dihydrate;
(iv) about 0.1 mg/mL L-methionine; and
(v) about 0.2 mg/mL polysorbate 20.

In some aspects, the invention comprises the following formulation:
(i) between about 10 to about 50 mg/mL Ab-[L1-FGF21ΔH-A129C]2;
(ii) about 30 mM lactic acid, pH 4.8±0.5;
(iii) about 90 mg/mL trehalose dehydrate;
(iv) about 0.05 mg/mL disodium EDTA dihydrate;
(vi) about 0.1 mg/mL L-methionine; and
(vi) about 0.2 mg/mL polysorbate 20.

In some aspects, the invention comprises the following formulation:
(i) between about 5 to about 25 mg/mL Ab-[L1-FGF21ΔH-A129C]2;
(ii) about 15 mM lactic acid, pH 4.8±0.5;
(iii) about 45 mg/mL trehalose dehydrate;
(iv) about 0.025 mg/mL disodium EDTA dihydrate;
(v) about 0.05 mg/mL L-methionine; and
(vi) about 0.1 mg/mL polysorbate 20.

Each of the above formulations may also comprise additional elements as described herein. In addition, each of the above formulations may also be suitable for subsequent lypholization and reconstitution at a lesser volume. In some aspects, the formulations may be concentrated by between about 2× and about 3×.

Example 68

Stability of [FGF21]-[1$^{st}$ Linker]-[Antibody]-[2$^{nd}$-Linker]-[Ex4]

Various formulations of [FGF21]-[1$^{st}$ Linker]-[Antibody]-[2$^{nd}$-Linker]-[Ex4] were prepared by buffer exchange using 10 kDa molecular weight cut-off dialysis cassettes, and then sterile filtered (all experiments used ABC-1). The formulations were subjected to a range of stress conditions (see Table 57). The samples were then analyzed using Appearance assay, UV (ultraviolet absorbance), and Size Exclusion Chromatography (SEC). Samples were analyzed at various time points (Table 57) to assess stability trend.
Appearance Assay
Turbidity increases upon storage at various temperatures: Both the 20 mM lactic acid and 20 mM histidine, pH5.8 formulation (Formulations C and D) showed turbidity increases following either 1 week storage at 40° C. or 2 week at 25° C. or 2 week at 40° C. These data suggest that formulations C and D lead to instability of Formulations of [FGF21]-[1$^{st}$ Linker]-[Antibody]-[2$^{nd}$-Linker]-[Ex4]. When stressed, both sodium acetate pH4.0 and glutamic acid pH4.0 showed no turbidity increase regardless of storage condition.
No significant change in UV was observed over time indicating that even if particulate formation was observed in some of the formulations listed in Table 57, the net concentration of protein in was not significantly affected over time.
High Molecular Weight Species (HMW) Formation
SE-HPLC was used to measure HMW formation for various formulations listed in Table 57. SE-HPLC is able to reliably separate HMW, and is an important stability-indicating assay for [FGF21]-[1$^{st}$ Linker]-[Antibody]-[2$^{nd}$-Linker]-[Ex4]. HMW in the SE-HPLC assay is defined as the species that elute prior to the [FGF21]-[1$^{st}$ Linker]-[Antibody]-[2$^{nd}$-Linker]-[Ex4] peak. Formulations in 20 mM histidine, pH5.8 and 20 mM phosphate, pH8.0 showed high initial as well as time-dependent formation of HMW. Nonlinear aggregation trend of protein formulations over time is known in literature. Formulations in 20 mM sodium acetate, pH4.0 and 20 mM glutamic acid pH4.0 showed the least amount of HMW when compared to other formulations. Therefore, formulations in 20 mM sodium acetate, pH4.0 and glutamic acid pH4.0 provide superior stability for HMW formation.
% HMW (high molecular weight species) measured by SE-HPLC. SE-HPLC conditions include: Toso Biosep G3000SWXL 5 μm, 7.8×300 mm SEC column, Mobile Phase: 200 mM Sodium Phosphate 100 mM Sodium Chloride buffer (pH7.0), Column Temperature: 25° C., Flow Rate: 0.3 ml/min (Isocratic), Detection: UV absorbance at 214 nm, Run Time: 42 mins.

Example 69 pH-Buffer Screen of [FGF21]-[1$^{st}$ Linker]-[Antibody]-[2$^{nd}$-Linker]-[Ex4]

The stability of [FGF21]-[1$^{st}$ Linker]-[Antibody]-[2$^{nd}$-Linker]-[Ex4] in various aqueous buffers was investigated with the goal of finding an appropriate stabilizing medium that can also be lyophilized (all experiments used ABC-1). Example 68 demonstrated the surprising result that compounds of the invention were most stable in sodium acetate and glutamic acid at pH4.0. However, sodium acetate sublimes, and accordingly is difficult to incorporate into a lyophilized buffer. There therefore exists a need to develop an alternative buffer for compounds of the invention that provides optimum long term stability in a lyophilized formulation. Instability of Linker, as well as any hydrolytic clipping of the protein components results in the generation of low molecular weight species (LMW). Additionally, high molecular weight species can be formed if the conjugates aggregate in the formulation tested. Formulations were prepared by buffer exchange into the desired formulation with a target protein concentration in the range of 7-9 mg/mL. Formulations were filtered using 0.2 μm filter, packaged in glass vials and stored at desired temperature. At indicated time points, samples were assayed.
Appearance Assay
Turbidity increases upon storage at various temperatures and conditions: Both the 20 mM citric acid (all pHs) and 20 mM succinic acid (>pH4.8) formulation (Formulations A-C, K and L) showed turbidity increases following either storage at 2 week at 25° C. or 2 week at 30° C. When stressed, both glutamic acid and lactic acid samples showed minimal turbidity increase regardless of storage condition.
With the exception of citric acid samples, no significant change in UV was observed over time indicating that even if particulate formation was observed in some of the formulations listed in Table 57, the net concentration of protein was not significantly affected over time.
HMW Measurement by SE-HPLC and LMW Monitoring by SDS-PAGE
Pronounced effect of buffer and pH was observed upon temperature stress over 2 weeks. The data is presented in Table 59. At initial time point, a trend of increasing HMW was seen in citric acid formulations and higher pH formulations (>4.8). Glutamic acid, pH4.2 and 4.5 formulations showed relatively superior performance for % HMW.

The LMW trend was directly proportionate to pH. Upon storage at 30° C. for 1 week, the lower pH formulations showed pronounced increase in % LMW presumably due to fragmentation. Among the glutamic acid formulations, a balance of pH of formulations is needed to prevent excessive fragmentation due to linker instability and protein clipping. For example, formulation D, pH4.2, in liquid state, produces substantial fragmentation compared to other glutamic acid formulations. The trend of pH-dependent % LMW suggests a pH4.5 formulation is suitable (borne out by SDS PAGE, data not shown).

TABLE 59

SEC data of formulations of [FGF21]-[$1^{st}$ Linker]-[Antibody]-[$2^{nd}$-Linker]-[Ex4].

| ID | Formulation | % HMW at initial | % HMW after 1 weeks at 30° C. | % HMW after 2 weeks at 25° C. | % HMW after 2 weeks at 30° C. |
|---|---|---|---|---|---|
| A | 20 mM citric acid pH 4.2 | 3.4 | 4.8 | 4.7 | 4.8 |
| B | 20 mM citric acid pH 4.5 | 3.5 | 5.5 | 5.4 | 5.6 |
| C | 20 mM citric acid pH 4.8 | 3.2 | 5.2 | 5.2 | 5.6 |
| D | 20 mM glutamic acid, pH 4.2 | 2.5 | 2.2 | 2.2 | 2.0 |
| E | 20 mM glutamic acid, pH 4.5 | 2.6 | 2.4 | 2.3 | 2.3 |
| F | 20 mM glutamic acid, pH 4.8 | 2.7 | 2.7 | 2.6 | 2.7 |
| G | 20 mM lactic acid, pH 4.2 | 2.6 | 3.1 | 2.6 | 2.8 |
| H | 20 mM lactic acid, pH 4.5 | 2.6 | 3.0 | 2.5 | 2.6 |
| I | 20 mM succinic acid, pH 4.2 | 2.6 | 2.6 | 2.3 | 2.6 |
| J | 20 mM succinic acid, pH 4.5 | 2.7 | 3.1 | 2.8 | 3.2 |
| K | 20 mM succinic acid, pH 4.8 | 2.9 | 3.6 | 3.3 | 3.9 |
| L | 20 mM succinic acid, pH 5.3 | 3.1 | 4.0 | 3.8 | 4.4 |

Additionally, the glutamic acid pH 4.5 formulation was also used to evaluate if the conjugates are soluble in aqueous buffered solvents at high concentration and to assess stability at high concentration. A concentration (A280) related increase was observed in % HMW upon storage. Results shown in Table 60.

TABLE 60

High concentration data of [FGF21]-[$1^{st}$ Linker]-[Antibody]-[$2^{nd}$-Linker]-[Ex4].

| Sample | A280 | Turbidity NTU | % HMW | % HMW 1w 2-8C |
|---|---|---|---|---|
| Initial | 8.9 | — | 2.4 | 2.4 |
| 17 min | 32.3 | 9.6 | 2.4 | 2.7 |
| 27 min | 48.9 | 11.2 | 2.5 | 2.8 |
| 42 min | 90 | 18.6 | 2.5 | 3.0 |

Example 70

Lyophilized Formulations of [FGF21]-[$1^{st}$ Linker]-[Antibody]-[$2^{nd}$-Linker]-[Ex4]

Although liquid formulations can be used with compounds of the invention, lyophilized formulations can provide greater longevity of stability. Examples 68 and 69 show that formulations of [FGF21]-[$1^{st}$ Linker]-[Antibody]-[$2^{nd}$-Linker]-[Ex4] with only glutamic acid, albeit superior to other buffers such as histidine, may not provide adequate stability for desired longer term use (all experiments used ABC-1). The combination of glutamic acid with various types of stabilizers such as a sugar or polyol serving as cryoprotectant and lyoprotectant (e.g. trehalose, sucrose, mannitol), and a surfactant for agitation stability (e.g. polysorbate 80, polysorbate 20, poloxamer), and a chelator (e.g. EDTA, DTPA) provides synergistic enhancement of stability. Therefore, the combinations clearly enhance stability of [FGF21]-[$1^{st}$ Linker]-[Antibody]-[$2^{nd}$-Linker]-[Ex4].

Formulations were prepared by buffer exchange and excipient addition with a target protein concentration that varied between formulations (all experiments used ABC-1). The prepared formulations were filtered using 0.2 μm filter, and packaged in glass vials. To prepare lyophilized formulations, the vials were lyophilized, stoppered and capped. At indicated time points, samples assayed by various analytical methods including SEC, iCE, and reduced cGE. Additionally, the liquid formulations were also evaluated for 4 weeks to evaluate stability trend of liquid formulations. Water content of the lyophilized formulations were tested after lyophilization, and were all below 0.5%.

The lyophilized formulations were stored under various temperature stresses, and Table 61 shows SEC, iCE, and reduced CGE (capillary gel electrophoresis) data at indicated time points. cGE produces semi-quantitative estimate of protein fragments. The lyophilized formulations showed better stability when compared to their liquid counterparts on all fronts (Δ% HMW, Δ% Acidic species and Δ% Frag). The lyophilized formulations of glutamic acid the presence of stabilizing excipients (in the presence of a cryoprotectant/lyoprotectant) showed good stability. Therefore, it is concluded that lyophilized glutamic acid formulations are appropriate to test for longer term storage stability. Finally, metal chelators (e.g. EDTA, DTPA) are expected to be beneficial to achieve stability.

Lyo formulation samples were also tested for relative bioactivity. Bioactivity was measured and expressed as relative % to that of a reference material using both a non-competitive Binding ELISA (FGF21) and GLP-1 Exendin potency assay (Ex4 peptide). Bioactivity data are presented in Table 62. These data provide further confidence in stability and functional integrity provided by the components of Lyo formulation.

Example 71

Stability of [FGF21]-[$1^{st}$ Linker]-[Antibody]-[$2^{nd}$-Linker]-[Ex4] Against Agitation The glutamic acid/trehalose/EDTA/PS80 formulation was prepared by buffer exchange and excipient addition with a target protein concentration in the range of 15 mg/mL. The prepared formulations were filtered using 0.2 μm filter, packaged in glass vials. Agitation was applied using an orbital shaker at 300 rpm speed. At indicated time points, samples were assayed. Results in Table 63 demonstrate that the presence of polysorbate 80 helps prevent agitation-induced instability (all experiments used ABC-1).

TABLE 63

Stability data of formulations against agitation stress.

| Formulation | Appearance at initial | Appearance after 24 hr agitation | Change in % HMW after 24 hr agitation |
|---|---|---|---|
| 20 mM glutamic acid, 85 mg/mL trehalose dihydrate, pH 4.5 | Clear | Milky liquid and precipitation | 0.1 |
| 20 mM glutamic acid, 85 mg/mL trehalose dihydrate, 0.2 mg/mL polysorbate 80, pH 4.5 | Clear | Clear with few particulates | 0.3 |

Accordingly, in some aspects the invention provides for a formulation comprising between about 0.1 and about 200 mg/ml of [FGF21]-[$1^{st}$ Linker]-[Antibody]-[$2^{nd}$-Linker]-[Ex4] and between about 1 and 150 mM glutamic acid, pH between about 4.0 and about 5.0; and at least one of the following:
 (i) between about 10 to about 150 mg/ml cryoprotectant;
 (ii) between about 0.001 and about 1.0 mg/ml chelator;
 (iii) between about 0.02-2.0 mg/mL surfactant.

In some aspects, formulations of the invention comprise one or more of (i) to (iv). In some aspects formulations of the invention comprise two or more of (i) to (iv). In some aspects, formulations of the invention comprise (i), (ii), and (iii).

In some aspects the invention provides for a lyophilized formulation comprising:
 (i) between about 0.1 and about 200 mg/ml of FGF21-conjugate
 (ii) between about 1 and 150 mM glutamic acid pH between about 4.0 and about 5.0; and
 (iii) between about 10 to about 150 mg/ml cryoprotectant;
 (iv) between about 0.02-2.0 mg/mL surfactant.

In some aspects, the lyophilized formulation may further comprise between about 0.001 and about 1.0 mg/ml chelator. The chelator may be EDTA or DTPA, and may be present in an amount of between about 0.02 to about 0.5 mg/mL. The chelator may be present in an amount of about 0.05 mg/mL.

In some aspects, the [FGF21]-[$1^{st}$ Linker]-[Antibody]-[$2^{nd}$-Linker]-[Ex4] is a compound of the invention as herein described. In some aspects, the FGF21-Ex4-conjugate is [FGF21]-[$1^{st}$ Linker]-[Antibody]-[$2^{nd}$-Linker]-[Ex4]. In some aspects, the FGF21-Ex4-conjugate is present in an amount of between about 5 mg/ml and about 200 mg/ml. In some aspects, the FGF21-Ex4-conjugate is present in an amount of between about 5 mg/ml and about 90 mg/ml. the FGF21-Ex4-conjugate is present in an amount of between about 5 mg/ml and about 50 mg/ml. the FGF21-conjugate is present in an amount of about 10 mg/ml.

In some aspects, the glutamic acid is present in an amount of between about 1 to about 100 mM. In some aspects, the glutamicic acid is present in an amount of between about 10 mM and about 50 mM. In some aspects, the glutamicic acid is present in an amount of about 20 mM. The pH may be between about 4.2 and about 5.3. The pH may be about 4.5±0.5. The pH may be about 4.5.

In some aspects, the cryoprotectant is selected from the group consisting of trehalose dihydrate, sucrose, and mannitol. The cryoprotectant may be trehalose dihydrate. The cryoprotectant may be present in an amount of between about 50 and about 120 mg/ml. The cryoprotectant may be present in an amount of about 85 mg/ml.

In some aspects, the surfactant may be selected from the group consisting of polysorbate 80, polysorbate 20 and poloxamer. The surfactant may be polysorbate 20. In some aspects, the surfactant is present in an amount of about 0.05 to about 1.0 mg/mL. In some aspects the surfactant is present in an amount of about 0.1 to about 0.5 mg/mL. In some aspects, the surfactant is present in an amount of about 0.2 mg/mL.

In some aspects, the invention comprises a formulation suitable for lyophlization comprising the following:
 (i) between about 30 and about 60 mg/mL [FGF21]-[$1^{st}$ Linker]-[Antibody]-[$2^{nd}$-Linker]-[Ex4];
 (ii) between about 10 and about 60 mM glutamic acid, pH 4.5±0.5;
 (iii) between about 50 and about 100 mg/mL trehalose dehydrate;
 (iv) between about 0.01 and about 0.0 mg/mL disodium EDTA dihydrate;
 (v) between about 0.1 and about 0.3 mg/mL polysorbate 20.

In some aspects, the invention comprises a formulation suitable for lyophlization comprising the following:
 (i) about 30 mg/mL [FGF21]-[$1^{st}$ Linker]-[Antibody]-[$2^{nd}$-Linker]-[Ex4];
 (ii) about 20 mM glutamic acid, pH 4.5±0.5;
 (iii) about 85 mg/mL trehalose dehydrate;
 (iv) about 0.05 mg/mL disodium EDTA dihydrate;
 (v) about 0.2 mg/mL polysorbate 20.

In some aspects, the invention comprises a formulation suitable for lyophlization comprising:
 (i) about 30 mg/ml [FGF21]-[$1^{st}$ Linker]-[Antibody]-[$2^{nd}$-Linker]-[Ex4];
 (ii) about 20 mM glutamic acid, pH 4.5±0.5;
 (iii) about 8.5% trehalose dehydrate;
 (iv) about 0.005% disodium EDTA dihydrate; and
 (v) about 0.02% polysorbate 80.

Example 72

Antibody Enrichment Process

In some situations when h38C2 is incubated with a peptide or protein for conjugation, the reaction does not go to completion, and some unreacted antibody remains. An analytical HIC assay (method described below) to investigate the phenomenon separated 2 early eluting peaks (typically about 0.6-1.8% of protein, and 16.9 and 19.4% protein respectively) and a main peak (typically about 75.2-79.5% protein, although variances of up to 73.5% and 83.3% protein were observed). The main peak protein was fully reactive while peak 1 and 2 were unreactive. Therefore, there was a need to develop an improved process for the purification of antibody h38C2.

HIC Method

This section describes the use of HIC chromatography to assess the percentage of different isoforms present in h38C2 antibody in-process and drug substance samples. These species are thought to be the starting material components which will conjugate zero (peak 1), one (peak 2), or two peptides (main peak) at the Lys-99 location (one for each of the two Fabs per h38C2). The separation and elution occurs by a salt reduction gradient with a simultaneous increase in the organic solvent (isopropyl alcohol) over the gradient in this method, which increases the affinity of the more hydrophobic proteins for the mobile phase, as in reversed phase chromatography. The peak areas are integrated to determine the relative abundance of each isoform.

An analytical HIC method with a TSK Gel Phenyl-5PW column, (7.5 mm×75 mm, 10 μm, TOSOH) was developed to separate unreactive (P1,P2) and reactive mAb main peak from the h38C2 IgG1 antibody. The mobile phases are A:0.75 M ammonium sulfate, 50 mM potassium phosphate, pH7.0 and B:50 mM potassium phosphate, pH7.0, 10% IPA. The column is run at 0.65 ml/minute at 35° C. with the absorbance measured at 214 nm. A 100 μg sample is prepared for injection by diluting the sample or standard to 1 mg/mL with diluent (mobile phase A: water, 50:50).

TABLE 64

Analytical HIC Method Mobile phases are A: 0.75 M ammonium sulfate, 50 mM potassium phosphate, pH 7.0 and B: 50 mM potassium phosphate, pH 7.0, 10%

| Time (minutes) | % B | Flow (ml/min) |
| --- | --- | --- |
| 0.0 | 0.0 | 0.65 |
| 6.8 | 50.0 | 0.65 |
| 42.8 | 81.0 | 0.65 |
| 43.0 | 95.0 | 0.65 |
| 48.0 | 95.0 | 0.65 |
| 48.1 | 0.0 | 0.65 |
| 53.0 | 0.0 | 0.65 |

Example 73 iCE, Met-Ox Data Correlation to Increase in Unreactive h38C2

A hold study was performed at 25° C. with clarified harvest broth of h38C2. The samples were frozen at the designated times. The samples were thawed and purified by Protein A spin columns and submitted for assays. There was a correlation between the increase in acidic and oxidized species and the increase in the non reactive form of the mAb (Table 65). There may be other factors involved in making h38C2 unreactive but the acidic species and oxidation of sulfur moities appear be two of the factors involved.

TABLE 65

Broth Hold Study results for levels of iCE, Met-Ox and Unreactive h38C2.

| Hrs incubation at 25° C. | NIC Non Reactive 2000 | Acidic Species | Met-Ox |
| --- | --- | --- | --- |
| 0 | 16.48 | 31.1 | 3.2 |
| 3 | 16.54 | 31.7 | 3.2 |
| 24 | 22.10 | 36.1 | 6.8 |
| 27 | 22.09 | 37.3 | 5.9 |
| 48 | 26.48 | 40.9 | 8 |
| 56 | 28.40 | 43.3 | 9.2 |
| 72.5 | 32.22 | 45.7 | 10.4 |
| 95 | 34.97 | 49.8 | 12.6 |
| 140 | 37.71 | 51.6 | 13.8 |

Example 74

Column Selection

Initially, a TSK gel Phenyl-5PW column (10 μM particle size) was used to develop an HIC assay to separate the conjugatable mAb from the unreactive form. A TSK gel Phenyl-5PW column (20 μM particle size) was scaled up to produce fully-reactive h38C2. The column capacity was 4-5 g/L and ran under high pressure. The following method had been used to make material for conjugation studies. The column was equilibrated with 0.5 to 1M NaCl in 50 mM sodium phosphate, pH 7 and loaded at 4-5 g/L resin. The column was not washed and was subjected to an elution buffer comprising 50 mM sodium phosphate, 20% IPA, pH7. A linear gradient of 42-60% of elution buffer in 50 mM sodium phosphate, pH7 was developed over 4.8 column volumes (CV), then the concentration was raised to 100% of the respective elution buffer until the material was collected and the absorbance returned to near baseline levels. Although this method was adequate for laboratory scale supplies, a higher throughput method with higher loading capacity was required. A variety of HIC resins were considered or tested (Table 66).

TABLE 66

HIC resins used for the analytical testing and purification of h38C2.

| Resin | Application | Particle size | Pore size | Capacity (g/L) |
| --- | --- | --- | --- | --- |
| TSK gel Phenyl 5 PW | analytical | 10 μM | 1000 Å | 4 |
| TSK gel Phenyl 5 PW | analytical | 20 μM | 1000 Å | ~4 |
| Phenyl 650 S | scalable | 35 μM | 750 Å | 18 |
| PPG 600 M | scalable | 65 μM | 750 Å | ~15-20 |
| Phenyl 600 M | scalable | 65 μM | 750 Å | ~50 |
| Phenyl Sepharose HP | scalable | 34 μM | NA | NA |
| Butyl 600 M | scalable | 65 μM | 750 Å | 20 |
| Butyl Sepharose HP | scalable | 34 μM | NA | NA |

NA = Not available.

For the Phenyl 5 PW, Phenyl 600 M, Butyl 600 M, and Phenyl 650 S chromatography, the equilibration buffer was 20 mM sodium phosphate, 1M NaCl, pH 7.0. The load was adjusted to a similar composition, having the same pH and conductivity. The loads ranged from 4-50 g/L resin on Phenyl 600 M (5-10 g/L, and 20 g/L), TSK gel Phenyl 5 PW, and Butyl 600 M. The loads on the Phenyl 650 S columns were 15-22 g mAb/L resin. The columns were equilibrated with 5CV of equilibration buffer (Table 67), then the column was loaded and washed with 1-2CV of equilibration buffer, then washed with 0-2CV of base buffer. The mAb was eluted with a 1-2CV step gradient of 40-43% elution buffer consisting of 20 mM sodium phosphate, 20% IPA, pH7.0. Next, a linear gradient of 5-10CV with 40-63% elution buffer. Finally the column was subjected to 3-6CV of elution buffer to ensure elution of the remaining mAb. The protein eluted over the course of 3-15CV depending on how fast the gradients were developed. The yields were 0-43% for the Phenyl 5 PW, Phenyl 600 M, and Butyl 600 M resins with product at a concentrations of 0.5-2 mg/mL. The mass balance was typically ~90-100%. The results for the Phenyl 650 S are described below.

TABLE 67

The HIC method used for initial column screening.

| Step | % B | CV's | Solution |
| --- | --- | --- | --- |
| Equilibration | | 5 | 20 mM Sodium Phosphate, 1 M NaCl, pH 7 (Buffer A) |
| Load | | N/A | 20 mM Sodium Phosphate, 1 M NaCl, pH 7 |
| Wash 1 | | 2 | 20 mM Sodium Phosphate, 1 M NaCl, pH 7 |
| Wash 2 | | 0-2 | 20 mM Sodium Phosphate, 1 M NaCl, pH 7 |
| Elution 1 | 40-43 | 1-2 | 20 mM Sodium Phosphate, 20% IPA, pH 7 |
| Elution 2 | 40-60 | 5-10 | 20 mM Sodium Phosphate, 20% IPA, pH 7 |
| Elution 3 | 100 | 5 | 20 mM Sodium Phosphate, 20% IPA, pH 7 |

Buffer B = 20 mM sodium phosphate pH 7 with 20% IPA.

The Phenyl 5 PW (20 μM) resin was tested in a 4 ml column but was not effective at enriching the main peak, only showing 90% reactive h38C2. Moreover, the Phenyl 5 PW was not scalable since it ran at high pressure with the 20 μM bead size and had low capacity, ~4-5 g/L resin. When the Butyl 600 M column was loaded at 23 g/L, it did not deliver any enrichment. The Phenyl 600 M column loaded at 20 g/L showed good enrichment of the main peak at 91-92% but the overall yield of about 43% was lower than the preferred minimum of about 50% yield and about 95% main peak. When the same column was under loaded at 5 g/L of resin, the peak fraction had less main peak than the load material, demonstrating a relationship between higher column load and higher product purity. The Phenyl 650 S with the 35 μM beads was then tested. The smaller beads provide more surface area and binding sites, which provide better resolution. By fine-tuning the salt concentrations and duration of the wash steps, most of the inactive form of the antibody was eliminated while more of the fully reactive (FR) h38C2 remained bound to the resin. Yields up to 57-58% and product pools containing 92-95% main peak were obtained.

Example 75

Development of Salt Reduction, Plateau, and Buffer Wash Steps

Several parameters were evaluated during the development of three wash steps to maximize product yield and purity. During the salt reduction linear gradient step, the slope, duration, and final concentration of the wash were tested. Following this, the optimum concentration and duration of the plateau wash, and the optimum duration of the buffer wash needed to be established. The results of several important experimental runs are shown in Table 68, with Table 69 comparing the HIC assay data from two of these experimental runs.

TABLE 68

Defining the Salt Reduction Wash Protocol for the Phenyl 650 S Column.

| Run | Salt Gradient (NaCl) | CV | Plateau | CV | Buffer | CV | Step 4 | CV | % Yield | % Yield of Main Peak |
|---|---|---|---|---|---|---|---|---|---|---|
| 140 | 1M-0M | 10 |  |  | 0M | 2 | — | — | 46 | 61 |
| 143 | 0.75M-0M | 8 |  |  | 0M | 5 | — | — | 11 | 15 |
| 152 | 1M-0.3M | 7 | 0.30M | 3 | *0.10M | 3 | — | — | 53 | 71 |
| 155 | 1M-0.35M | 3 | 0.35M | 3 | — | — | — | — | 45 | 57 |
| 159 | 1M-0.44M | 7 | 0.44M | 4 | *0.3M | 4 | 0M | 2 | 50 | NA |
| 167 | 1M-0.3M | 7 | 0.30M | 8 | 0M | 2 | — | — | 47 | 65 |
| 171 | 1M-0.33M | 7 | 0.33M | 6 | 0M | 2 | — | — | 57 | 75 |
| **177 | 1M-0.30M | 7 | 0.30M | 2 | 0M | 4 | — | — | 73 | 96 |
| 185 | 1M-0.33M | 7 | 0.33M | 6 | 0M | 3 | — | — | 58 | 76 |
| 9.5 L scale | 1M-0.33M | 7 | 0.33M | 6 | 0M | 3 |  |  | 72 | 93 |
| 33 L GLP | 1M-0.33M | 7 | 0.33M | 6 | 0M | 2 |  |  | 75 | 94 |

NA =- not available.
*This was not a base buffer wash, it also contained NaCl as listed.
**This run used 20 mM sodium phosphate, 1, 6, hexanediol, pH 7.0, the others were eluted with 20% IPA in base buffer.

TABLE 69

HIC assay data.

| Run-Fraction | Peak 1 | Peak 2 | Main Peak |
|---|---|---|---|
| Reference Standard | 1.2 | 19.4 | *75.6 |
| 140 fraction 6 | 3 | 86.8 | 10.2 |
| 140 fraction 10 | 0 | 11.1 | 88.9 |
| 140 fraction 12 | 0 | 11.2 | 88.8 |
| 140 fraction 22 | 0 | 9.7 | 90.3 |
| Reference Standard | 1.8 | 19.2 | 75.2 |
| 152 fraction 10 | 2.3 | 66.2 | 31.5 |
| 152 fraction 14 | 0 | 9.5 | 90.5 |

TABLE 69-continued

HIC assay data.

| Run-Fraction | Peak 1 | Peak 2 | Main Peak |
|---|---|---|---|
| 152 fraction 20 | 0 | 5.9 | 94.1 |
| 152 fraction 22 | 0 | 2.9 | 97.1 |
| 152 fraction 24 | 0 | 8.1 | 91.9 |
| Reference Standard | 0.6 | 17.9 | 77.1 |
| 9.5 L scale product pool | ND | 7.2 | 90.7 |
| Reference Standard | 1.7 | 16.9 | 79.5 |
| 33 L scale, Cycle A, GLP | 0.16 | 9.73 | 88.7 |

Peak 1 and 2 are unreactive/partially active. Main peak is fully in conjugation reactions.
*The reference standard has been measured at 73.5-83.3% in the HIC assay on different days.

The Phenyl 650 S run 140 (Table 68) showed a significant amount of protein in both the wash and elution phase of the run. In these initial runs a 1M to 0 M NaCl linear gradient over 10CV was used. The gradient was followed by a 2CV base buffer wash of 20 mM sodium phosphate. This was the first run that demonstrated the potential to remove the unreactive component and obtain more acceptable yields of fully reactive h38C2. This is shown in greater detail in Table 69, where fraction 6 (wash) contains 86.2% unreactive h38C2 but only 10.2% main peak. During the elution with 20% IPA, 3 fractions contained 90% reactive mAb and the amount of unreactive mAb was reduced to ~10%.

The Phenyl 650 S run 143 (Table 68) used a 0.75 M to 0 M NaCl linear gradient over 8CV. The gradient was followed by a 5CV base buffer wash which had much more protein in the wash phase than the previous run, with a concomitant low yield of 11%. Based on the surprisingly poor yield obtained from this run, it was postulated that the resin may benefit from salt equilibration to provide tighter protein binding. It was also postulated that a balance must be struck between using a sufficient volume of base buffer to remove the salt and the unreactive mAb, while minimizing product loss.

Many of the subsequent runs used 2-3 volumes of base buffer rather than 5CV. The Phenyl 650 S run 152 used a 1M to 0.30 M NaCl linear gradient over 7CV. The gradient was followed by a 3CV plateau wash with 0.30 M NaCl in base buffer and then a 3CV plateau wash with 0.10 M NaCl in base buffer which contained even less protein in the wash and a concomitant increase in the elution peak, giving a 53% yield (Table 68). The initiation of a plateau in the salt reduction step at 300 mM NaCl was a critical discovery which ultimately led to the required improvements. Two elution fractions from run 152 contained 94 and 97% main peak (Table 69) demonstrating that the method worked to achieve the goal of >50% yield and >90% main peak in the Phenyl 650 S product pool. The wash fraction 10 had 31.5% main peak which showed that a plateau wash with more than 0.30 M NaCl could possibly retain more product on the column.

The Phenyl 650 S run 155 used a 1M to 0.35 M NaCl linear gradient over 3CV (Table 68). The gradient was followed by a 3CV plateau wash with 0.35 M NaCl in base buffer which delivered a 43% yield, lower than the previous run. One factor was that a double load, 45 g/L was applied to the column. Most of the protein exited the column in the flow-through and wash, effectively making the load 16 g/L. The steeper slope of the salt reduction gradient, which washed off more of the main peak, also reduced the yield.

The Phenyl 650 S run 159 used a 1M to 0.44M NaCl linear gradient over 7CV (Table 68). The gradient was followed by a 4CV plateau wash with 0.44M NaCl in base buffer, followed by a 4CV plateau wash with 0.3M NaCl in base buffer a 2CV plateau wash with base buffer which delivered a 50% yield, which was lower than a previous run. However, optimizing the base buffer wash was another key discovery that helped maximized both the purity and yields.

The Phenyl 650 S run 167 used a 1M to 0.3M NaCl linear gradient over 7CV (Table 68). The gradient was followed by a 8CV plateau wash with 0.3M NaCl in base buffer, followed by a 2CV plateau wash with base buffer. The yield was 51%. It was postulated that the yield may have been greater had the concentration of the 0.3M NaCl wash been greater.

The Phenyl 650 S run 171 used a 1M to 0.33M NaCl linear gradient over 7CV (Table 68). The gradient was followed by a 6CV plateau wash with 0.33M NaCl in base buffer, followed by a 2CV wash with base buffer which delivered a 57% yield.

A final process development run was conducted to fine-tune the conditions for eliminating NaCl during the 20 mM phosphate wash. The wash steps were established over the course of several experiments, the final refinements in the wash steps were completed as shown in runs 171 and 185 (Table 68) which provided the elution of most of the unreactive mAb. After the column was loaded and washed with 1 CV of 1M NaCl buffer, a 1-0.33M NaCl linear gradient over 7CV efficiently removed the unreactive mAb. A plateau wash of 0.33 M NaCl for 5-6CV allowed the unreactive material to be thoroughly washed from the column. A 2-3CV wash with base buffer removed the remaining salt to condition the column for elution, and was established as the method of choice. Subsequently for the 33 L scale pilot plant runs, the 0.33M NaCl wash was reduced to 5CV and the 20 mM sodium phosphate was reduced to 2CV without losing product quality.

The elution buffer was changed from 14% IPA to 15% 1,6 hexanediol. The goal was to eliminate the flammability potential of IPA at large-scale. The IPA concentration in the elution buffer was established at 14% since a high yield of the fully-reactive h38C2 was collected at lab scale, usually within 1.5CV. The hexanediol elution buffer was tested at small scale in run 177 (Table 68). The product pool was collected in 1.5CV, with a yield of 73% and contained 88% main peak. Individual fractions were collected for the lab scale column runs. The fractions pooled were generally collected at 200 mAU on the ascending peak and between 200 and 400 mAU on the descending peak. After reviewing the product quality of the shoulders, they were sufficiently high in % of main peak so that the pooling strategy for the 33 L column runs was to collect the product peak from 100 AU to 100 mAu.

Example 76

Aqueous Elution Screening

Another consideration was to find a column that could be eluted without organic components in the elution buffer while still enriching the fully-reactive h38C2. More hydrophilic columns were selected for this screen so that the mAb would not bind as tightly to the resin. With the protein less tightly bound, the potential to elute the mAb with an aqueous buffer was greater. In order to be an effective approach the method still needed to separate the fully reactive and unreactive h38C2. PPG 600 M, Butyl HP, and Phenyl HP columns were tested using methodology very similar to the processes developed with the Phenyl 650 S column described herein (Table 70). For PPG 600 M, Butyl HP, and Phenyl HP chromatography (4 mL scale) the equilibration buffer was 20 mM sodium phosphate, 2.5 M NaCl, pH7.0. The load was adjusted to a similar composition, having the same pH and conductivity. The load of 18-19 g mAb/L resin was followed by a 5CV wash with equilibration buffer. Next, a salt reduction wash from 2.5 M to 0 M NaCl over 13-15CV, followed by 3CV of 20 mM phosphate buffer. Alternatively, one Butyl run had a salt reduction wash from 1M to 0.3M NaCl, followed by 3CV of 20 mM phosphate buffer. The columns were stripped with 5CV 20 mM sodium phosphate, 20% IPA, pH7.0.

TABLE 70

Operating conditions for PPG 600 M, Butyl HP and Phenyl HP columns.

| Step | Linear Flow rate | Volume | Solution |
|---|---|---|---|
| Pre-equilibration | 200 cm/h | 5 CV | A: 2.5 M NaCl, 20 mM Na-Phosphate, pH 7.0 |
| Load | 120 cm/h | 15 mL | 5 g/L h38C2 in 2.5 M NaCl, 20 mM Na-Phosphate, pH 7.0 |
| Wash | 100 cm/h | 5 CV | A: 2.5 MNaCl, 20 mM Na-Phosphate, pH 7.0 |
| Elution | 100 cm/h | 0-100% B over 13-15 CV, hold at 100% B for 3 CV | B: 20 mM Na-Phosphate, pH 7.0 |
| Strip | 200 cm/h | 5 CV | 20% v/v IPA in 20 mM Na-Phosphate, pH 7.0 |
| Cleaning | 200 cm/h | 3 CV | 0.5 N NaOH |
| Storage | 200 cm/h | 3 CV | 0.1 N NaOH |

A = 20 mM sodium phosphate, 1 M NaCl, pH 7.
B = 20 mM sodium phosphate, pH 7.

The PPG 600 M column was slightly overloaded at 18 g/L with about 5% of the mAb flowing through during the high-salt wash. The mAb eluted as the conductivity dropped. However, there was a large, broad peak without definition that indicates a separation of the reactive/non-reactive species. The Butyl HP column held the most promise, in fact, a substantial amount of mAb eluted during the lower salt elution. However, the HIC assay results showed the pool contained 43% peak 2 and 53% main peak species. The h38C2 did not elute in the aqueous phase during the salt reduction wash from the Phenyl HP column. Enriched h38C2 was only eluted with an IPA gradient. Since the mAb could only be eluted with IPA, the Phenyl HP column was not suitable for an aqueous elution method. Therefore, none of these columns were able to provide an alternate purification strategy or a reason to switch from the Phenyl 650 S resin.

Example 77

Refined Phenyl 650S Purification Process h38C2 at 20 g/L mAb was thawed and diluted 1:1 with 40 mM sodium phosphate, 2M NaCl, pH7, filtered through a 0.45 /0.2 µM filter, and was loaded at 16-18 g/L on a Phenyl 650 S HIC column (TOSOH) that was equilibrated with 20 mM sodium phosphate, 1M NaCl, pH7.0 (Table 71). The column was washed with 1 CV of equilibration buffer and then a 7CV gradient was developed from 1 to 0.33M NaCl in 20 mM sodium phosphate, pH7. The gradient was held at 0.33M NaCl in 20 mM sodium phosphate, pH7.0 for 5CV and was followed by a 2CV wash with the base buffer, 20 mM sodium phosphate, pH7. The less reactive forms of h38C2 eluted during the application of these wash steps. For the elution phase, a 0-15% 1,6 hexanediol gradient was developed over 1 CV and held at 15% until the elution is complete. The fully reactive h38C2 product was collected as a pool of about 1-2CV.

TABLE 71

The Phenyl 650 S HIC Column Method.

| Step | Linear Flow (cm/hr) | CV's | % B | Solution |
|---|---|---|---|---|
| Flush | 60 | 3 | — | Milli-Q |
| Equilibration | 80 | 5 | — | 20 mM Sodium Phosphate pH 7, 1 M NaCl |
| Load | 80 | N/A | — | ~10 g/L in 20 mM sodium phosphate pH 7, 1 M NaCl |
| Wash | 80 | 1 | — | 20 mM Sodium Phosphate pH 7, 1 M NaCl |
| Salt gradient | 80 | 7 | 0-67 | 20 mM Sodium Phosphate pH 7, 1 M –0.33 M NaCl |
| Salt plateau | 80 | 5 | 67 | 20 mM Sodium Phosphate pH 7, 0.33 M NaCl |
| Buffer wash | 80 | 2 | 100 | 20 mM Sodium Phosphate pH 7 |
| Elution | 60 | 1 | 0-75 | 20 mM Sodium Phosphate pH 7, 20% 1,6, hexanediol, |
| Elution | 60 | 5 | 75 | 20 mM Sodium Phosphate pH 7, 20% 1,6, hexanediol, |
| Flush | 60 | 3 | — | Purified $H_2O$ (WFI: water for injection) |
| *Cleaning | 60 | 3 | — | 0.5 M Sodium Hydroxide |
| Flush | 60 | 3 | — | WFI |
| Storage | 60 | 2 | — | 20 mM Sodium Phosphate pH 7, 20% ethanol, |

*Direction of flow is bottom to top. All other steps have to bottom flow direction. The feed rate was limited by a maximum system pressure of 3 bar. Protein binding under these load conditions was 100%. All operations were carried out at room temperature (18-22° C.).
B: 20 mM sodium phosphate, pH 7.0.

The Phenyl 650 S product pool containing 90-95% fully reactive h38C2 was then diafiltered into 10 mM histidine (8 diavolumes) with a 30 kD Hydrosart membrane (3 m² by Sartorius) at 130-280 g of mAb/m² of membrane. The UF retentate was adjusted to 25 g/L with the appropriate amount of UF rinse of UF buffer. A stock solution containing a 4-5× amount of the remaining excipients was spiked into the diafiltered protein solution in order to establish the final bulk drug substance intermediate formulation. The final formulation was: 10 mM histidine, 10 mM glycine, 2% sucrose, pH6.5±0.3. The formulated DS intermediate solution was passed through a 0.45/0.2 µM final filter and was stored in appropriately-sized Stedium bags or the equivalent up to six months @ 2-8° C. For longer term storage, the DS intermediate was frozen at –70 to –80° C. in 1 L or 4 L PETG bottles.

Tables 72 & 73 show yields from GLP and GMP grade process runs using the refined phenyl 650 S process.

TABLE 72 h38C2 fully reactive (FR) Purification Table at 1.1 kg Scale to GLP (Good Laboratory Practice) standard

| Step | [mAb] (g/L) | Volume (L) | Mass (g) | Total mAb Yield (%) | Main Peak, h38C2 (%) | Yield of h38C2 Main Peak (%) |
|---|---|---|---|---|---|---|
| P 650 S Load cycle A, B | 9.65 | 56 × 2 | 540 | 100 | 79.8 | — |
| P 650 S Pool cycle A | 11.08 | 37.25 | 413 | 76 | 88.7 | 92 |
| P 650 S Pool cycle B | 11.4 | 36 | 411 | 76 | *77 | 91 |
| UF Pool 1 | 25.4 | 15.9 | 403 | 98 | — | — |
| UF Pool 2 | 25 | 16.4 | 411 | 100 | — | — |
| h38C2 FR (Formulated) | 19.9 | 40 | 796 | 98 | — | — |

*A sampling error occurred and the actual product pool was not obtained. The sample analyzed had a protein concentration of 2 g/L instead of 11.4 g/L.

TABLE 73 h38C2 fully reactive (FR) Purification Table at 1.2 kg Scale to GMP (Good Manufacturing Practice) standard.

| Step | [mAb] (g/L) | Volume (L) | Mass (g) | Total mAb Yield (%) | Main Peak, h38C2 (%) | Yield of h38C2 Main Peak (%) |
|---|---|---|---|---|---|---|
| P 650 S Load cycle A, B | 10.27 | 57.3 | 588.5 | — | 83.3 | — |
| P 650 S Pool cycle A | 9.03 | 43.1 | 389.2 | *66 | 94.3 | 79 |
| P 650 S Pool cycle B | 8.41 | 53.68 | 451.4 | 77 | 91.5 | 92 |

TABLE 73-continued h38C2 fully reactive (FR) Purification Table at 1.2 kg Scale to GMP (Good Manufacturing Practice) standard.

| Step | [mAb] (g/L) | Volume (L) | Mass (g) | Total mAb Yield (%) | Main Peak, h38C2 (%) | Yield of h38C2 Main Peak (%) |
|---|---|---|---|---|---|---|
| UF Pool | 25.4 | 32.6 | 828 | 99.5 | — | — |
| h38C2 FR (Formulated) | 19.7 | 40.8 | 804 | 97 | — | — |

*A program error occurred which skipped the salt reduction and plateau wash step, displacing some of the protein from the column. The entire wash step was repeated. The main peak in the fraction was 94.3%, slightly higher than the 91.3% in cycle B. The yield was within the 60-75% range.

Example 78

Conjugation Efficiency of Fully-Reactive h38C2 with Ex4-Linker

The relationship between the HIC assay results reporting the main peak in samples and the ability of both conjugation sites to react with substrate are shown in (Table 74) below. Following the different HIC purification runs, each sample of h38C2 was incubated with a 1:3 molar ratio of [SEQ ID NO:53-L1], and then the number of E4-linker conjugations per antibody were counted using size exclusion chromatography.

h38C2 FR run 171 was purified on Phenyl 650 S according to the Refined process of Example 77 and was contained in a solution of base buffer and 15% IPA. Elution fractions totalling 3CV from h38C2 FR run 171 were pooled and the pool showed 92.4% main peak by HIC assay. The h38C2 was incubated with a 1:3 molar ratio of Ex4-linker. The conjugation reaction went to 87.8% completion and 11.8% of the mAb reacted with one peptide.

h38C2 FR run 177 was purified on Phenyl 650 S according to the Refined process of Example 77 and was contained in a solution of base buffer and 15% 1,6 hexandiol, was then diafiltered into 10 mM glycine, 10 mM histidine pH6.5. Elution fractions totalling 1.5CV from h38C2 FR run 177 were pooled and the pool showed 88% main peak. The h38C2 was incubated with a 1:3 molar ratio of Ex4-linker. The conjugation reaction went to 96% completion and 3.9% of the mAb reacted with one peptide.

Comparing runs 171 and 177, it was evident that the IPA interfered with the reaction since run 177 had higher conjugation efficiency without IPA, and everything else was equivalent.

h38C2 FR run "E-tox" was purified on Phenyl 650 S according to the Refined process of Example 77 and was contained in a solution of base buffer and 15% IPA. Elution fractions totalling 5CV from h38C2 FR run 'E-tox' were pooled and the pool showed 90.7% main peak by HIC assay. The h38C2 was incubated with a 1:3 molar ratio of Ex4-linker. The conjugation reaction went to 93.2% completion and 6.7% of the mAb reacted with one peptide.

It can be seen from Table 74 that the size exclusion analysis, which measures the amount of fully reactive antibody in a sample, correlates very well with the main peak analysis.

TABLE 74

Conjugation efficiency of fully-reactive h38C2 with Ex4-linker.

| h38C2 conjugation with Ex4-linker | HIC assay with TSK gel Phenyl-5PW column Main Peak h38C2 (%) | HIC-TSK gel Butyl NBR column assay to determine conjugation efficiency | | |
|---|---|---|---|---|
| | | h38C2 (%) | h38C2 +1 Ex4-linker (%) | h38C2 +2 Ex4-linker (%) |
| h38C2 FR 171 in 15% IPA | 92.4 | 0.4 | 11.8 | 87.8 |
| h38C2 FR 177 post UF/DF 182 | 88.0 | 0.1 | 3.9 | 96 |
| 124652-198: E-Tox Run | 90.7 | 0.1 | 6.7 | 93.2 |

Example 79

Important Phenyl 650 S Development Findings

The Phenyl 650 S column was chosen after screening several HIC resins from TOSOH™ and other vendors. The resin has a high loading capacity (range of about 16 to about 18 g/L, for a HIC resin. The 35 μM particle size offers the resolution necessary to remove the non-conjuagtable mAb while enriching the reactive form of the antibody. At large scale, columns with 10, 13.5, and 20 cm bed heights have been used. The flow rates are about 2 to about 4 fold higher for the two shorter columns, and accordingly, the invention provides for the use of columns column bed heights of about 10 cm to about 20 cm, and preferably about 10 cm to about 15 cm, enabling more efficient processing at lower pressure. A 20 cm column bed height could be used to meet processing requirements but would require longer process times. The column load range and wash strategy described above has been optimized for both enrichment and yield of fully reactive h38C2. Previous strategies and the other resins delivered protein recoveries of about 11 to about 55% and did not achieve the desired enrichment levels of fully reactive h38C2. The small scale development work employed 20% IPA in 20 mM sodium phosphate, pH7.0 as the elution buffer. The present invention provides for the use of 1,6,hexanediol to avoid using IPA to avoid flammability issues at large scale.

The Phenyl 650 S column is robust and has a four-fold higher loading capacity than the Phenyl 5PW column, achieves higher flow rates than the Phenyl 5 PW column, due to larger particle size, and is scalable and reproducible.

The results with the developed process using Phenyl 650 S at 4 ml, 75 ml, 9.5 L, and 33 L scales with similar purification methods all achieve excellent yields and produced fully reactive h38C2. The 9.5 L scale run delivered 110 g of h38C2 FR (well over the target of 80-90 g) that represented a total protein yield of 72%. The HIC assay showed that the main peak comprised 93% of the total protein.

The present invention provides a process to deliver fully reactive h38C2 at a main peak yield of at least about 85% and preferably at least about 90%, more preferably at least about 92%, more preferably at least about 95%, with a total protein yield of at least about 65%, more preferably at least about 70%, and most preferably at least about 72%.

The purification process delivered the fully reactive h38C2 required for conjugation to FGF21 and subsequently to the Ex4 peptide for the preparation of ABC1.

The total protein yields at the large scales with the Phenyl 650 S column have been optimized to achieve at least about 55%, preferably at least about 60%, more preferably at least about 65%, more preferably at least about 68%, more preferably at least about 70%, and most preferably at least about 75%. The present invention also provides for a process to deliver at least about 85%, preferably at least about 88%, more preferably at least about 90% of fully reactive h38C2.

Successful enrichment of fully-reactive h38C2 for conjugation was achieved with the Phenyl 650 S resin. The maximum loading capacity of the Phenyl 650 S column was approximately 20-22 g/L.

The maximum loading capacity is ascertained by equilibrating the column with buffer then applying the protein load until an absorbance breakthrough is observed. The level of breakthrough is usually set at 5-10% of maximum absorbance. The column loading is stopped and the breakthrough is collected while washing the column with equilibration buffer. The difference between the mass of protein applied minus the amount of protein breakthrough is the maximum loading capacity. On another column run, the calculated maximum load is applied to the column to verify that amount of protein will bind to the column.

The 650 S column gave optimum performance when loaded to at least 2/3 capacity. Column loads were generally ~15-18 g/L, which is about 70-80% of the maximum loading capacity. It was found to be advantageous to load near the column's binding capacity. If the column has too many available binding sites after loading then the elution of the unreactive mAb could be retarded during the wash steps and not be removed prior to elution of the fully conjugatable form. Accordingly, in some aspects, the column may be loaded to at least about 50% capacity, and preferably at least about 60%, more preferably at least about 70%, even more preferably at least about 80%. In run 155 (Table 67) the column was overloaded at 45 g/L and most of the material did not bind to the column. The column run was continued and the protein recovered from the rest of the run. The calculation of total load minus the amount of protein in the breakthrough gave a practical load of 16 g/L. The column was overloaded past the normal break through point and more protein was washed off the column than expected. The binding capacity of the Phenyl 650 S column is between about 22-30 g/L, near or above the 22 g/L tested without seeing breakthrough.

An important part of the purification is to define a 3 step aqueous salt reduction wash that elutes the unreactive antibody. By fine-tuning the target salt concentrations, slope of the salt reduction wash, and duration of the wash, most of the inactive form was eluted from the column while most of the fully-reactive h38C2 remains bound to the resin. The elution is accomplished in the reverse phase mode by either isopropyl alcohol (IPA) or 1,6 hexandiol. Although additional column testing was performed to identify aqueous elution conditions, a suitable method was not identified.

Accordingly, in some aspects, the invention provides the surprising refinement of a process to purify h38C2. In some aspects, h38C2 comprises SEQ ID NO:25 and 26. In some aspects, invention provides a process for the refinement h38C2 and variants thereof. In this context, "variants thereof" relates to antibodies that comprise a light chain variable region ($V_L$) comprising a $V_L$ CDR1, $V_L$ CDR2, and $V_L$ CDR3 of the $V_L$ sequence shown in SEQ ID NO:27; and a heavy chain variable region ($V_H$) comprising a $V_H$ CDR1, $V_H$ CDR2, and $V_H$ CDR3 of the $V_H$ sequence shown in SEQ ID NO:28. Preferably, the h38C2 is an IgG1 antibody. Preferably the h38C2 variant comprises the $V_L$ as set forth in SEQ ID NO:27 and the $V_H$ as set forth in SEQ ID NO:28, and further comprises a light chain constant region at least 95% identical to one or more of SEQ ID NOs:78, 79, 80 and 81, and a heavy chain constant region at least 95% identical to SEQ ID NO:82. In some aspects, the identity of each constant chain independently to one of SEQ ID NO:27 or 28 may be at least 96%, at least 97%, at least 98% or at least 99%. In some aspects, the light chain constant region differs by no more than 5 amino acid residues from one or more of SEQ ID NOs:78, 79, 80 and 81. In some aspects, the light chain constant region comprises SEQ ID NO:81. In some aspects, the light chain constant region differs by no more than 5, 4, 3, 2, or 1 amino acid from SEQ ID NO:81.

In some aspects, the invention provides for a process for extracting fully reactive h38C2 or variant thereof from a mixture of partially unreactive h38C2 or variant thereof and wholly unreactive h38C2 or variant thereof, comprising subjecting the sample to reverse phase chromatography over a phenyl column.

In some aspects, the invention relates to a composition comprising fully reactive h38C2 or variant thereof. A reactive sample of h38C2 or variant thereof may be defined as a sample of h38C2 or variant thereof wherein both antigen binding sites are fully available for antigen binding in at least about 85%, about 88% about 90%, of the antibodies in the sample.

Where the antibody is a catalytic antibody, such as h38C2 or variant thereof, the reactive antigen binding sites will be available to catalyse the respective reaction, and in the case of h38C2 or variant thereof, form covalent conjugates to linkers of the formulae X-Y-Z as herein described. Without wishing to be bound by theory, one hypothesis for the presence of partially and wholly unreactive antibodies in a sample is where one or both antigen binding sites of an antibody has bound with 'sticky' small molecules naturally present at some point throughout the preceding production cycle.

The particle size of the column beads may be below about 50 μm in diameter. The particle size of the column beads may be below about 40 μm. The particle size of the column beads may be between about 50 μm and about 20 μm. The particle size of the column beads may be between about 40 μm and about 30 μm. The particle size of the column beads may be about 35 μm. In some aspects, a phenyl column of "S" grade may be used.

In some aspects, the beads may comprise pores of at least about 500 Å. In some aspects, the beads may comprise pores of at least about 650 Å. In some aspects, the beads may comprise pores of at least about 700 Å. In some aspects, the beads may comprise pores of between about 500 Å and 1000 Å. In some aspects, the beads may comprise pores of between about 700 Å and 800 Å.

In some aspects, the HIC column may comprise phenyl conjugated resin beads of about 35 μM comprising pores of about 750 Å. In some aspects, the column may be a phenyl 650 S column.

The HIC may be carried out between about 0° C. and 37° C. This may be at RT (about 15° C. to about 25° C.). This may be at a temperature of between about 16° C. to about 23° C.

The linear flow rate of the column may be between about 10 and about 100 cm/hr. The preferred flow rates may be between about 50 and about 90 cm/hr.

Base buffer may comprise a buffering agent selected from the group consisting of sodium phosphate, potassium phosphate, ammonium phosphate, HEPES, Tris, or bis-Tris, and preferably sodium phosphate, in a concentration of between about 15 mM and about 100 mM, and preferably between about 20 mM and about 70 mM, and more preferably between about 20 mM and about 50 mM, and most preferably about 20 mM. Below a concentration of about 5 mm, there is likely to be too weak a salt concentration to buffer effectively, and above about 100 mM the increased salt concentration may negatively impact the solubility of the solution. The pH may be between about 6.5 and about 7.5, and more preferably between about 6.8 and about 7.2, and most preferably about 7.

In some aspects, the column may be subjected to a pre-load equilibration wash before loading. The pre-load equilibration wash may comprise base buffer and between about 0.5 M and about 1.5 M salt.

In some aspects, the column may be subjected to a post-loading equilibration wash, comprising base buffer and further comprising between about 0.5 M and about 1.5 M salt.

The salt for any of the steps (including pre-load, load, and post load equilibration buffers) may be at a concentration range whose lower limit is selected from the group consisting of about 0.5 M, 0.6M, 0.7M, 0.75 M and 0.8M, and whose upper limit is selected from the group consisting of about 0.8M, 0.9M, 1 M, 1.1M, 1.2M, 1.3M, 1.4M and 1.5 M. The salt concentration may be about 0.75 M. The salt concentration may be about 0.5 M. The salt concentration may be about 1 M. The salt may be selected from the group consisting of NaCl, KCl, and monosodium citrate. The salt may be NaCl. The salt may be NaCl at about 1M.

In some aspects, the column may be subjected to a linear salt gradient in base buffer, wherein the starting salt concentration is between about 0.5 and about 1.5 M, and is preferably about 1M, and whose final concentration is between about 0.25 and about 0.4M, and is preferably between about 0.3M and about 0.35 M, and is more preferably about 0.33M. It has been found that particularly advantageous results are obtained when the reduction in the concentration of the salt (in particular NaCl) across the gradient equals a decrease of 90-100 mM per 1 CV (for example, between about 10-11 CV would be used to reduce the salt concentration from 1.5 M to 0.5 M). Accordingly, in some aspects, the linear salt gradient is characterized by a reduction in salt concentration of between about 90 mM and 100 mM per 1 CV. Accordingly, it has been found that where using a NaCl gradient, it is desirable to maintain at least about 0.65-0.7M NaCl per about 7CV, and in some aspects about 0.67M of NaCl per about 7CV. The linear gradient may comprise at least about 4, preferably at least about 4.5, and more preferably at least about 5CV. Too small a volume of linear gradient may result in the slope of the gradient being too steep, and there being insufficient time for unreactive material to elute. In some aspects, the linear salt gradient may comprise between about 4 and about 10CV. In some aspects, the linear salt gradient may comprise between about 5 and about 7CV. In some aspects, the linear salt gradient may comprise about 7CV. The salt may be selected from the group consisting of NaCl, KCl, and monosodium citrate. The salt may be NaCl.

Favourably, the column may then be subjected to a plateau wash in base buffer, comprising between about 0.25 M and about 0.4M salt (as above), and preferably 0.33M salt, for between about 4CV and about 7CV, and preferably about 6CV, and more preferably about 5CV. The salt may be NaCl. The NaCl may be at 0.33M.

In some aspects, the column may then be subjected to a further wash with base buffer in a range of CVs whose lower limit is selected from the group consisting of about 1, 2, 3, 4, and 5, and whose upper limit is selected from the group consisting of about 5, 6, 7, 8, 9, and 10, and wherein the range may be between about 1 and about 10, or about 2 and about 8, or about 3 and about 8, or between about 5 and about 6. In some aspects, the further wash in base buffer is in between about 2 to about 3 CV of base buffer.

In some aspects, the elution on the column may be conducted using base buffer and a linear concentration gradient of 1,6 hexanediol. The elution linear gradient may progress from an initial concentration of 1,6 hexanediol of between about 0 to about 1%, and preferably about 0%, to an upper limit selected from the group consisting of about 13%, about 14%, about 15%, about 16%, about 17%, about 18%, about 19%, about 20%, about 21%, and about 22%. The hexanediol elution may be increased over a column volume of between about 0.5CV and about 3CV of elution buffer or until the elution pool is collected. In some aspects, a further elution step may be run, comprising the base buffer and 1,6 hexanediol at a concentration selected from the group consisting of about 13%, about 14%, about 15%, about 16%, about 17%, about 18%, about 19%, about 20%, about 21%, and 22% about 0% to about 22%, for up to 5CV or until the elution pool is collected. In some aspects, the total elution CV is about 7CV. In some aspects the total elution CV is about 6CV.

Although 20% hexanediol worked well, it was found that 15% permitted a better flow rate on UF/DF.

The eluted h38C2 may then be diafiltered into suitable buffer (for example, about 10 mM histidine about 10 mM glycine, about 2% sucrose pH 6.5+/−0.3).

In some aspects, the invention provides a process for purifying a sample of h38C2 or variant thereof wherein both antigen binding sites are fully available for antigen binding in at least about 85% of the antibodies in the sample, comprising
  (i) Equilibrating a HIC column with a pre-loading equilibration wash comprising a base buffer that comprises between about 15 mM and about 100 mM sodium phosphate, potassium phosphate or ammonium phosphate HEPES, Tris and bis-Tris, at between about pH6.5 to about 7.5, and further comprises a salt selected from the group consisting of NaCl, KCl, and monosodium citrate, at a first concentration of between about 0.5 M and 1.5 M; wherein the HIC column comprises phenyl conjugated resin beads below about 50 μm in diameter and comprising pores of at least about 500 Å;
  (ii) Loading the column with a sample of h38C2 at between about 4 and about 80 g/L in loading buffer comprising the base buffer and further comprising the salt at the first concentration;
  (iii) Washing the column with post-loading equilibration wash comprising the base buffer and the salt at the first concentration;
  (iv) Washing the column with a salt gradient, comprising the base buffer and further comprising a linear concentration gradient from about 1.5 M to about 0.25 M of the salt, characterised in that the salt concentration decreases by between about 90 mM and 100 mM per 1 CV;

(v) Washing the column with a salt plateau wash, comprising between about 4CV and about 8CV of the salt at between about 0.25 M and about 0.4M in the base buffer;

(vi) Washing the column with a buffer wash comprising the base buffer;

(vii) Eluting the h38C2 with an elution buffer, comprising the base buffer and a linear concentration gradient of 1,6 hexanediol beginning at a concentration of between about 0 to about 1% of 1,6 hexanediol and ending at an upper limit selected from the group consisting of about 13%, about 14%, about 15%, about 16%, about 17%, about 18%, about 19%, about 20%, about 21%, and 22% about 0% to about 22% of 1,6 hexanediol for between about 0.5CV to about 3CV or until the elution pool is collected;

(viii) Optionally running a further elution step comprising the base buffer and 1,6 hexanediol at a concentration selected from the group consisting of about 13%, about 14%, about 15%, about 16%, about 17%, about 18%, about 19%, about 20%, about 21%, and 22% about 0% to about 22%, for up to 5CV or until the elution pool is collected.

In some aspects, the invention provides a process for purifying a sample of h38C2 or variant thereof wherein both antigen binding sites are fully available for antigen binding in at least about 85% of the antibodies in the sample comprising (i) Equilibrating a Phenyl 650 S HIC column with a pre-loading equilibration wash comprising about 20 mM sodium phosphate, about 1M NaCl, about pH7;

(ii) Loading the column with a sample of h38C2 at between about 5 and about 20 g/L in about 20 mM sodium phosphate at about pH7;

(iii) Washing the column with post-loading equilibration wash comprising about 1 CV of 1M NaCl in about 20 mM sodium phosphate at about pH7;

(iv) Washing the column with a NaCl gradient, comprising 20 mM sodium phosphate pH7, and further comprising a linear concentration gradient from about 1M to about 0.33M of NaCl, characterised in that the salt concentration decreases by between about 90 mM and 100 mM per 1 CV;

(v) Washing the column with a NaCl plateau wash, comprising about 5 CV about 0.33M of NaCl in about 20 mM sodium phosphate at about pH 7;

(vi) Washing the column with a buffer wash comprising about 2CV of 20 mM sodium phosphate at about pH7;

(vii) Eluting the h38C2 with an elution buffer, comprising 20 mM sodium phosphate pH7 and a linear concentration gradient of 1,6 hexanediol beginning at a concentration of between about 0 to about 1% of 1,6 hexanediol and ending at an upper limit selected from the group consisting of about 14%, about 15%, or about 16%, of 1,6 hexanediol for about 1 CV.

(viii) Running a further elution step comprising 20 mM sodium phosphate pH7 and 1,6 hexanediol at a concentration selected from the group consisting of about 14%, about 15%, and about 16%, for about 2 to about 5CV or until the elution pool is collected.

Example 80

Adipocyte Analysis Following ABC-1 Treatment

In addition to gene expression analysis by array in white adipose tissue, histochemical assessment was undertaken on white adipose tissue from DIO mice treated with ABC-1, Ab[Ex4]$_2$ or Ab[FGF21]$_2$. Compounds were dosed once weekly (days 0 and 7), and body weight and food intake were measured twice weekly. On the day of termination (day 10), one gonadal white adipose depot was excised, weighed, fixed, paraffin-embedded, and sectioned for histochemical analysis of cell size and apoptosis (TUNEL staining). ABC-1 significantly reduced body weight and adipose tissue wet weight, as well as adipocyte size, with a trend toward reduced adipocyte apoptosis.

TABLE 75

Body weight change, food intake, adipose depot weight, adipocyte size and TUNEL staining on day 10, after two weekly SC injection of compounds in DIO mice.

| Treatment | Mean Body Weight Change (g) | Mean Cumulative Food Intake (g) | Mean Adipose Tissue Weight (g) | Mean Adipocyte Size (pixel area) | TUNEL staining (pixel area) |
| --- | --- | --- | --- | --- | --- |
| Vehicle | +2.2 | 30.8 | 0.6 | 3336 | 43.6 |
| ABC-1 10 mg/kg | −7.9 | 23.6 | 0.3 | 1652 | 32.0 |
| ABC-1 3 mg/kg | −3.6 | 25.4 | 0.4 | 2111 | 30.8 |
| Ab[Ex4]$_2$ 0.3 mg/kg | −1.0 | 19.2 | 0.7 | 3148 | 48.2 |
| Ab[FGF21]$_2$ 10 mg/kg | −2.5 | 29.4 | 0.7 | 2990 | 41.0 |

Example 81

ABC-1 Effect on Monkeys after High Fat Diet

In a study designed to investigate the efficacy of ABC-1 in cynomolgus monkeys after feeding on a high fat diet for 6 months, 8 adult male were dosed with ABC-1 intravenously twice weekly for two weeks at a dose levels of 1.0 mg/kg (Weeks 1 and 2), 3.0 mg/kg (Weeks 3 and 4) and 10 mg/kg (Weeks 5 and 6). Whole-body DXA scans were taken under anesthesia after an overnight fast at baseline and at the end of the 6 weeks dosing period. Composition of the 3 body compartments consisting of fat mass, lean body mass, and bone mineral content (BMC) were analyzed and estimated. No remarkable change in body weights were noted between the baseline and the 1.0 mg/kg and 3.0 mg/kg dosing periods. However, at the end of the 10.0 mg/kg treatment a considerable decrease in mean body weight was observed (9.0% with a standard error of ±5.4%). The mean Body Mass Index (BMI) values were lower by 12.09% at the end of the dosing period (Week 6) as compared to the mean baseline values. DXA body composition analysis showed lower mean percent values for tissue (−34.9±12.9%) and regional (−35.6±12.9%) percentage fat and fat mass (−42.1±14.0%) involving the trunk and total body recorded at the end of the dosing periods (Week 6), relative to the baseline values. No remarkable changes in the lean tissue mass, bone mineral content (BMC), and total mass were noted during the entire observation periods, suggesting that weight loss induced by ABC-1 is targeted uniquely to a loss of fat mass.

TABLE 76

Effect of ABC-1 on cynomolgus monkeys after 6-months high fat diet.

| | Body Weight (kg) | BMI (kg/m$^2$) | Total Mass by DXA (kg) | Lean Mass by DXA (kg) | Fat Mass by DXA (kg) | BMC by DXA (kg) |
|---|---|---|---|---|---|---|
| Baseline | 5.9 ± 0.3 | 33.6 ± 1.3 | 6.0 ± 0.3 | 4.7 ± 0.2 | 1.1 ± 0.1 | 0.27 ± 0.02 |
| Week 6 | 5.2 ± 0.2 | 29.6 ± 0.9 | 5.3 ± 0.3 | 4.5 ± 0.2 | 0.58 ± 0.07 | 0.27 ± 0.02 |

Unless otherwise indicated, where the term "Ab-L1-FGF21ΔH-A129C" is used in the context of the specific examples, this refers to the h38C2 antibody (SEQ ID NO:25 and 26), with each arm of the antibody covalently linked through $K^{99}$ of SEQ ID NO:26 to linker-1(L1), and each L1 molecule covalently conjugated to the thiol group of $Cys^{129}$ in SEQ ID NO:10 (according to the numbering of SEQ ID NO:1). The compound may also be described as Ab-(FGF21ΔH-A129C-L1)$_2$, h38C2-(FGF21ΔH-A129C-L1)$_2$, and h38C2-(SEQ ID NO:10-L1)$_2$. It will be apparent that minor modifications to the sequence of the antibody, specific linker and FGF21 molecule may be possible, in particular known polymorphic sites, such as position 146, which may be L or P. It is noted that P146 and L146 variants of FGF21 do not appear to show any biological difference.

Where asymmetric bifunctional conjugate (ABC) molecules and intermediates and derivatives thereof are described in the context of specific examples, a subscript 1 or 2 denotes the number of conjugated protein-linker or peptide-linker species per antibody.

Where letters are used in the context of describing linker groups, or chemical variables (e.g. Y to define a recognition group), the formula may be represented by a combination of uppercase and lowercase version of the letter, or double lowercase, to avoid any possible confusion between the formula represented by the single letter and an amino acid or nucleotide denoted by the one-letter IUPAC code. Thus, Y, as a recognition group, may also be described as Yy or yy.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description.

The use of the term "or" in the claims is used to mean "and/or" unless explicitly indicated to refer to alternatives only or the alternative are mutually exclusive, although the disclosure supports a definition that refers to only alternatives and "and/or."

As used herein the specification, "a" or "an" may mean one or more, unless clearly indicated otherwise. As used herein in the claim (s), when used in conjunction with the word "comprising", the words "a" or "an" may mean one or more than one. As used herein "another" may mean at least a second or more.

The words "comprises/comprising" and the words "having/including" when used herein with reference to the present invention are used to specify the presence of stated features, integers, steps or components but does not preclude the presence or addition of one or more other features, integers, steps, components or groups thereof.

TABLE 57

Formulations of [FGF21]-[1st Linker]-[Antibody]-[2nd-Linker]-[Ex4] (ABC-1)

| | Formulation | Protein (mg/mL) | pH | Appearance (NTU) | | | | | | | SE-HPLC (% HMW) | | | | | | |
|---|---|---|---|---|---|---|---|---|---|---|---|---|---|---|---|---|---|
| | | | | Initial | 1 wk 5° C. | 2 wks 5° C. | 1 wk 25° C. | 2 wks 25° C. | 1 wk 40° C. | 2 wks 40° C. | Initial | 1 wk 5° C. | 2 wks 5° C. | 1 wk 25° C. | 2 wks 25° C. | 1 wk 40° C. | 2 wks 40° C. |
| A | 20 mM sodium acetate, pH 4.0 | 7-9 | 4.0 | 4 | 6 | 4 | 6 | 3 | 4 | 11 | 2.7 | 2.3 | 2.4 | 2.3 | 2.5 | 3.0 | 4.3 |
| B | 20 mM glutamic acid, pH 4.0 | 7-9 | 4.0 | 6 | 7 | 4 | 4 | 3 | 3 | 6 | 2.5 | 2.2 | 2.3 | 2.2 | 2.1 | 2.0 | 2.0 |
| C | 20 mM lactic acid, pH 4.8 | 7-9 | 4.8 | 4 | 6 | 6 | 11 | 28 | 75 | 40 | 2.7 | 2.5 | 2.6 | 2.6 | 2.7 | 3.8 | 5.2 |
| D | 20 mM histidine, pH 5.8 | 7-9 | 5.9 | 5 | 7 | 4 | 5 | 28 | 334 | 357 | 4.3 | 4.5 | 4.8 | 4.0 | 4.2 | 3.8 | 4.0 |
| E | 20 mM sodium phosphate, pH 8.0 | 7-9 | 7.9 | 7 | 8 | 4 | 7 | 8 | 6 | 7 | 4.0 | 4.6 | 5.1 | 6.8 | 7.2 | 5.4 | 5.6 |

TABLE 58

Appearance and UV data of [FGF21]-[1st Linker]-[Antibody]-[2nd-Linker]-[Ex4] (ABC-1)

| | | Appearance (NTU) | | | | Concentration (mg/mL) | | | |
|---|---|---|---|---|---|---|---|---|---|
| | Formulation | Initial | 1 wk 30° C. | 2 wks 25° C. | 2 wks 30° C. | Initial | 1 wk 30° C. | 2 wks 25° C. | 2 wks 30° C. |
| A | 20 mM citric acid pH 4.2 | 12 | 530 | 296 | 362 | 8.1 | 5.5 | 5.9 | 5.5 |
| B | 20 mM citric acid pH 4.5 | 84 | 519 | 580 | 528 | 8.4 | 5.0 | 5.3 | 4.8 |
| C | 20 mM citric acid pH 4.8 | 55 | 498 | 522 | 530 | 8.0 | 4.8 | 5.3 | 4.4 |
| D | 20 mM glutamic acid, pH 4.2 | 7 | 6 | 5 | 3 | 8.4 | 8.3 | 8.6 | 8.5 |
| E | 20 mM glutamic acid, pH 4.5 | 7 | 7 | 6 | 6 | 8.3 | 8.3 | 8.5 | 8.5 |
| F | 20 mM glutamic acid, pH 4.8 | 6 | 58 | 17 | 34 | 8.3 | 8.4 | 8.7 | 8.6 |
| G | 20 mM lactic acid, pH 4.2 | 6 | 5 | 6 | 5 | 8.3 | 8.4 | 8.7 | 8.6 |
| H | 20 mM lactic acid, pH 4.5 | 8 | 9 | 7 | 9 | 8.4 | 8.4 | 8.7 | 8.6 |
| I | 20 mM succinic acid, pH 4.2 | 6 | 4 | 7 | 7 | 8.3 | 8.4 | 8.6 | 8.5 |
| J | 20 mM succinic acid, pH 4.5 | 7 | 13 | 9 | 13 | 8.3 | 8.5 | 8.6 | 8.7 |
| K | 20 mM succinic acid, pH 4.8 | 6 | 315 | 39 | 291 | 8.3 | 8.2 | 8.6 | 8.2 |
| L | 20 mM succinic acid, pH 5.3 | 6 | 390 | 12 | 368 | 8.2 | 8.1 | 8.5 | 8.1 |

TABLE 61

Lyophilized formulations of [FGF21]-[1st Linker]-[Antibody]-[2nd-Linker]-[Ex4] (ABC-1); (Liq = Liquid, Lyo = lyophilized)

| ID | protein conc mg/mL | Buffer | pH | Excipients | Liq/Lyo | % HMW at initial | % HMW after 4 weeks at 5° C. | % HMW after 4 weeks at 25° C. | % Acidic species at initial | % Acidic species after 4 wks at 25° C. | % Frag at initial | % Frag after 4 weeks at 5° C. |
|---|---|---|---|---|---|---|---|---|---|---|---|---|
| A | 15 | 20 mM Glutamic Acid | 4.5 | 85 mg/mL Trehalose dihydrate, 0.05 mg/mL EDTA, 0.5 mg/mL PS80 | Liq | 1.0 | 1.2 | 1.7 | 39.62 | 49.61 | 1.3 | 2.3 |
| B | 30 | 20 mM Glutamic Acid | 4.5 | 85 mg/mL Trehalose dihydrate, 0.05 mg/mL EDTA, 0.5 mg/mL PS80 | Lyo | 1.4 | 1.5 | 1.6 | 42.19 | 41.63 | 1.5 | 1.5 |

TABLE 62

Bioactivity (relative %) data of selected Lyophilized formulations of [FGF21]-[1st Linker]-[Antibody]-[2nd-Linker]-[Ex4] listed in Table 61

| Test | Bioactivity after lyophilization t = 0 | Bioactivity after 1 month at 5° C. | Bioactivity after 1month at 25° C. | Bioactivity after 3 months at 5° C. | Bioactivity after 3 months at 25° C. |
|---|---|---|---|---|---|
| FGF21 | 93.0 | 89 | 78 | 87 | 99 |
| Ex4 | 116.0 | 127 | 113 | 112 | 124 |

What is claimed:

1. A process for purifying a sample of h38C2 antibody or variant thereof, wherein both antigen binding sites are fully available for antigen binding in at least about 85% of the antibodies in the sample, comprising
  (a) Equilibrating a hydrophobic interaction chromatography (HIC) column with a pre-loading equilibration wash comprising a base buffer that comprises between about 15 mM and about 100 mM sodium phosphate, potassium phosphate or ammonium phosphate HEPES, Tris and bis-Tris, at between about pH6.5 to about 7.5, and further comprises a salt selected from the group consisting of NaCl, KCl, and monosodium citrate, at a first concentration of between about 0.5 M and 1.5 M; wherein the HIC column comprises phenyl conjugated resin beads below about 50 µm in diameter and comprising pores of at least about 500 Å;
  (b) Loading the column with a sample of h38C2 at between about 4 and about 80 g/L in loading buffer comprising the base buffer and further comprising the salt at the first concentration;
  (c) Washing the column with post-loading equilibration wash comprising the base buffer and the salt at the first concentration;
  (d) Washing the column with a salt gradient, comprising the base buffer and further comprising a linear concentration gradient from about 1.5 M to about 0.25 M of the salt, characterised in that the salt concentration decreases by between about -90 mM and 100 mM per 1column volume CV;
  (e) Washing the column with a salt plateau wash, comprising between about 4CV and about -8CV of the salt at between about 0.25 M and about 0.4M in the base buffer;
  (f) Washing the column with a buffer wash comprising the base buffer;
  (g) Eluting the h38C2 with an elution buffer, comprising the base buffer and a linear concentration gradient of 1,6 hexanediol beginning at a concentration of between about 0 to about 1% of 1,6 hexanediol and ending at an upper limit selected from the group consisting of about 13%, about 14%, about 15%, about 16%, about 17%, about 18%, about 19%, about 20%, about 21%, and 22% about 0% to about 22% of 1,6 hexanediol for between about 0.5CV to about 3CV or until the elution pool is collected,
  (h) Optionally running a further elution step comprising the base buffer and 1,6 hexanediol at a concentration selected from the group consisting of about 13%, about 14%, about 15%, about 16%, about 17%, about 18%, about 19%, about 20%, about 21%, and 22% about 0% to about 22%, for up to 5CV or until the elution pool is collected;
wherein the h38C2 antibody or variant thereof is an IgG1 aldolase antibody comprising a light chain variable region ($V_L$) as set forth in SEQ ID NO:27; and a heavy chain variable region ($V_H$) as set forth in SEQ ID NO:28.

2. The process as claimed in claim 1, wherein the antibody further comprises a light chain constant region at least 95% identical to one or more of SEQ ID NOs:78, 79, 80 and 81, and a heavy chain constant region at least 95% identical to SEQ ID NO:82.

3. The process as claimed in claim 1, wherein the antibody is an IgG1, and may comprise SEQ ID NO:25 and 26.

4. The process as claimed in claim 1, wherein HIC column comprises phenyl conjugated resin beads of about 35 µM comprising pores of about 750 Å.

5. The process as claimed in claim 1, wherein the pre-loading equilibration wash of step (a) comprises about 20 mM sodium phosphate, about 1M NaCl, about pH7.

6. The process as claimed in claim 1, wherein at step (b), the column is loaded with a sample of h38C2 at between about 15 and about 18 g/L in about 20 mM sodium phosphate at about pH7.

7. The process as claimed in claim 1, step (c), the post-loading equilibration wash comprises about 1 CV of 1M NaCl in about 20 mM sodium phosphate at about pH7.

8. The process as claimed in claim 1, wherein at step (d), the salt gradient comprises 20 mM sodium phosphate pH7, and wherein and the linear concentration gradient is from about 1M to about 0.33M of NaCl, and the salt concentration decreases by between about 90 mM and 100 mM per 1 CV.

9. The process as claimed in claim 1, wherein at step (d), the linear salt gradient comprises at least about 4 CV.

10. The process as claimed in claim 1, wherein the salt plateau wash of step (e) comprises about 5 CV and about 0.33M of NaCl in about 20 mM sodium phosphate at about pH 7.

11. The process as claimed in claim 1, wherein the base buffer at step (f) comprises about 2CV of 20 mM sodium phosphate at about pH7.

12. The process as claimed in claim 1, wherein the elution buffer of step (g) comprises 20 mM sodium phosphate pH7.

13. The process as claimed in claim 1, wherein the linear concentration gradient of step (g) comprises a linear concentration gradient of 1,6 hexanediol beginning at a concentration of between about 0 to about 1% of 1,6 hexanediol and ending at an upper limit selected from the group consisting of about 14%, about 15%, or about 16%, of 1,6 hexanediol for about 1 CV.

14. The process as claimed in claim 1, wherein the further elution step of step (h) comprises 20 mM sodium phosphate pH7 and 1,6 hexanediol at a concentration selected from the group consisting of about 14%, about 15%, and about 16%, for about 2 to about 5CV or until the elution pool is collected.

* * * * *

SEQUENCE LISTING

<160> NUMBER OF SEQ ID NOS: 82

<210> SEQ ID NO 1
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or absent
<220> FEATURE:
<221> NAME/KEY: MISC_FEATURE
<222> LOCATION: (146)..(146)
<223> OTHER INFORMATION: X = L or P

<400> SEQUENCE: 1

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 180
<212> TYPE: PRT
<213> ORGANISM: Homo sapiens

<400> SEQUENCE: 2

Pro Ile Pro Asp Ser Ser Pro Leu Leu Gln Phe Gly Gly Gln Val Arg

```
  1               5                   10                  15
Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
            35                  40                  45

Glu Ser Leu Leu Gln Leu Lys Ala Leu Lys Pro Gly Val Ile Gln Ile
            50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro His Arg Asp Pro Ala
                115                 120                 125

Pro Arg Gly Pro Ala Arg Phe Leu Pro Leu Pro Gly Leu Pro Pro Ala
            130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 3
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or absent
<220> FEATURE:
<221> NAME/KEY: MISC_FEATURE
<222> LOCATION: (79)..(79)
<223> OTHER INFORMATION: X = D or C
<220> FEATURE:
<221> NAME/KEY: MISC_FEATURE
<222> LOCATION: (125)..(125)
<223> OTHER INFORMATION: X = H or C
<220> FEATURE:
<221> NAME/KEY: MISC_FEATURE
<222> LOCATION: (129)..(129)
<223> OTHER INFORMATION: X = A or C
<220> FEATURE:
<221> NAME/KEY: MISC_FEATURE
<222> LOCATION: (146)..(146)
<223> OTHER INFORMATION: X = P or L

<400> SEQUENCE: 3

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
            50                  55                  60

Ile Leu Gly Val Lys Thr Ser Arg Phe Leu Cys Gln Arg Pro Xaa Gly
65                  70                  75                  80

Ala Leu Tyr Gly Ser Leu His Phe Asp Pro Glu Ala Cys Ser Phe Arg
```

```
              85                  90                  95
Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Xaa Arg Asp Pro
            115                 120                 125

Xaa Pro Arg Gly Pro Ala Arg Phe Leu Pro Leu Pro Gly Leu Pro Pro
130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 4
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (125)..(125)
<223> OTHER INFORMATION: X = C or H
<220> FEATURE:
<221> NAME/KEY: MISC_FEATURE
<222> LOCATION: (129)..(129)
<223> OTHER INFORMATION: X = A or C
<220> FEATURE:
<221> NAME/KEY: MISC_FEATURE
<222> LOCATION: (146)..(146)
<223> OTHER INFORMATION: X = L or P

<400> SEQUENCE: 4

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Xaa Arg Asp Pro
            115                 120                 125

Xaa Pro Arg Gly Pro Ala Arg Phe Leu Pro Leu Pro Gly Leu Pro Pro
130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180
```

```
<210> SEQ ID NO 5
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (146)..(146)
<223> OTHER INFORMATION: X = L or P

<400> SEQUENCE: 5

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Cys Arg Asp Pro
        115                 120                 125

Ala Pro Arg Gly Pro Ala Arg Phe Leu Pro Leu Pro Gly Leu Pro Pro
    130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 6
<211> LENGTH: 180
<212> TYPE: PRT
<213> ORGANISM: Homo sapiens

<400> SEQUENCE: 6

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
    50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95
```

```
Leu Leu Leu Glu Asp Gly Tyr Asn Val Tyr Gln Ser Glu Ala His Gly
                100                 105                 110

Leu Pro Leu His Leu Pro Gly Asn Lys Ser Pro Cys Arg Asp Pro Ala
            115                 120                 125

Pro Arg Gly Pro Ala Arg Phe Leu Pro Leu Pro Gly Leu Pro Pro Ala
        130                 135                 140

Pro Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 7
<211> LENGTH: 180
<212> TYPE: PRT
<213> ORGANISM: Homo sapiens

<400> SEQUENCE: 7

Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
    50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro Cys Arg Asp Pro Ala
            115                 120                 125

Pro Arg Gly Pro Ala Arg Phe Leu Pro Leu Pro Gly Leu Pro Pro Ala
        130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 8
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (146)..(146)
<223> OTHER INFORMATION: X = L or P

<400> SEQUENCE: 8

Xaa Pro Ile Pro Asp Ser Ser Pro Leu Leu Gln Phe Gly Gly Gln Val
```

```
                1               5                   10                  15
            Arg Gln Arg Tyr Leu Tyr Thr Asp Asp Ala Gln Gln Thr Glu Ala His
                            20                  25                  30

Leu Glu Ile Arg Glu Asp Gly Thr Val Gly Gly Ala Ala Asp Gln Ser
                            35                  40                  45

Pro Glu Ser Leu Leu Gln Leu Lys Ala Leu Lys Pro Gly Val Ile Gln
                            50                  55                  60

Ile Leu Gly Val Lys Thr Ser Arg Phe Leu Cys Gln Arg Pro Asp Gly
             65                  70                  75                  80

Ala Leu Tyr Gly Ser Leu His Phe Asp Pro Glu Ala Cys Ser Phe Arg
                            85                  90                  95

Glu Leu Leu Glu Asp Gly Tyr Asn Val Tyr Gln Ser Glu Ala His
                            100                 105                 110

Gly Leu Pro Leu His Leu Pro Gly Asn Lys Ser Pro His Arg Asp Pro
                            115                 120                 125

Cys Pro Arg Gly Pro Ala Arg Phe Leu Pro Leu Pro Gly Leu Pro Pro
                            130                 135                 140

Ala Xaa Pro Glu Pro Pro Gly Ile Leu Ala Pro Gln Pro Pro Asp Val
             145                 150                 155                 160

Gly Ser Ser Asp Pro Leu Ser Met Val Gly Pro Ser Gln Gly Arg Ser
                            165                 170                 175

Pro Ser Tyr Ala Ser
                            180

<210> SEQ ID NO 9
            <211> LENGTH: 180
            <212> TYPE: PRT
            <213> ORGANISM: Homo sapiens

<400> SEQUENCE: 9

Pro Ile Pro Asp Ser Ser Pro Leu Leu Gln Phe Gly Gly Gln Val Arg
             1               5                   10                  15

Gln Arg Tyr Leu Tyr Thr Asp Asp Ala Gln Gln Thr Glu Ala His Leu
                            20                  25                  30

Glu Ile Arg Glu Asp Gly Thr Val Gly Gly Ala Ala Asp Gln Ser Pro
                            35                  40                  45

Glu Ser Leu Leu Gln Leu Lys Ala Leu Lys Pro Gly Val Ile Gln Ile
                            50                  55                  60

Leu Gly Val Lys Thr Ser Arg Phe Leu Cys Gln Arg Pro Asp Gly Ala
             65                  70                  75                  80

Leu Tyr Gly Ser Leu His Phe Asp Pro Glu Ala Cys Ser Phe Arg Glu
                            85                  90                  95

Leu Leu Leu Glu Asp Gly Tyr Asn Val Tyr Gln Ser Glu Ala His Gly
                            100                 105                 110

Leu Pro Leu His Leu Pro Gly Asn Lys Ser Pro His Arg Asp Pro Cys
                            115                 120                 125

Pro Arg Gly Pro Ala Arg Phe Leu Pro Leu Pro Gly Leu Pro Pro Ala
                            130                 135                 140

Pro Pro Glu Pro Pro Gly Ile Leu Ala Pro Gln Pro Pro Asp Val Gly
             145                 150                 155                 160

Ser Ser Asp Pro Leu Ser Met Val Gly Pro Ser Gln Gly Arg Ser Pro
                            165                 170                 175

Ser Tyr Ala Ser
                            180
```

<210> SEQ ID NO 10
<211> LENGTH: 180
<212> TYPE: PRT
<213> ORGANISM: Homo sapiens

<400> SEQUENCE: 10

```
Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro His Arg Asp Pro Cys
        115                 120                 125

Pro Arg Gly Pro Ala Arg Phe Leu Pro Leu Pro Gly Leu Pro Pro Ala
130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180
```

<210> SEQ ID NO 11
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (146)..(146)
<223> OTHER INFORMATION: X = P or L

<400> SEQUENCE: 11

```
Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Cys Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
```

```
            100                 105                 110
Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 12
<211> LENGTH: 180
<212> TYPE: PRT
<213> ORGANISM: Homo sapiens

<400> SEQUENCE: 12

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
    50                  55                  60

Leu Gly Val Lys Thr Ser Arg Phe Leu Cys Gln Arg Pro Cys Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 13
<211> LENGTH: 180
<212> TYPE: PRT
<213> ORGANISM: Homo sapiens

<400> SEQUENCE: 13

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
```

```
                    50                  55                  60

Leu Gly Val Lys Thr Ser Arg Phe Leu Cys Gln Arg Pro Cys Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Pro Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 14
<211> LENGTH: 180
<212> TYPE: PRT
<213> ORGANISM: Homo sapiens

<400> SEQUENCE: 14

Pro Ile Pro Asp Ser Ser Pro Leu Leu Gln Phe Gly Gly Gln Val Arg
 1               5                  10                  15

Gln Arg Tyr Leu Tyr Thr Asp Asp Ala Gln Gln Thr Glu Ala His Leu
             20                  25                  30

Glu Ile Arg Glu Asp Gly Thr Val Gly Gly Ala Ala Asp Gln Ser Pro
         35                  40                  45

Glu Ser Leu Leu Gln Leu Lys Ala Leu Lys Pro Gly Val Ile Gln Ile
     50                  55                  60

Leu Gly Val Lys Thr Ser Arg Phe Leu Cys Gln Arg Pro Asp Gly Ala
 65                  70                  75                  80

Leu Tyr Gly Ser Cys His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 15
<211> LENGTH: 180
<212> TYPE: PRT
<213> ORGANISM: Homo sapiens

<400> SEQUENCE: 15

Pro Ile Pro Asp Ser Ser Pro Leu Leu Gln Phe Gly Gly Gln Val Arg
```

```
                1               5                   10                  15
        Gln Arg Tyr Leu Tyr Thr Asp Asp Ala Gln Gln Thr Glu Ala His Leu
                        20                  25                  30

Glu Ile Arg Glu Asp Gly Cys Val Gly Gly Ala Ala Asp Gln Ser Pro
                        35                  40                  45

Glu Ser Leu Leu Gln Leu Lys Ala Leu Lys Pro Gly Val Ile Gln Ile
                50                  55                  60

Leu Gly Val Lys Thr Ser Arg Phe Leu Cys Gln Arg Pro Asp Gly Ala
        65                  70                  75                  80

Leu Tyr Gly Ser Leu His Phe Asp Pro Glu Ala Cys Ser Phe Arg Glu
                        85                  90                  95

Leu Leu Leu Glu Asp Gly Tyr Asn Val Tyr Gln Ser Glu Ala His Gly
                        100                 105                 110

Leu Pro Leu His Leu Pro Gly Asn Lys Ser Pro His Arg Asp Pro Ala
                        115                 120                 125

Pro Arg Gly Pro Ala Arg Phe Leu Pro Leu Pro Gly Leu Pro Pro Ala
                        130                 135                 140

Leu Pro Glu Pro Pro Gly Ile Leu Ala Pro Gln Pro Pro Asp Val Gly
        145                 150                 155                 160

Ser Ser Asp Pro Leu Ser Met Val Gly Pro Ser Gln Gly Arg Ser Pro
                        165                 170                 175

Ser Tyr Ala Ser
                        180

<210> SEQ ID NO 16
<211> LENGTH: 181
<212> TYPE: PRT
<213> ORGANISM: Homo sapiens

<400> SEQUENCE: 16

Cys Pro Ile Pro Asp Ser Ser Pro Leu Leu Gln Phe Gly Gly Gln Val
        1               5                   10                  15

Arg Gln Arg Tyr Leu Tyr Thr Asp Asp Ala Gln Gln Thr Glu Ala His
                        20                  25                  30

Leu Glu Ile Arg Glu Asp Gly Thr Val Gly Gly Ala Ala Asp Gln Ser
                        35                  40                  45

Pro Glu Ser Leu Leu Gln Leu Lys Ala Leu Lys Pro Gly Val Ile Gln
                50                  55                  60

Ile Leu Gly Val Lys Thr Ser Arg Phe Leu Cys Gln Arg Pro Asp Gly
        65                  70                  75                  80

Ala Leu Tyr Gly Ser Leu His Phe Asp Pro Glu Ala Cys Ser Phe Arg
                        85                  90                  95

Glu Leu Leu Leu Glu Asp Gly Tyr Asn Val Tyr Gln Ser Glu Ala His
                        100                 105                 110

Gly Leu Pro Leu His Leu Pro Gly Asn Lys Ser Pro His Arg Asp Pro
                        115                 120                 125

Ala Pro Arg Gly Pro Ala Arg Phe Leu Pro Leu Pro Gly Leu Pro Pro
                        130                 135                 140

Ala Leu Pro Glu Pro Pro Gly Ile Leu Ala Pro Gln Pro Pro Asp Val
        145                 150                 155                 160

Gly Ser Ser Asp Pro Leu Ser Met Val Gly Pro Ser Gln Gly Arg Ser
                        165                 170                 175

Pro Ser Tyr Ala Ser
                        180
```

```
<210> SEQ ID NO 17
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (56)..(56)
<223> OTHER INFORMATION: X = K or R
<220> FEATURE:
<221> NAME/KEY: MISC_FEATURE
<222> LOCATION: (59)..(59)
<223> OTHER INFORMATION: X = K or R
<220> FEATURE:
<221> NAME/KEY: MISC_FEATURE
<222> LOCATION: (69)..(69)
<223> OTHER INFORMATION: X = K or R
<220> FEATURE:
<221> NAME/KEY: MISC_FEATURE
<222> LOCATION: (122)..(122)
<223> OTHER INFORMATION: X = K or R
<220> FEATURE:
<221> NAME/KEY: MISC_FEATURE
<222> LOCATION: (146)..(146)
<223> OTHER INFORMATION: X = L or P

<400> SEQUENCE: 17

Xaa Pro Ile Pro Asp Ser Ser Pro Leu Leu Gln Phe Gly Gly Gln Val
 1               5                  10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Xaa Ala Leu Xaa Pro Gly Val Ile Gln
    50                  55                  60

Ile Leu Gly Val Xaa Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Xaa Ser Pro His Arg Asp Pro
        115                 120                 125

Ala Pro Arg Gly Pro Ala Arg Phe Leu Pro Leu Pro Gly Leu Pro Pro
    130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 18
<211> LENGTH: 180
<212> TYPE: PRT
<213> ORGANISM: Homo sapiens

<400> SEQUENCE: 18

Pro Ile Pro Asp Ser Ser Pro Leu Leu Gln Phe Gly Gly Gln Val Arg
 1               5                  10                  15
```

```
Gln Arg Tyr Leu Tyr Thr Asp Asp Ala Gln Gln Thr Glu Ala His Leu
             20                  25                  30

Glu Ile Arg Glu Asp Gly Thr Val Gly Gly Ala Ala Asp Gln Ser Pro
         35                  40                  45

Glu Ser Leu Leu Gln Leu Lys Ala Leu Arg Pro Gly Val Ile Gln Ile
     50                  55                  60

Leu Gly Val Arg Thr Ser Arg Phe Leu Cys Gln Arg Pro Asp Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                 110

Leu Pro Leu His Leu Pro Gly Asn Arg Ser Pro His Arg Asp Pro Ala
            115                 120                 125

Pro Arg Gly Pro Ala Arg Phe Leu Pro Leu Pro Gly Leu Pro Pro Ala
        130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 19
<211> LENGTH: 180
<212> TYPE: PRT
<213> ORGANISM: Homo sapiens

<400> SEQUENCE: 19

Pro Ile Pro Asp Ser Ser Pro Leu Leu Gln Phe Gly Gly Gln Val Arg
  1               5                  10                  15

Gln Arg Tyr Leu Tyr Thr Asp Asp Ala Gln Gln Thr Glu Ala His Leu
             20                  25                  30

Glu Ile Arg Glu Asp Gly Thr Val Gly Gly Ala Ala Asp Gln Ser Pro
         35                  40                  45

Glu Ser Leu Leu Gln Leu Arg Ala Leu Lys Pro Gly Val Ile Gln Ile
     50                  55                  60

Leu Gly Val Arg Thr Ser Arg Phe Leu Cys Gln Arg Pro Asp Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                 110

Leu Pro Leu His Leu Pro Gly Asn Arg Ser Pro His Arg Asp Pro Ala
            115                 120                 125

Pro Arg Gly Pro Ala Arg Phe Leu Pro Leu Pro Gly Leu Pro Pro Ala
        130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 20
```

<211> LENGTH: 180
<212> TYPE: PRT
<213> ORGANISM: Homo sapiens

<400> SEQUENCE: 20

```
Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Arg Ala Leu Arg Pro Gly Val Ile Gln Ile
    50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Arg Ser Pro His Arg Asp Pro Ala
        115                 120                 125

Pro Arg Gly Pro Ala Arg Phe Leu Pro Leu Pro Gly Leu Pro Pro Ala
    130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180
```

<210> SEQ ID NO 21
<211> LENGTH: 180
<212> TYPE: PRT
<213> ORGANISM: Homo sapiens

<400> SEQUENCE: 21

```
Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Arg Ala Leu Arg Pro Gly Val Ile Gln Ile
    50                  55                  60

Leu Gly Val Arg Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro His Arg Asp Pro Ala
        115                 120                 125

Pro Arg Gly Pro Ala Arg Phe Leu Pro Leu Pro Gly Leu Pro Pro Ala
    130                 135                 140

Leu Pro Glu Pro Pro Gly Ile Leu Ala Pro Gln Pro Pro Asp Val Gly
145                 150                 155                 160
```

```
Ser Ser Asp Pro Leu Ser Met Val Gly Pro Ser Gln Gly Arg Ser Pro
                165                 170                 175

Ser Tyr Ala Ser
            180
```

<210> SEQ ID NO 22
<211> LENGTH: 180
<212> TYPE: PRT
<213> ORGANISM: Homo sapiens

<400> SEQUENCE: 22

```
Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
            20                  25                  30

Glu Ile Arg Glu Asp Gly Thr Val Gly Gly Ala Ala Asp Gln Ser Pro
            35                  40                  45

Glu Ser Leu Leu Gln Leu Arg Ala Leu Arg Pro Gly Val Ile Gln Ile
    50                  55                  60

Leu Gly Val Arg Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Arg Ser Pro His Arg Asp Pro Ala
        115                 120                 125

Pro Arg Gly Pro Ala Arg Phe Leu Pro Leu Pro Gly Leu Pro Pro Ala
    130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180
```

<210> SEQ ID NO 23
<211> LENGTH: 181
<212> TYPE: PRT
<213> ORGANISM: Homo sapiens

<400> SEQUENCE: 23

```
Lys Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110
```

```
Gly Leu Pro Leu His Leu Pro Gly Asn Arg Ser Pro His Arg Asp Pro
            115                 120                 125
Ala Pro Arg Gly Pro Ala Arg Phe Leu Pro Leu Pro Gly Leu Pro Pro
130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Gly Pro Ser Gln Gly Arg Ser
                165                 170                 175
Pro Ser Tyr Ala Ser
            180

<210> SEQ ID NO 24
<211> LENGTH: 180
<212> TYPE: PRT
<213> ORGANISM: Homo sapiens

<400> SEQUENCE: 24

Pro Ile Pro Asp Ser Ser Pro Leu Leu Gln Phe Gly Gly Gln Val Arg
1               5                   10                  15
Gln Arg Tyr Leu Tyr Thr Asp Asp Ala Gln Gln Thr Glu Ala His Leu
            20                  25                  30
Glu Ile Arg Glu Asp Gly Thr Val Gly Gly Ala Ala Asp Gln Ser Pro
        35                  40                  45
Glu Ser Leu Leu Gln Leu Arg Ala Leu Arg Pro Gly Val Ile Gln Ile
50                  55                  60
Leu Gly Val Arg Thr Ser Arg Phe Leu Cys Gln Arg Pro Asp Gly Ala
65                  70                  75                  80
Leu Tyr Gly Ser Leu His Phe Asp Pro Glu Ala Cys Ser Phe Arg Glu
                85                  90                  95
Leu Leu Leu Glu Asp Gly Tyr Asn Val Tyr Gln Ser Glu Ala His Gly
            100                 105                 110
Leu Pro Leu His Leu Pro Gly Asn Arg Ser Pro His Arg Asp Pro Ala
        115                 120                 125
Pro Arg Gly Pro Ala Arg Phe Leu Pro Leu Pro Gly Leu Pro Pro Ala
    130                 135                 140
Leu Pro Glu Pro Pro Gly Ile Leu Ala Pro Gln Pro Pro Asp Val Gly
145                 150                 155                 160
Ser Ser Asp Pro Leu Ser Met Val Gly Pro Ser Gln Gly Arg Ser Pro
                165                 170                 175
Ser Tyr Ala Lys
            180

<210> SEQ ID NO 25
<211> LENGTH: 219
<212> TYPE: PRT
<213> ORGANISM: Homo sapiens

<400> SEQUENCE: 25

Glu Leu Gln Met Thr Gln Ser Pro Ser Ser Leu Ser Ala Ser Val Gly
1               5                   10                  15
Asp Arg Val Thr Ile Thr Cys Arg Ser Ser Gln Ser Leu Leu His Thr
            20                  25                  30
Tyr Gly Ser Pro Tyr Leu Asn Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
```

```
Ser Arg Phe Ser Gly Ser Gly Ser Gly Thr Asp Phe Thr Leu Thr Ile
 65                  70                  75                  80

Ser Ser Leu Gln Pro Glu Asp Phe Ala Val Tyr Phe Cys Ser Gln Gly
                 85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 448
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Trp Met Ser Trp Val Arg Gln Ser Pro Glu Lys Gly Leu Glu Trp Val
         35                  40                  45

Ser Glu Ile Arg Leu Arg Ser Asp Asn Tyr Ala Thr His Tyr Ala Glu
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Gly Ile Tyr
                 85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 27
<211> LENGTH: 112
<212> TYPE: PRT
<213> ORGANISM: Homo sapiens

<400> SEQUENCE: 27

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

<210> SEQ ID NO 28
<211> LENGTH: 118
<212> TYPE: PRT
<213> ORGANISM: Homo sapiens
```

```
<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser
        115

<210> SEQ ID NO 29
<211> LENGTH: 112
<212> TYPE: PRT
<213> ORGANISM: Mus musculus

<400> SEQUENCE: 29

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Gly
                85                  90                  95

Thr His Leu Pro Tyr Thr Phe Gly Gly Gly Thr Lys Leu Glu Ile Lys
            100                 105                 110

<210> SEQ ID NO 30
<211> LENGTH: 118
<212> TYPE: PRT
<213> ORGANISM: Mus musculus

<400> SEQUENCE: 30

Glu Val Lys Leu Val Glu Ser Gly Gly Gly Leu Val Gln Pro Gly Gly
1               5                   10                  15

Thr Met Lys Leu Ser Cys Glu Ile Ser Gly Leu Thr Phe Arg Asn Tyr
            20                  25                  30

Trp Met Ser Trp Val Arg Gln Ser Pro Glu Lys Gly Leu Glu Trp Val
        35                  40                  45

Ala Glu Ile Arg Leu Arg Ser Asp Asn Tyr Ala Thr His Tyr Ala Glu
50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Thr Glu Asp Thr Gly Ile Tyr
```

-continued

```
                    85                  90                  95
Tyr Cys Lys Tyr Tyr Phe Tyr Ser Phe Ser Tyr Trp Gly Gln Gly Thr
                100                 105                 110

Leu Val Thr Val Ser Ala
        115

<210> SEQ ID NO 31
<211> LENGTH: 15
<212> TYPE: PRT
<213> ORGANISM: Artificial Sequence
<220> FEATURE:
<223> OTHER INFORMATION: Polypeptide Linker

<400> SEQUENCE: 31

Gly Gly Gly Gly Ser Gly Gly Gly Ser Gly Gly Gly Gly Ser
1               5                   10                  15

<210> SEQ ID NO 32
<211> LENGTH: 28
<212> TYPE: PRT
<213> ORGANISM: Homo sapiens

<400> SEQUENCE: 32

Met Asn Ser Asn Glu Thr Gly Phe Glu His Ser Gly Leu Trp Val Ser
1               5                   10                  15

Val Leu Ala Gly Leu Leu Gly Ala Cys Gln Ala
            20                  25

<210> SEQ ID NO 33
<211> LENGTH: 209
<212> TYPE: PRT
<213> ORGANISM: Homo sapiens

<400> SEQUENCE: 33

Met Asn Ser Asn Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Leu Pro Glu
                165                 170                 175

Pro Pro Gly Ile Leu Ala Pro Gln Pro Pro Asp Val Gly Ser Ser Asp
                180                 185                 190
```

```
Pro Leu Ser Met Val Gly Pro Ser Gln Gly Arg Ser Pro Ser Tyr Ala
        195                 200                 205
Ser

<210> SEQ ID NO 34
<211> LENGTH: 30
<212> TYPE: PRT
<213> ORGANISM: Homo sapiens

<400> SEQUENCE: 34

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 35
<211> LENGTH: 39
<212> TYPE: PRT
<213> ORGANISM: Homo sapiens

<400> SEQUENCE: 35

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 36

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 37
<211> LENGTH: 40
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (40)..(40)
<223> OTHER INFORMATION: X = K, KSH, KSMAL, Dap, Dab, R, Y, C, T, S
      homocysteine, or homoserine

<400> SEQUENCE: 37

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Ser Xaa
        35                  40
```

<210> SEQ ID NO 38
<211> LENGTH: 40
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (40)..(40)
<223> OTHER INFORMATION: X = K, KSH, KSMAL, Dap, Dab, R, Y, C, T, S homocysteine, homoserine, or is absent

<400> SEQUENCE: 38

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40
```

<210> SEQ ID NO 39
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (38)..(38)
<223> OTHER INFORMATION: X = K, KSH, KSMAL, Dap, Dab, R, Y, C, T, S homocysteine, or homoserine

<400> SEQUENCE: 39

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Xaa Ser
        35
```

<210> SEQ ID NO 40
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (36)..(36)
<223> OTHER INFORMATION: X = K, KSH, KSMAL, Dap, Dab, R, Y, C, T, S homocysteine, or homoserine

<400> SEQUENCE: 40

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Pro Pro Ser
        35
```

<210> SEQ ID NO 41
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (34)..(34)
<223> OTHER INFORMATION: X = K, KSH, KSMAL, Dap, Dab, R, Y, C, T, S homocysteine, or homoserine

<400> SEQUENCE: 41

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Xaa Ala Pro Pro Pro Ser
        35
```

<210> SEQ ID NO 42
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (32)..(32)
<223> OTHER INFORMATION: X = K, KSH, KSMAL, Dap, Dab, R, Y, C, T, S homocysteine, or homoserine

<400> SEQUENCE: 42

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Xaa
            20                  25                  30

Ser Gly Ala Pro Pro Pro Ser
        35
```

<210> SEQ ID NO 43
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (28)..(28)

<223> OTHER INFORMATION: X = K, KSH, KSMAL, Dap, Dab, R, Y, C, T, S homocysteine, or homoserine

<400> SEQUENCE: 43

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (27)..(27)
<223> OTHER INFORMATION: X = K, KSH, KSMAL, Dap, Dab, R, Y, C, T, S homocysteine, or homoserine

<400> SEQUENCE: 44

His Xaa Glu Gly Thr Phe Thr Ser Asp Leu Ser Lys Gln Met Glu Glu
1               5                   10                  15

Glu Ala Val Arg Leu Phe Ile Glu Trp Leu Xaa Asn Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (26)..(26)
<223> OTHER INFORMATION: X = K, KSH, KSMAL, Dap, Dab, R, Y, C, T, S homocysteine, or homoserine

<400> SEQUENCE: 45

His Xaa Glu Gly Thr Phe Thr Ser Asp Leu Ser Lys Gln Met Glu Glu
1               5                   10                  15

Glu Ala Val Arg Leu Phe Ile Glu Trp Xaa Lys Asn Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE

```
<222> LOCATION: (2)..(2)
<223> OTHER INFORMATION: X = Aib
<220> FEATURE:
<221> NAME/KEY: MISC_FEATURE
<222> LOCATION: (24)..(24)
<223> OTHER INFORMATION: X = K, KSH, KSMAL, Dap, Dab, R, Y, C, T, S
      homocysteine, or homoserine

<400> SEQUENCE: 46

His Xaa Glu Gly Thr Phe Thr Ser Asp Leu Ser Lys Gln Met Glu Glu
1               5                   10                  15

Glu Ala Val Arg Leu Phe Ile Xaa Trp Leu Lys Asn Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (23)..(23)
<223> OTHER INFORMATION: X = K, KSH, KSMAL, Dap, Dab, R, Y, C, T, S
      homocysteine, or homoserine

<400> SEQUENCE: 47

His Xaa Glu Gly Thr Phe Thr Ser Asp Leu Ser Lys Gln Met Glu Glu
1               5                   10                  15

Glu Ala Val Arg Leu Phe Xaa Glu Trp Leu Lys Asn Gly Gly Pro Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (21)..(21)
<223> OTHER INFORMATION: X = K, KSH, KSMAL, Dap, Dab, R, Y, C, T, S
      homocysteine, or homoserine

<400> SEQUENCE: 48

His Xaa Glu Gly Thr Phe Thr Ser Asp Leu Ser Lys Gln Met Glu Glu
1               5                   10                  15

Glu Ala Val Arg Xaa Phe Ile Glu Trp Leu Lys Asn Gly Gly Pro Ser
            20                  25                  30

Ser Gly Ala Pro Pro Pro Ser
        35

<210> SEQ ID NO 49
<211> LENGTH: 39
<212> TYPE: PRT
```

```
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (20)..(20)
<223> OTHER INFORMATION: X = K, KSH, KSMAL, Dap, Dab, R, Y, C, T, S
      homocysteine, or homoserine

<400> SEQUENCE: 49

His Xaa Glu Gly Thr Phe Thr Ser Asp Leu Ser Lys Gln Met Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (19)..(19)
<223> OTHER INFORMATION: X = K, KSH, KSMAL, Dap, Dab, R, Y, C, T, S
      homocysteine, or homoserine

<400> SEQUENCE: 50

His Xaa Glu Gly Thr Phe Thr Ser Asp Leu Ser Lys Gln Met Glu Glu
1               5                   10                  15

Glu Ala Xaa Arg Leu Phe Ile Glu Trp Leu Lys Asn Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (17)..(17)
<223> OTHER INFORMATION: X = K, KSH, KSMAL, Dap, Dab, R, Y, C, T, S
      homocysteine, or homoserine

<400> SEQUENCE: 51

His Xaa Glu Gly Thr Phe Thr Ser Asp Leu Ser Lys Gln Met Glu Glu
1               5                   10                  15

Xaa Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 52
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (16)..(16)
<223> OTHER INFORMATION: X = K, KSH, KSMAL, Dap, Dab, R, Y, C, T, S
      homocysteine, or homoserine

<400> SEQUENCE: 52

His Xaa Glu Gly Thr Phe Thr Ser Asp Leu Ser Lys Gln Met Glu Xaa
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (14)..(14)
<223> OTHER INFORMATION: X = K, KSH, KSMAL, Dap, Dab, R, Y, C, T, S
      homocysteine, or homoserine

<400> SEQUENCE: 53

His Xaa Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 54
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (13)..(13)
<223> OTHER INFORMATION: X = K, KSH, KSMAL, Dap, Dab, R, Y, C, T, S
      homocysteine, or homoserine

<400> SEQUENCE: 54

His Xaa Glu Gly Thr Phe Thr Ser Asp Leu Ser Lys Xaa Met Glu Glu
1               5                   10                  15
```

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 55
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (12)..(12)
<223> OTHER INFORMATION: X = K, KSH, KSMAL, Dap, Dab, R, Y, C, T, S homocysteine, or homoserine

<400> SEQUENCE: 55

His Xaa Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (11)..(11)
<223> OTHER INFORMATION: X = K, KSH, KSMAL, Dap, Dab, R, Y, C, T, S homocysteine, or homoserine

<400> SEQUENCE: 56

His Xaa Glu Gly Thr Phe Thr Ser Asp Leu Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 57
<211> LENGTH: 31
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (31)..(31)
<223> OTHER INFORMATION: X = K, KSH, KSMAL, Dap, Dab, R, Y, C, T, S homocysteine, or homoserine

<400> SEQUENCE: 57

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 58
<211> LENGTH: 33
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (21)..(21)
<223> OTHER INFORMATION: X = K, KSH, KSMAL, Dap, Dab, R, Y, C, T, S
      homocysteine, or homoserine

<400> SEQUENCE: 58

His Xaa Glu Gly Thr Phe Thr Ser Asp Leu Ser Lys Gln Met Glu Glu
1               5                   10                  15

Glu Ala Val Arg Xaa Phe Ile Glu Trp Leu Lys Asn Gly Gly Pro Ser
            20                  25                  30

Ser

<210> SEQ ID NO 59
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (1)..(1)
<223> OTHER INFORMATION: X = d-His
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (14)..(14)
<223> OTHER INFORMATION: X = K, KSH, KSMAL, Dap, Dab, R, Y, C, T, S
      homocysteine, or homoserine

<400> SEQUENCE: 59

Xaa Xaa Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 60
<211> LENGTH: 40
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:

```
<221> NAME/KEY: MISC_FEATURE
<222> LOCATION: (12)..(12)
<223> OTHER INFORMATION: X = K, KSH, KSMAL, Dap, Dab, R, Y, C, T, S
      homocysteine, or homoserine
<220> FEATURE:
<221> NAME/KEY: MISC_FEATURE
<222> LOCATION: (14)..(14)
<223> OTHER INFORMATION: X = M, K, KSH, KSMAL, Dap, Dab, R, Y, C, T, S
      homocysteine, or homoserine
<220> FEATURE:
<221> NAME/KEY: MISC_FEATURE
<222> LOCATION: (19)..(19)
<223> OTHER INFORMATION: X = V, K, KSH, KSMAL, Dap, Dab, R, Y, C, T, S
      homocysteine, or homoserine
<220> FEATURE:
<221> NAME/KEY: MISC_FEATURE
<222> LOCATION: (20)..(20)
<223> OTHER INFORMATION: X = R, K, KSH, KSMAL, Dap, Dab, R, Y, C, T, S
      homocysteine, or homoserine
<220> FEATURE:
<221> NAME/KEY: MISC_FEATURE
<222> LOCATION: (21)..(21)
<223> OTHER INFORMATION: X = L, K, KSH, KSMAL, Dap, Dab, R, Y, C, T, S
      homocysteine, or homoserine
<220> FEATURE:
<221> NAME/KEY: MISC_FEATURE
<222> LOCATION: (40)..(40)
<223> OTHER INFORMATION: X = Absent or any amino acid

<400> SEQUENCE: 60

His Xaa Glu Gly Thr Phe Thr Ser Asp Leu Ser Xaa Gln Xaa Glu Glu
1               5                   10                  15

Glu Ala Xaa Xaa Xaa Phe Ile Glu Trp Leu Lys Asn Gly Gly Pro Ser
            20                  25                  30

Ser Gly Ala Pro Pro Pro Ser Xaa
        35                  40

<210> SEQ ID NO 61
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 61

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 62
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (12)..(12)
<223> OTHER INFORMATION: X = KSH
```

```
<400> SEQUENCE: 62

His Xaa Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 63

His Xaa Glu Gly Thr Phe Thr Ser Asp Leu Ser Lys Gln Lys Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (14)..(14)
<223> OTHER INFORMATION: X = KSH

<400> SEQUENCE: 64

His Xaa Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 65
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 65

His Xaa Glu Gly Thr Phe Thr Ser Asp Leu Ser Lys Gln Met Glu Glu
1               5                   10                  15

Glu Ala Lys Arg Leu Phe Ile Glu Trp Leu Lys Asn Gly Gly Pro Ser
```

```
            20                  25                  30

Ser Gly Ala Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (19)..(19)
<223> OTHER INFORMATION: X = KSH

<400> SEQUENCE: 66

His Xaa Glu Gly Thr Phe Thr Ser Asp Leu Ser Lys Gln Met Glu Glu
1               5                   10                  15

Glu Ala Xaa Arg Leu Phe Ile Glu Trp Leu Lys Asn Gly Gly Pro Ser
            20                  25                  30

Ser Gly Ala Pro Pro Ser
        35

<210> SEQ ID NO 67
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 67

His Xaa Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (20)..(20)
<223> OTHER INFORMATION: X = KSH

<400> SEQUENCE: 68

His Xaa Glu Gly Thr Phe Thr Ser Asp Leu Ser Lys Gln Met Glu Glu
1               5                   10                  15

Glu Ala Val Xaa Leu Phe Ile Glu Trp Leu Lys Asn Gly Gly Pro Ser
            20                  25                  30
```

Ser Gly Ala Pro Pro Pro Ser
            35

<210> SEQ ID NO 69
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 69

His Xaa Glu Gly Thr Phe Thr Ser Asp Leu Ser Lys Gln Met Glu Glu
1               5                   10                  15

Glu Ala Val Arg Lys Phe Ile Glu Trp Leu Lys Asn Gly Gly Pro Ser
            20                  25                  30

Ser Gly Ala Pro Pro Pro Ser
            35

<210> SEQ ID NO 70
<211> LENGTH: 39
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (21)..(21)
<223> OTHER INFORMATION: X = KSH

<400> SEQUENCE: 70

His Xaa Glu Gly Thr Phe Thr Ser Asp Leu Ser Lys Gln Met Glu Glu
1               5                   10                  15

Glu Ala Val Arg Xaa Phe Ile Glu Trp Leu Lys Asn Gly Gly Pro Ser
            20                  25                  30

Ser Gly Ala Pro Pro Pro Ser
            35

<210> SEQ ID NO 71
<211> LENGTH: 40
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib

<400> SEQUENCE: 71

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
            35                  40

<210> SEQ ID NO 72
<211> LENGTH: 40

```
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (40)..(40)
<223> OTHER INFORMATION: X = KSH

<400> SEQUENCE: 72

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 73
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (146)..(146)
<223> OTHER INFORMATION: X = L or P

<400> SEQUENCE: 73

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Cys Ser Gln Gly Arg Ser
                165                 170                 175

Pro Ser Tyr Ala Ser
            180

<210> SEQ ID NO 74
<211> LENGTH: 181
```

```
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or absent

<400> SEQUENCE: 74
```

| Xaa | Pro | Ile | Pro | Asp | Ser | Ser | Pro | Leu | Leu | Gln | Phe | Gly | Gly | Gln | Val |
|---|---|---|---|---|---|---|---|---|---|---|---|---|---|---|---|
| 1 | | | | 5 | | | | | 10 | | | | | 15 | |

| Arg | Gln | Arg | Tyr | Leu | Tyr | Thr | Asp | Asp | Ala | Gln | Gln | Thr | Glu | Ala | His |
|---|---|---|---|---|---|---|---|---|---|---|---|---|---|---|---|
| | | | 20 | | | | | 25 | | | | | 30 | | |

| Leu | Glu | Ile | Arg | Glu | Asp | Gly | Thr | Val | Gly | Gly | Ala | Ala | Asp | Gln | Ser |
|---|---|---|---|---|---|---|---|---|---|---|---|---|---|---|---|
| | | | 35 | | | | | 40 | | | | | 45 | | |

| Pro | Glu | Ser | Leu | Leu | Gln | Leu | Lys | Ala | Leu | Lys | Pro | Gly | Val | Ile | Gln |
|---|---|---|---|---|---|---|---|---|---|---|---|---|---|---|---|
| | 50 | | | | | 55 | | | | | 60 | | | | |

| Ile | Leu | Gly | Val | Lys | Thr | Ser | Arg | Phe | Leu | Cys | Gln | Arg | Pro | Asp | Gly |
|---|---|---|---|---|---|---|---|---|---|---|---|---|---|---|---|
| 65 | | | | | 70 | | | | | 75 | | | | | 80 |

| Ala | Leu | Tyr | Gly | Ser | Leu | His | Phe | Asp | Pro | Glu | Ala | Cys | Ser | Phe | Arg |
|---|---|---|---|---|---|---|---|---|---|---|---|---|---|---|---|
| | | | | 85 | | | | | 90 | | | | | 95 | |

| Glu | Leu | Leu | Leu | Glu | Asp | Gly | Tyr | Asn | Val | Tyr | Gln | Ser | Glu | Ala | His |
|---|---|---|---|---|---|---|---|---|---|---|---|---|---|---|---|
| | | | 100 | | | | | 105 | | | | | 110 | | |

| Gly | Leu | Pro | Leu | His | Leu | Pro | Gly | Asn | Lys | Ser | Pro | His | Arg | Asp | Pro |
|---|---|---|---|---|---|---|---|---|---|---|---|---|---|---|---|
| | | 115 | | | | | 120 | | | | | 125 | | | |

| Ala | Pro | Arg | Gly | Pro | Ala | Arg | Phe | Leu | Pro | Leu | Pro | Gly | Leu | Pro | Pro |
|---|---|---|---|---|---|---|---|---|---|---|---|---|---|---|---|
| | 130 | | | | | 135 | | | | | 140 | | | | |

| Ala | Leu | Pro | Glu | Pro | Pro | Gly | Ile | Leu | Ala | Pro | Gln | Pro | Pro | Asp | Val |
|---|---|---|---|---|---|---|---|---|---|---|---|---|---|---|---|
| 145 | | | | | 150 | | | | | 155 | | | | | 160 |

| Gly | Ser | Ser | Asp | Pro | Leu | Ser | Met | Val | Gly | Cys | Ser | Gln | Gly | Arg | Ser |
|---|---|---|---|---|---|---|---|---|---|---|---|---|---|---|---|
| | | | | 165 | | | | | 170 | | | | | 175 | |

| Pro | Ser | Tyr | Ala | Ser |
|---|---|---|---|---|
| | | | | 180 |

```
<210> SEQ ID NO 75
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent

<400> SEQUENCE: 75
```

| Xaa | Pro | Ile | Pro | Asp | Ser | Ser | Pro | Leu | Leu | Gln | Phe | Gly | Gly | Gln | Val |
|---|---|---|---|---|---|---|---|---|---|---|---|---|---|---|---|
| 1 | | | | 5 | | | | | 10 | | | | | 15 | |

| Arg | Gln | Arg | Tyr | Leu | Tyr | Thr | Asp | Asp | Ala | Gln | Gln | Thr | Glu | Ala | His |
|---|---|---|---|---|---|---|---|---|---|---|---|---|---|---|---|
| | | | 20 | | | | | 25 | | | | | 30 | | |

| Leu | Glu | Ile | Arg | Glu | Asp | Gly | Thr | Val | Gly | Gly | Ala | Ala | Asp | Gln | Ser |
|---|---|---|---|---|---|---|---|---|---|---|---|---|---|---|---|
| | | | 35 | | | | | 40 | | | | | 45 | | |

| Pro | Glu | Ser | Leu | Leu | Gln | Leu | Lys | Ala | Leu | Lys | Pro | Gly | Val | Ile | Gln |
|---|---|---|---|---|---|---|---|---|---|---|---|---|---|---|---|
| | 50 | | | | | 55 | | | | | 60 | | | | |

| Ile | Leu | Gly | Val | Lys | Thr | Ser | Arg | Phe | Leu | Cys | Gln | Arg | Pro | Asp | Gly |
|---|---|---|---|---|---|---|---|---|---|---|---|---|---|---|---|
| 65 | | | | | 70 | | | | | 75 | | | | | 80 |

| Ala | Leu | Tyr | Gly | Ser | Leu | His | Phe | Asp | Pro | Glu | Ala | Cys | Ser | Phe | Arg |
|---|---|---|---|---|---|---|---|---|---|---|---|---|---|---|---|
| | | | | 85 | | | | | 90 | | | | | 95 | |

| Glu | Leu | Leu | Leu | Glu | Asp | Gly | Tyr | Asn | Val | Tyr | Gln | Ser | Glu | Ala | His |
|---|---|---|---|---|---|---|---|---|---|---|---|---|---|---|---|
| | | | 100 | | | | | 105 | | | | | 110 | | |

| Gly | Leu | Pro | Leu | His | Leu | Pro | Gly | Asn | Lys | Ser | Pro | His | Arg | Asp | Pro |
|---|---|---|---|---|---|---|---|---|---|---|---|---|---|---|---|

```
            115                 120                 125
Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Cys Ser Gln Gly Arg Ser
                165                 170                 175

Pro Ser Tyr Ala Ser
            180

<210> SEQ ID NO 76
<211> LENGTH: 444
<212> TYPE: PRT
<213> ORGANISM: Homo sapiens

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300
```

```
Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 77
<211> LENGTH: 41
<212> TYPE: PRT
<213> ORGANISM: Artificial Sequence
<220> FEATURE:
<223> OTHER INFORMATION: Synthetic Analogs of Human Exendin-4
<220> FEATURE:
<221> NAME/KEY: MISC_FEATURE
<222> LOCATION: (1)..(1)
<223> OTHER INFORMATION: X = C(O)CH3
<220> FEATURE:
<221> NAME/KEY: MISC_FEATURE
<222> LOCATION: (3)..(3)
<223> OTHER INFORMATION: X = Aib
<220> FEATURE:
<221> NAME/KEY: MISC_FEATURE
<222> LOCATION: (15)..(15)
<223> OTHER INFORMATION: X = KSH
<220> FEATURE:
<221> NAME/KEY: MISC_FEATURE
<222> LOCATION: (41)..(41)
<223> OTHER INFORMATION: X = NH2

<400> SEQUENCE: 77

Xaa His Xaa Glu Gly Thr Phe Thr Ser Asp Leu Ser Lys Gln Xaa Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser Xaa
            35                  40

<210> SEQ ID NO 78
<211> LENGTH: 107
<212> TYPE: PRT
<213> ORGANISM: Homo sapiens
<220> FEATURE:
<221> NAME/KEY: MISC_FEATURE
<222> LOCATION: (46)..(46)
<223> OTHER INFORMATION: X = V or A
<220> FEATURE:
<221> NAME/KEY: MISC_FEATURE
<222> LOCATION: (84)..(84)
<223> OTHER INFORMATION: X = V or L

<400> SEQUENCE: 78

Arg Thr Val Ala Ala Pro Ser Val Phe Ile Phe Pro Pro Ser Asp Glu
```

```
                1               5                   10                  15
        Gln Leu Lys Ser Gly Thr Ala Ser Val Val Cys Leu Leu Asn Asn Phe
                        20                  25                  30

Tyr Pro Arg Glu Ala Lys Val Gln Trp Lys Val Asp Asn Xaa Leu Gln
                        35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
        65                  70                  75                  80

Lys His Lys Xaa Tyr Ala Cys Glu Val Thr His Gln Gly Leu Ser Ser
                        85                  90                  95

Pro Val Thr Lys Ser Phe Asn Arg Gly Glu Cys
                        100                 105

<210> SEQ ID NO 79
<211> LENGTH: 107
<212> TYPE: PRT
<213> ORGANISM: Homo sapiens

<400> SEQUENCE: 79

Arg Thr Val Ala Ala Pro Ser Val Phe Ile Phe Pro Pro Ser Asp Glu
        1               5                   10                  15

Gln Leu Lys Ser Gly Thr Ala Ser Val Val Cys Leu Leu Asn Asn Phe
                        20                  25                  30

Tyr Pro Arg Glu Ala Lys Val Gln Trp Lys Val Asp Asn Val Leu Gln
                        35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
        65                  70                  75                  80

Lys His Lys Leu Tyr Ala Cys Glu Val Thr His Gln Gly Leu Ser Ser
                        85                  90                  95

Pro Val Thr Lys Ser Phe Asn Arg Gly Glu Cys
                        100                 105

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
        1               5                   10                  15

Gln Leu Lys Ser Gly Thr Ala Ser Val Val Cys Leu Leu Asn Asn Phe
                        20                  25                  30

Tyr Pro Arg Glu Ala Lys Val Gln Trp Lys Val Asp Asn Ala Leu Gln
                        35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
        65                  70                  75                  80

Lys His Lys Leu Tyr Ala Cys Glu Val Thr His Gln Gly Leu Ser Ser
                        85                  90                  95

Pro Val Thr Lys Ser Phe Asn Arg Gly Glu Cys
                        100                 105
```

<210> SEQ ID NO 81
<211> LENGTH: 107
<212> TYPE: PRT
<213> ORGANISM: Homo sapiens

<400> SEQUENCE: 81

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 82
<211> LENGTH: 330
<212> TYPE: PRT
<213> ORGANISM: Homo sapiens

<400> SEQUENCE: 82

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

-continued

```
                225                 230                 235                 240
Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330
```